US012644101B2

(12) United States Patent
Wilson et al.

(10) Patent No.: US 12,644,101 B2
(45) Date of Patent: Jun. 2, 2026

(54) ADENO-ASSOCIATED VIRUS (AAV) CLADE F VECTOR AND USES THEREFOR

(71) Applicant: The Trustees of the University of Pennsylvania, Philadelphia, PA (US)

(72) Inventors: James M. Wilson, Philadelphia, PA (US); Qiang Wang, Philadelphia, PA (US); April Tepe, Laurel, MD (US); Kevin Turner, Newtown Square, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 18/484,856

(22) Filed: Oct. 11, 2023

(65) Prior Publication Data

US 2024/0117322 A1 Apr. 11, 2024

Related U.S. Application Data

(63) Continuation of application No. 16/487,674, filed as application No. PCT/US2018/019992 on Feb. 27, 2018, now Pat. No. 11,827,906.

(60) Provisional application No. 62/614,002, filed on Jan. 5, 2018, provisional application No. 62/591,002, filed on Nov. 27, 2017, provisional application No. 62/464,748, filed on Feb. 28, 2017.

(51) Int. Cl.

*C12N 7/00* (2006.01)
*A61K 35/761* (2015.01)
*C07K 14/005* (2006.01)
*C07K 16/32* (2006.01)

(52) U.S. Cl.

CPC .............. *C12N 7/00* (2013.01); *A61K 35/761* (2013.01); *C07K 14/005* (2013.01); *C07K 16/32* (2013.01); *C12N 2750/14121* (2013.01); *C12N 2750/14122* (2013.01); *C12N 2750/14143* (2013.01)

(58) Field of Classification Search

None

See application file for complete search history.

(56) References Cited

U.S. PATENT DOCUMENTS

| | | | |
|---|---|---|---|
| 4,816,567 | A | 3/1989 | Cabilly et al. |
| 5,139,941 | A | 8/1992 | Muzyczka et al. |
| 5,478,745 | A | 12/1995 | Samulski et al. |
| 5,741,683 | A | 4/1998 | Zhou et al. |
| 5,811,524 | A | 9/1998 | Brams et al. |
| 5,830,462 | A | 11/1998 | Crabtree et al. |
| 5,834,266 | A | 11/1998 | Crabtree et al. |
| 5,869,337 | A | 2/1999 | Crabtree et al. |
| 5,871,753 | A | 2/1999 | Crabtree et al. |
| 6,011,018 | A | 1/2000 | Crabtree et al. |
| 6,015,709 | A | 1/2000 | Natesan |
| 6,043,082 | A | 3/2000 | Crabtree et al. |
| 6,046,047 | A | 4/2000 | Crabtree et al. |
| 6,057,152 | A | 5/2000 | Samulski et al. |
| 6,063,625 | A | 5/2000 | Crabtree et al. |
| 6,117,680 | A | 9/2000 | Natesan et al. |
| 6,127,521 | A | 10/2000 | Berlin et al. |
| 6,133,456 | A | 10/2000 | Holt et al. |
| 6,140,120 | A | 10/2000 | Crabtree et al. |
| 6,150,137 | A | 11/2000 | Berlin et al. |
| 6,150,527 | A | 11/2000 | Holt et al. |
| 6,165,787 | A | 12/2000 | Crabtree et al. |
| 6,166,197 | A | 12/2000 | Cook et al. |
| 6,187,757 | B1 | 2/2001 | Clackson et al. |
| 6,200,560 | B1 | 3/2001 | Couto et al. |
| 6,204,059 | B1 | 3/2001 | Samulski et al. |
| 6,221,349 | B1 | 4/2001 | Couto et al. |
| 6,258,603 | B1 | 7/2001 | Carlson et al. |
| 6,258,823 | B1 | 7/2001 | Holt et al. |
| 6,268,213 | B1 | 7/2001 | Samulski et al. |
| 6,326,166 | B1 | 12/2001 | Pomerantz et al. |
| 6,464,374 | B2 | 10/2002 | Akiyama et al. |
| 6,464,974 | B1 | 10/2002 | Berlin et al. |

(Continued)

FOREIGN PATENT DOCUMENTS

| | | |
|---|---|---|
| EP | 1310571 | 5/2003 |
| EP | 2296700 A2 | 3/2011 |

(Continued)

OTHER PUBLICATIONS

Adam VS et al., Adeno-associated virus 9-mediated airway expression of antibody protects old and immunodeficient mice against influenza virus. Clin. Vaccine Immunol., 21(11):1528-33, Nov. 2014. (Epub Sep. 10, 2014).
Afonine PV et al., Towards automated crystallographic structure refinement with phenix.refine, Acta Crystallogr. D Biol. Crystallogr., 68(Pt 4):352-67, Apr. 2012. (Epub Mar. 16, 2012).
Alexander MC et al., Insulin stimulates glyceraldehyde-3-phosphate dehydrogenase gene expression through cis-acting DNA sequences, Proc Natl Acad Sci USA, 85(14):5092-6, Jul. 1988.
Ali MY, Histology of the Human Nasopharyngeal Mucosa, J. Anat., 99(3):657-672, 1965.
Almond B. and Schenborn ET, A Comparison of pCI-neo Vector and pcDNA4/HisMax Vector, Promega Corporation Website, Updated 2000, Available from: http://www.promega.com/resources/pubhub/enotes/a-comparison-of-pcineo-vector-and-pcdna4hismax-vector/.
Amara JF et al., A versatile synthetic dimerizer for the regulation of protein-protein interactions, Proc. Natl. Acad. Sci. USA, 94(20):10618-23, Sep. 1997.

(Continued)

*Primary Examiner* — Benjamin P Blumel
(74) *Attorney, Agent, or Firm* — Howson & Howson LLP; Cathy A. Kodroff

(57) ABSTRACT

A recombinant adeno-associated virus (rAAV) vector comprising an AAVhu68 capsid produced in a production system comprising a nucleotide sequence of SEQ ID NO: 1, or a sequence at least 75% identical thereto which encodes SEQ ID NO:2. The AAVhu68 capsid comprises subpopulations of highly deamidated asparagine residues in asparagine-glycine pairs in the amino acid sequence of SEQ ID NO: 2. Also provided are compositions containing the rAAV and uses thereof. Additionally, rAAV having an engineered AAV capsid comprising at least one subpopulation of vp1 or vp2 proteins having a Val at amino acid position 157 with reference to the AAVhu68 vp1 numbering are provided.

7 Claims, 23 Drawing Sheets

Specification includes a Sequence Listing.

(56) References Cited

U.S. PATENT DOCUMENTS

| | | | |
|---|---|---|---|
| 6,476,200 | B1 | 11/2002 | Sabatini et al. |
| 6,479,653 | B1 | 11/2002 | Natesan et al. |
| 6,491,907 | B1 | 12/2002 | Rabinowitz et al. |
| 6,506,379 | B1 | 1/2003 | Clackson et al. |
| 6,509,152 | B1 | 1/2003 | Berlin et al. |
| 6,596,535 | B1 | 7/2003 | Carter |
| 6,649,595 | B2 | 11/2003 | Clackson et al. |
| 6,660,514 | B1 | 12/2003 | Zolotukhin et al. |
| 6,693,189 | B2 | 2/2004 | Holt et al. |
| 6,780,639 | B1 | 8/2004 | Chtarto et al. |
| 6,951,753 | B2 | 10/2005 | Shenk et al. |
| 6,972,193 | B1 | 12/2005 | Crabtree et al. |
| 6,984,635 | B1 | 1/2006 | Schreiber et al. |
| 7,008,780 | B2 | 3/2006 | Pomerantz et al. |
| 7,045,315 | B2 | 5/2006 | Evans et al. |
| 7,067,526 | B1 | 6/2006 | Yang et al. |
| 7,091,038 | B2 | 8/2006 | Palli et al. |
| 7,094,604 | B2 | 8/2006 | Snyder et al. |
| 7,109,317 | B1 | 9/2006 | Clemons et al. |
| 7,125,717 | B2 | 10/2006 | Carter |
| 7,172,893 | B2 | 2/2007 | Rabinowitz et al. |
| 7,196,192 | B2 | 3/2007 | Yang et al. |
| 7,201,898 | B2 | 4/2007 | Monahan et al. |
| 7,229,823 | B2 | 6/2007 | Samulski et al. |
| 7,282,199 | B2 | 10/2007 | Gao et al. |
| 7,439,065 | B2 | 10/2008 | Ferrari et al. |
| 7,442,373 | B2 | 10/2008 | Morrow et al. |
| 7,456,683 | B2 | 11/2008 | Takano et al. |
| 7,485,441 | B2 | 2/2009 | Pomerantz et al. |
| 7,588,772 | B2 | 9/2009 | Kay et al. |
| 7,785,888 | B2 | 8/2010 | Carter |
| 7,790,449 | B2 | 9/2010 | Gao et al. |
| 7,838,657 | B2 | 11/2010 | Singh et al. |
| 7,846,729 | B2 | 12/2010 | Carter |
| 7,906,111 | B2 | 3/2011 | Wilson et al. |
| 7,985,565 | B2 | 7/2011 | Mayer et al. |
| 8,008,005 | B2 | 8/2011 | Belshaw et al. |
| 8,093,054 | B2 | 1/2012 | Carter |
| 8,110,560 | B2 | 2/2012 | Singh et al. |
| 8,114,402 | B2 | 2/2012 | Grandea et al. |
| 8,124,092 | B2 | 2/2012 | Lanzavecchia |
| 8,211,631 | B2 | 7/2012 | Svendsen et al. |
| 8,361,977 | B2 | 1/2013 | Baker et al. |
| 8,734,809 | B2 | 5/2014 | Gao et al. |
| 8,852,595 | B2 | 10/2014 | Vogels et al. |
| 8,927,514 | B2 | 1/2015 | Chatterjee et al. |
| 8,961,978 | B2 | 2/2015 | Kwaks et al. |
| 8,980,853 | B2 | 3/2015 | Bennett et al. |
| 9,034,836 | B2 | 5/2015 | Dodge et al. |
| 9,340,603 | B2 | 5/2016 | Lanzavecchia |
| 9,719,106 | B2 | 8/2017 | Wilson et al. |
| 10,265,417 | B2 | 4/2019 | Wilson et al. |
| 10,370,435 | B2 | 8/2019 | Brandenburg et al. |
| 10,485,883 | B2 | 11/2019 | Wilson et al. |
| 10,695,441 | B2 | 6/2020 | Wilson et al. |
| 10,722,598 | B2 | 7/2020 | Wilson et al. |
| 10,786,568 | B2 | 9/2020 | Limberis et al. |
| 10,973,928 | B2 | 4/2021 | Wilson et al. |
| 11,827,906 | B2 * | 11/2023 | Wilson ................. A61K 35/761 |
| 2002/0110861 | A1 | 8/2002 | Dhadialla et al. |
| 2002/0173474 | A1 | 11/2002 | Schreiber et al. |
| 2004/0033600 | A1 | 2/2004 | Palli et al. |
| 2004/0096942 | A1 | 5/2004 | Kapitskaya et al. |
| 2005/0266457 | A1 | 12/2005 | Palli et al. |
| 2006/0014711 | A1 | 1/2006 | Evans et al. |
| 2006/0100416 | A1 | 5/2006 | Palli et al. |
| 2006/0136184 | A1 | 6/2006 | Gustafsson et al. |
| 2007/0036760 | A1 | 2/2007 | Wilson et al. |
| 2007/0161086 | A1 | 7/2007 | Palli et al. |
| 2009/0100535 | A1 | 4/2009 | Pomerantz et al. |
| 2009/0104232 | A1 | 4/2009 | Crystal et al. |
| 2009/0197338 | A1 | 8/2009 | Vandenberghe et al. |
| 2009/0275107 | A1 | 11/2009 | Lock et al. |
| 2010/0080813 | A1 | 4/2010 | Lanzavecchia |
| 2011/0076265 | A1 | 3/2011 | Burioni et al. |
| 2011/0150904 | A1 | 6/2011 | Schiltz et al. |
| 2011/0236353 | A1 | 9/2011 | Wilson et al. |
| 2011/0274702 | A1 | 11/2011 | Lanzavecchia |
| 2012/0232133 | A1 | 9/2012 | Balazs et al. |
| 2012/0282695 | A1 | 11/2012 | Blain et al. |
| 2013/0045186 | A1 | 2/2013 | Gao et al. |
| 2013/0243792 | A1 | 9/2013 | Vogels et al. |
| 2014/0032186 | A1 | 1/2014 | Gustafsson et al. |
| 2014/0037637 | A1 | 2/2014 | McNally et al. |
| 2014/0065666 | A1 | 3/2014 | Simpson et al. |
| 2014/0094392 | A1 | 4/2014 | Bowers et al. |
| 2014/0127749 | A1 | 5/2014 | Mason et al. |
| 2015/0344911 | A1 | 12/2015 | Chatterjee et al. |
| 2016/0074474 | A1 | 3/2016 | Passini et al. |
| 2017/0028082 | A1 | 2/2017 | Wilson et al. |
| 2017/0043035 | A1 | 2/2017 | Wilson et al. |
| 2017/0081392 | A1 | 3/2017 | Wilson et al. |
| 2017/0101458 | A1 | 4/2017 | Wilson et al. |
| 2017/0159027 | A1 | 6/2017 | Wilson et al. |
| 2017/0292132 | A1 | 10/2017 | Wilson et al. |
| 2018/0243416 | A1 | 8/2018 | Limberis et al. |
| 2018/0353624 | A1 | 12/2018 | Wilson et al. |
| 2019/0015527 | A1 | 1/2019 | Wilson et al. |
| 2019/0054188 | A1 | 2/2019 | Wilson et al. |
| 2019/0216841 | A1 | 7/2019 | Wilson et al. |
| 2020/0056159 | A1 | 2/2020 | Wilson et al. |
| 2020/0056205 | A1 | 2/2020 | Wilson et al. |
| 2020/0155704 | A1 | 5/2020 | Wilson et al. |
| 2020/0390888 | A1 | 12/2020 | Limberies et al. |
| 2021/0170050 | A1 | 6/2021 | Wilson et al. |

FOREIGN PATENT DOCUMENTS

| | | | |
|---|---|---|---|
| EP | 3589730 | B1 | 12/2023 |
| WO | WO 1994/18347 | | 8/1994 |
| WO | WO 1995/33052 | | 12/1995 |
| WO | WO 1996/06097 | | 2/1996 |
| WO | WO 1996/009378 | | 3/1996 |
| WO | WO 1996/020951 | | 7/1996 |
| WO | WO 1996/41865 | | 12/1996 |
| WO | WO 1997/31898 | | 9/1997 |
| WO | WO 1998/02441 | | 1/1998 |
| WO | WO 1999/10508 | | 3/1999 |
| WO | WO 1999/10510 | | 3/1999 |
| WO | WO 1999/36553 | | 7/1999 |
| WO | WO 1999/41258 | | 8/1999 |
| WO | WO 2001/114387 | | 3/2001 |
| WO | WO 2001/70816 | | 9/2001 |
| WO | WO 2002/29075 | | 4/2002 |
| WO | WO 2002/066612 | | 8/2002 |
| WO | WO 2002/066613 | | 8/2002 |
| WO | WO 2002/066614 | | 8/2002 |
| WO | WO 2002/066615 | | 8/2002 |
| WO | WO 2003/042397 | | 5/2003 |
| WO | WO 2005/033321 | | 4/2005 |
| WO | WO 2005/108617 | | 11/2005 |
| WO | WO 2006/110689 | | 10/2006 |
| WO | WO 2007/127264 | | 11/2007 |
| WO | WO 2008/156763 | | 12/2008 |
| WO | WO 2009/079259 | A2 | 6/2009 |
| WO | WO 2009/115972 | | 9/2009 |
| WO | WO 2009/121004 | A2 | 10/2009 |
| WO | WO 2010/010466 | | 1/2010 |
| WO | WO 2010/044921 | A2 | 4/2010 |
| WO | WO 2010/053572 | | 5/2010 |
| WO | WO 2010/071832 | A1 | 6/2010 |
| WO | WO 2010/130636 | | 11/2010 |
| WO | WO 2010/140114 | | 12/2010 |
| WO | WO 2010/151673 | | 12/2010 |
| WO | WO 2011/126808 | | 3/2011 |
| WO | WO 2012/145572 | | 10/2012 |
| WO | WO 2012/170930 | | 12/2012 |
| WO | WO 2013/007770 | | 1/2013 |
| WO | WO 2013/049492 | | 4/2013 |
| WO | WO 2013/049493 | | 4/2013 |
| WO | WO 2013/114885 | | 8/2013 |
| WO | WO 2013/132007 | | 9/2013 |
| WO | WO 2013/155222 | | 10/2013 |
| WO | WO 2013/182683 | | 12/2013 |

(56) References Cited

FOREIGN PATENT DOCUMENTS

| | | |
|---|---|---|
| WO | WO 2013/190059 | 12/2013 |
| WO | WO 2015/012924 | 1/2015 |
| WO | WO 2015/127136 | 8/2015 |
| WO | WO 2015/164757 | 10/2015 |
| WO | WO 2016/049230 | 3/2016 |
| WO | WO 2016/054598 | 4/2016 |
| WO | WO 2016/124768 | 8/2016 |
| WO | WO 2016/200543 | 12/2016 |
| WO | WO 2017/075119 | 5/2017 |
| WO | WO 2017/100674 | 6/2017 |
| WO | WO 2017/100676 | 6/2017 |
| WO | WO 2017/100704 | 6/2017 |
| WO | WO 2017/106244 | 6/2017 |
| WO | WO 2017/106326 | 6/2017 |
| WO | WO 2017/106354 | 6/2017 |
| WO | WO 2017/136500 | 8/2017 |
| WO | WO 2017/160360 | 9/2017 |
| WO | WO 2018/035059 | 2/2018 |
| WO | WO 2018/057916 | 3/2018 |
| WO | WO-2018/160573 | 9/2018 |

OTHER PUBLICATIONS

An W et al., Active retrotransposition by a synthetic L1 element in mice, Proc Natl Acad Sci U S A, 103(49):18662-7, Dec. 5, 2006. (Epub Nov. 21, 2006).

Andersson R et al, An atlas of active enhancers across human cell types and tissues, Nature, 507(7493):455-61, Mar. 27, 2014.

Aquino TL et al., Influenza Outbreak in a Vaccinated Population—USS Ardent, Feb. 2014. MMWR Morb Mortal Wkly Rep, 63(42):947-9, Oct. 24, 2014.

Arkblad et al., A population-based study of genotypic and phenotypic variability in children with spinal muscular atrophy. Acta Paediatr. May 2009;98(5):865-72. Epub Jan. 20, 2009.

Armbruster et al., Efficacy and biodistribution analysis of intracerebroventricular administration of an optimized scAAV9-SMN1 vector in a mouse model of spinal muscular atrophy, Molecular Therapy: Methods & Clinical Development, vol. 14:3:16060(1-8), Sep. 2016.

Arnold et al., Spinal muscular atrophy: diagnosis and management in a new therapeutic era. Muscle Nerve. Feb. 2015;51(2):157-67. Epub Dec. 16, 2014.

Aschauer et el., Analysis of transduction efficiency, tropism and axonal transport of AAV serotypes 1, 2, 5, 6, 8 and 9 in the mouse brain, PLoS One, vol. 8(9):e76310(1-16), Sep. 2013.

Ashkenazi A et al., Immunoadhesins, International reviews of immunology, 10(2):219-227, 1993.

Balazs AB et al., Antibody-based protection against HIV infection by vectored immunoprophylaxis, Nature, 481(7379):81-4, Nov. 30, 2011.

Ballay A et al., In vitro and in vivo synthesis of the hepatitis B virus surface antigen and of the receptor for polymerized human serum albumin from recombinant human adenoviruses, EMBO J., 4(13B):3861-5, Dec. 30, 1985.

Bankiewicz et al., Long-term clinical improvement in MPTP-lesioned primates after gene therapy with AAV-hAADC. Mol Ther. Oct. 2006;14(4):564-70. Epub Jul. 7, 2006.

Bartus et al., Parkinson's Disease Gene Therapy: Success by Design Meets Failure by Efficacy. Mol Ther. Mar. 2014; 22(3): 487-497.

Bell et al., An optimized protocol for detection of *E. coli* beta-galactosidase in lung tissue following gene transfer. Histochem Cell Biol. Jul. 2005;124(1):77-85. Epub Jun. 10, 2005.

Bell et al., Analysis of Tumors Arising in Male B6C3F1 Mice with and without AAV Vector Delivery to Liver. Mol Ther. Jul. 2006;14(1):34-44. Epub May 6, 2006.

Bell et al., Identification of the galactose binding domain of the adeno-associated virus serotype 9 capsid. J Virol. Jul. 2012;86(13):7326-33. Epub Apr. 18, 2012.

Bell et al., No Evidence for Tumorigenesis of AAV Vectors in a Large-Scale Study in Mice. Mol Ther. Aug. 2005;12(2):299-306.

Bell P et al. Motor neuron transduction after intracisternal delivery of AAV9 in a cynomolgus macaque. Hum Gene Ther Methods. Apr. 2015;26(2):43-4.

Bell et al., The AAV9 receptor and its modification to improve in vivo lung gene transfer in mice. J Clin Invest. Jun. 2011;121(6):2427-35. Epub May 16, 2011.

Bendell, et al, Central nervous system metastases in women who receive trastuzumab-based therapy for metastatic breast carcinoma. Cancer. 97, 2972-2977 (2003).

Benkhelifa-Ziyyat et al., Intramuscular scAAV9-SMN injection mediates widespread gene delivery to the spinal cord and decreases disease severity in SMA mice. Mol Ther. Feb. 2013;21(2):282-90. Epub Jan. 8, 2013.

Berezov A et al., Disabling erbB receptors with rationally designed exocyclic mimetics of antibodies: structure-function analysis, J. Med. Chem., 44(16):2565-74, Aug. 2001.

Bergman et al., Pharmacokinetics of IgG and IgM anti-ganglioside antibodies in rats and monkeys after intrathecal administration. J Pharmacol Exp Ther. Jan. 1998;284(1):111-5.

Bevan et al., Early heart failure in the SMNDelta7 model of spinal muscular atrophy and correction by postnatal scAAV9-SMN delivery. Hum Mol Genet. Oct. 15, 2010;19(20):3895-905. Epub Jul. 16, 2010.

Beyer We et al., Cochrane re-arranged: support for policies to vaccinate elderly people against influenza, Vaccine, 31(50):6030-3, Dec. 2013. (Epub Oct. 3, 2013).

Bousquet et al., Intrathecal Trastuzumab Halts Progression of CNS Metastases in Breast Cancer. J Clin Oncol. Jun. 1, 2016;34(16):e151-5. Epub Dec. 29, 2014.

Bouvier NM et al., The biology of influenza viruses, Vaccine, 26 Suppl 4:D49-53, Sep. 2008.

Boyer JL et al., 853. Persistent expression of single chain antibodies mediated by AAV5 and AAVrh. 10 vectors, Molecular Therapy, 11(Supp. 1):331-2, May 2005.

Brandenburg B et al., Mechanisms of hemagglutinin targeted influenza virus neutralization, PLoS One, 8(12):e80034(1-14), Dec. 11, 2013.

Brantly et al., Sustained transgene expression despite T lymphocyte responses in a clinical trial of rAAVI-AAT gene therapy. Proc Natl Acad Sci U S A. Sep. 22, 2009;106(38):16363-8. Epub Aug. 1, 2009.

Brinster et al., Regulation of metallothionein-thymidine kinase fusion plasmids injected into mouse eggs, Nature, 296:39-42, Mar. 4, 1982.

Bryant et al. Lessons learned from the clinical development and market authorization of Glybera. Hum Gene Ther Clin Dev. Jun. 2013;24(2):55-64. Epub Jun. 29, 2013.

Bucher et al., Intracisternal delivery of AAV9 results in oligodendrocyte and motor neuron transduction in the whole central nervous system of cats. Gene Ther. May 2014;21(5):522-8. Epub Feb. 27, 2014.

Buning et al., Recent developments in adeno-associated virus vector technology, J Gene Med. Jul. 2008;10(7):717-33.

Bussaglia et al., A frame-shift deletion in the survival motor neuron gene in Spanish spinal muscular atrophy patients. Nat Genet. Nov. 1995;11(3):335-7.

Calcedo et al., Worldwide epidemiology of neutralizing antibodies to adeno-associated viruses. J Infect Dis. Feb. 1, 2009;199(3):381-90.

Cao et al., Distance, Depth and Puncture Angle for Cisterna Magna in Chinese Adults as Read from Magnetic Resonance Imaging. Chin Med J (Engl). Jun. 20, 2015;128(12):1683-5.

Carragher B et al., Leginon: an automated system for acquisition of images from vitreous ice specimens, J. Struct. Biol., 132(1):33-45, Oct. 2000.

Carter BJ, Chapter 10: The Growth Cycle of Adeno-associated Virus, in CRC Handbook of Parvoviruses, ed. P. Tijsser, CRC Press, p. 155-68, 1990.

Castle et al., Adeno-associated virus serotypes 1, 8, and 9 share conserved mechanisms for anterograde and retrograde axonal transport. Hum Gene Ther. Aug. 2014;25(8):705-20. Epub May 2, 2014.

(56)                References Cited

OTHER PUBLICATIONS

Castle et al., Long-distance axonal transport of AAV9 is driven by dynein and kinesin-2 and is trafficked in a highly motile Rab7-positive compartment. Mol Ther. Mar. 2014;22(3):554-566. Epub Oct. 8, 2013.

Cearley et al., Expanded repertoire of AAV vector serotypes mediate unique patterns of transduction in mouse brain. Mol Ther. Oct. 2008;16(10):1710-8. Epub Aug. 19, 2008.

Center for Disease Control and Prevention, "Types of Influenza Viruses" Web page <https://www.cdc.gov/flu/about/viruses/types.htm>, 2 pages, Apr. 4, 2016, page last updated Aug. 19, 2014, retrieved from Internet Archive Wayback Machine <https://web.archive.org/web/20160404144120/https://www.cdc.gov/flu/about/viruses/types.htm> on May 11, 2018.

Centers for Disease Control and Prevention, Estimates of deaths associated with seasonal influenza: United States, 1976-2007, available in MMWR Morb. Mortal. Wkly. Rep. 59:1057-1062, Aug. 27, 2010.

Chamow SM and Ashkenazi, Immunoadhesins: principles and applications, Trends in biotechnology, 14(2):52-60, Feb. 1996.

Chandler et al., Vector design influences hepatic genotoxicity after adeno-associated virus gene therapy. J Clin Invest. Feb. 2015;125(2):870-80. Epub Jan. 20, 2015.

Chen H et al., Avian flu: H5N1 virus outbreak in migratory waterfowl. Nature, 436(7048):191-2, Jul. 14, 2005.

Chen et al., Prevalence and risk factors for feeding and swallowing difficulties in spinal muscular atrophy types II and III. J Pediatr. Mar. 2012;160(3):447-451.el. Epub Sep. 1, 2011.

Ch'ng JL et al., Antisense RNA complementary to 3' coding and noncoding sequences of creatine kinase is a potent inhibitor of translation in vivo, Proc. Natl. Acad. Sci. USA, 86(24):10006-10, Dec. 1989.

Cho and Dreyfuss, A degron created by SMN2 exon 7 skipping is a principal contributor to spinal muscular atrophy severity. Genes Dev. Mar. 1, 2010;24(5):438-42.

Ciesielska et al., Cerebral infusion of AAV9 vector-encoding non-self proteins can elicit cell-mediated immune responses. Mol Ther. Jan. 2013;21(1):158-66. Epub Aug. 2, 2012.

Cobleigh, et al, Multinational study of the efficacy and safety of humanized anti-HER2 monoclonal antibody in women who have HER2-overexpressing metastatic breast cancer that has progressed after chemotherapy for metastatic disease. J. Clin. Oncol. 17, 2639-2648 (1999).

Colle et al., Efficient intracerebral delivery of AAV5 vector encoding human ARSA in non-human primate. Hum Mol Genet. Jan. 1, 2010;19(1):147-58.

Coovert et al., The survival motor neuron protein in spinal muscular atrophy. Human Molecular Genetics. 1997;6(8):1205-14.

Corti D et al., A neutralizing antibody selected from plasma cells that binds to group 1 and group 2 influenza A hemagglutinins, Science, 333:850-6, Aug. 12, 2011. (Epub Jul. 28, 2011).

Cox F et al., Protection against H5N1 influenza virus induced by matrix-M adjuvanted seasonal virosomal vaccine in mice requires both antibodies and T cells, PLoS One, 10(12):e0145243, Dec. 22, 2015.

Crawford & Pardo. The neurobiology of childhood spinal muscular atrophy. Neurobiol Dis. Apr. 1996;3(2):97-110.

Crawford et al., Evaluation of SMN protein, transcript, and copy number in the biomarkers for spinal muscular atrophy (BforSMA) clinical study. PLoS One. 2012;7(4):e33572. Epub Apr. 27, 2012.

Crosariol M, et al., Effective AAV9 Vector Delivery to Nasal Mucosa for Protection Against Airborne Challenge With Influenza A and B, Abstract 699, Molecular Therapy, 24(Supp. 1):S276, May 2016.

Daley, J., Severe Toxicity Reported in High-Dose AAV Gene Therapy in Animals. The Scientist, Jan. 31, 2018, printed from https://www.the-scientist.com/the-nutshell/severe-toxicity-reported-in-high-dose-aav-gene-therapy-in-animals-30348.

David et al., Recombinant adeno-associated virus-mediated in utero gene transfer gives therapeutic transgene expression in the sheep., Hum Gene Ther. Apr. 2011;22(4):419-26. Epub Feb. 2, 2011.

Davidson E et al., Mechanism of Binding to Ebola Virus Glycoprotein by the ZMapp, ZMAb, and MB-003 Cocktail Antibodies, 89(21):10982-92, Nov. 2015. (Epub Aug. 26, 2015).

Dawood FS et al., Estimated global mortality associated with the first 12 months of 2009 pandemic influenza A H1N1 virus circulation: a modelling study, Lancet Infect Dis, 12(9):687-95, Sep. 2012. (Epub Jun. 26, 2012).

De BP et al., Abstract 611—Induction of Persistent Passive Immunity Against Anthrax Toxin by an Adeno-Associated Virus Type rh1O Vector Expressing Anti-Protective Antigen Antibody, Molecular Therapy, 13(Suppl. 1):S236, May 2006.

De BP et al, Rapid/ Sustained Anti-anthrax Passive Immunity Mediated by co-administration od Ad/AAV, Molecular Therapy, 6(1):203-9, Jan. 2008.

De BP et al., High levels of persistent expression of alpha 1-antitrypsin mediated by the nonhuman primate serotype rh. 10 adeno-associated virus despite preexisting immunity to common human adeno-associated viruses, Mol. Ther., 13(1):67-76, Jan. 2006.

Dekaban, Changes in brain weights during the span of human life: relation of brain weights to body heights and body weights. Ann Neurol. Oct. 1978;4(4):345-56.

Delzor et al., Restricted transgene expression in the brain with cell-type specific neuronal promoters. Human Gene Therapy Methods. Hum Gene Ther Methods. Aug. 2012;23(4):242-54. Epub Aug. 30, 2012.

Deuschle U et al., Tetracycline-Reversible Silencing of Eukaryotic Promoters, Mol Cell Biol., 15(4):1907-14, Apr. 1995.

Deverman et al., Cre-dependent selection yields AAV variants for widespread gene transfer to the adult brain. Nat Biotechnol. Feb. 2016;34(2):204-9. Epub Feb. 1, 2016.

Dhuria SV et al., Intranasal Delivery to the Central Nervous System: Mechanisms and Experimental Considerations, Journal of Pharmaceutical Sciences, 99(4):1654-73, Apr. 2010. (Epub Oct. 29, 2009).

Didonato et al., Cloning, characterization, and copy number of the murine survival motor neuron gene: homolog of the spinal muscular atrophy-determining gene. Genome Res. Apr. 1997;7(4):339-52.

Dilillo DJ et al., Broadly neutralizing anti-influenza antibodies require Fc receptor engagement for in vivo protection, J. Clin. Invest., 126(2):605-10, Feb. 2016. (Epub Jan. 5, 2016).

Dilillo DJ et al., Broadly neutralizing hemagglutinin stalk-specific antibodies require FcγR interactions for protection against influenza virus in vivo, Nat. Med., 20(2):143-51, Feb. 2014. (Epub Jan. 12, 2014).

Dimattia et al., Structural insight into the unique properties of adeno-associated virus serotype 9. J Virol. Jun. 2012;86(12):6947-58. Epub Apr. 11, 2012.

Dirren et al., Intracerebroventricular Injection of Adeno-Associated Virus 6 and 9 Vectors for Cell Type-Specific Transgene Expression in the Spinal Cord. Hum Gene Ther. Feb. 2014;25(2):109-20. Epub Jan. 15, 2014.

Djupesland PG, Nasal drug delivery devices: characteristics and performance in a clinical perspective-a review, Drug Deliv Transl Res, 3(1):42-62, Feb. 2013. (Epub Oct. 18, 2012).

Dominguez et al., Intravenous scAAV9 delivery of a codon-optimized SMN1 sequence rescues SMA mice. Hum Mol Genet. Hum Mol Genet. Feb. 15, 2011;20(4):681-93. Epub Nov. 30, 2010.

Donnelly MLL et al., The cleavage activities of aphthovirus and cardiovirus 2A proteins, J. Gen. Virol., 78(Pt 1):13-21, Jan. 1997.

Donsante et al., Observed incidence of tumorigenesis in long-term rodent studies of rAAV vectors. Gene Ther. Sep. 2001;8(17):1343-6.

Dreyfus C et al., Highly conserved protective epitopes on influenza B viruses, Science, 337:1343-8, Sep. 14, 2012. (Epub Aug. 9, 2012).

Dul et al., Intranasal vaccination of recombinant adeno-associated virus encoding receptor-binding domain of severe acute respiratory syndrome coronavirus (SARS-CoV) spike protein induces strong mucosal immune responses and provides long-term protection against SARS-COV infection, J Immunology, 180(2):948-956, Jan. 2008.

Dubowitz, Very severe spinal muscular atrophy (SMA type 0): an expanding clinical phenotype. Eur J Paediatr Neurol. 1999;3(2):49-51.

(56) References Cited

OTHER PUBLICATIONS

Duque et al., A large animal model of spinal muscular atrophy and correction of phenotype. Ann Neurol. Mar. 2015;77(3):399-414. Epub Feb. 9, 2015.
Duque et al., Intravenous administration of self-complementary AAV9 enables transgene delivery to adult motor neurons. Mol Ther. Jul. 2009;17(7):1187-96. Epub Apr. 14, 2009.
Ekiert DC et al., A highly conserved neutralizing epitope on group 2 influenza A viruses, Science, 333(6044):843-50, Aug. 12, 2011. (Epub Jul. 7, 2011).
Ekiert DC et al., Antibody recognition of a highly conserved influenza virus epitope, Science, 324(5924):246-51, Apr. 10, 2009. (Epub Feb. 26, 2009).
Ekiert DC et al., Cross-neutralization of influenza A viruses mediated by a single antibody loop, Nature, 489(7417):526-32, Sep. 27, 2012. (Epub Sep. 16, 2012).
El-Khodor et al., Identification of a battery of tests for drug candidate evaluation in the SMNΔ7 neonate model of spinal muscular atrophy. Exp Neurol. Jul. 2008;212(1):29-43. Epub Mar. 18, 2008.
Ellinwood et al. Safe, Efficient, and Reproducible Gene Therapy of the Brain in the Dog Models of Sanfilippo and Hurler Syndromes. Mol Ther. Feb. 2011;19(2):251-259.
Emsley P et al., Cowtan, Features and development of Coot, Acta Crystallogr. D Biol. Crystallogr., 66(Pt 4):486-501, Apr. 2010. (Epub Mar. 24, 2010).
Ercolani L et al., Isolation and complete sequence of a functional human glyceraldehyde-3-phosphate dehydrogenase gene, J Biol Chem, 263(30):15335-41, Oct. 25, 1988.
European Medicines Agency, Guideline on Development, Production, Characterisation and Specifications for Monoclonal Antibodies and Related Products (EMEA/CHMP/BWP/157653/2007), published Dec. 2008.
European Medicines Agency, Guideline on Development, Production, Characterization and Specifications for Monoclonal Antibodies and Related Products (EMEA/CHMP/BWP/532517/2008), p. 1-13, published Dec. 2008.
Fang J et al., An antibody delivery system for regulated expression of therapeutic levels of monoclonal antibodies in vivo, Mol. Ther., 15(6);1153-9, Jun. 2007. (Epub Mar. 20, 2007).
Fang et al. Molecular characterization and copy No. of SMN1, SMN2 and NAIP in Chinese patients with spinal muscular atrophy and unrelated healthy controls. BMC Musculoskelet Disord. 2015; 16(1): 11.
Faravelli, et al. Spinal muscular atrophy—recent therapeutic advances for an old challenge. Nat Rev Neurol. Jun. 2015;11(6):351-9. Epub May 19, 2015.
Federici et al., Robust spinal motor neuron transduction following intrathecal delivery of AAV9 in pigs. Gene Ther. Aug. 2012;19(8):852-9. Epub Sep. 15, 2011.
Feldkotter et al., Quantitative analyses of SMN1 and SMN2 based on real-time lightCycler PCR: fast and highly reliable carrier testing and prediction of severity of spinal muscular atrophy. Am J Hum Genet. Feb. 2002;70(2):358-68. Epub Dec. 21, 2001.
Finkel et al. 209th ENMC International Workshop: Outcome Measures and Clinical Trial Readiness in Spinal Muscular Atrophy Nov. 7-9, 2014, Heemskerk, The Netherlands. Neuromuscul Disord. Jul. 2015;25(7):593-602. Epub Apr. 28, 2015.
Finkel et al., Nusinersen versus Sham Control in Infantile-Onset Spinal Muscular Atrophy. N Engl J Med. Nov. 2, 2017;377(18):1723-1732.
Finkel et al., Observational study of spinal muscular atrophy type I and implications for clinical trials. Neurology. Aug. 26, 2014;83(9):810-7. Epub Jul. 30, 2014.
Finkel, Electrophysiological and motor function scale association in a pre-symptomatic infant with spinal muscular atrophy type I. Neuromuscul Disord. Feb. 2013;23(2):112-5. Epub Nov. 10, 2012.
Fisher et al., Transduction with recombinant adeno-associated virus for gene therapy is limited by leading-strand synthesis. J Virol. Jan. 1996;70(1):520-32.
Flotte TR et al., Stable in vivo expression of the cystic fibrosis transmembrane conductance regulator with an adeno-associated virus vector. Proc Natl Acad Sci U S A. 90(22):10613-7, Nov. 15, 1993.
Flotte and Buning, Severe Toxicity in Nonhuman Primates and Piglets with Systemic High-Dose Administration of Adeno-Associated Virus Serotype 9-Like Vectors: Putting Patients First. Hum Gene Ther. Mar. 2018;29(3):283-284. Epub Feb. 7, 2018.
Forsman A et al., Llama antibody fragments with cross-subtype human immunodeficiency virus type 1 (HIV-1)-neutralizing properties and high affinity for HIV-1 gp120. J. Virol., 82(24):12069-81, Dec. 2008. (Epub Oct. 8, 2008).
Foster et al., Codon and mRNA sequence optimization for microdystrophin transgenes improves expression and physiological outcome in dystrophic mdx mice following AAV2/8 gene transfer. Mol. Ther. 2008; 16:1825-32 and Supplementary Material, Figure S1 and S2. Epub Sep. 2, 2008.
Foust et al., Intravascular AAV9 preferentially targets neonatal neurons and adult astrocytes, Nat Biotechnol. Jan. 2009;27(1):59-65. Epub Dec. 21, 2008.
Friedmann, Gene therapy for spinomuscular atrophy: a biomedical advance, a missed opportunity for more equitable drug pricing. Gene Ther. Sep. 2017;24(9):503-505. Epub Jun. 22, 2017.
Friesen RH et al., A common solution to group 2 influenza virus neutralization. Proc. Natl. Acad. Sci. U.S.A., vol. 111(1):445-50, Jan. 7, 2014. (Epub Dec. 11, 2013).
Furler S et al., Recombinant AAV vectors containing the foot and mouth disease virus 2A sequence confer efficient bicistronic gene expression in cultured cells and rat substantia nigra neurons, Gene Ther., 8(11):864-73, Jun. 2001.
Gamblin SJ et al., Influenza hemagglutinin and neuraminidase membrane glycoproteins, Journal of Biological Chemistry, 285(37):28403-9, Sep. 10, 2010. (Epub Jun. 10, 2010).
Gao R et al., Human infection with a novel avian-origin influenza A (H7N9) virus. N. Engl. J. Med., 368:1888-97, May 16, 2013. (Epub Apr. 11, 2013).
Gao et al., Adeno-associated viruses undergo substantial evolution in primates during natural infections. Proc Natl Acad Sci U S A. May 13, 2003;100(10):6081-6. Epub Apr. 25, 2003.
Gao et al., Clades of Adeno-associated viruses are widely disseminated in human tissues. J Virol. Jun. 2004;78(12):6381-8.
Gao et al., Novel adeno-associated viruses from rhesus monkeys as vectors for human gene therapy. Proc Natl Acad Sci U S A. Sep. 3, 2002;99(18):11854-9. Epub Aug. 21, 2002.
Gao et al., Purification of recombinant adeno-associated virus vectors by column chromatography and its performance in vivo. Hum Gene Ther. Oct. 10, 2000;11(15):2079-91.
Garcia et al., Peripheral motor and sensory nerve conduction studies in normal infants and children. Clin Neurophysiol. Mar. 2000;111(3):513-20.
GenBank Accession AAS99264.1, capsid protein VP1 [Adeno-associated virus 9, Jun. 2004.
GenBank: AAB86861.1, Web page <https://www.ncbi.nlm.nih.gov/protein/AAB86861.1>, 1 page, retrieved from Internet on May 11, 2018.
GenBank: ACJ71709.1, Web page <https://www.ncbi.nlm.nih.gov/protein/ACJ71709.1>, 2 pages, retrieved from Internet on May 11, 2018.
GenBank: AEL31303.1, Web page <https://www.ncbi.nlm.nih.gov/protein/AEL31303.1>, 2 pages, retrieved from Internet on May 11, 2018.
GenBank: AFP87542.1, Web page <https://www.ncbi.nlm.nih.gov/protein/AFP87542.1>, 2 pages, retrieved from Internet on May 11, 2018.
GenBank: AGH70219.1, Web page <https://www.ncbi.nlm.nih.gov/protein/AGH70219.1>, 1 page, retrieved from Internet on May 11, 2018.
GenBank Accession AY530553.1, Adeno-associated virus isolate pi. 1 capsid protein VP1 (cap) gene, complete cds, Jun. 2004.
GenBank: BAF64540.1, Web page <https://www.ncbi.nlm.nih.gov/protein/BAF64540.1>, 2 pages, retrieved from Internet on May 11, 2018.

(56) References Cited

OTHER PUBLICATIONS

GenBank: CAA24362.1, Web page <https://www.ncbi.nlm.nih.gov/protein/AGH70219.1>, 1 page, retrieved from Internet on May 11, 2018.
GenBank Accession K03104.1, Human cytomegalovirus major immediate-early gene, enhancer, Aug. 1993.
GenBank Accession NC_001401.2, Adeno-associated virus—2, complete genome, Dec. 2014.
GenBank Accession NM_000344.3, *Homo sapiens* survival of motor neuron 1, telomeric (SMN1), transcript variant d, mRNA, Jan. 22, 2018.
GenBank Accession NM_001297715.1, *Homo sapiens* survival of motor neuron 1, telomeric (SMN1), transcript variant a, mRNA, Sep. 2016.
GenBank Accession NM_022874.2, *Homo sapiens* survival of motor neuron 1, telomeric (SMN1), transcript variant b, mRNA, Sep. 2016.
GenBank Accession NP 000335.1, survival motor neuron protein isoform d [*Homo sapiens*], Apr. 22, 2016.
GenBank Accession NP 001284644.1, survival motor neuron protein isoform a [*Homo sapiens*], Sep. 2016.
GenBank: V00882.1, Web page <https://www.ncbi.nlm.nih.gov/protein/AGH70219.1>, 2 pages, retrieved from Internet on May 11, 2018.
GenBank Accession X00182.1, Gallus gallus cytoplasmic beta-actin gene, Nov. 2006.
George et al., Hemophilia B Gene Therapy with a High-Specific-Activity Factor IX Variant. N Engl J Med. Dec. 7, 2017;377(23):2215-2227.
Giles et al., Deamidation of Amino Acids on the Surface of Adeno-Associated Virus Capsids Leads to Charge Heterogeneity and Altered Vector Function. Mol Ther. Dec. 5, 2018;26(12):2848-2862. Epub Oct. 18, 2018.
Gil-Farina et al., Recombinant AAV Integration Is Not Associated With Hepatic Genotoxicity in Nonhuman Primates and Patients. Mol Ther. Jun. 2016;24(6):1100-1105. Epub Mar. 7, 2016.
Glaven RH et al., Linking Single Domain Antibodies that Recognize Different Epitopes on the Same Target, Biosensors (Basel), 2(1):43-56, Feb. 1, 2012.
Glezen WP et al., The burden of influenza B: a structured literature review, Am J Public Health, 103(3):e43-51, Mar. 2013. (Epub Jan. 17, 2013).
Gordeeva et al., Improved PCR-based gene synthesis method and its application to the Citrobacter freundii phytase gene codon modification. J Microbiol Methods. May 2010;81(2):147-52. Epub Mar. 10, 2010.
Gossen M and Bujard H, Tight control of gene expression in mammalian cells by tetracycline-responsive promoters, Proc. Natl. Acad. Sci. USA, 89:5547-51, Jun. 1992.
Gossen M et al., Transcriptional activation by tetracyclines in mammalian cells, Science 268(5218):1766-9, Jun. 23, 1995.
Graham et al., Characteristics of a human cell line transformed by DNA from human adenovirus type 5. J Gen Virol. Jul. 1977;36(1):59-74.
Gray et al., Global CNS gene delivery and evasion of anti-AAV-neutralizing antibodies by intrathecal AAV administration in non-human primates. Gene Ther. Apr. 2013;20(4):450-9. Epub Jan. 10, 2013.
Gray et al., Preclinical differences of intravascular AAV9 delivery to neurons and glia: a comparative study of adult mice and nonhuman primates. Mol Ther. Jun. 2011;19(6):1058-69. Epub Apr. 12, 2011.
Gregoretti et al., Survival of patients with spinal muscular atrophy type 1. Pediatrics. May 2013;131(5):e1509-14. Epub Apr. 22, 2013.
Greig et al., Intramuscular Injection of AAV8 in Mice and Macaques Is Associated with Substantial Hepatic Targeting and Transgene Expression, PLoS One. Nov. 13, 2014;9(11):e112268. doi: 10.1371/journal.pone.0112268. eCollection 2014.
Grieger & Samulski, Adeno-associated virus as a gene therapy vector: Vector development, production and clinical applications, Adv. Biochem. Engin/Biotechnol. 2005;99: 119-145.
Grimm et al., Titration of AAV-2 particles via a novel capsid ELISA: packaging of genomes can limit production of recombinant AAV-2. Gene Ther. Jul. 1999;6(7):1322-30.
Gupta P, Preclinical pharmacokinetics of MHAA4549A, a human monoclonal antibody to influenza A virus, and the prediction of its efficacious clinical dose for the treatment of patients hospitalized with influenza A, Mabs, 8(5):991-7, Jul. 2016. (Epub Mar. 31, 2016).
Gurda et al., Evaluation of AAV-mediated Gene Therapy for Central Nervous System Disease in Canine Mucopolysaccharidosis VII. Mol Ther. Feb. 2016;24(2):206-216. Epub Oct. 8, 2015.
Haaker and Fujak, Proximal spinal muscular atrophy: current orthopedic perspective. Appl Clin Genet. Nov. 14, 2013;6(11):113-20.
Harris A et al., Influenza virus pleiomorphy characterized by cryoelectron tomograph, Proc. Natl. Acad. Sci. U.S.A., 103(50)19123-7, Dec. 12, 2006. (Epub Dec. 4, 2006).
Helmken et al., Evidence for a modifying pathway in SMA discordant families: reduced SMN level decreases the amount of its interacting partners and Htra2-beta1. Hum Genet. Dec. 2003;114(1):11-21. Epub Oct. 1, 2003.
Hessell AJ et al., Fc receptor but not complement binding is important in antibody protection against HIV, Nature, 449(7158):101-104, Sep. 6, 2007.
Hinderer et al., Neonatal Systemic AAV Induces Tolerance to CNS Gene Therapy in MPS I Dogs and Nonhuman Primates. Mol Ther. Aug. 2015; 23(8):1298-1307. Prepublished online May 29, 2015. Published online Jun. 30, 2015.
Hinderer et al., Widespread gene transfer in the central nervous system of cynomolgus macaques following delivery of AAV9 into the cisterna magna. Mol Ther Methods Clin Dev. Dec. 10, 2014;1:14051.
Hinderer et al., Neonatal tolerance induction enables accurate evaluation of gene therapy for MPS I in a canine model. Mol Genet Metab. Sep. 2016;119(1-2):124-30. Epub Jun. 8, 2016.
Hinderer, et al. Intrathecal gene therapy corrects CNS pathology in a feline model of mucopolysaccharidosis I. Mol Ther. Dec. 2014;22(12):2018-27. Epub Jul. 16, 2014.
Hinderer, et al. Delivery of an Adeno-Associated Virus Vector into Cerebrospinal Fluid Attenuates Central Nervous System Disease in Mucopolysaccharidosis Type II Mice. Hum Gene Ther. Nov. 2016;27(11):906-915. Epub Aug. 10, 2016.
Hinderer, et al. Severe Toxicity in Nonhuman Primates and Piglets Following High-Dose Intravenous Administration of an Adeno-Associated Virus Vector Expressing Human SMN.Hum Gene Ther. Mar. 2018;29(3):285-298. Epub Feb. 12, 2018.
Hioki et al., Efficient gene transduction of neurons by lentivirus with enhanced neuron-specific promoters. Gene Ther. Jun. 2007;14(11):872-82. Epub Mar. 15, 2007.
Hohn M et al., SPARX, a new environment for Cryo-EM image processing, J. Struct. Biol., 157(1):47-55, Jan. 2007. (Epub Jul. 16, 2006).
Holehonnur et al., Adeno-associated viral serotypes produce differing titers and differentially transduce neurons within the rat basal and lateral amygdala. BMC Neurosci. Feb. 18, 2014;15:28.
Hoogenboom HR et al., By-passing immunisation: Human antibodies from synthetic repertoires of germline VH gene segments rearranged in vitro, J. Mil. Biol., 227(2):381-8, Sep. 1992.
Hordeaux et al., The Neurotropic Properties of AAV-PHP.B Are Limited to C57BL/6J Mice. Mol Ther. Mar. 7, 2018;26(3):664-668. Epub Feb. 2, 2018.
Hu et al., RH10 provides superior transgene expression in mice when compared with natural AAV serotypes for neonatal gene therapy. J Gene Med. Sep. 2010;12(9):766-78.
Hua et al., Antisense masking of an hnRNP A1/A2 intronic splicing silencer corrects SMN2 splicing in transgenic mice. Am J Hum Genet. Apr. 2008;82(4):834-48. Epub Mar. 27, 2008.
Hua et al., Peripheral SMN restoration is essential for long-term rescue of a severe spinal muscular atrophy mouse model. Nature. Oct. 5, 2011;478(7367):123-6.
Hufton SE et al. The breadth of cross sub-type neutralisation activity of a single domain antibody to influenza hemagglutinin can be increased by antibody valency, PLoS One, vol. 9(8):e103294(1-19), Aug. 1, 2014.

(56) References Cited

OTHER PUBLICATIONS

Hultberg A et al., Llama-derived single domain antibodies to build multivalent, superpotent and broadened neutralizing anti-viral molecules, PLoS One vol. 6(4):e17665(1-12), Apr. 1, 2011.
Hynes et al., Hormone-responsive expression of an endogenous proviral gene of mouse mammary tumor virus after molecular cloning and gene transfer into cultured cells, Proc. Natl. Acad. Sci. USA, 78(4):2038-42, Apr. 1981.
Iliff et al., A paravascular pathway facilitates CSF flow through the brain parenchyma and the clearance of interstitial solutes, including amyloid β. Sci Transl Med. Aug. 15, 2012;4(147):147ra111.
Iliff et al., Cerebral arterial pulsation drives paravascular CSF-interstitial fluid exchange in the murine brain. J Neurosci. Nov. 13, 2013;33(46):18190-9.
Invivogen, IgG-Fc Engineering for Therapeutic Use, available online at www.invivogen.com/docs/Insight200605.pdf, p. 1-4, Apr./May 2006.
Irani V et al., Molecular properties of human IgG subclasses and their implications for designing therapeutic monoclonal antibodies against infectious diseases, Molecular immunology, 67(2):171-82, Oct. 2015. (Epub Apr. 18, 2015).
Israel DI and Kaufman RJ, Highly inducible expression from vectors containing multiple GRE's in CHO cells overexpressing the glucocorticoid receptor, Nucl. Acids Res., 17(12):2589-2604, Nov. 12, 1989.
James et al., Predictors of outcome after acetaminophen poisoning in children and adolescents. J Pediatr. May 2002;140(5):522-6.
Janson, et al. Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.
Jedrzejowska et al., Incidence of spinal muscular atrophy in Poland—more frequent than predicted? Neuroepidemiology. 2010;34(3):152-7. Epub Jan. 15, 2010.
Jegaskanda PC et al., Influenza-specific antibody-dependent cellular cytotoxicity: toward a universal influenza vaccine, J. Immunol. 193(2):469-75, Jul. 15, 2014.
Jin et al., Direct Liquid Chromatography/Mass Spectrometry Analysis for Complete Characterization of Recombinant Adeno-Associated Virus Capsid Proteins. Hum Gene Ther Methods. Oct. 2017;28(5):255-267. Epub Jun. 16, 2017.
Johnson PR et al., Vector-mediated gene transfer engenders long-lived neutralizing activity and protection against SIV infection in monkeys, Nat Med., 15(8):901-6, Aug. 2009. (Epub May 17, 2009).
Jones PT et al., Replacing the complementarity-determining regions in a human antibody with those from a mouse, Nature, 321(6069):522-5, May 1986.
Julien JP et al., Structural insights into key sites of vulnerability on HIV-1 Env and influenza HA, Immunol. Rev., 250(1):180-98, Nov. 2012.
Juno J et al., Immunogenetic Factors Associated with Severe Respiratory Illness Caused by Zoonotic H1N1 and H5N1 Influenza Viruses, Clinical and Developmental Immunology, vol. 2012:797180(1-9), (Epub Nov. 3, 2011).
Kabsch W, XDS, Acta Crystallogr. D Biol. Crystallogr., 66(Pt 2):125-32, Feb. 2010. (Epub Jan. 22, 2010).
Kaplitt MG, et al. Long-term gene expression and phenotypic correction using adeno-associated virus vectors in the mammalian brain. Nat Genet., 8(2):148-54, Oct. 1, 1994.
Kaplitt, et al. Safety and tolerability of gene therapy with an adeno-associated virus (AAV) borne GAD gene for Parkinson's disease: an open label, phase I trial.Lancet. Lancet. Jun. 23, 2007;369(9579):2097-105.
Kashima, et al., An intronic element contributes to splicing repression in spinal muscular atrophy. Proc Natl Acad Sci U S A. Feb. 27, 2007;104(9):3426-31. Epub Feb. 16, 2007.
Kashyap AK et al., Combinatorial antibody libraries from survivors of the Turkish H5N1 avian influenza outbreak reveal virus neutralization strategies, Proc. Natl. Acad. Sci. U.S.A., 105(16):5986-91, Apr. 22, 2008. (Epub Apr. 14, 2008).
Kashyap AK et al., Protection from the 2009 H1N1 Pandemic Influenza by an Antibody from Combinatorial Survivor-Based Libraries, PLoS Pathog., 6(7):e1000990, Jul. 2010.
Kay et al., Evidence for gene transfer and expression of factor IX in haemophilia B patients treated with an AAV vector. Nat Genet. Mar. 2000;24(3):257-61.
Kelly S et al., Splicing of many human genes involves sites embedded within introns, Nucleic Acids Research, 43(9):4721-32, May 19, 2015. (Epub Apr. 20, 2015).
Kerr, New insights into haemostasis in liver failure. Blood Coagul Fibrinolysis. Jun. 2003;14 Suppl 1:S43-5.
Khan et al., Mitigation of septic shock in mice and rhesus monkeys by human chorionic gonadotrophin-related oligopeptides. Clin Exp Immunol. Jun. 2010;160(3):466-78. Epub Mar. 16, 2010.
Kim et al., Intracerebroventricular viral injection of the neonatal mouse brain for persistent and widespread neuronal transduction. Journal of Visualized Experiments, J Vis Exp. Sep. 15, 2014;(91):51863.
Klein C et al., Progress in overcoming the chain association issue in bispecific heterodimeric IgG antibodies, mAbs, 4(6):653-63, Nov.-Dec. 2012. (Epub Aug. 27, 2012).
Klock G et al., Oestrogen and glucocorticoid responsive elements are closely related but distinct, Nature, 329(6141):734-6, Oct. 22-28, 1987.
Klump H et al., Retroviral vector-mediated expression of HoxB4 in hematopoietic cells using a novel coexpression strategy, Gene Ther., 8(10):811-7, May 2001.
Kohler et al., Continuous cultures of fused cells secreting antibody of predefined specificity, Nature, 256(5517):495-7, Aug. 1975.
Kolb & Kissel, Spinal Muscular Atrophy. Neurol Clin. Nov. 2015;33(4):831-46.
Kortt AA et al., Recombinant anti-sialidase single-chain variable fragment antibody. Characterization, formation of dimer and higher-molecular-mass multimers and the solution of the crystal structure of the single-chain variable fragment/sialidase complex, Eur. J. Biochem., 221(1):151-7, Apr. 1994.
Krah S et al., Single-domain antibodies for biomedical applications, Immunopharmacol. Immunotoxicol., 38(1):2128, 2016. (Epub Nov. 9, 2015).
Kramer RA et al., A novel helper phage that improves phage display selection efficiency by preventing the amplification of phages without recombinant protein. Nucleic Acids Res., 31(11):e59, Jun. 1, 2003.
Kramer RA et al., The human antibody repertoire specific for rabies virus glycoprotein as selected from immune libraries, Eur. J. Immunol., 35(7):2131-45, Jul. 2005.
Krause et al., Human Monoclonal Antibodies to Pandemic 1957 H2N2 and Pandemic 1968 H3N2 Influence Viruses, Journal of Virology, 86(11):6334-6340, Jun. 2012.
Kuo TT et al., Neonatal Fc Receptor and IgG-Based Therapeutics, mAbs, 3(5):422-30, Sep.-Oct. 2011. (Epub Sep. 1, 2011).
Labrijn et al., Efficient generation of stable bispecific IgG1 by controlled Fab-arm exchange, Proc Natl Acad Sci USA, 110(13):5145-50, Mar. 26, 2013. (Epub Mar. 11, 2013).
Lai et al., Antisense RNA complimentary to 3' coding and noncoding sequences of creatine kinase is a potent inhibitor of translation in vivo, Proc. Natl. Acad. Sci. USA, vol. 86(24):10006-10 (Dec. 1989).
Lander et al., Appion: an integrated, database-driven pipeline to facilitate EM image processing, J. Struct. Biol., 166(1):95-102, Apr. 2009.
Laube et al., The expanding role of aerosols in systemic drug delivery, gene therapy and vaccination: an update. Transl. Respir. Med., vol. 2:3(1-12), Jan. 2014 (Epub Jan. 13, 2014).
Laursen S and Wilson IA, Broadly neutralizing antibodies against influenza viruses, Antiviral. Res. 98(3):476-83, Jun. 2013. (Epub Apr. 9, 2013).
Le et al., SMNDelta7, the major product of the centromeric survival motor neuron (SMN2) gene, extends survival in mice with spinal muscular atrophy and associates with full-length SMN. Hum Mol Genet. Mar. 15, 2005;14(6):845-57. Epub Feb. 9, 2005.
Lee F et al., Glucocorticoids regulate expression of dihydrofolate reductase cDNA in mouse mammary tumour virus chimaeric plasmids, Nature 294(5838):228-32, Nov. 19, 1981.

(56) References Cited

OTHER PUBLICATIONS

Lee PS et al., Heterosubtypic antibody recognition of the influenza virus hemagglutinin receptor binding site enhanced by avidity. Proc. Natl. Acad. Sci. U.S.A. 109(42):17040-5, Oct. 16, 2012. (Epub Oct. 1, 2012).
Lefebvre et al., Correlation between severity and SMN protein level in spinal muscular atrophy. Nat Genet. Jul. 1997;16(3):265-9.
Lefebvre et al., Identification and characterization of a spinal muscular atrophy-determining gene. Cell. Jan. 13, 1995;80(1):155-65.
Levitt N et al., Definition of an efficient synthetic poly(A) site, Genes Dev., 3(7):1019-25, Jul. 1989.
Li et al., Adeno-associated virus capsid antigen presentation is dependent on endosomal escape. J Clin Invest. Mar. 2013;123(3):1390-401. Epub Feb. 1, 2013.
Li et al., Assessing the potential for AAV vector genotoxicity in a murine model. Blood. Mar. 24, 2011;117(12):3311-9. Epub Nov. 24, 2010.
Limberis MP, AAV Vectors for Rapid and Effective Prophylaxis against Airborne Viruses, presented on Feb. 14, 2018 at 2018 ASM Biothreats meeting in Baltimore, Maryland, pp. 1-34.
Limberis MP et al., Establishment of a New AAV Clinical Candidate for Prophylaxis Against Influenza A and B (Abstract 398), Poster presented at American Society of Gene & Cell Therapy 2017 Annual Meeting on May 11, 2017.
Limberis MP et al., Adeno-Associated Virus Serotype 9-Expressed ZMapp in Mice Confers Protection Against Systemic and Airway-Acquired Ebola Virus Infection, J Infect Dis., 214(12):1975-79, Dec. 2016. (Epub Sep. 28, 2016).
Limberis MP et al., Intranasal Antibody Gene Transfer in Mice and Ferrets Elicits Broad Protection Against Pandemic Influenza, Science Translational Medicine, vol. 5(187):187ra72(1-19), May 29, 2013.
Limberis et al., Vectored expression of the broadly neutralizing antibody FI6 in mouse airway provides partial protection against a new avian influenza A virus, H7N9., Clin Vaccine Immunol, 20(12):1836-7. Dec. 2013. (Epub Oct. 16, 2013).
Limberis MP et al., Transduction efficiencies of novel AAV vectors in mouse airway epithelium in vivo and human ciliated airway epithelium in vitro, Mol. Ther., 17(2):294-301, Feb. 2009. (Epub Dec. 9, 2008).
Limberis MP and Wilson JM, Adeno-associated virus serotype 9 vectors transduce murine alveolar and nasal epithelia and can be readministered 2006, Proc Natl Acad Sci USA, 103(35):12993-8, Aug. 29, 2006. (Epub Aug. 22, 2006).
Liu J et al., Highly pathogenic H5N1 influenza virus infection in migratory birds, Science, vol. 309(5738):1206, Aug. 19, 2005. (Epub Jul. 6, 2005).
Ljungman P, Vaccination of immunocompromised patients, Clin Microbiol Infect, 18 Suppl 5:93-9, Oct. 2012.
Lobner E et al., Engineered IgG1-Fc-one fragment to bind them all, Immunological reviews, 270(1):113-131, Mar. 2016. (Epub Feb. 10, 2016).
Lock et al., Characterization of a recombinant adeno-associated virus type 2 Reference Standard Material. Hum Gene Ther. Oct. 2010;21(10):1273-85.
Lock M et al., Rapid, simple, and versatile manufacturing of recombinant adeno-associated viral vectors at scale, Hum Gene Ther. 21(10):1259-71, Oct. 2010. (Published online Sep. 24, 2010).
Lock et al., Absolute determination of single-stranded and self-complementary adeno-associated viral vector genome titers by droplet digital PCR. Hum Gene Ther Methods. Apr. 2014;25(2):115-25. Epub Feb. 14, 2014.
Luo et al., Adeno-associated virus-mediated cancer gene therapy: current status. Cancer Lett. Jan. 28, 2015;356(2 Pt B):347-56. Epub Nov. 10, 2014.
Maclaren et al., Retinal gene therapy in patients with choroideremia: initial findings from a phase 1/2 clinical trial. Lancet. Mar. 29, 2014;383(9923):1129-37. Epub Jan. 16, 2014.
Macleod et al., Prenatal onset spinal muscular atrophy. Eur J Paediatr Neurol. 1999;3(2):65-72.
Maguire et al., Safety and efficacy of gene transfer for Leber's congenital amaurosis. N Engl J Med. May 22, 2008;358(21):2240-8. Epub Apr. 27, 2008.
Malkova et al., Longitudinal magnetic resonance imaging study of rhesus monkey brain development. Eur J Neurosci. Dec. 2006;24(11):3204-12.
Manno et al., Successful transduction of liver in hemophilia by AAV-Factor IX and limitations imposed by the host immune response. Nat Med. Mar. 2006;12(3):342-7. Epub Feb. 12, 2006.
Marks JD et al., By-passing immunization. Human antibodies from V-gene libraries displayed on phage, J. Mol. Biol., 222(3):381-97, Dec. 1991.
Martino et al., Engineered AAV vector minimizes in vivo targeting of transduced hepatocytes by capsid-specific CD8+ T cells. Blood. Mar. 21, 2013;121(12):2224-33. Epub Jan. 16, 2013.
Mayer, et al. Respiratory inductance plethysmography in healthy 3-to 5-year-old children. Chest. Nov. 2003;124(5):1812-9.
Mayo KE et al. The mouse metallothionein-I gene is transcriptionally regulated by cadmium following transfection into human or mouse cells, Cell, 29(1):99-108, May 1982.
Mazzone, et al. Assessing upper limb function in nonambulant SMA patients: development of a new module. Neuromuscul Disord. Jun. 2011;21(6):406-12. Epub Mar. 21, 2011.
Mcandrew et al., Identification of proximal spinal muscular atrophy carriers and patients by analysis of SMNT and SMNC gene copy number. Am J Hum Genet. Jun. 1997;60(6):1411-22.
Mcbride JM et al. Phase 2 Randomized Trial of the Safety and Efficacy of MHAA4549A, a Broadly Neutralizing Monoclonal Antibody, in a Human Influenza A Virus Challenge Model. Antimicrob Agents Chemother, vol. 61(11):e01154-17, Oct. 2017 (Accepted manuscript posted online Aug. 14, 2017).
Mccarty et al., Self-complementary recombinant adeno-associated virus (scAAV) vectors promote efficient transduction independently of DNA synthesis. Gene Ther. Aug. 2001;8(16):1248-54.
Mccarty et al., Integration of adeno-associated virus (AAV) and recombinant AAV vectors. Annu Rev Genet. 2004;38:819-45.
Mccoy AJ et al., Likelihood-enhanced fast translation functions. Acta Crystallogr. D Biol. Crystallogr. 61(Pt 4):458-64, Apr. 2005. (Epub Mar. 24, 2005).
Mclellan JS et al., Structure of respiratory syncytial virus fusion glycoprotein in the postfusion conformation reveals preservation of neutralizing epitopes, J Virol., 85(15):7788-96, Aug. 2011. (Epub May 25, 2011).
Medina RA, Influenza A viruses: new research developments, Nat Rev Microbiol., 9(8):590-603, Jul. 11, 2011.
Meister et al., SMN-mediated assembly of RNPs: a complex story. Trends Cell Biol. Oct. 2002;12(10):472-8.
Melnick JL et al., Association of 20-Millimicron Particles with Adenoviruses, J Bacteriol., 90(1):271-4, Jul. 1965.
Mendell et al., Abstract: AVXS-101 Phase 1 Gene Therapy Clinical Trial in SMA Type 1: Event Free Survival and Achievement of developmental milestones (CT.003). Neurology. Apr. 2017;88(16 Supplement).
Mendell et al., Single-Dose Gene-Replacement Therapy for Spinal Muscular Atrophy. N Engl J Med. Nov. 2, 2017;377(18):1713-22.
Mercuri et al., Childhood spinal muscular atrophy: controversies and challenges. Lancet Neurol. May 2012;11(5):443-52.
Mercuri et al., Efficacy and safety of nusinersen in children with later-onset spinal muscular atrophy (SMA): end of study results from the phase 3 CHERISH study. Oct. 2017, vol. 27, Supplement 2, p. S210.
Mercuri et al., Nusinersen versus Sham Control in Later-Onset Spinal Muscular Atrophy. N Engl J Med. Feb. 15, 2018;378(7):625-635.
Mercuri et al., Patterns of disease progression in type 2 and 3 SMA: Implications for clinical trials. Neuromuscul Disord. Feb. 2016;26(2):126-31. Epub Dec. 3, 2015.
Merrifield, Solid Phase Peptide Synthesis I. The Synthesis of a Tetrapepide, J. Am. Chem. Soc., vol. 85(14):2149-2154, Jan. 1963.
Meyer et al., Improving Single Injection CSF Delivery of AAV9-mediated Gene Therapy for SMA: A Dose-response Study in Mice

(56) References Cited

OTHER PUBLICATIONS and Nonhuman Primates, The American Society of Gene & Cell Therapy; vol. 23(3):477-487, Mar. 2015.
Miller AD et al., Expression of a retrovirus encoding human HPRT in mice, Science, 225(4662):630-2, Aug. 10, 1984.
Miller, Glybera and the future of gene therapy in the European Union. Nat Rev Drug Discov. May 2012;11(5):419.
Miller MA et al. Visualization of murine intranasal dosing efficiency using luminescent Francisella tularensis: effect of instillation volume and form of anesthesia. PLoS One, vol. 7(2):e31359(1-8), 2012. (Epub Feb. 24, 2012).
Mittermeyer et al., Long-term evaluation of a phase 1 study of AADC gene therapy for Parkinson's disease. Hum Gene Ther. Apr. 2012;23(4):377-81. Epub Apr. 10, 2012.
Mizukami et al., A Protocol for AAV vector production and purification. Diss. Division of Genetic Therapeutics, Center for Molecular Medicine, 1998.
Molinari N-A M et al., The annual impact of seasonal influenza in the US: measuring disease burden and costs, Vaccine, 25(27):5086-96, Jun. 28, 2007. (Epub Apr. 20, 2007).
Monani et al., A single nucleotide difference that alters splicing patterns distinguishes the SMA gene SMN1 from the copy gene SMN2. Hum Mol Genet. Jul. 1999;8(7):1177-83.
Monani et al., The human centromeric survival motor neuron gene (SMN2) rescues embryonic lethality in Smn(−/−) mice and results in a mouse with spinal muscular atrophy. Hum Mol Genet. Feb. 12, 2000;9(3):333-9.
Morford et al., Preclinical safety evaluations supporting pediatric drug development with biopharmaceuticals: strategy, challenges, current practices. Birth Defects Res B Dev Reprod Toxicol. Aug. 2011;92(4):359-80. Epub Jul. 18, 2011.
Mouquet H et al., Enhanced HIV-1 neutralization by antibody heteroligation, Proc. Natl. Acad. Sci. U.S.A., 109(3):875-80, Jan. 17, 2012. (Epub Jan. 4, 2012).
Mueller et al., Human Treg responses allow sustained recombinant adeno-associated virus-mediated transgene expression. J Clin Invest. Dec. 2013;123(12):5310-8. Epub Nov. 15, 2013.
Muraszko et al., Pharmacokinetics and toxicology of immunotoxins administered into the subarachnoid space in nonhuman primates and rodents. Cancer Res. Aug. 15, 1993;53(16):3752-7.
Murshudov GN et al., Refinement of macromolecular structures by the maximum-likelihood method, Acta Crystallogr. D Biol. Crystallogr., 53(Pt 3):240-55, May 1, 1997.
Nakamura G et al., An in vivo human-plasmablast enrichment technique allows rapid identification of therapeutic A antibodies. Cell Host Microbe, 14(1):93-103, Jul. 17, 2013.
Nathwani et al., Adenovirus-associated virus vector-mediated gene transfer in hemophilia B. N Engl J Med. Dec. 22, 2011;365(25):2357-65. Epub Dec. 10, 2011.
Neubert et al., Connectivity reveals relationship of brain areas for reward-guided learning and decision making in human and monkey frontal cortex. Proc Natl Acad Sci U S A. May 19, 2015;112(20):E2695-704. Epub May 6, 2015.
Ng S-Y et al., Regulation of the human beta-actin promoter by upstream and intron domains, Nuc. Nucleic Acids Res., 17(2): 601-615, Jan. 25, 1989.
Nieto K et al., Combined prophylactic and therapeutic intranasal vaccination against human papillomavirus type- 16 using different adeno-associated virus serotype vectors, Antiviral Ther., 14(8):1125-37, 2009.
Ogino et al., New insights on the evolution of the SMN1 and SMN2 region: simulation and meta-analysis for allele and haplotype frequency calculations. Eur J Hum Genet. Dec. 2004;12(12):1015-23.
Ogino et al., Spinal muscular atrophy: molecular genetics and diagnostics. Expert Rev Mol Diagn. Jan. 2004;4(1):15-29.
Ogura T et al., Topology representing network enables highly accurate classification of protein images taken by cryo electron-microscope without masking, J. Struct. Biol., 143(3):185-200, Sep. 2003.
O'Hagen et al., An expanded version of the Hammersmith Functional Motor Scale for SMA II and III patients. Neuromuscul Disord. Oct. 2007;17(9-10):693-7. Epub Jul. 19, 2007.
Oliveira EC et al., Influenza in the intensive care unit. J Intensive Care Med, 18(2):80-91, Mar.-Apr. 2003. (First Published Mar. 1, 2003 ).
Oshio et al., Reduced cerebrospinal fluid production and intracranial pressure in mice lacking choroid plexus water channel Aquaporin-1. FASEB J. Jan. 2005;19(1):76-8. Epub Nov. 8, 2004.
Osterholm MT et al., Efficacy and effectiveness of influenza vaccines: a systematic review and meta-analysis. Lancet Infect Dis. 12(1):36-44, Jan. 2012. (Epub Oct. 25, 2011).
Ostrowski LE et al., Targeting expression of a transgene to the airway surface epithelium using a ciliated cell-specific promoter, Molecular Therapy, 8(4):637-45, Oct. 2003.
Park et al., Spinal muscular atrophy: new and emerging insights from model mice. Curr Neurol Neurosci Rep. Mar. 2010;10(2):108-17.
Parsons et al., An 11 Base Pair Duplication in Exon 6 of the SMN Gene Produces a Type I Spinal Muscular Atrophy (SMA) Phenotype: Further Evidence For SMN as the Primary SMA-Determining Gene. Human Molecular Genetics. Nov. 1996;5(11):1727-32.
Passini et al., Antisense Oligonucleotides Delivered to the Mouse CNS Ameliorate Symptoms of Severe Spinal Muscular Atrophy. Sci Transl Med. Mar. 2, 2011;3(72):72ra18.
Passini et al., CNS-targeted gene therapy improves survival and motor function in a mouse model of spinal muscular atrophy. J Clin Invest. Apr. 2010;120(4):1253-64. Epub Mar. 15, 2010.
Passini et al., Translational fidelity of intrathecal delivery of self-complementary AAV9-survival motor neuron 1 for spinal muscular atrophy. Hum Gene Ther. Jul. 2014;25(7):619-30. Epub Apr. 28, 2014.
Patrizi et al. SMN protein analysis in fibroblast, amniocyte and CVS cultures from spinal muscular atrophy patients and its relevance for diagnosis. Eur J Hum Genet. Apr. 1999;7(3):301-9.
Payen et al., Prothrombin time prolongation in paracetamol poisoning: a relevant marker of hepatic failure? Hum Exp Toxicol. Nov. 2003;22(11):617-21.
Pellizzoni et al., A novel function for SMN, the spinal muscular atrophy disease gene product, in pre-mRNA splicing. Cell. Nov. 25, 1998;95(5):615-24.
Pellizzoni et al., Essential role for the SMN complex in the specificity of snRNP assembly. Science. Nov. 29, 2002;298(5599):1775-9.
Pellizzoni et al., The survival of motor neurons (SMN) protein interacts with the snoRNP proteins fibrillarin and GAR1. Curr Biol. Jul. 24, 2001;11(14):1079-88.
Petrone et al. Noninvasive ventilation in children with spinal muscular atrophy types 1 and 2. Am J Phys Med Rehabil. Mar. 2007;86(3):216-21.
Petrosyan et al., Transduction efficiency of neurons and glial cells by AAV-1, -5, -9, -rh10 and -hu11 serotypes in rat spinal cord following contusion injury. Gene Ther. Dec. 2014;21(12):991-1000. Epub Aug. 14, 2014.
Pettersen EF et al., UCSF Chimera—a visualization system for exploratory research and analysis, J. Comput. Chem., 25(13):1605-12, Oct. 2004.
PDB: 2J6E_A, Web page <https://www.ncbi.nlm.nih.gov/protein/2J6E_A>, 2 pages, retrieved from Internet on May 11, 2018.
PDB: 4FQL_H, Web page <https://www.ncbi.nlm.nih.gov/protein/4FQL_H>, 3 pages, retrieved from Internet on May 11, 2018.
Prior and Finanger, Spinal Muscular Atrophy, Feb. 24, 2000 [Updated Dec. 22, 2016]. In: Adam MP, Ardinger HH, Pagon RA, et al., editors. GeneReviews® [Internet]. Seattle (WA): University of Washington, Seattle; 1993-2019.
Prior et al., Homozygous SMN1 deletions in unaffected family members and modification of the phenotype by SMN2. Am J Med Genet A. Oct. 15, 2004;130A(3):307-10.
Prior et al., Spinal muscular atrophy: newborn and carrier screening. Obstet Gynecol Clin North Am. Mar. 2010;37(1):23-36.
Prior, Perspectives and diagnostic considerations in spinal muscular atrophy. Genet Med. Mar. 2010;12(3):145-52.

(56) References Cited

OTHER PUBLICATIONS

Pulicherla et al., Engineering liver-detargeted AAV9 vectors for cardiac and musculoskeletal gene transfer. Mol Ther. Jun. 2011;19(6):1070-8. pub Mar. 1, 2011.

Quitschke WW et al., The beta actin promoter, High levels of transcription depend upon a CCAAT binding factor, 264(16):9539-46, Jun. 5, 1989.

Radcliffe PA et al., Multiple gene products from a single vector: 'self-cleaving' 2A peptides, Gene Therapy, 11(23): 1673-4, 2004. (Published Oct. 26, 2004).

Rath T et al., Fc-fusion proteins and FcRn: structural insights for longer-lasting and more effective therapeutics, Critical reviews in biotechnology, 35(2):235-54, Jun. 2015. (Epub Oct. 24, 2013).

Riechmann L et al., Reshaping human antibodies for therapy, Nature, 332(6162):323-7, Mar. 1988.

Roderick et al., Genetic and phenotypic variation in weight of brain and spinal cord between inbred strains of mice. Brain Res. Dec. 21, 1973;64:345-53.

Rosas et al., Patterns of scAAV vector insertion associated with oncogenic events in a mouse model for genotoxicity. Mol Ther. Nov. 2012;20(11):2098-110. Epub Sep. 18, 2012.

Roscilli G et al., Long-Term and Tight Control of Gene Expression in Mouse Skeletal Muscle by a New Hybrid Human Transcription Factor, Mol. Ther., 6(5):653-63, Nov. 2002.

Roseman Am, FindEM—a fast, efficient program for automatic selection of particles from electron micrographs, J. Struct. Biol., 145(1-2):91-9, Jan.-Feb. 2004.

Royo et al., Specific AAV serotypes stably transduce primary hippocampal and cortical cultures with high efficiency and low toxicity. Brain Res. Jan. 23, 2008;1190:15-22. Epub Nov. 17, 2007.

Rudnik-Schoneborn et al., The predictive value of achieved motor milestones assessed in 441 patients with infantile spinal muscular atrophy types II and III. Eur Neurol. 2001;45(3):174-81.

Russman, Spinal muscular atrophy: clinical classification and disease heterogeneity. J Child Neurol. Aug. 2007;22(8):946-51.

Sanner MF et al., Reduced surface: an efficient way to compute molecular surfaces, Biopolymers, 38(3):305-20, Mar. 1996.

Sahashi et al., Pathological impact of SMN2 mis-splicing in adult SMA mice. EMBO Mol Med. Oct. 2013;5(10):1586-601. Epub Sep. 9, 2013.

Saunders and Riordan, Cisternal or Suboccipital Puncture: A Report of 2019 Punctures. The New England Journal of Medicine, 1929;201(4):168-8.

Sawada-Hirai et al., Human anti-anthrax protective antigen neutralizing monoclonal antibodies derived from donors vaccinated with anthrax vaccine adsorbed. J Immune Based Ther Vaccines. May 12, 2004;2(1):5.

Saxena A and Wu D, Advances in therapeutic Fc engineering-modulation of IgG-Associated effector functions and serum half-life, Frontiers in immunology, 7:580, Dec. 12, 2016.

Scharfmann R et al., Long-term in vivo expression of retrovirus-mediated gene transfer in mouse fibroblast implants, Proc. Natl. Acad. Sci. USA, 88(11):4626-30, Jun. 1, 1991.

Scheres SH, A Bayesian view on cryo-EM structure determination, J. Mol. Biol., 415(2):406-18, Jan. 13, 2012. (Epub Nov. 12, 2011).

Schillinger KJ et al., Regulatable atrial natriuretic peptide gene therapy for hypertension, Proc. Natl. Acad. Sci. U S A., 102(39):13789-94, Sep. 27, 2005. (Epub Sep. 14, 2005).

Schrank et al., Inactivation of the survival motor neuron gene, a candidate gene for human spinal muscular atrophy, leads to massive cell death in early mouse embryos. Proc Natl Acad Sci U S A. Sep. 2, 1997;94(18):9920-5.

Searle et al., Building a Metal-Responsive Promoter with Synthetic Regulatory Elements, Mol. Cell. Biol., 5(6):1480-9, Jun. 1985.

Shapiro RJ, The Potential American Market for Generic Biological Treatments and the Associated Cost Savings, SONECON, No. vol., p. 1-20, Feb. 2008, Available from: http://www.sonecon.com/docs/studies/0208_GenericBiologicsStudy.pdf.

Shapshak P et al., The Influenza Pandemic of 2009: Lessons and Implications, Mol Diagn Ther., 15(2):63-81, Apr. 1, 2011.

Shepelev V and Fedorov A. Advances in the Exon-Intron Database. Briefings in Bioinformatics, 7(2):178-85, Jun. 2006. (Epub Mar. 9, 2006).

Sivo et al. Upper limb module in non-ambulant patients with spinal muscular atrophy: 12 month changes. Neuromuscul Disord. Mar. 2015;25(3):212-5. Epub Nov. 22, 2014.

Skaricic D et al., Genetic delivery of an anti-RSV antibody to protect against pulmonary infection with RSV, Virology, 378(1):79-85, Aug. 2008.

Slamon et al., Use of Chemotherapy plus a Monoclonal Antibody against HER2 for Metastatic Breast Cancer That Overexpresses HER2. N Engl J Med. Mar. 15, 2001;344(11):783-92.

Sleigh et al., The contribution of mouse models to understanding the pathogenesis of spinal muscular atrophy. Dis Model Mech. Jul. 2011;4(4):457-67.

Snyder et al., Comparison of Adeno-Associated Viral Vector Serotypes for Spinal Cord and Motor Neuron Gene Delivery. Hum Gene Ther. Sep. 2011;22(9):1129-35. Epub Jul. 25, 2011.

Sommer et al., Quantification of adeno-associated virus particles and empty capsids by optical density measurement. Mol Ther. Jan. 2003;7(1):122-8.

Staropoli et al., Rescue of gene-expression changes in an induced mouse model of spinal muscular atrophy by an antisense oligonucleotide that promotes inclusion of SMN2 exon 7. Genomics. Apr. 2015;105(4):220-8. Epub Jan. 31, 2015.

Stetefeld et al., Dynamic light scattering: a practical guide and applications in biomedical sciences. Biophys Rev. Dec. 2016;8(4):409-427. Epub Oct. 6, 2016.

Stratford-Perricaudet LD et al., Evaluation of the transfer and expression in mice of an enzyme-encoding gene using a human adenovirus vector, Hum Gene Ther., 1(3):241-56, 1990.

Strohl WR, Optimization of Fc-Mediated Effector Functions of Monoclonal Antibodies, Current Opinion in Biotechnology, 20(6):685-91, Dec. 2009. (Epub Nov. 4, 2009).

Su et al., In vitro and in vivo mRNA delivery using lipid-enveloped pH-responsive polymer nanoparticles. Mol Pharm. Jun. 6, 2011;8(3):774-87. Epub Apr. 1, 2011.

Sugarman et al., Pan-ethnic carrier screening and prenatal diagnosis for spinal muscular atrophy: clinical laboratory analysis of >72,400 specimens.

Sui J et al., Structural and functional bases for broad-spectrum neutralization of avian and human influenza A viruses, Nature structural & molecular biology, 16(3):265-73. (Epub Feb. 22, 2009).

Swoboda et al., Natural history of denervation in SMA: relation to age, SMN2 copy number, and function. Ann Neurol. May 2005;57(5):704-12.

Swoboda et al., SMA CARNI-VAL trial part I: double-blind, randomized, placebo-controlled trial of L-carnitine and valproic acid in spinal muscular atrophy. PLoS One. Aug. 19, 2010;5(8):e12140.

Talbot et al., Characterization of a gene encoding survival motor neuron (SMN)-related protein, a constituent of the spliceosome complex. Hum Mol Genet. Dec. 1998;7(13):2149-56.

Tan GS et al., A pan-H1 anti-hemagglutinin monoclonal antibody with potent broad-spectrum efficacy in vivo, 86(11):6179-88, Jun. 2012. (Epub Apr. 4, 2012).

Tang G et al., EMAN2: an extensible image processing suite for electron microscopy, J. Struct. Biol., 157(1):38-46, Jan. 2007. (Epub Jun. 8, 2006).

Tanguy et al., Systemic AAVrh10 provides higher transgene expression than AAV9 in the brain and the spinal cord of neonatal mice. Front Mol Neurosci. Jul. 28, 2015;8:36.

Tardieu et al., Intracerebral administration of adeno-associated viral vector serotype rh. 10 carrying human SGSH and SUMF1 cDNAs in children with mucopolysaccharidosis type IIIA disease: results of a phase I/II trial. Hum Gene Ther. Jun. 2014;25(6):506-16. Epub May 5, 2014.

Thompson et al., A comprehensive comparison of multiple sequence alignment programs. Nucleic Acids Res. Jul. 1, 1999;27(13):2682-90.

Throsby M et al., Heterosubtypic neutralizing monoclonal antibodies cross-protective against H5N1 and H1N1 recovered from human IgM+ memory B cells, PLoS One, vol. 3(12): e3942, 2008. (Epub Dec. 16, 2008).

(56) References Cited

OTHER PUBLICATIONS

Tillib et al., Formatted single-domain antibodies can protect mice against infection with influenza virus (H5N2), Antiviral Research. 97(3):245-54, Mar. 2013. (Epub Dec. 25, 2012).
Tsibane et al., Influenza human monoclonal antibody 1F1 interacts with three major antigenic sites and residues mediating human receptor specificity in H1N1 viruses, PLoS Pathog., 8(12):e1003067, 2012. (Epub Dec. 6, 2012).
Tycko J et al. 701. Intranasal Delivery of Neutralizing Antibodies by AAV9 to Protect Mice Against RSV Infection. Vaccines and Immunotherapy, Molecular Therapy, vol. 22, Supplement 1, pS271, May 2014.
UniProtKB—P60568 (IL2_HUMAN), Web page http://www.uniprot.org/uniprot/P60568, 9 pages, retrieved from Internet on May 11, 2018.
U.S. Department of Health and Human Services, Food and Drug Administration, Center for Biologics Evaluation, "Research Points to Consider in the Manufacture and Testing of Monoclonal Ab Products for Human Use," Center for Biologics Evaluation and Research, Center for Drug Evaluation and Research, published in Feb. 1997, Available from https://www.fda.gov/regulatory-information/search-fda-guidance-documents/points-consider-manufacture-and-testing-monoclonal-antibody-products-human-use.
U.S. Department of Health and Human Services Food and Drug Administration Center for Biologics Evaluation and Research, Guidance for Industry Preclinical Assessment of Investigational Cellular and Gene Therapy Products, Nov. 2013.
Urrutia R., KRAB-containing zinc-finger repressor proteins, Genome Biol., 4(10):231, 2003. (Epub Sep. 23, 2003).
Vafa O et al., An engineered Fc variant of an IgG eliminates all immune effector functions via structural perturbations, Methods, 65(1):114-26, Jan. 1, 2014. (Epub Jul. 17, 2013).
Vanlandschoot P et al., Nanobodies: new ammunition to battle viruses, Antiviral Res., 92(3):389-407, Dec. 2011. (Epub Sep. 10, 2011).
Verhoeyen M et al., Reshaping human antibodies: grafting an antilysozyme activity, Science, 239(4847):1534-6, Mar. 1988.
Vincent-Lacaze et al., Structure of Adeno-Associated Virus Vector DNA following Transduction of the Skeletal Muscle. J Virol. Mar. 1999;73(3):1949-55.
Viollet et al., cDNA isolation, expression, and chromosomal localization of the mouse survival motor neuron gene (Smn). Genomics. Feb. 15, 1997;40(1):185-8.
Vite et al., Effective gene therapy for an inherited CNS disease in a large animal model. Ann Neurol. Mar. 2005;57(3):355-64.
Wang and Lunn, Spinal muscular atrophy: advances in research and consensus on care of patients. Curr Treat Options Neurol. Nov. 2008;10(6):420-8.
Wang et al., Consensus statement for standard of care in spinal muscular atrophy. J Child Neurol. Aug. 2007;22(8):1027-49.
Wang TT et al., Broadly protective monoclonal antibodies against H3 influenza viruses following sequential immunization with different hemagglutinins, PLoS Pathog., 6(2):e1000796, Feb. 26, 2010.
Wang Y et al., A regulatory system for use in gene transfer, Proc. Natl. Acad. Sci. USA., 91(17):8180-4, Aug. 1994.
Ward et al., Codon optimization of human factor VIII cDNA leads to high-level expression, Blood, Jan. 20, 2011; 117(3):798-807. DOI: 10.1182/blood-2010-05-282707 Epub Nov. 1, 2010.
Wang et al., Impact of pre-existing immunity on gene transfer to nonhuman primate liver with adeno-associated virus 8 vectors. Hum Gene Ther. Nov. 2011;22(11):1389-401. Epub Jun. 8, 2011.
Wang et al., The pleiotropic effects of natural AAV infections on liver-directed gene transfer in macaques. Mol Ther. Jan. 2010;18(1):126-34. Epub Nov. 3, 2009.
WHO Manual on Animal Influenza Diagnosis and Surveillance, Geneva: World Health Organization, 2002, Version 2002.5, p. 1-105, n.d.
Willey R et al., Neutralizing antibody titers conferring protection to macaques from a simian/human immunodeficiency virus challenge using the TZM-bl assay, AIDS research and human retroviruses, 26(1):89-98, Jan. 10, 2010.
Williams DA et al., Introduction of new genetic material into pluripotent haematopoietic stem cells of the mouse, Nature, 310(5977):476-80, Aug. 9, 1984.
Wirth, Mildly affected patients with spinal muscular atrophy are partially protected by an increased SMN2 copy number. Hum Genet. May 2006;119(4):422- 8. Epub Mar. 1, 2006.
Wobus et al., Monoclonal antibodies against the adeno-associated virus type 2 (AAV-2) capsid: epitope mapping and identification of capsid domains involved in AAV-2-cell interaction and neutralization of AAV-2 infection. J Virol. Oct. 2000;74(19):9281-93.
Worgall, et al. Treatment of late infantile neuronal ceroid lipofuscinosis by CNS administration of a serotype 2 adeno-associated virus expressing CLN2 cDNA. Hum Gene Ther. May 2008;19(5):463-74.
Wright, Product-Related Impurities in Clinical-Grade Recombinant AAV Vectors: Characterization and Risk Assessment, Biomedicines. Mar. 3, 2014;2(1):80-97.
Wu Y et al., A potent broad-spectrum protective human monoclonal antibody crosslinking two haemagglutinin monomers of influenza A virus, Nat. Commun., 6:7708, Jul. 21, 2015.
Xia H et al., siRNA-mediated gene silencing in vitro and in vivo, Nat Biotechnol, 20(10):1006-10, Oct. 2002. (Epub Sep. 16, 2002).
Xie H et al., H3N2 Mismatch of 2014-15 Northern Hemisphere Influenza Vaccines and Head-to-head Comparison between Human and Ferret Antisera derived Antigenic Maps, Sci. Rep., 5:15279, Oct. 16, 2015.
Xin K-Q et al., A novel recombinant adeno-associated virus vaccine induces a long-term humoral immune response to human immunodeficiency virus, Human Gene Ther., 12(9):1047-61, Jun. 2001.
Xiong et al., PCR-based accurate synthesis of long DNA sequences. Nat Protoc. 2006;1(2):791-7.
Xu R et al., Structural basis of preexisting immunity to the 2009 H1N1 pandemic influenza virus, Science, 328(5976):357-60, Apr. 16, 2010. (Epub Mar. 25, 2010).
Yang et al., Evaluating glymphatic pathway function utilizing clinically relevant intrathecal infusion of CSF tracer. J Transl Med. May 1, 2013;11:107.
Yang Z et al., Iterative stable alignment and clustering of 2D transmission electron microscope images, Structure, 20(2):237-47, Feb. 8, 2012.
Yoshida R et al., Cross-protective potential of a novel monoclonal antibody directed against antigenic site B of the hemagglutinin of influenza A viruses, PLoS Pathog., 5(3):e1000350, Mar. 2009. (Epub Mar. 20, 2009).
Young and Dong, Two-step total gene synthesis method. Nucleic Acids Res. Apr. 15, 2004;32(7):e59.
Young et al., The relationship between SMN, the spinal muscular atrophy protein, and nuclear coiled bodies in differentiated tissues and cultured cells. Exp Cell Res. May 1, 2000;256(2):365-74.
Yu et al. Recent patents on oligonucleotide synthesis and gene synthesis. Recent Pat DNA Gene Seq. Apr. 2012;6(1):10-21.
Zagouri et al., Intrathecal administration of trastuzumab for the treatment of meningeal carcinomatosis in HER2-positive metastatic breast cancer: a systematic review and pooled analysis. Breast Cancer Res Treat. May 2013;139(1):13-22.
Zanta-Boussif et al., Validation of a mutated PRE sequence allowing high and sustained transgene expression while abrogating WHV-X protein synthesis: application to the gene therapy of WAS. Gene Ther. May 2009;16(5):605-19.
Zerres & Rudnik-Schoneborn, Natural history in proximal spinal muscular atrophy. Clinical analysis of 445 patients and suggestions for a modification of existing classifications. Arch Neurol. May 1995;52(5):518-23.
Zhang et al., Adenovirus-adeno-associated virus hybrid for large-scale recombinant adeno-associated virus production. Hum Gene Ther. Sep. 2009;20(9):922-9.
Zhang L et al., Alteration in the IL-2 signal peptide affects secretion of proteins in vitro and in vivo, J Gene Med., 7(3):354-65, Mar.

(56) References Cited

OTHER PUBLICATIONS 2005. (Published online Dec. 23, 2004 )WHO Manual on Animal Influenza Diagnosis and Surveillance, Geneva: World Health Organisation, 2002, version 2002.5.
Zolgensma Package Insert, May 2019.
International Search Report and Written Opinion issued in International Patent Application No. PCT/US2018/019992, mailed Sep. 21, 2018.
Communication issued in corresponding European Patent Application No. 18711202.4, dated Mar. 1, 2021.
Office Action issued in corresponding Chilean Patent Application No. 2019-2474, dated Aug. 27, 2020, with translated summary provided by local Agent.
Office Action dated Sep. 21, 2022 issued in corresponding Egyptian Patent Application No. 1367/2019, with unofficial English translation provided by local Agent.
Substantive Examination Report dated Nov. 8, 2022 issued in corresponding Saudi Arabian Patent Application No. 519402565, with unofficial English translation provided by local Agent.
Communication dated Sep. 26, 2022 issued in corresponding European Patent Application No. 18711202.4.
Substantive Examination Report issued in corresponding Saudi Arabian Patent Application No. 519402565, dated Oct. 31, 2021, with unofficial English translation from local Agent.
Office Action dated Jan. 29, 2022 issued in corresponding Japanese Patent Application No. 2019-547088, with unofficial English translation provided by local Agent.
Office Action dated Mar. 14, 2022 issued in corresponding Eurasian Patent Application No. 201992023, with unofficial English translation provided by local Agent.
Substantive Examination Report dated Apr. 13, 2022 issued in corresponding Indonesian Patent Application No. P00201908032, with unofficial translation provided by local agent.
Communication dated Jan. 13, 2025, issued in related European Patent Application No. 23183607.3.
Certificate of Grant of Standard Patent dated Sep. 19, 2024, issued in related Australian Patent Application No. 2018227440.
Office Action dated Jan. 12, 2024, issued in related Peruvian Patent Application No. 001786-2019/DIN, with unofficial English translation provided by local Agent.
Office Action dated Feb. 14, 2024, issued in related Japanese Patent Application No. 2023-064895, with unofficial English translation provided by local Agent.
Office Action dated Nov. 20, 2024, issued in related Japanese Patent Application No. 2023-064895, with unofficial English translation provided by local Agent.
Decision for Patent Grant dated Nov. 25, 2024, issued in related Korean Patent Application No. 10-2019-7027807, with unofficial English translation provided by local Agent.
Notice of Allowance dated Aug. 1, 2024, issued in Mexican Patent Application No. MX/A/2019/010275, with unofficial English translation provided by local Agent.
Notification Prior to Acceptance dated Oct. 1, 2024, issued in Israeli Patent Application No. 268644, with unofficial English translation provided by local Agent.
Notification of Readiness to Grant dated Jun. 18, 2024, issued in Eurasian Patent Application No. 201992023, with unofficial English translation provided by local Agent.
Office Action dated Jan. 15, 2024, issued in Chinese Patent Application No. 201880028016.X, with unofficial English translation provided by local Agent.
Notification to Grant Patent Right dated Jun. 17, 2024, issued in Chinese Patent Application No. 201880028016.X, with unofficial English translation provided by local Agent.
Office Action dated Jan. 8, 2024, issued in Canadian Patent Application No. 3,053,399.
Communication pursuant to Article 94(3) EPC issued on corresponding European Patent Application No. 23183607.3, dated Jan. 13, 2025.
Office Action dated May 21, 2025, issued in corresponding Japanese Patent Application No. 2023-064895, with unofficial English translation provided by local Agent.
Preliminary Office Action dated Apr. 1, 2025, issued in corresponding Brazilian Patent Application No. BR112019017839-2, with unofficial English translation provided by local Agent.
Office Action dated Jul. 4, 2025, issued in corresponding Canadian Patent Application No. 3,053,399.

* cited by examiner

| | | |
|---|---|---|
| AAV9 | (501) | FAWPGASSWALNGRNSLMNPGPAMASHKEGEDRFFPLSGSLIFGKQGTGRDNVDADKVMITNEEEIKTTNPVATESYGQVATNHQSAQAQAQTGWVQNQG |
| hu.68.VP1 | (501) | FAWPGASSWALNGRNSLMNPGPAMASHKEGEDRFFPLSGSLIFGKQGTGRDNVDADKVMITNEEEIKTTNPVATESYGQVATNHQSAQAQAQTGWVQNQG |
| hu.31 | (501) | FAWPGASSWALNGRNSLMNPGPAMASHKEGEDRFFPLSGSLIFGKQGTGRDNVDADKVMITNEEEIKTTNPVATESYGQVATNHQSAQAQAQTGWVQNQG |
| hu.32 | (501) | FAWPGASSWALNGRNSLMNPGPAMASHKEGEDRFFPLSGSLIFGKQGTGRDNVDADKVMITNEEEIKTTNPVATESYGQVATNHQSAQAQAQTGWVQNQG |
| | | 601 700 |
| AAV9 | (601) | ILPGMVWQDRDVYLQGPIWAKIPHTDGNFHPSPLMGGFMKHPPPQILIKNTPVPADPPTAFNKDKLNSFITQYSTGQVSVEIEWELQKENSKRWNPEIQ |
| hu.68.VP1 | (601) | ILPGMVWQDRDVYLQGPIWAKIPHTDGNFHPSPLMGGFMKHPPPQILIKNTPVPADPPTAFNKDKLNSFITQYSTGQVSVEIEWELQKENSKRWNPEIQ |
| hu.31 | (601) | ILPGMVWQDRDVYLQGPIWAKIPHTDGNFHPSPLMGGFMKHPPPQILIKNTPVPADPPTAFNKDKLNSFITQYSTGQVSVEIEWELQKENSKRWNPEIQ |
| hu.32 | (601) | ILPGMVWQDRDVYLQGPIWAKIPHTDGNFHPSPLMGGFMKHPPPQILIKNTPVPADPPTAFNKDKLNSFITQYSTGQVSVEIEWELQKENSKRWNPEIQ |
| | | 701 736 |
| AAV9 | (701) | YTSNYYKSNNVEFAVNTEGVYSEPRPIGTRYLTRNL |
| hu.68.VP1 | (701) | YTSNYYKSNNVEFAVNTEGVYSEPRPIGTRYLTRNL |
| hu.31 | (701) | YTSNYYKSNNVEFAVSTEGVYSEPRPIGTRYLTRNL |
| hu.32 | (701) | YTSNYYKSNNVEFAVNTEGVYSEPRPIGTRYLTRNL |

FIG 1B

AAV9 (1)
hu.68 VP1 (1)
hu.31 (1)
hu.32 (1)

AAV9 (101)
hu.68 VP1 (101)
hu.31 (101)
hu.32 (101)

AAV9 (201)
hu.68 VP1 (201)
hu.31 (201)
hu.32 (201)

AAV9 (301)
hu.68 VP1 (301)
hu.31 (301)
hu.32 (301)

AAV9 (401)
hu.68 VP1 (401)
hu.31 (401)
hu.32 (401)

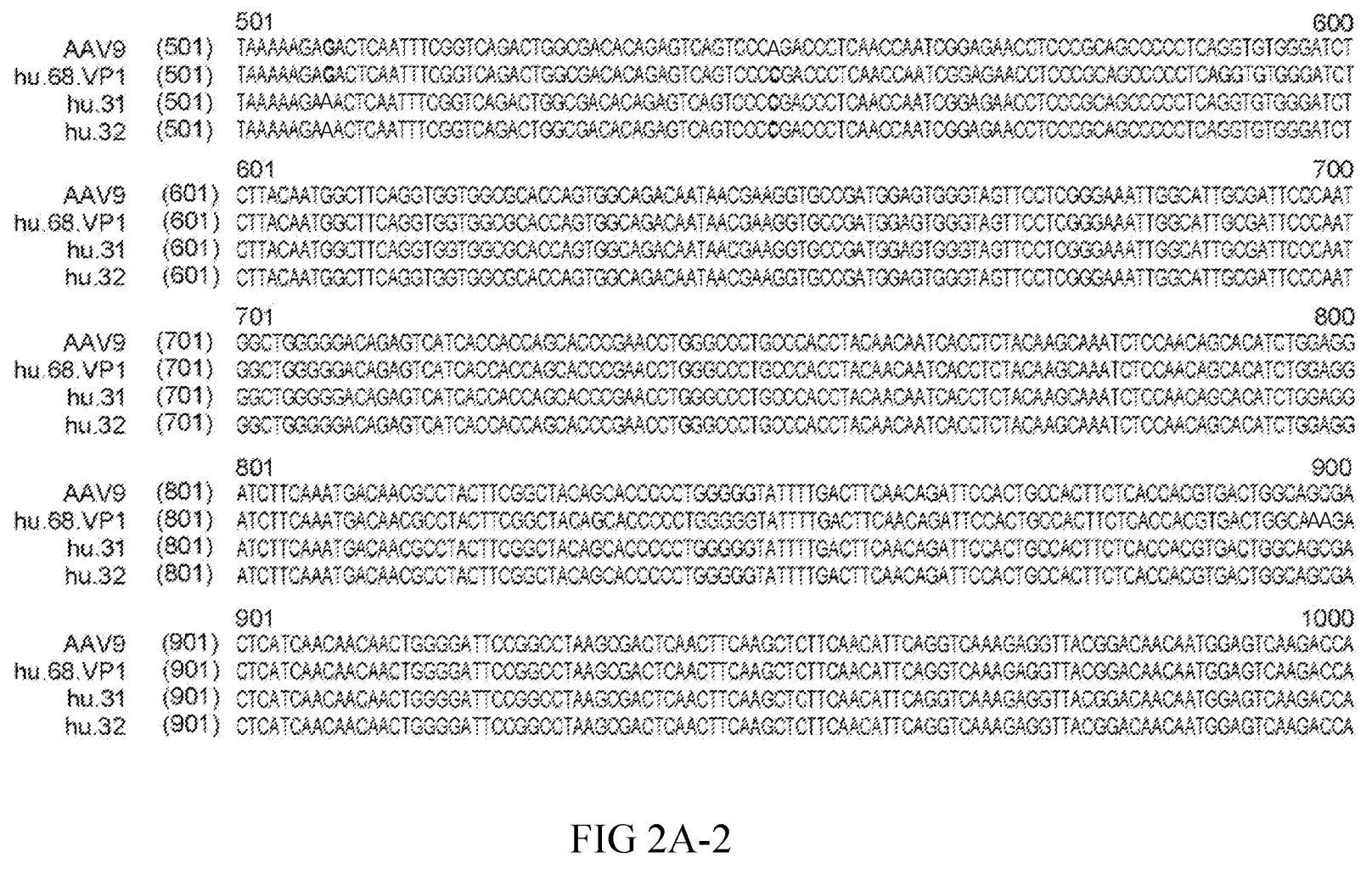

| | | 501 600 |
|---|---|---|
| AAV9 | (501) | TAAAAAGAGACTCAATTTCGGTCAGACTGGCGACACAGAGTCAGTCCCAGACCCTCAACCAATCGGAGAACCTCCCGCAGCCCCCTCAGGTGTGGGATCT |
| hu.68.VP1 | (501) | TAAAAAGAGACTCAATTTCGGTCAGACTGGCGACACAGAGTCAGTCCCCGACCCTCAACCAATCGGAGAACCTCCCGCAGCCCCCTCAGGTGTGGGATCT |
| hu.31 | (501) | TAAAAAGAAACTCAATTTCGGTCAGACTGGCGACACAGAGTCAGTCCCCGACCCTCAACCAATCGGAGAACCTCCCGCAGCCCCCTCAGGTGTGGGATCT |
| hu.32 | (501) | TAAAAAGAAACTCAATTTCGGTCAGACTGGCGACACAGAGTCAGTCCCCGACCCTCAACCAATCGGAGAACCTCCCGCAGCCCCCTCAGGTGTGGGATCT |

| | | 601 700 |
|---|---|---|
| AAV9 | (601) | CTTACAATGGCTTCAGGTGGTGGCGCACCAGTGGCAGACAATAACGAAGGTGCCGATGGAGTGGGTAGTTCCTCGGGAAATTGGCATTGCGATTCCCAAT |
| hu.68.VP1 | (601) | CTTACAATGGCTTCAGGTGGTGGCGCACCAGTGGCAGACAATAACGAAGGTGCCGATGGAGTGGGTAGTTCCTCGGGAAATTGGCATTGCGATTCCCAAT |
| hu.31 | (601) | CTTACAATGGCTTCAGGTGGTGGCGCACCAGTGGCAGACAATAACGAAGGTGCCGATGGAGTGGGTAGTTCCTCGGGAAATTGGCATTGCGATTCCCAAT |
| hu.32 | (601) | CTTACAATGGCTTCAGGTGGTGGCGCACCAGTGGCAGACAATAACGAAGGTGCCGATGGAGTGGGTAGTTCCTCGGGAAATTGGCATTGCGATTCCCAAT |

| | | 701 800 |
|---|---|---|
| AAV9 | (701) | GGCTGGGGGACAGAGTCATCACCACCAGCACCCGAACCTGGGCCCTGCCCACCTACAACAATCACCTCTACAAGCAAATCTCCAACAGCACATCTGGAGG |
| hu.68.VP1 | (701) | GGCTGGGGGACAGAGTCATCACCACCAGCACCCGAACCTGGGCCCTGCCCACCTACAACAATCACCTCTACAAGCAAATCTCCAACAGCACATCTGGAGG |
| hu.31 | (701) | GGCTGGGGGACAGAGTCATCACCACCAGCACCCGAACCTGGGCCCTGCCCACCTACAACAATCACCTCTACAAGCAAATCTCCAACAGCACATCTGGAGG |
| hu.32 | (701) | GGCTGGGGGACAGAGTCATCACCACCAGCACCCGAACCTGGGCCCTGCCCACCTACAACAATCACCTCTACAAGCAAATCTCCAACAGCACATCTGGAGG |

| | | 801 900 |
|---|---|---|
| AAV9 | (801) | ATCTTCAAATGACAACGCCTACTTCGGCTACAGCACCCCCTGGGGGTATTTTGACTTCAACAGATTCCACTGCCACTTCTCACCACGTGACTGGCAGCGA |
| hu.68.VP1 | (801) | ATCTTCAAATGACAACGCCTACTTCGGCTACAGCACCCCCTGGGGGTATTTTGACTTCAACAGATTCCACTGCCACTTCTCACCACGTGACTGGCAAAGA |
| hu.31 | (801) | ATCTTCAAATGACAACGCCTACTTCGGCTACAGCACCCCCTGGGGGTATTTTGACTTCAACAGATTCCACTGCCACTTCTCACCACGTGACTGGCAGCGA |
| hu.32 | (801) | ATCTTCAAATGACAACGCCTACTTCGGCTACAGCACCCCCTGGGGGTATTTTGACTTCAACAGATTCCACTGCCACTTCTCACCACGTGACTGGCAGCGA |

| | | 901 1000 |
|---|---|---|
| AAV9 | (901) | CTCATCAACAACAACTGGGGATTCCGGCCTAAGCGACTCAACTTCAAGCTCTTCAACATTCAGGTCAAAGAGGTTACGGACAACAATGGAGTCAAGACCA |
| hu.68.VP1 | (901) | CTCATCAACAACAACTGGGGATTCCGGCCTAAGCGACTCAACTTCAAGCTCTTCAACATTCAGGTCAAAGAGGTTACGGACAACAATGGAGTCAAGACCA |
| hu.31 | (901) | CTCATCAACAACAACTGGGGATTCCGGCCTAAGCGACTCAACTTCAAGCTCTTCAACATTCAGGTCAAAGAGGTTACGGACAACAATGGAGTCAAGACCA |
| hu.32 | (901) | CTCATCAACAACAACTGGGGATTCCGGCCTAAGCGACTCAACTTCAAGCTCTTCAACATTCAGGTCAAAGAGGTTACGGACAACAATGGAGTCAAGACCA |

FIG 2A-2

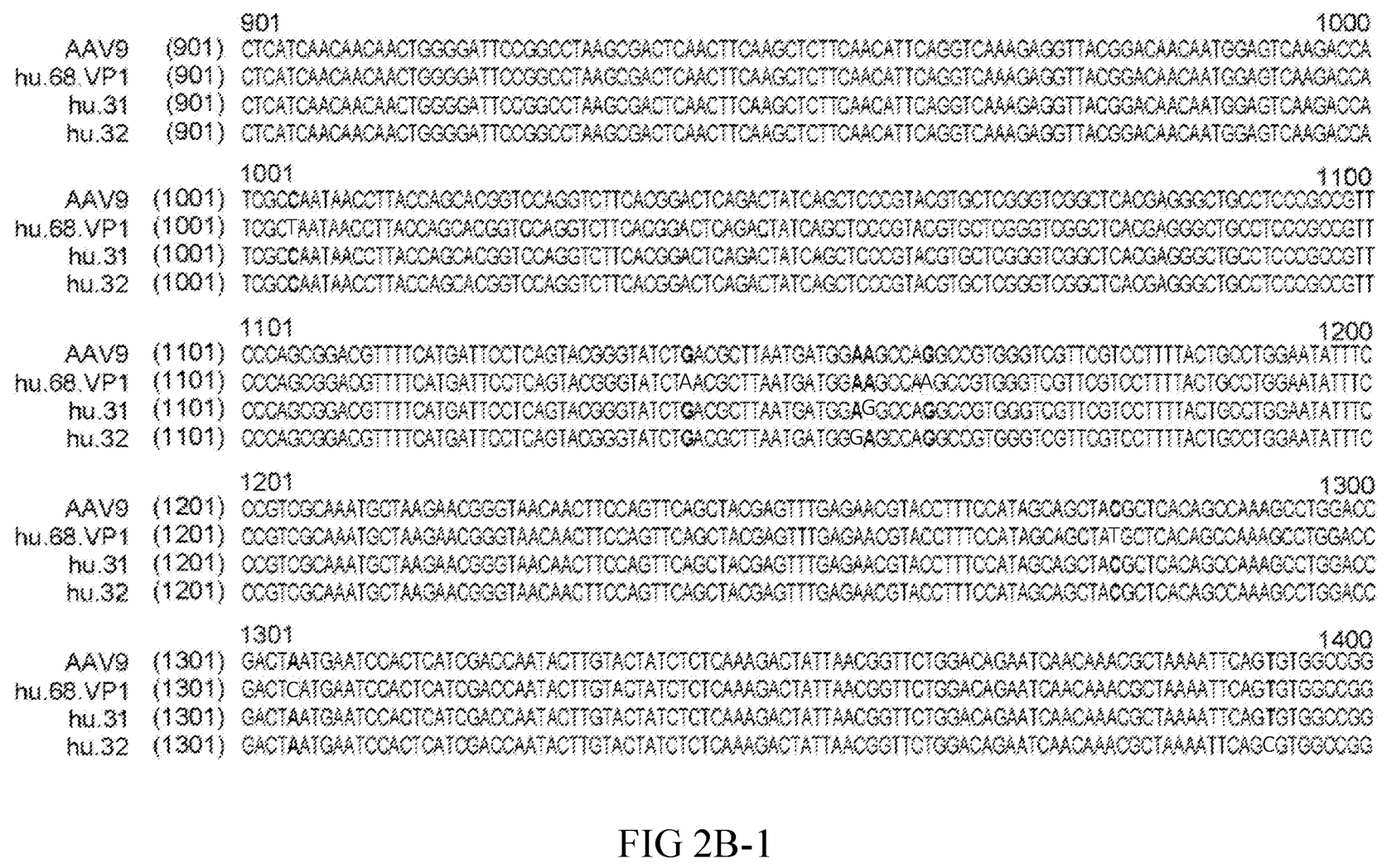

```
                    901                                                                                                 1000
    AAV9    (901)   CTCATCAACAACAACTGGGGATTCCGGCCTAAGCGACTCAACTTCAAGCTCTTCAACATTCAGGTCAAAGAGGTTACGGACAACAATGGAGTCAAGACCA
hu.68.VP1   (901)   CTCATCAACAACAACTGGGGATTCCGGCCTAAGCGACTCAACTTCAAGCTCTTCAACATTCAGGTCAAAGAGGTTACGGACAACAATGGAGTCAAGACCA
    hu.31   (901)   CTCATCAACAACAACTGGGGATTCCGGCCTAAGCGACTCAACTTCAAGCTCTTCAACATTCAGGTCAAAGAGGTTACGGACAACAATGGAGTCAAGACCA
    hu.32   (901)   CTCATCAACAACAACTGGGGATTCCGGCCTAAGCGACTCAACTTCAAGCTCTTCAACATTCAGGTCAAAGAGGTTACGGACAACAATGGAGTCAAGACCA

                    1001                                                                                                1100
    AAV9   (1001)   TCGCCAATAACCTTACCAGCACGGTCCAGGTCTTCACGGACTCAGACTATCAGCTCCCGTACGTGCTCGGGTCGGCTCACGAGGGCTGCCTCCCGCCGTT
hu.68.VP1  (1001)   TCGCTAATAACCTTACCAGCACGGTCCAGGTCTTCACGGACTCAGACTATCAGCTCCCGTACGTGCTCGGGTCGGCTCACGAGGGCTGCCTCCCGCCGTT
    hu.31  (1001)   TCGCCAATAACCTTACCAGCACGGTCCAGGTCTTCACGGACTCAGACTATCAGCTCCCGTACGTGCTCGGGTCGGCTCACGAGGGCTGCCTCCCGCCGTT
    hu.32  (1001)   TCGCCAATAACCTTACCAGCACGGTCCAGGTCTTCACGGACTCAGACTATCAGCTCCCGTACGTGCTCGGGTCGGCTCACGAGGGCTGCCTCCCGCCGTT

                    1101                                                                                                1200
    AAV9   (1101)   CCCAGCGGACGTTTTCATGATTCCTCAGTACGGGTATCTGACGCTTAATGATGGAAGCCAGGCCGTGGGTCGTTCGTCCTTTTACTGCCTGGAATATTTC
hu.68.VP1  (1101)   CCCAGCGGACGTTTTCATGATTCCTCAGTACGGGTATCTAACGCTTAATGATGGAAGCCAAGCCGTGGGTCGTTCGTCCTTTTACTGCCTGGAATATTTC
    hu.31  (1101)   CCCAGCGGACGTTTTCATGATTCCTCAGTACGGGTATCTGACGCTTAATGATGGAGGCCAGGCCGTGGGTCGTTCGTCCTTTTACTGCCTGGAATATTTC
    hu.32  (1101)   CCCAGCGGACGTTTTCATGATTCCTCAGTACGGGTATCTGACGCTTAATGATGGGAGCCAGGCCGTGGGTCGTTCGTCCTTTTACTGCCTGGAATATTTC

                    1201                                                                                                1300
    AAV9   (1201)   CCGTCGCAAATGCTAAGAACGGGTAACAACTTCCAGTTCAGCTACGAGTTTGAGAACGTACCTTTCCATAGCAGCTACGCTCACAGCCAAAGCCTGGACC
hu.68.VP1  (1201)   CCGTCGCAAATGCTAAGAACGGGTAACAACTTCCAGTTCAGCTACGAGTTTGAGAACGTACCTTTCCATAGCAGCTATGCTCACAGCCAAAGCCTGGACC
    hu.31  (1201)   CCGTCGCAAATGCTAAGAACGGGTAACAACTTCCAGTTCAGCTACGAGTTTGAGAACGTACCTTTCCATAGCAGCTACGCTCACAGCCAAAGCCTGGACC
    hu.32  (1201)   CCGTCGCAAATGCTAAGAACGGGTAACAACTTCCAGTTCAGCTACGAGTTTGAGAACGTACCTTTCCATAGCAGCTACGCTCACAGCCAAAGCCTGGACC

                    1301                                                                                                1400
    AAV9   (1301)   GACTAATGAATCCACTCATCGACCAATACTTGTACTATCTCTCAAAGACTATTAACGGTTCTGGACAGAATCAACAAACGCTAAAATTCAGTGTGGCCGG
hu.68.VP1  (1301)   GACTCATGAATCCACTCATCGACCAATACTTGTACTATCTCTCAAAGACTATTAACGGTTCTGGACAGAATCAACAAACGCTAAAATTCAGTGTGGCCGG
    hu.31  (1301)   GACTAATGAATCCACTCATCGACCAATACTTGTACTATCTCTCAAAGACTATTAACGGTTCTGGACAGAATCAACAAACGCTAAAATTCAGTGTGGCCGG
    hu.32  (1301)   GACTAATGAATCCACTCATCGACCAATACTTGTACTATCTCTCAAAGACTATTAACGGTTCTGGACAGAATCAACAAACGCTAAAATTCAGCGTGGCCGG
```

FIG 2B-1

| | | |
|---|---|---|
| | | 1801 1900 |
| AAV9 | (1801) | ATACTTCCGGGTATGGTTTGGCAGGACAGAGATGTGTACCTGCAAGGACCCATTTGGGCCAAAATTCCTCACACGGACGGCAACTTTCACCCTTCTCCGC |
| hu.68.VP1 | (1801) | ATACTTCCGGGTATGGTTTGGCAGGACAGAGATGTGTACCTGCAAGGACCCATTTGGGCCAAAATTCCTCACACGGACGGCAACTTTCACCCTTCTCCGC |
| hu.31 | (1801) | ATACTTCCGGGTATGGTTTGGCAGGACAGAGATGTGTACCTGCAAGGACCCATTTGGGCCAAAATTCCTCACACGGACGGCAACTTTCACCCTTCTCCGC |
| hu.32 | (1801) | ATACTTCCGGGTATGGTTTGGCAGGACAGAGATGTGTACCTGCAAGGACCCATTTGGGCCAAAATTCCTCACACGGACGGCAACTTTCACCCTTCTCCGC |
| | | 1901 2000 |
| AAV9 | (1901) | TGATGGGAGGGTTTGGAATGAAGCACCCGCCTCCTCAGATCCTCATCAAAAACACACCTGTACCTGCGGATCCTCCAACGGCCTTCAACAAGGACAAGCT |
| hu.68.VP1 | (1901) | TGATGGGAGGGTTTGGAATGAAGCACCCGCCTCCTCAGATCCTCATCAAAAACACACCTGTACCTGCGGATCCTCCAACGGCTTTCAACAAGGACAAGCT |
| hu.31 | (1901) | TAATGGGAGGGTTTGGAATGAAGCACCCGCCTCCTCAGATCCTCATCAAAAACACACCTGTACCTGCGGATCCTCCAACGGCTTTCAATAAGGACAAGCT |
| hu.32 | (1901) | TAATGGGAGGGTTTGGAATGAAGCACCCGCCTCCTCAGATCCTCATCAAAAACACACCTGTACCTGCGGATCCTCCAACGGCTTTCAATAAGGACAAGCT |
| | | 2001 2100 |
| AAV9 | (2001) | GAACTCTTTCATCACCCAGTATTCTACTGGCCAAGTCAGCGTGGAGATCGAGTGGGAGCTGCAGAAGGAAAACAGCAAGCGCTGGAACCCGGAGATCCAG |
| hu.68.VP1 | (2001) | GAACTCTTTCATCACCCAGTATTCTACTGGCCAAGTCAGCGTGGAGATTGAGTGGGAGCTGCAGAAGGAAAACAGCAAGCGCTGGAACCCGGAGATCCAG |
| hu.31 | (2001) | GAACTCTTTCATCACCCAGTATTCTACTGGCCAAGTCAGCGTGGAGATTGAGTGGGAGCTGCAGAAGGAAAACAGCAAGCGCTGGAACCCGGAGATCCAG |
| hu.32 | (2001) | GAACTCTTTCATCACCCAGTATTCTACTGGCCAAGTCAGCGTGGAGATTGAGTGGGAGCTGCAGAAGGAAAACAGCAAGCGCTGGAACCCGGAGATCCAG |
| | | 2101 2200 |
| AAV9 | (2101) | TACACTTCCAACTATTACAAGTCTAATAATGTTGAATTTGCTGTTAATACTGAAGGTGTATATAGTGAACCCCGCCCCATTGGCACCAGATACCTGACTC |
| hu.68.VP1 | (2101) | TACACTTCCAACTATTACAAGTCTAATAATGTTGAATTTGCTGTTAATACTGAAGGTGTTTATTCTGAACCCCGCCCCATTGGCACCAGATACCTGACTC |
| hu.31 | (2101) | TACACTTCCAACTATTACAAGTCTAATAATGTTGAATTTGCTGTTAGTACTGAAGGTGTATATAGTGAACCCCGCCCCATTGGCACCAGATACCTGACTC |
| hu.32 | (2101) | TACACTTCCAACTATTACAAGTCTAATAATGTTGAATTTGCTGTTAATACTGAAGGTGTATATAGTGAACCCCGCCCCATTGGCACCAGATACCTGACTC |
| | | 2201 2211 |
| AAV9 | (2201) | GTAATCTGTAA |
| hu.68.VP1 | (2201) | GTAATCTGTAA |
| hu.31 | (2201) | GTAATCTGTAA |
| hu.32 | (2201) | GTAATCTGTAA |

FIG 2C $5x10^{11}$GC AAVhu68.CB7.LacZ, IN administration, mouse

Kidney

ADENO-ASSOCIATED VIRUS (AAV) CLADE F VECTOR AND USES THEREFOR

STATEMENT REGARDING FEDERALLY SPONSORED RESEARCH OR DEVELOPMENT

This application contains work supported by Defense Advanced Research Projects Agency (DARPA) under W911NF-13-2-0036. The US government may have certain rights in this invention.

REFERENCE TO AN ELECTRONIC SEQUENCE LISTING

The electronic sequence listing filed herewith named "UPN-17-7986.US.C1_ST26_Seq Listing_ver2.xml" with size of 54,729 bytes, created on date of 30 Oct. 2023, and the contents of the electronic sequence listing (e.g., the sequences and text therein) are incorporated herein by reference in entirety.

BACKGROUND OF THE INVENTION

Adeno-associated virus (AAV), a member of the Parvovirus family, is a small non-enveloped, icosahedral virus with single-stranded linear DNA (ssDNA) genomes of about 4.7 kilobases (kb) long. The wild-type genome comprises inverted terminal repeats (ITRs) at both ends of the DNA strand, and two open reading frames (ORFs): rep and cap. Rep is composed of four overlapping genes encoding rep proteins required for the AAV life cycle, and cap contains overlapping nucleotide sequences of capsid proteins: VP1, VP2 and VP3, which self-assemble to form a capsid of an icosahedral symmetry.

AAV is assigned to the genus, Dependovirus, because the virus was discovered as a contaminant in purified adenovirus stocks. AAV's life cycle includes a latent phase at which AAV genomes, after infection, are site specifically integrated into host chromosomes and an infectious phase in which, following either adenovirus or herpes simplex virus infection, the integrated genomes are subsequently rescued, replicated, and packaged into infectious viruses. The properties of non-pathogenicity, broad host range of infectivity, including non-dividing cells, and potential site-specific chromosomal integration make AAV an attractive tool for gene transfer.

Recombinant adeno-associated virus (rAAV) vectors derived from the replication defective human parvovirus have been described as suitable vehicles for gene delivery. Typically, functional rep genes and the cap gene are removed from the vector, resulting in a replication-incompetent vector. These functions are provided during the vector production system but absent in the final vector.

To date, there have been several different well-characterized AAVs isolated from human or non-human primates (NHP). It has been found that AAVs of different serotypes exhibit different transfection efficiencies, and exhibit tropism for different cells or tissues. Many different AAV clades have been described in WO 2005/033321, including clade F which is identified therein as having just three members, AAV9, AAVhu31 and AAVhu32. A structural analysis of AAV9 is provided in M. A. DiMattia et al, J. Virol. (June 2012) vol. 86 no. 12 6947-6958. This paper reports that AAV9 has 60 copies (in total) of the three variable proteins (vps) that are encoded by the cap gene and have overlapping sequences. These include VP1 (87 kDa), VP2 (73 kDa), and VP3 (62 kDa), which are present in a predicted ratio of 1:1:10, respectively. The entire sequence of VP3 is within VP2, and all of VP2 is within VP1. VP1 has a unique N-terminal domain. The refined coordinates and structure factors are available under accession no. 3UX1 from the RCSB PDB database.

Several different AAV9 variants have been engineered in order to detarget or target different tissue. See, e.g., N. Pulicheria, "Engineering Liver-detargeted AAV9 Vectors for Cardiac and Musculoskeletal Gene Transfer", Molecular Therapy, Vol, 19, no. 6, p. 1070-1078 (June 2011). The development of AAV9 variants to deliver gene across the blood-brain barrier has also been reported. See, e.g., B. E. Deverman et al, Nature Biotech, Vol. 34, No. 2, p 204-211 (published online 1 Feb. 2016) and Caltech press release, A. Wetherston, www.neurology-central.com/2016/02/10/successful-delivery-of-genes-through-the-blood-brain-barrier/, accessed Oct. 5, 2016. See, also, WO 2016/0492301 and U.S. Pat. No. 8,734,809.

What is desirable are AAV-based constructs for delivery of heterologous molecules.

SUMMARY OF THE INVENTION

Novel AAVhu68 capsid and rep sequences are described, which are useful in manufacturing and in vectors for delivery of nucleic acid molecules to host cells. In certain embodiments, a recombinant AAV is provided which has an AAVhu68 capsid which is encoded by a nucleic acid sequence of SEQ ID NO: 1 or a nucleic acid sequence at least 70% identical to SEQ ID NO: 1, at least 75%, at least 80%, at least 85%, at least 90%, at least 95%, at least 97%, or at least 99% identical to SEQ ID NO:1, which encodes the amino acid sequence of SEQ ID NO: 2.

In one embodiment, a recombinant adeno-associated virus (rAAV) is provided which comprises: (A) an AAV68 capsid comprising one or more of: (1) AAV hu68 capsid proteins comprising: AAVhu68 vp1 proteins produced by expression from a nucleic acid sequence which encodes the predicted amino acid sequence of 1 to 736 of SEQ ID NO:2, vp1 proteins produced from SEQ ID NO:1, or vp1 proteins produced from a nucleic acid sequence at least 70% identical to SEQ ID NO:1 which encodes the predicted amino acid sequence of 1 to 736 of SEQ ID NO:2, AAVhu68 vp2 proteins produced by expression from a nucleic acid sequence which encodes the predicted amino acid sequence of at least about amino acids 138 to 736 of SEQ ID NO:2, vp2 proteins produced from a sequence comprising at least nucleotides 412 to 2211 of SEQ ID NO:1, or vp2 proteins produced from a nucleic acid sequence at least 70% identical to at least nucleotides 412 to 2211 of SEQ ID NO:1 which encodes the predicted amino acid sequence of at least about amino acids 138 to 736 of SEQ ID NO:2, AAVhu68 vp3 proteins produced by expression from a nucleic acid sequence which encodes the predicted amino acid sequence of at least about amino acids 203 to 736 of SEQ ID NO:2, vp3 proteins produced from a sequence comprising at least nucleotides 607 to 2211 of SEQ ID NO:1, or vp3 proteins produced from a nucleic acid sequence at least 70% identical to at least nucleotides 607 to 2211 of SEQ ID NO:1 which encodes the predicted amino acid sequence of at least about amino acids 203 to 736 of SEQ ID NO:2; and/or (2) AAV capsid proteins comprising a heterogenous population of vp1 proteins optionally comprising a valine at position 157 and/or a glutamic acid at position 67, a heterogenous population of vp2 proteins optionally comprising a valine at position 157, and a heterogenous population of vp3 proteins, wherein at least a subpopulation of the vp1 and vp2 proteins comprise a valine at position 157 and optionally further comprising a glutamic acid at position 67 based on the numbering of the vp1 capsid of SEQ ID NO:2; and/or (3) a heterogenous population of vp1 proteins which are the product of a nucleic acid sequence encoding the amino acid sequence of SEQ ID NO: 2, a heterogenous population of vp2 proteins which are the product of a nucleic acid sequence encoding the amino acid sequence of at least about amino acids 138 to 736 of SEQ ID NO: 2, and a heterogenous population of vp3 proteins which are the product of a nucleic acid sequence encoding at least amino acids 203 to 736 of SEQ ID NO:2, wherein: the vp1, vp2 and vp3 proteins contain subpopulations with amino acid modifications comprising at least two highly deamidated asparagines (N) in asparagine-glycine pairs in SEQ ID NO: 2 and optionally further comprising subpopulations comprising other deamidated amino acids, wherein the deamidation results in an amino acid change; and (B) a vector genome in the AAVhu68 capsid, the vector genome comprising a nucleic acid molecule comprising AAV inverted terminal repeat sequences and a non-AAV nucleic acid sequence encoding a product operably linked to sequences which direct expression of the product in a host cell. For example, four residues (N57, N329, N452, N512) routinely display high levels of deamidation. Additional residues (N94, N253, N270, N304, N409, N477 and Q599) also display deamidation levels up to ~20% across various lots.

In certain embodiments, the deamidated asparagines are deamidated to aspartic acid, isoaspartic acid, an interconverting aspartic acid/isoaspartic acid pair, or combinations thereof. In certain embodiments, the deamidated glutamine (s) are deamidated to (α)-glutamic acid, γ-glutamic acid, an interconverting (α)-glutamic acid/γ-glutamic acid pair, or combinations thereof.

In certain embodiments, the AAVhu68 capsid comprises subpopulations having one or more of: (a) at least 65% of asparagines (N) in asparagine-glycine pairs located at positions 57 of the vp1 proteins are deamidated, based on the numbering of SEQ ID NO:2; (b) at least 75% of N in asparagine-glycine pairs in position 329 of the vp1, v2 and vp3 proteins are deamidated, based on the residue numbering of the amino acid sequence of SEQ ID NO: 2; (c) at least 50% of N in asparagine-glycine pairs in position 452 of the vp1, v2 and vp3 proteins are deamidated, based on the residue numbering of the amino acid sequence of SEQ ID NO: 2; and/or (d) at least 75% of N in asparagine-glycine pairs in position 512 of the vp1, v2 and vp3 proteins are deamidated, based on the residue numbering of the amino acid sequence of SEQ ID NO: 2. In certain embodiments, the hu68 capsid comprises a subpopulation of vp1 in which 75% to 100% of the N at position 57 of the vp1 proteins are deamidated, as determined using mass spectrometry. In certain embodiments, the hu68 capsid comprises subpopulation of vp1 proteins, vp2 proteins, and/or vp3 proteins in which 75% to 100% of the N at position 329, based on the numbering of SEQ ID NO:2, are deamidated as determined using mass spectrometry. In certain embodiments, the hu68 capsid comprises subpopulation of vp1 proteins, vp2 proteins, and/or vp3 proteins in which 75% to 100% of the N at position 452, based on the numbering of SEQ ID NO:2, are deamidated as determined using mass spectrometry. In certain embodiments, the hu68 capsid comprises subpopulation of vp1 proteins, vp2 proteins, and/or vp3 proteins in which 75% to 100% of the N at position 512, based on the numbering of SEQ ID NO:2, are deamidated. In certain embodiments, the nucleic acid sequence encoding the proteins is SEQ ID NO: 1, or a sequence at least 80% to at least 99% identical to SEQ ID NO: 1 which encodes the amino acid sequence of SEQ ID NO:2. In certain embodiments, the sequence is at least 80% to 97% identical to SEQ ID NO: 1. In certain embodiments, the rAAVhu68 capsid further comprises at least subpopulation of vp1, vp2 and/or vp3 proteins having amino acid modifications from SEQ ID NO: 2 comprising at least about 50 to 100% deamidation at least four positions selected from one or more of N57, 329, 452, 512, or combinations thereof. In certain embodiments, the hu68 capsid comprises subpopulations of vp1, vp2 and/or vp3 proteins which further comprise 1% to about 40% deamidation in at least one or more of positions N94, N113, N252, N253, Q259, N270, N303, N304, N305, N319, N328, N336, N409, N410, N477, N515, N598, Q599, N628, N651, N663, N709, or combinations thereof. In certain embodiments, the hu68 capsid comprises subpopulations of vp1, vp2 and/or vp3 proteins which further comprise one or more modifications selected from one or more modification in one or more of the following: acetylated lysine, phosphorylated serine and/or threonine, isomerized aspartic acid, oxidized tryptophan and/or methionine, or an amidated amino acid. In certain embodiments, the rAAVhu68 comprises about 60 total capsid proteins in a ratio of about 1 vp1 to about 1 to 1.5 vp2 to 3 to 10 vp3 proteins. In certain embodiments, the AAVhu68 capsid about 60 total capsid proteins in a ratio of about 1 vp1 to about 1 vp2 to 3 to 9 vp3 proteins. In certain embodiments, the vector genome comprises AAV ITR sequences from an AAV source other than AAVhu68.

In certain embodiments, a composition is provided which comprises a mixed population of recombinant adeno-associated virus hu68 (rAAVhu68), wherein each of the rAAVhu68 is independently selected from an rAAVhu68 as described herein. In certain embodiments, the average AAVhu68 capsid comprises about 60 total capsid proteins in a ratio of about 1 vp1 to about 1 to 1.5 vp2 to 3 to 10 vp3 proteins. In certain embodiments, the average AAVhu68 capsid comprises about 60 total capsid proteins in a ratio of about 1 vp1 to about 1 vp2 to 3 to 6 vp3 proteins. In certain embodiments, the composition is formulated for intrathecal delivery and vector genome comprises a nucleic acid sequence encoding a product for delivery to the central nervous system. In certain embodiments, the composition is formulated for intravenous delivery. In certain embodiments, the vector genome comprises a nucleic acid sequence encoding an anti-HER2 antibody. In certain embodiments, the composition is formulated for intranasal or intramuscular delivery. In certain embodiments, a composition comprises at least an rAAVhu68 vector stock and an optional carrier, excipient and/or preservative.

In certain embodiments, use of an rAAVhu68 or a composition as described herein for delivering a desired gene product to a subject in need thereof is provided.

In certain embodiments, an rAAV production system useful for producing a recombinant AAVhu68 is provided. The production system comprises: (a) an AAVhu68 capsid nucleic acid sequence encoding the amino acid sequence of SEQ ID NO:2; (b) a nucleic acid molecule suitable for packaging into the AAVhu68 capsid, said nucleic acid molecule comprising at least one AAV inverted terminal repeat (ITR) and a non-AAV nucleic acid sequence encoding a gene product operably linked to sequences which direct expression of the product in a host cell; and (c) sufficient AAV rep functions and helper functions to permit packaging of the nucleic acid molecule into the recombinant AAVhu68 capsid. In certain embodiments, the nucleic acid sequence of (a) comprises at least SEQ ID NO: 1, or a sequence at least 70% to at least 99% identical to SEQ ID NO: 1 which encodes the amino acid sequence of SEQ ID NO:2. In certain embodiments, the system optionally further comprises a nucleic acid sequence of about nt 607 to about nt 2211 of SEQ ID NO:1 encoding the AAVhu68 vp3 of about aa 203 to about amino acid 736 of SEQ ID NO: 2. In certain embodiments, the system comprises human embryonic kidney 293 cells or a baculovirus system.

In certain embodiments, a method for reducing deamidation of an AAVhu68 capsid is provided. The method comprises producing an AAVhu68 capsid from a nucleic acid sequence containing modified AAVhu68 vp codons, the nucleic acid sequence comprising independently modified glycine codons at one to three of the arginine-glycine pairs located at position 58, 330, 453 and/or 513 in SEQ ID NO: 2, such that the modified codon encodes an amino acid other than glycine. In certain embodiments, the method comprises producing an AAVhu68 capsid from a nucleic acid sequence containing modified AAVhu68 vp codons, the nucleic acid sequence comprising independently modified arginine codons at one to three of the arginine-glycine pairs located at position 57, 329, 452 and/or 512 in SEQ ID NO: 2, such that the modified codon encodes an amino acid other than arginine. In certain embodiments, each modified codon encodes a different amino acid. In certain embodiments, two or more modified codons encode the same amino acid. In certain embodiments, a mutant AAVhu68 capsid as described herein contains a mutation in an arginine-glycine pair, such that the glycine is changed to an alanine or a serine. A mutant AAVhu68 capsid may contain one, two or three mutants where the reference AAVhu68 natively contains four NG pairs. In certain embodiments, a mutant AAVhu68 capsid contains only a single mutation in an NG pair. In certain embodiments, a mutant AAV capsid contains mutations in two different NG pairs. In certain embodiments, a mutant AAVhu68 capsid contains mutation is two different NG pairs which are located in structurally separate location in the AAVhu68 capsid. In certain embodiments, the mutation is not in the VP1-unique region. In certain embodiments, one of the mutations is in the VP1-unique region. Optionally, a mutant AAVhu6 capsid contains no modifications in the NG pairs, but contains mutations to minimize or eliminate deamidation in one or more asparagines, or a glutamine, located outside of an NG pair.

In certain embodiments, a mutant rAAVhu68 is provided which comprises a modified rAAVhu68 capsid with reduced deamidation as compared to an unmodified AAVhu68 capsid, which is produced using the method described herein.

In still a further aspect, a method for increasing yield and/or packaging efficiency of a recombinant adeno-associated (rAAV) vector is provided. The method comprising engineering an AAV capsid gene to express a vp1 protein Val at amino acid position 157, wherein the numbering of the amino acid residues is based on full-length vp1 of AAVhu68 [SEQ ID NO: 2]. In certain embodiments, a clade F rAAV is provided having a glutamic acid (Glu or E) at amino acid position 67 based on the numbering of SEQ ID NO:2.

In still a further embodiment, an engineered rAAV produced according to this method is provided.

In a further embodiment, an AAVhu68 particle which expressing an anti-HER2 antibody useful for treatment and/or prophylaxis of HER2+ cancers is provided.

In yet a further embodiment, a nucleic acid molecule comprising a nucleic acid sequence encoding an AAVhu68 rep protein or a functional fragment thereof under the control of exogenous regulatory control sequences which direct expression thereof in a host cell is provided. In one embodiment, the rep protein has the amino acid sequence of SEQ ID NO: 4, or a functional fragment thereof.

These and other aspects of the invention will be apparent from the following detailed description of the invention.

BRIEF DESCRIPTION OF THE DRAWINGS

FIGS. 1A-1B provides an alignment showing the amino acid sequence of the vp1 capsid protein of AAVhu68 [SEQ ID NO:16] (labelled hu.68.vp1 in alignment), with AAV9 [SEQ ID NO: 6], AAVhu31 (labelled hu.31 in alignment) [SEQ ID NO: 10] and AAVhu32 (labelled hu.32 in alignment) [SEQ ID NO: 11]. Compared to AAV9, AAVhu31 and AAVhu32, two mutations (A67E and A 157V) were found critical in AAVhu68 and circled in the figures.

FIGS. 2A-2C provide an alignment of the nucleic acid sequence encoding the vp1 capsid protein of AAVhu68, with AAV9, AAVhu31 [SEQ ID NO: 12] and AAVhu32 [SEQ ID NO: 13].

FIG. 3A shows yields of AAVhu.68 and AAV9 from the total lysate. P value was calculated as 0.4173 and determined not significant.

FIG. 3B shows yields of AAVhu.68 and AAV9 from the culture supernatant. The yield of AAVhu.68 in the supernatant is significantly higher than that of AAV9 with a p value at 0.0003.

FIG. 4A provides immunohistochemistry staining of various organs (heart, liver, lung and muscle) from mice administrated with $5\times10^{11}$ GC AAVhu68.CB7.nLacZ intravenously (IV). All tested organs demonstrated AAVhu68 transduction while a tropism favoring heart and liver over lung and muscle was observed.

FIG. 4B provides immunohistochemistry staining of various organs (heart, liver, lung and muscle) from mice administrated with $5\times10^{11}$ GC AAVhu68.CB7.nLacZ intramuscularly (IM). Heart, liver and muscle demonstrated high transduction rate of AAVhu68 while no detectable transduction in lung was observed.

FIG. 4C provides immunohistochemistry staining of various organs (heart, liver, lung and muscle) from mice administrated with $5\times10^{11}$ GC AAVhu68.CB7.nLacZ intranasally (IN). Scattered transduction was observed in heart, liver, muscle and lung.

FIG. 5A provides fluorescent microscopic images of hippocampus slides from mice administrated with AAVhu68.GFP or AAV9.GFP at the doses of $1\times10^{10}$ GC or $1\times10^{11}$ GC. Corresponding samples from untreated mice stained with nucleic acid dye shown in blue were provided as negative control. Transduction of the AAV vectors was observed in all tested samples except one from mice injected with $1\times10^{10}$ GC of AAV9.GFP.

FIG. 5B provides fluorescent microscopic images of motor cortexes from mice administrated with AAVhu68.GFP or AAV9.GFP at the doses of $1\times10^{10}$ GC or $1\times10^{11}$ GC. A better transduction of AAVhu68.GFP compared to that of AAV9 was observed.

FIG. 5C provides fluorescent microscopic images of cerebellum slides from mice administrated with AAVhu68.GFP or AAV9.GFP at the doses of $1\times10^{10}$ GC or $1\times10^{11}$ GC. A successful transduction of AAVhu68.GFP was observed when mice were injected with $1\times10^{11}$ GC of the vector.

FIG. 6A provides microscopic images of a representative liver section from mice administrated with AAVhu68.GFP intravenously. Positive signal shown in green was observed.

FIG. 6B provides microscopic images of a representative kidney section from mice administrated with AAVhu68.GFP intravenously. Positive signal shown in green was observed.

FIG. 6C provides microscopic images of a representative heart section from mice administrated with AAVhu68.GFP intravenously. Positive signal shown in green was observed.

FIG. 6D provides microscopic images of a representative pancreas section from mice administrated with AAVhu68.GFP intravenously. Positive signal shown in green was observed.

DETAILED DESCRIPTION OF THE INVENTION

Figure 1A:
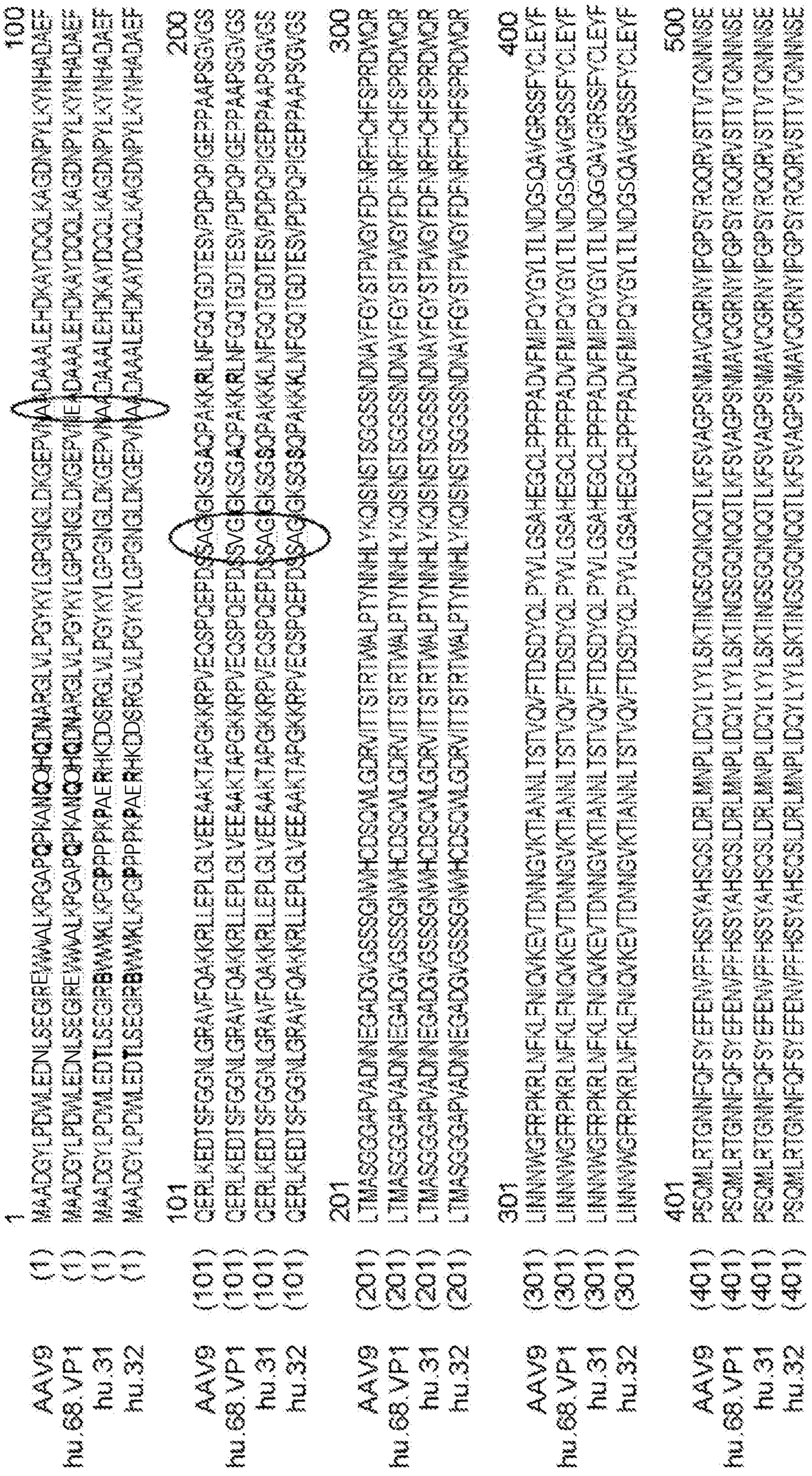

Provided herein are nucleic acid sequences and amino acids of a novel isolated adeno-associated virus (AAV), which is termed herein AAVhu68, which is within clade F. AAVhu68 (previously termed herein AAV3G2) varies from another Clade F virus AAV9 (SEQ ID NO: 5) by two encoded amino acids at positions 67 and 157 of vp1, SEQ ID NO: 2. In contrast, the other Clade F AAV (AAV9, hu31, hu31) have an Ala at position 67 and an Ala at position 157. Provided are novel AAVhu68 capsids and/or engineered AAV capsids having valine (Val or V) at position 157 based on the numbering of SEQ ID NO: 2 and optionally, a glutamic acid (Glu or E) at position 67. In certain embodiments, the ratio of vp3 proteins in the AAVhu68 capsid relative to vp1 and vp2 proteins is lower than previously described for the capsids of AAV9 and other clade F AAVs. In certain embodiments, the AAVhu68 capsid is composed of AAVhu68 vp1 proteins, AAVhu68 vp2 proteins, and AAVhu68 vp3 proteins in a ratio of about 1 vp1:1 to about 1.5 vp2:to 3 to about 10 vp3. In certain embodiments, a rAAVhu68 virus stock or a population of rAAVhu68 is a composition has an average of about 60 total vp 1, vp2 and vp3 proteins in the AAVhu68 capsid, which are present in average vp1:vp2:vp3 ratio of about 1:about 1:to about 3 to 6. These AAV capsids described herein are useful for generating recombinant AAV (rAAV) vectors that are provide good yield and/or packaging efficiency, and providing rAAV vectors useful in transducing a number of different cell and tissue types. Such cells and tissue types may include, without limitation, lung, heart, muscle, liver, pancreas, kidney, brain, hippocampus, motor cortex, cerebellum, nasal epithelial cells, cardiac muscle cells or cardiomyocytes, hepatocytes, pulmonary endothelial cells, myocytes, pulmonary epithelial cells, islet cells, acinar cells, renal cells, and motor neurons.

A "recombinant AAV" or "rAAV" is a DNAse-resistant viral particle containing two elements, an AAV capsid and a vector genome containing at least non-AAV coding sequences packaged within the AAV capsid. Unless otherwise specified, this term may be used interchangeably with the phrase "rAAV vector". The rAAV is a "replication-defective virus" or "viral vector", as it lacks any functional AAV rep gene or functional AAV cap gene and cannot generate progeny. In certain embodiments, the only AAV sequences are the AAV inverted terminal repeat sequences (ITRs), typically located at the extreme 5' and 3' ends of the vector genome in order to allow the gene and regulatory sequences located between the ITRs to be packaged within the AAV capsid.

As used herein, a "vector genome" refers to the nucleic acid sequence packaged inside the rAAV capsid which forms a viral particle. Such a nucleic acid sequence contains AAV inverted terminal repeat sequences (ITRs). In the examples herein, a vector genome contains, at a minimum, from 5' to 3', an AAV 5' ITR, coding sequence(s), and an AAV 3' ITR. ITRs from AAV2, a different source AAV than the capsid, or other than full-length ITRs may be selected. In certain embodiments, the ITRs are from the same AAV source as the AAV which provides the rep function during production or a transcomplementing AAV. Further, other ITRs may be used. Further, the vector genome contains regulatory sequences which direct expression of the gene products. Suitable components of a vector genome are discussed in more detail herein.

A rAAVhu68 is composed of an AAVhu68 capsid and a vector genome. An AAVhu68 capsid is an assembly of a heterogenous population of vp1, a heterogenous population of vp2, and a heterogenous population of vp3 proteins. As used herein when used to refer to vp capsid proteins, the term "heterogenous" or any grammatical variation thereof, refers to a population consisting of elements that are not the same, for example, having vp1, vp2 or vp3 monomers (proteins) with different modified amino acid sequences. SEQ ID NO: 2 provides the encoded amino acid sequence of the AAVhu68 vp1 protein.

The AAVhu68 capsid contains subpopulations within the vp1 proteins, within the vp2 proteins and within the vp3 proteins which have modifications from the predicted amino acid residues in SEQ ID NO:2. These subpopulations include, at a minimum, certain deamidated asparagine (N or Asn) residues. For example, certain subpopulations comprise at least one, two, three or four highly deamidated asparagines (N) positions in asparagine-glycine pairs in SEQ ID NO: 2 and optionally further comprising other deamidated amino acids, wherein the deamidation results in an amino acid change and other optional modifications. SEQ ID NO: 14 provide an amino acid sequence of a modified AAVhu68 capsid, illustrating positions which may have some percentage of deamidated or otherwise modified amino acids. The various combinations of these and other modifications are described herein.

As used herein, a "subpopulation" of vp proteins refers to a group of vp proteins which has at least one defined characteristic in common and which consists of at least one group member to less than all members of the reference group, unless otherwise specified. For example, a "subpopulation" of vp1 proteins is at least one (1) vp1 protein and less than all vp1 proteins in an assembled AAV capsid, unless otherwise specified. A "subpopulation" of vp3 proteins may be one (1) vp3 protein to less than all vp3 proteins in an assembled AAV capsid, unless otherwise specified. For example, vp1 proteins may be a subpopulation of vp proteins; vp2 proteins may be a separate subpopulation of vp proteins, and vp3 are yet a further subpopulation of vp proteins in an assembled AAV capsid. In another example, vp1, vp2 and vp3 proteins may contain subpopulations having different modifications, e.g., at least one, two, three or four highly deamidated asparagines, e.g., at asparagine-glycine pairs.

Unless otherwise specified, highly deamidated refers to at least 45% deamidated, at least 50% deamidated, at least 60% deamidated, at least 65% deamidated, at least 70%, at least 75%, at least 80%, at least 85%, at least 90%, at least 95%, 97%, 99%, up to about 100% deamidated at a referenced amino acid position, as compared to the predicted amino acid sequence at the reference amino acid position (e.g., at least 80% of the asparagines at amino acid 57 of SEQ ID NO:2 may be deamidated based on the total vp1 proteins or 20% of the asparagines at amino acid 409 of SEQ ID NO: 2 may be deamidated based on the total vp1, vp2 and vp3 proteins). Such percentages may be determined using 2D-gel, mass spectrometry techniques, or other suitable techniques.

Without wishing to be bound by theory, the deamidation of at least highly deamidated residues in the vp proteins in the AAVhu68 capsid is believed to be primarily non-enzymatic in nature, being caused by functional groups within the capsid protein which deamidate selected asparagines, and to a lesser extent, glutamine residues. Efficient capsid assembly of the majority of deamidation vp1 proteins indicates that either these events occur following capsid assembly or that deamidation in individual monomers (vp1, vp2 or vp3) is well-tolerated structurally and largely does not affect assembly dynamics. Extensive deamidation in the VP1-unique (VP1-u) region (~aa 1-137), generally considered to be located internally prior to cellular entry, suggests that VP deamidation may occur prior to capsid assembly.

Without wishing to be bound by theory, the deamidation of N may occur through its C-terminus residue's backbone nitrogen atom conducts a nucleophilic attack to the Asn's side chain amide group carbon atom. An intermediate ring-closed succinimide residue is believed to form. The succinimide residue then conducts fast hydrolysis to lead to the final product aspartic acid (Asp) or iso aspartic acid (IsoAsp). Therefore, in certain embodiments, the deamidation of asparagine (N or Asn) leads to an Asp or IsoAsp, which may interconvert through the succinimide intermediate e.g., as illustrated below.

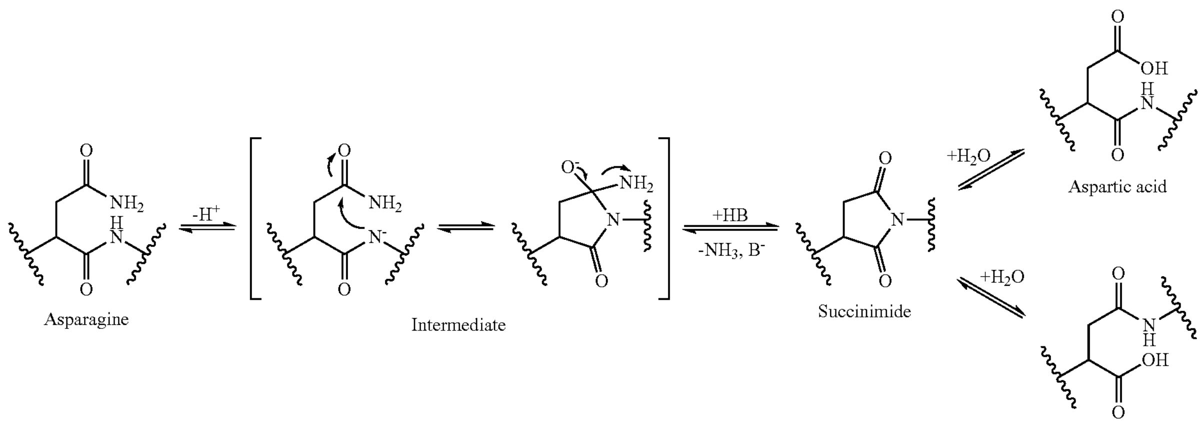

Asparagine
Intermediate
Succinimide
Aspartic acid
Isoaspartic acid

As provided herein, each deamidated N of SEQ ID NO: 2 may independently be aspartic acid (Asp), isoaspartic acid (isoAsp), aspartate, and/or an interconverting blend of Asp and isoAsp, or combinations thereof. Any suitable ratio of α- and isoaspartic acid may be present. For example, in certain embodiments, the ratio may be from 10:1 to 1:10 aspartic to isoaspartic, about 50:50 aspartic:isoaspartic, or about 1:3 aspartic:isoaspartic, or another selected ratio.

In certain embodiments, one or more glutamine (Q) in SEQ ID NO: 2 deamidates to glutamic acid (Glu), i.e., α-glutamic acid, γ-glutamic acid (Glu), or a blend of α- and γ-glutamic acid, which may interconvert through a common glutarinimide intermediate. Any suitable ratio of α- and γ-glutamic acid may be present. For example, in certain embodiments, the ratio may be from 10:1 to 1:10 α to γ, about 50:50 α: γ, or about 1:3 α: γ, or another selected ratio.

vp3 proteins produced by expression from a nucleic acid sequence which encodes the predicted amino acid sequence of at least about amino acids 203 to 736 of SEQ ID NO:2, vp3 proteins produced from a sequence comprising at least nucleotides 607 to 2211 of SEQ ID NO:1, or vp3 proteins produced from a nucleic acid sequence at least 70% identical to at least nucleotides 607 to 2211 of SEQ ID NO:1 which encodes the predicted amino acid sequence of at least about amino acids 203 to 736 of SEQ ID NO:2.

Additionally or alternatively, an AAV capsid is provided which comprise a heterogenous population of vp1 proteins optionally comprising a valine at position 157, a heterogenous population of vp2 proteins optionally comprising a

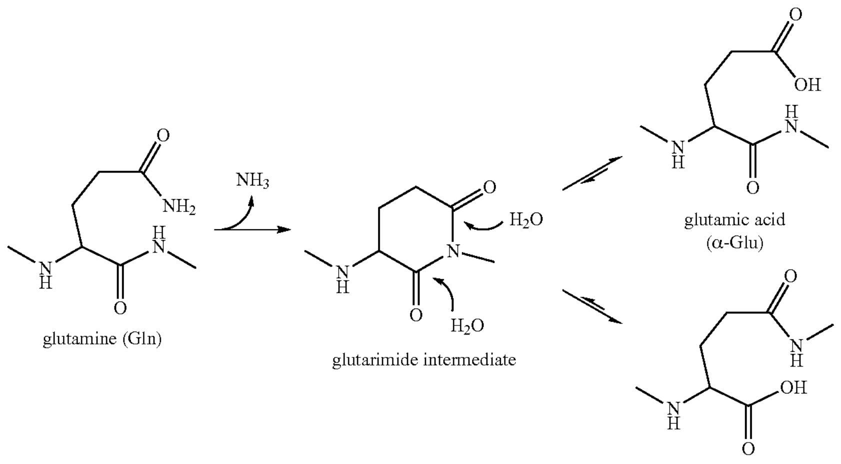

glutamine (Gln)

glutarimide intermediate glutamic acid (α-Glu)

isoglutamic acid (γ-Glu)

Thus, an rAAVhu68 includes subpopulations within the rAAVhu68 capsid of vp1, vp2 and/or vp3 proteins with deamidated amino acids, including at a minimum, at least one subpopulation comprising at least one highly deamidated asparagine. In addition, other modifications may include isomerization, particularly at selected aspartic acid (D or Asp) residue positions. In still other embodiments, modifications may include an amidation at an Asp position.

In certain embodiments, an AAVhu68 capsid contains subpopulations of vp1, vp2 and vp3 having at least 4 to at least about 25 deamidated amino acid residue positions, of which at least 1 to 10% are deamidated as compared to the encoded amino acid sequence of SEQ ID NO: 2. The majority of these may be N residues. However, Q residues may also be deamidated.

In certain embodiments, an AAV68 capsid is further characterized by one or more of the following. AAV hu68 capsid proteins comprise: AAVhu68 vp1 proteins produced by expression from a nucleic acid sequence which encodes the predicted amino acid sequence of 1 to 736 of SEQ ID NO:2, vp1 proteins produced from SEQ ID NO:1, or vp1 proteins produced from a nucleic acid sequence at least 70% identical to SEQ ID NO:1 which encodes the predicted amino acid sequence of 1 to 736 of SEQ ID NO:2; AAVhu68 vp2 proteins produced by expression from a nucleic acid sequence which encodes the predicted amino acid sequence of at least about amino acids 138 to 736 of SEQ ID NO:2, vp2 proteins produced from a sequence comprising at least nucleotides 412 to 2211 of SEQ ID NO:1, or vp2 proteins produced from a nucleic acid sequence at least 70% identical to at least nucleotides 412 to 2211 of SEQ ID NO:1 which encodes the predicted amino acid sequence of at least about amino acids 138 to 736 of SEQ ID NO:2, and/or AAVhu68 valine at position 157, and a heterogenous population of vp3 proteins, wherein at least a subpopulation of the vp1 and vp2 proteins comprise a valine at position 157 and optionally further comprising a glutamic acid at position 67 based on the numbering of the vp1 capsid of SEQ ID NO:2. Additionally or alternatively, an AAVhu68 capsid is provided which comprises a heterogenous population of vp1 proteins which are the product of a nucleic acid sequence encoding the amino acid sequence of SEQ ID NO: 2, a heterogenous population of vp2 proteins which are the product of a nucleic acid sequence encoding the amino acid sequence of at least about amino acids 138 to 736 of SEQ ID NO: 2, and a heterogenous population of vp3 proteins which are the product of a nucleic acid sequence encoding at least amino acids 203 to 736 of SEQ ID NO:2, wherein: the vp1, vp2 and vp3 proteins contain subpopulations with amino acid modifications The AAVhu68 vp1, vp2 and vp3 proteins are typically expressed as alternative splice variants encoded by the same nucleic acid sequence which encodes the full-length vp1 amino acid sequence of SEQ ID NO: 2 (amino acid 1 to 736). Optionally the vp1-encoding sequence is used alone to express the vp1, vp2 and vp3 proteins. Alternatively, this sequence may be co-expressed with one or more of a nucleic acid sequence which encodes the AAVhu68 vp3 amino acid sequence of SEQ ID NO: 2 (about aa 203 to 736) without the vp1-unique region (about aa 1 to about aa 137) and/or vp2-unique regions (about aa 1 to about aa 202), or a strand complementary thereto, the corresponding mRNA or tRNA (about nt 607 to about nt 2211 of SEQ ID NO: 1), or a sequence at least 70% to at least 99% (e.g., at least 85%, at least 90%, at least 95%, at least 97%, at least 98% or at least 99%) identical to SEQ ID NO: 1 which encodes aa 203 to 736 of SEQ ID NO: 2. Additionally, or alternatively, the vp1-encoding and/or the vp2-encoding sequence may be co-expressed with the nucleic acid sequence which encodes the AAVhu68 vp2 amino acid sequence of SEQ ID NO: 2 (about aa 138 to 736) without the vp1-unique region (about aa 1 to about 137), or a strand complementary thereto, the corresponding mRNA or tRNA (nt 412 to 22121 of SEQ ID NO: 1), or a sequence at least 70% to at least 99% (e.g., at least 85%, at least 90%, at least 95%, at least 97%, at least 98% or at least 99%) identical to SEQ ID NO: 1 which encodes about aa 138 to 736 of SEQ ID NO: 2.

As described herein, a rAAVhu68 has a rAAVhu68 capsid produced in a production system expressing capsids from an AAVhu68 nucleic acid which encodes the vp1 amino acid sequence of SEQ ID NO: 2, and optionally additional nucleic acid sequences, e.g., encoding a vp 3 protein free of the vp1 and/or vp2-unique regions. The rAAVhu68 resulting from production using a single nucleic acid sequence vp1 produces the heterogenous populations of vp1 proteins, vp2 proteins and vp3 proteins. More particularly, the AAVhu68 capsid contains subpopulations within the vp1 proteins, within the vp2 proteins and within the vp3 proteins which have modifications from the predicted amino acid residues in SEQ ID NO:2. These subpopulations include, at a minimum, deamidated asparagine (N or Asn) residues. For example, asparagines in asparagine-glycine pairs are highly deamidated.

In one embodiment, the AAVhu68 vp1 nucleic acid sequence has the sequence of SEQ ID NO: 1, or a strand complementary thereto, e.g., the corresponding mRNA or tRNA. In certain embodiments, the vp2 and/or vp3 proteins may be expressed additionally or alternatively from different nucleic acid sequences than the vp1, e.g., to alter the ratio of the vp proteins in a selected expression system. In certain embodiments, also provided is a nucleic acid sequence which encodes the AAVhu68 vp3 amino acid sequence of SEQ ID NO: 2 (about aa 203 to 736) without the vp1-unique region (about aa 1 to about aa 137) and/or vp2-unique regions (about aa 1 to about aa 202), or a strand complementary thereto, the corresponding mRNA or tRNA (about nt 607 to about nt 2211 of SEQ ID NO: 1). In certain embodiments, also provided is a nucleic acid sequence which encodes the AAVhu68 vp2 amino acid sequence of SEQ ID NO: 2 (about aa 138 to 736) without the vp1-unique region (about aa 1 to about 137), or a strand complementary thereto, the corresponding mRNA or tRNA (nt 412 to 2211 of SEQ ID NO: 1).

However, other nucleic acid sequences which encode the amino acid sequence of SEQ ID NO: 2 may be selected for use in producing rAAVhu68 capsids. In certain embodiments, the nucleic acid sequence has the nucleic acid sequence of SEQ ID NO: 1 or a sequence at least 70% to 99% identical, at least 75%, at least 80%, at least 85%, at least 90%, at least 95%, at least 97%, at least 99%, identical to SEQ ID NO: 1 which encodes SEQ ID NO: 2. In certain embodiments, the nucleic acid sequence has the nucleic acid sequence of SEQ ID NO: 1 or a sequence at least 70% to 99.%, at least 75%, at least 80%, at least 85%, at least 90%, at least 95%, at least 97%, at least 99%, identical to about nt 412 to about nt 2211 of SEQ ID NO: 1 which encodes the vp2 capsid protein (about aa 138 to 736) of SEQ ID NO: 2. In certain embodiments, the nucleic acid sequence has the nucleic acid sequence of about nt 607 to about nt 2211 of SEQ ID NO:1 or a sequence at least 70% to 99.%, at least 75%, at least 80%, at least 85%, at least 90%, at least 95%, at least 97%, at least 99%, identical to nt SEQ ID NO: 1 which encodes the vp3 capsid protein (about aa 203 to 736) of SEQ ID NO: 2.

It is within the skill in the art to design nucleic acid sequences encoding this AAVhu68 capsid, including DNA (genomic or cDNA), or RNA (e.g., mRNA). In certain embodiments, the nucleic acid sequence encoding the AAVhu68 vp1 capsid protein is provided in SEQ ID NO: 1. See, also, FIGS. 1B-1D. In other embodiments, a nucleic acid sequence of 70% to 99.9% identity to SEQ ID NO: 1 may be selected to express the AAVhu68 capsid proteins. In certain other embodiments, the nucleic acid sequence is at least about 75% identical, at least 80% identical, at least 85%, at least 90%, at least 95%, at least 97% identical, or at least 99% to 99.9% identical to SEQ ID NO: 1. Such nucleic acid sequences may be codon-optimized for expression in a selected system (i.e., cell type) can be designed by various methods. This optimization may be performed using methods which are available on-line (e.g., GeneArt), published methods, or a company which provides codon optimizing services, e.g., DNA2.0 (Menlo Park, CA). One codon optimizing method is described, e.g., in US International Patent Publication No. WO 2015/012924, which is incorporated by reference herein in its entirety. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence and produce a nucleic acid fragment of a codon-optimized coding region which encodes the polypeptide. A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In certain embodiments, the asparagine (N) in N-G pairs in the AAVhu68 vp1, vp2 and vp3 proteins are highly deamidated. In certain embodiments, an AAVhu68 capsid contains subpopulations of AAV vp 1, vp2 and/or vp3 capsid proteins having at least four asparagine (N) positions in the AAVhu68 capsid proteins which are highly deamidated. In certain embodiments, about 20 to 50% of the N—N pairs (exclusive of N—N—N triplets) show deamidation. In certain embodiments, the first N is deamidated. In certain embodiments, the second N is deamidated. In certain embodiments, the deamidation is between about 15% to about 25% deamidation. Deamidation at the Q at position 259 of SEQ ID NO: 2 is about 8% to about 42% of the AAVhu68 vp1, vp2 and vp3 capsid proteins of an AAVhu68 protein.

In certain embodiments, the rAAVhu68 capsid is further characterized by an amidation in D297 the vp1, vp2 and vp3 proteins. In certain embodiments, about 70% to about 75% of the D at position 297 of the vp1, vp2 and/or vp3 proteins in a AAVhu68 capsid are amidated, based on the numbering of SEQ ID NO: 2.

In certain embodiments, at least one Asp in the vp1, vp2 and/or vp3 of the capsid is isomerized to D-Asp. Such isomers are generally present in an amount of less than about 1% of the Asp at one or more of residue positions 97, 107, 384, based on the numbering of SEQ ID NO: 2.

In certain embodiments, a rAAVhu68 has an AAVhu68 capsid having vp1, vp2 and vp3 proteins having subpopulations comprising combinations of one, two, three, four or more deamidated residues at the positions set forth in the table below. Deamidation in the rAAV may be determined using 2D gel electrophoresis, and/or mass spectrometry, and/or protein modelling techniques. Online chromatography may be performed with an Acclaim PepMap column and a Thermo UltiMate 3000 RSLC system (Thermo Fisher Scientific) coupled to a Q Exactive HF with a NanoFlex source (Thermo Fisher Scientific). MS data is acquired using a data-dependent top-20 method for the Q Exactive HF, dynamically choosing the most abundant not-yet-sequenced precursor ions from the survey scans (200-2000 m/z). Sequencing is performed via higher energy collisional dissociation fragmentation with a target value of 1e5 ions determined with predictive automatic gain control and an isolation of precursors was performed with a window of 4 m/z. Survey scans were acquired at a resolution of 120,000 at m/z 200. Resolution for HCD spectra may be set to 30,000 at m/z200 with a maximum ion injection time of 50 ms and a normalized collision energy of 30. The S-lens RF level may be set at 50, to give optimal transmission of the m/z region occupied by the peptides from the digest. Precursor ions may be excluded with single, unassigned, or six and higher charge states from fragmentation selection. BioPharma Finder 1.0 software (Thermo Fischer Scientific) may be used for analysis of the data acquired. For peptide mapping, searches are performed using a single-entry protein FASTA database with carbamidomethylation set as a fixed modification; and oxidation, deamidation, and phosphorylation set as variable modifications, a 10-ppm mass accuracy, a high protease specificity, and a confidence level of 0.8 for MS/MS spectra. Examples of suitable proteases may include, e.g., trypsin or chymotrypsin. Mass spectrometric identification of deamidated peptides is relatively straightforward, as deamidation adds to the mass of intact molecule+0.984 Da (the mass difference between —OH and —$NH_2$ groups). The percent deamidation of a particular peptide is determined mass area of the deamidated peptide divided by the sum of the area of the deamidated and native peptides. Considering the number of possible deamidation sites, isobaric species which are deamidated at different sites may co-migrate in a single peak. Consequently, fragment ions originating from peptides with multiple potential deamidation sites can be used to locate or differentiate multiple sites of deamidation. In these cases, the relative intensities within the observed isotope patterns can be used to specifically determine the relative abundance of the different deamidated peptide isomers. This method assumes that the fragmentation efficiency for all isomeric species is the same and independent on the site of deamidation. It will be understood by one of skill in the art that a number of variations on these illustrative methods can be used. For example, suitable mass spectrometers may include, e.g. a quadrupole time of flight mass spectrometer (QTOF), such as a Waters Xevo or Agilent 6530 or an orbitrap instrument, such as the Orbitrap Fusion or Orbitrap Velos (Thermo Fisher). Suitably liquid chromatography systems include, e.g., Acquity UPLC system from Waters or Agilent systems (1100 or 1200 series). Suitable data analysis software may include, e.g., MassLynx (Waters), Pinpoint and Pepfinder (Thermo Fischer Scientific), Mascot (Matrix Science), Peaks DB (Bioinformatics Solutions). Still other techniques may be described, e.g., in X. Jin et al, Hu Gene Therapy Methods, Vol. 28, No. 5, pp. 255-267, published online Jun. 16, 2017.

| Deamidation Based on Predicted AAVHu68 [SEQ ID NO: 2] | Average % Based on VP1/VP2/VP3 Proteins in AAVhu68 Capsid | |
|---|---|---|
| Deamidated Residue + 1 (Neighboring AA) | Broad Range of Percentages (%) | Narrow Ranges (%) |
| N57 (N-G) | 78 to 100% | 80 to 100, 85 to 97 |
| N66 (N-E) | 0 to 5 | 0, 1 to 5 |
| N94 (N-H) | 0 to 15, | 0, 1 to 15, 5 to 12, 8 |
| N113 (N-L) | 0 to 2 | 0, 1 to 2 |
| ~N253 (N-N) | 10 to 25 | 15 to 22 |
| Q259 (Q-I) | 8 to 42 | 10 to 40, 20 to 35 |
| ~N270 (N-D) | 12 to 30 | 15 to 28 |
| ~N304 (N-N) (position 303 also N) | 0 to 5 | 1 to 4 |
| N319 (N-I) | 0 to 5 | 0, 1 to 5, 1 to 3 |
| N329 * (N-G)*(position 328 also N) | 65 to 100 | 70 to 95, 85 to 95, 80 to 100, 85 to 100, |
| N336 (N-N) | 0 to 100 | 0, 1 to 10, 25 to 100, 30 to 100, 30 to 95 |
| ~N409 (N-N) | 15 to 30 | 20 to 25 |
| N452 (N-G) | 75 to 100 | 80 to 100, 90 to 100, 95 to 100, |
| N477 (N-Y) | 0 to 8 | 0, 1 to 5 |
| N512 (N-G) | 65 to 100 | 70 to 95, 85 to 95, 80 to 100, 85 to 100, |
| ~N515 (N-S) | 0 to 25 | 0, 1 to 10, 5 to 25, 15 to 25 |
| ~Q599 (Asn-Q-Gly) | 1 to 20 | 2 to 20, 5 to 15 |
| N628 (N-F) | 0 to 10 | 0, 1 to 10, 2 to 8 |
| N651 (N-T) | 0 to 3 | 0, 1 to 3 |
| N663 (N-K) | 0 to 5 | 0, 1 to 5, 2 to 4 |
| N709 (N-N) | 0 to 25 | 0,1 to 22, 15 to 25 |
| N735 | 0 to 40 | 0. 1 to 35, 5 to 50, 20 to 35 |

In certain embodiments, the AAVhu68 capsid is characterized, by having, capsid proteins in which at least 45% of N residues are deamidated at least one of positions N57, N329, N452, and/or N512 based on the numbering of amino acid sequence of SEQ ID NO: 2. In certain embodiments, at least about 60%, at least about 70%, at least about 80%, or at least 90% of the N residues at one or more of these N-G positions (i.e., N57, N329, N452, and/or N512, based on the numbering of amino acid sequence of SEQ ID NO: 2) are deamidated. In these and other embodiments, an AAVhu68 capsid is further characterized by having a population of proteins in which about 1% to about 20% of the N residues have deamidations at one or more of positions: N94, N253, N270, N304, N409, N477, and/or Q599, based on the numbering of amino acid sequence of SEQ ID NO: 2. In certain embodiments, the AAVhu68 comprises at least a subpopulation of vp1, vp2 and/or vp3 proteins which are deamidated at one or more of positions N35, N57, N66, N94, N113, N252, N253, Q259, N270, N303, N304, N305, N319, N328, N329, N336, N409, N410, N452, N477, N515, N598, Q599, N628, N651, N663, N709, N735, based on the numbering of amino acid sequence of SEQ ID NO: 2, or combinations thereof. In certain embodiments, the capsid proteins may have one or more amidated amino acids.

Still other modifications are observed, most of which do not result in conversion of one amino acid to a different amino acid residue. Optionally, at least one Lys in the vp1, vp2 and vp3 of the capsid are acetylated. Optionally, at least one Asp in the vp1, vp2 and/or vp3 of the capsid is isomerized to D-Asp. Optionally, at least one S (Ser, Serine) in the vp1, vp2 and/or vp3 of the capsid is phosphorylated. Optionally, at least one T (Thr, Threonine) in the vp1, vp2 and/or vp3 of the capsid is phosphorylated. Optionally, at least one W (trp, tryptophan) in the vp1, vp2 and/or vp3 of the capsid is oxidized. Optionally, at least one M (Met, Methionine) in the vp1, vp2 and/or vp3 of the capsid is oxidized. In certain embodiments, the capsid proteins have one or more phosphorylations. For example, certain vp1 capsid proteins may be phosphorylated at position 149.

In certain embodiments, an AAVhu68 capsid comprises a heterogenous population of vp1 proteins which are the product of a nucleic acid sequence encoding the amino acid sequence of SEQ ID NO: 2, wherein the vp1 proteins comprise a Glutamic acid (Glu) at position 67 and/or a valine (Val) at position 157; a heterogenous population of vp2 proteins optionally comprising a valine (Val) at position 157; and a heterogenous population of vp3 proteins. The AAVhu68 capsid contains at least one subpopulation in which at least 65% of asparagines (N) in asparagine-glycine pairs located at position 57 of the vp1 proteins and at least 70% of asparagines (N) in asparagine-glycine pairs at positions 329, 452 and/or 512 of the vp1, v2 and vp3 proteins are deamidated, based on the residue numbering of the amino acid sequence of SEQ ID NO: 2, wherein the deamidation results in an amino acid change.

As discussed in more detail herein, the deamidated asparagines may be deamidated to aspartic acid, isoaspartic acid, an interconverting aspartic acid/isoaspartic acid pair, or combinations thereof. In certain embodiments, the rAAVhu68 are further characterized by one or more of: (a) each of the vp2 proteins is independently the product of a nucleic acid sequence encoding at least the vp2 protein of SEQ ID NO: 2; (b) each of the vp3 proteins is independently the product of a nucleic acid sequence encoding at least the vp3 protein of SEQ ID NO: 2; (c) the nucleic acid sequence encoding the vp1 proteins is SEQ ID NO: 1, or a sequence at least 70% to at least 99% (e.g., at least 85%, at least 90%, at least 95%, at least 97%, at least 98% or at least 99%) identical to SEQ ID NO: 1 which encodes the amino acid sequence of SEQ ID NO:2. Optionally that sequence is used alone to express the vp1, vp2 and vp3 proteins. Alternatively, this sequence may be co-expressed with one or more of a nucleic acid sequence which encodes the AAVhu68 vp3 amino acid sequence of SEQ ID NO: 2 (about aa 203 to 736) without the vp1-unique region (about aa 1 to about aa 137) and/or vp2-unique regions (about aa 1 to about aa 202), or a strand complementary thereto, the corresponding mRNA or tRNA (about nt 607 to about nt 2211 of SEQ ID NO: 1), or a sequence at least 70% to at least 99% (e.g., at least 85%, at least 90%, at least 95%, at least 97%, at least 98% or at least 99%) identical to SEQ ID NO: 1 which encodes aa 203 to 736 of SEQ ID NO: 2. Additionally, or alternatively, the vp1-encoding and/or the vp2-encoding sequence may be co-expressed with the nucleic acid sequence which encodes the AAVhu68 vp2 amino acid sequence of SEQ ID NO: 2 (about aa 138 to 736) without the vp1-unique region (about aa 1 to about 137), or a strand complementary thereto, the corresponding mRNA or tRNA (nt 412 to 2211 of SEQ ID NO: 1), or a sequence at least 70% to at least 99% (e.g., at least 85%, at least 90%, at least 95%, at least 97%, at least 98% or at least 99%) identical to SEQ ID NO: 1 which encodes about aa 138 to 736 of SEQ ID NO: 2.

Additionally or alternatively, the rAAVhu68 capsid comprises at least a subpopulation of vp1, vp2 and/or vp3 proteins which are deamidated at one or more of positions N57, N66, N94, N113, N252, N253, Q259, N270, N303, N304, N305, N319, N328, N329, N336, N409, N410, N452, N477, N512, N515, N598, Q599, N628, N651, N663, N709, based on the numbering of SEQ ID NO:2, or combinations thereof; (e) rAAVhu68 capsid comprises a subpopulation of vp1, vp2 and/or vp3 proteins which comprise 1% to 20% deamidation at one or more of positions N66, N94, N113, N252, N253, Q259, N270, N303, N304, N305, N319, N328, N336, N409, N410, N477, N515, N598, Q599, N628, N651, N663, N709, based on the numbering of SEQ ID NO:2, or combinations thereof; (f) the rAAVhu68 capsid comprises a subpopulation of vp1 in which 65% to 100% of the N at position 57 of the vp1 proteins, based on the numbering of SEQ ID NO:2, are deamidated; (g) the rAAVhu68 capsid comprises subpopulation of vp1 proteins in which 75% to 100% of the N at position 57 of the vp1 proteins are deamidated; (h) the rAAVhu68 capsid comprises subpopulation of vp1 proteins, vp2 proteins, and/or vp3 proteins in which 80% to 100% of the N at position 329, based on the numbering of SEQ ID NO:2, are deamidated; (i) the rAAVhu68 capsid comprises subpopulation of vp1 proteins, vp2 proteins, and/or vp3 proteins in which 80% to 100% of the N at position 452, based on the numbering of SEQ ID NO:2, are deamidated; (j) the rAAVhu68 capsid comprises subpopulation of vp1 proteins, vp2 proteins, and/or vp3 proteins in which 80% to 100% of the N at position 512, based on the numbering of SEQ ID NO:2, are deamidated; (k) the rAAV comprises about 60 total capsid proteins in a ratio of about 1 vp1 to about 1 to 1.5 vp2 to 3 to 10 vp3 proteins; (l) the rAAV comprises about 60 total capsid proteins in a ratio of about 1 vp1 to about 1 vp2 to 3 to 9 vp3 proteins.

In certain embodiments, the AAVhu68 is modified to change the glycine in an asparagine-glycine pair, in order to reduce deamidation. In other embodiments, the asparagine is altered to a different amino acid, e.g., a glutamine which deamidates at a slower rate; or to an amino acid which lacks amide groups (e.g., glutamine and asparagine contain amide groups); and/or to an amino acid which lacks amine groups (e.g., lysine, arginine and histidine contain amide groups). As used herein, amino acids lacking amide or amine side groups refer to, e.g., glycine, alanine, valine, leucine, isoleucine, serine, threonine, cystine, phenylalanine, tyrosine, or tryptophan, and/or proline. Modifications such as described may be in one, two, or three of the asparagine-glycine pairs found in the encoded AAVhu68 amino acid sequence. In certain embodiments, such modifications are not made in all four of the asparagine-glycine pairs. Thus, a method for reducing deamidation of AAVhu68 and/or engineered AAVhu68 variants having lower deamidation rates. Additionally, or alternative one or more other amide amino acids may be changed to a non-amide amino acid to reduce deamidation of the AAVhu68.

These amino acid modifications may be made by conventional genetic engineering techniques. For example, a nucleic acid sequence containing modified AAVhu68 vp codons may be generated in which one to three of the codons encoding glycine at position 58, 330, 453 and/or 513 in SEQ ID NO: 2 (arginine-glycine pairs) are modified to encode an amino acid other than glycine. In certain embodiments, a nucleic acid sequence containing modified arginine codons may be engineered at one to three of the arginine-glycine pairs located at position 57, 329, 452 and/or 512 in SEQ ID NO: 2, such that the modified codon encodes an amino acid other than arginine. Each modified codon may encode a different amino acid. Alternatively, one or more of the altered codons may encode the same amino acid. In certain embodiments, these modified AAVhu68 nucleic acid sequences may be used to generate a mutant rAAVhu68 having a capsid with lower deamidation than the native hu68 capsid. Such mutant rAAVhu68 may have reduced immunogenicity and/or increase stability on storage, particularly storage in suspension form. As used herein, a "codon" refers to three nucleotides in a sequence which encodes an amino acid.

As used herein, "encoded amino acid sequence" refers to the amino acid which is predicted based on the translation of a known DNA codon of a referenced nucleic acid sequence being translated to an amino acid. The following table illustrates DNA codons and twenty common amino acids, showing both the single letter code (SLC) and three letter code (3LC).

| Amino Acid | SLC | 3 LC | DNA codons |
|---|---|---|---|
| Isoleucine | I | Ile | ATT, ATC, ATA |
| Leucine | L | Leu | CTT, CTC, CTA, CTG, TTA, TTG |
| Valine | V | Val | GTT, GTC, GTA, GTG |
| Phenylalanine | F | Phe | TTT, TTC |
| Methionine | M | Met | ATG |
| Cysteine | C | Cys | TGT, TGC |
| Alanine | A | Ala | GCT, GCC, GCA, GCG |
| Glycine | G | Gly | GGT, GGC, GGA, GGG |
| Proline | P | Pro | CCT, CCC, CCA, CCG |
| Threonine | T | Thr | ACT, ACC, ACA, ACG |
| Serine | S | Ser | TCT, TCC, TCA, TCG, AGT, AGC |
| Tyrosine | Y | Tyr | TAT, TAC |
| Tryptophan | W | Trp | TGG |
| Glutamine | Q | Gln | CAA, CAG |
| Asparagine | N | Asn | AAT, AAC |
| Histidine | H | His | CAT, CAC |
| Glutamic acid | E | Glu | GAA, GAG |
| Aspartic acid | D | Asp | GAT, GAC |
| Lysine | K | Lys | AAA, AAG |
| Arginine | R | Arg | CGT, CGC, CGA, CGG, AGA, AGG |
| Stop codons | Stop | | TAA, TAG, TGA |

AAVhu68 capsids may be useful in certain embodiments. For example, such capsids may be used in generating monoclonal antibodies and/or generating reagents useful in assays for monitoring AAVhu68 concentration levels in gene therapy patients. Techniques for generating useful anti-AAVhu68 antibodies, labelling such antibodies or empty capsids, and suitable assay formats are known to those of skill in the art.

In certain embodiments, provided herein is a nucleic acid sequence of SEQ ID NO: 1 or a sequence at least 70%, at least 75%, at least 80%, at least 85%, at least 90%, at least 95%, at least 97%, at least 99%, which encodes the vp1 amino acid sequence of SEQ ID NO: 2 with a modification (e.g., deamidated amino acid) as described herein. In certain embodiments, the vp1 amino acid sequence is reproduced in SEQ ID NO: 14.

As used herein, the term "clade" as it relates to groups of AAV refers to a group of AAV which are phylogenetically related to one another as determined using a Neighbor-Joining algorithm by a bootstrap value of at least 75% (of at least 1000 replicates) and a Poisson correction distance measurement of no more than 0.05, based on alignment of the AAV vp1 amino acid sequence. The Neighbor-Joining algorithm has been described in the literature. See, e.g., M. Nei and S. Kumar, *Molecular Evolution and Phylogenetics* (Oxford University Press, New York (2000). Computer programs are available that can be used to implement this algorithm. For example, the MEGA v2.1 program implements the modified Nei-Gojobori method. Using these techniques and computer programs, and the sequence of an AAV vp1 capsid protein, one of skill in the art can readily determine whether a selected AAV is contained in one of the clades identified herein, in another clade, or is outside these clades. See. e.g., G Gao, et al, J Virol, 2004 June; 78(10: 6381-6388, which identifies Clades A, B, C, D, E and F, and provides nucleic acid sequences of novel AAV, GenBank Accession Numbers AY530553 to AY530629. See, also, WO 2005/033321.

In one embodiment, the invention provides an engineered molecule comprising a spacer sequence between the AAVhu68 vp1 coding sequence and the AAVhu68 rep coding sequences. This coding sequence is: atgacttaaaccaggt, SEQ ID NO: 9. The coding sequence for rep52 of AAVhu68 is reproduced in SEQ ID NO: 3. The rep52 protein sequence is reproduced in SEQ ID NO: 4.

In one embodiment, a method of increasing yields of a rAAV and thus, increasing the amount of an rAAV which is present in supernatant prior to, or without requiring cell lysis is provided. This method involves engineering an AAV VP1capsid gene to express a capsid protein having the Glu at position 67, and not the Val at position 157 based on an alignment having the amino acid numbering of the AAVhu68 vp1 capsid protein. In other embodiments, the method involves engineering an AAVhu68 VP1 capsid gene to express a capsid protein having the Val at position 157, and not the Glu at position 67. Such other AAV may be readily selected from other Clade F AAV, or AAV in Clade A, B, C, D, or E. In certain embodiments, the AAV are selected from Clade C, D, E, or F. In other embodiments, the AAV are selected from Clade C, D or E.

In other embodiments, the method involves increasing yield of a rAAV and thus, increasing the amount of an rAAV which is present in supernatant prior to, or without requiring cell lysis. This method involves engineering an AAV VP1capsid gene to express a capsid protein having Glu at position 67, Val at position 157, or both based on an alignment having the amino acid numbering of the AAVhu68 vp1 capsid protein. In other embodiments, the method involves engineering the VP2 capsid gene to express a capsid protein having the Val at position 157. In still other embodiments, the rAAV has a modified capsid comprising both vp1 and vp2 capsid proteins Glu at position 67 and Val at position 157.

In still other embodiments, AAVhu68 may be engineered to have a Ser, Gly, Ser or Thr at position 67, with reference to the vp1 numbering [SEQ ID NO: 2], while retaining the Val at position 157. In still further embodiments, AAVhu68 may be engineered to have an Ile or Leu at position 157, with reference to the vp1 numbering [SEQ ID NO:2]. In yet another embodiment, AAVhu68 may be engineered to have a Ser, Gly, Ser or Thr at position 67 and an Ile or Leu at position 157, with reference to the vp1 numbering [SEQ ID NO:2].

In a further embodiment, a method for packaging a transgene into a Clade F AAV which provides at least a 15% increase in yield of packaged vector as compared to AAV9, said method comprising: culturing a host cell culture according to suitable conditions. In certain embodiments, the increase is an at least 90% increase in yield. In other embodiments, the increase is an at least 200% increase in yield.

In a comparison between AAVhu68 and AAVrh10, AAVhu68 has been found to provide better transduction efficiency than AAVrh10 at low dose (e.g. about $1\times10^9$ GC) following intracerebroventricular administration. In a further comparison between AAVhu68 and AAV9, AAVhu68 has been found to provide better transduction efficiency than AAV9 in cerebellum, motor cortex and hippocampus of brain (e.g. at about $1\times10^{11}$ GC) following intracerebroventricular administration.

In certain embodiments, the invention provides an AAVhu68 vector comprising a vector genome which expresses an antibody directed against a HER2 receptor. Such a vector is useful in the treatment and/or prevention of cancers.

As used herein, an "AAV9 capsid" is a self-assembled AAV capsid composed of multiple AAV9 vp proteins. The AAV9 vp proteins are typically expressed as alternative splice variants encoded by a nucleic acid sequence of SEQ ID NO: 5 or a sequence at least 70%, at least 75%, at least 80%, at least 85%, at least 90%, at least 95%, at least 97%, at least 99% thereto, which encodes the vp1 amino acid sequence of SEQ ID NO: 6 (GenBank accession: AAS99264). These splice variants result in proteins of different length of SEQ ID NO: 6. In certain embodiments, "AAV9 capsid" includes an AAV having an amino acid sequence which is 99% identical to AAS99264 or 99% identical to SEQ ID NO: 6. See, also U.S. Pat. No. 7,906,111 and WO 2005/033321. As used herein "AAV9 variants" include those described in, e.g., WO2016/049230, U.S. Pat. No. 8,927,514, US 2015/0344911, and U.S. Pat. No. 8,734,809.

Methods of generating the capsid, coding sequences therefore, and methods for production of rAAV viral vectors have been described. See. e.g., Gao, et al, Proc. Natl. Acad. Sci. U.S.A. 100 (10), 6081-6086 (2003) and US 2013/0045186A1.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The terms "sequence identity" "percent sequence identity" or "percent identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length and may be up to about 700 amino acids. Examples of suitable fragments are described herein.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. In the examples, AAV alignments are performed using the published AAV9 sequences as a reference point. Alignments are performed using any of a variety of publicly or commercially available Multiple Sequence Alignment Programs. Examples of such programs include, "Clustal Omega", "Clustal W", "CAP Sequence Assembly", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference. Multiple sequence alignment programs are also available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See. e.g., J. D. Thomson et al, Nucl. Acids. Res., "A comprehensive comparison of multiple sequence alignments", 27(13): 2682-2690 (1999).

I. rAAV Vectors

As indicated above, the novel AAVhu68 sequences and proteins are useful in production of rAAV, and are also useful in recombinant AAV vectors which may be antisense delivery vectors, gene therapy vectors, or vaccine vectors. Additionally, the engineered AAV capsids described herein, e.g., those having mutant amino acids at position 67, 157 or both relative to the numbering of the vp1 capsid protein in SEQ ID NO:2, may be used to engineer rAAV vectors for delivery of a number of suitable nucleic acid molecules to target cells and tissues.

Genomic sequences which are packaged into an AAV capsid and delivered to a host cell are typically composed of, at a minimum, a transgene and its regulatory sequences, and AAV inverted terminal repeats (ITRs). Both single-stranded AAV and self-complementary (sc) AAV are encompassed with the rAAV. The transgene is a nucleic acid coding sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J. Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. In one embodiment, the ITRs are from an AAV different than that supplying a capsid. In one embodiment, the ITR sequences from AAV2. A shortened version of the 5' ITR, termed ΔITR, has been described in which the D-sequence and terminal resolution site (trs) are deleted. In other embodiments, the full-length AAV 5' and 3' ITRs are used. However, ITRs from other AAV sources may be selected. Where the source of the ITRs is from AAV2 and the AAV capsid is from another AAV source, the resulting vector may be termed pseudotyped. However, other configurations of these elements may be suitable.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

The regulatory control elements typically contain a promoter sequence as part of the expression control sequences, e.g., located between the selected 5' ITR sequence and the coding sequence. Constitutive promoters, regulatable promoters [see, e.g., WO 2011/126808 and WO 2013/04943], tissue specific promoters, or a promoter responsive to physiologic cues may be used may be utilized in the vectors described herein. The promoter(s) can be selected from different sources, e.g., human cytomegalovirus (CMV) immediate-early enhancer/promoter, the SV40 early enhancer/promoter, the JC polymovirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter. In addition to a promoter a vector may contain one or more other appropriate transcription initiation, termination, enhancer sequences, efficient RNA processing signals such as splicing and polyadenylation (polyA) signals; sequences that stabilize cytoplasmic mRNA for example WPRE; sequences that enhance translation efficiency (i.e., Kozak consensus sequence); sequences that enhance protein stability; and when desired, sequences that enhance secretion of the encoded product. An example of a suitable enhancer is the CMV enhancer. Other suitable enhancers include those that are appropriate for desired target tissue indications. In one embodiment, the expression cassette comprises one or more expression enhancers. In one embodiment, the expression cassette contains two or more expression enhancers. These enhancers may be the same or may differ from one another. For example, an enhancer may include a CMV immediate early enhancer. This enhancer may be present in two copies which are located adjacent to one another. Alternatively, the dual copies of the enhancer may be separated by one or more sequences. In still another embodiment, the expression cassette further contains an intron, e.g, the chicken beta-actin intron. Other suitable introns include those known in the art, e.g., such as are described in WO 2011/126808. Examples of suitable polyA sequences include, e.g., SV40, SV50, bovine growth hormone (bGH), human growth hormone, and synthetic polyAs. Optionally, one or more sequences may be selected to stabilize mRNA. An example of such a sequence is a modified WPRE sequence, which may be engineered upstream of the polyA sequence and downstream of the coding sequence [see, e.g., MA Zanta-Boussif, et al, Gene Therapy (2009) 16: 605-619.

These rAAVs are particularly well suited to gene delivery for therapeutic purposes and for immunization, including inducing protective immunity. Further, the compositions of the invention may also be used for production of a desired gene product in vitro. For in vitro production, a desired product (e.g., a protein) may be obtained from a desired culture following transfection of host cells with a rAAV containing the molecule encoding the desired product and culturing the cell culture under conditions which permit expression. The expressed product may then be purified and isolated, as desired. Suitable techniques for transfection, cell culturing, purification, and isolation are known to those of skill in the art.

In certain embodiments, a rAAV or composition as provided herein does not contain an anti-influenza antibody or immunoglobulin construct. In certain embodiments, a rAAV or composition as provided herein does not contain an SMN coding sequence.

Therapeutic Genes and Gene Products

Useful products encoded by the transgene include a variety of gene products which replace a defective or deficient gene, inactivate or "knock-out", or "knock-down" or reduce the expression of a gene which is expressing at an undesirably high level, or delivering a gene product which has a desired therapeutic effect. In most embodiments, the therapy will be "somatic gene therapy", i.e., transfer of genes to a cell of the body which does not produce sperm or eggs. In certain embodiments, the transgenes express proteins have the sequence of native human sequences. However, in other embodiments, synthetic proteins are expressed. Such proteins may be intended for treatment of humans, or in other embodiments, designed for treatment of animals, including companion animals such as canine or feline populations, or for treatment of livestock or other animals which come into contact with human populations.

Examples of suitable gene products may include those associated with familial hypercholesterolemia, muscular dystrophy, cystic fibrosis, and rare or orphan diseases. Examples of such rare disease may include spinal muscular atrophy (SMA), Huntingdon's Disease, Rett Syndrome (e.g., methyl-CpG-binding protein 2 (MeCP2); UniProtKB-P51608), Amyotrophic Lateral Sclerosis (ALS), Duchenne Type Muscular dystrophy, Friedrichs Ataxia (e.g., frataxin), progranulin (PRGN) (associated with non-Alzheimer's cerebral degenerations, including, frontotemporal dementia (FTD), progressive non-fluent aphasia (PNFA) and semantic demential), among others. See, e.g., www.orpha.net/consor/cgi-bin/Disease_Search_List.php; rarediseases.info.nih.gov/diseases.

Examples of suitable genes may include, e.g., hormones and growth and differentiation factors including, without limitation, insulin, glucagon, glucagon-like peptide-1 (GLP1), growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO) (including, e.g., human, canine or feline epo), connective tissue growth factor (CTGF), neutrophic factors including, e.g., basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor α superfamily, including TGFα, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-36 (including, e.g., human interleukins IL-1, IL-1α, IL-1β, IL-2, IL-3, IL-4, IL-6, IL-8, IL-12, IL-11, IL-12, IL-13, IL-18, IL-31, IL-35), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. For example, in certain embodiments, the rAAV antibodies may be designed to delivery canine or feline antibodies, e.g., such as anti-IgE, anti-IL31, anti-CD20, anti-NGF, anti-GnRH. Useful gene products also include complement regulatory proteins such as complement regulatory proteins, membrane cofactor protein (MCP), decay accelerating factor (DAF), CR1, CF2, CD59, and C1 esterase inhibitor (C1-INH).

Still other useful gene products include any one of the receptors for the hormones, growth factors, cytokines, lymphokines, regulatory proteins and immune system proteins. The invention encompasses receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses gene products such as members of the steroid hormone receptor superfamily including glucocorticoid receptors and estrogen receptors, Vitamin D receptors and other nuclear receptors. In addition, useful gene products include transcription factors such as jun,fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase (OTC), arginosuccinate synthetase, arginosuccinate lyase (ASL) for treatment of arginosuccinate lyase deficiency, arginase, fumarylacetate hydrolase, phenylalanine hydroxylase, alpha-1 antitrypsin, rhesus alpha-fetoprotein (AFP), rhesus chorionic gonadotrophin (CG), glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin gene product [e.g., a mini- or micro-dystrophin]. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)).

In certain embodiments, the rAAV may be used in gene editing systems, which system may involve one rAAV or co-administration of multiple rAAV stocks. For example, the rAAV may be engineered to deliver SpCas9, SaCas9, ARCUS, Cpf1, and other suitable gene editing constructs.

Still other useful gene products include those used for treatment of hemophilia, including hemophilia B (including Factor IX) and hemophilia A (including Factor VIII and its variants, such as the light chain and heavy chain of the heterodimer and the B-deleted domain; U.S. Pat. Nos. 6,200,560 and 6,221,349). In some embodiments, the minigene comprises first 57 base pairs of the Factor VIII heavy chain which encodes the 10 amino acid signal sequence, as well as the human growth hormone (hGH) polyadenylation sequence. In alternative embodiments, the minigene further comprises the A 1 and A2 domains, as well as 5 amino acids from the N-terminus of the B domain, and/or 85 amino acids of the C-terminus of the B domain, as well as the A3, C1 and C2 domains. In yet other embodiments, the nucleic acids encoding Factor VIII heavy chain and light chain are provided in a single minigene separated by 42 nucleic acids coding for 14 amino acids of the B domain [U.S. Pat. No. 6,200,560].

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce "self"-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

Further illustrative genes which may be delivered via the rAAV include, without limitation, glucose-6-phosphatase, associated with glycogen storage disease or deficiency type IA (GSD1), phosphoenolpyruvate-carboxykinase (PEPCK), associated with PEPCK deficiency; cyclin-dependent kinase-like 5 (CDKL5), also known as serine/threonine kinase 9 (STK9) associated with seizures and severe neurodevelopmental impairment; galactose-1 phosphate uridyl transferase, associated with galactosemia; phenylalanine hydroxylase, associated with phenylketonuria (PKU); branched chain alpha-ketoacid dehydrogenase, associated with Maple syrup urine disease; fumarylacetoacetate hydrolase, associated with tyrosinemia type 1; methylmalonyl-CoA mutase, associated with methylmalonic acidemia; medium chain acyl CoA dehydrogenase, associated with medium chain acetyl CoA deficiency; ornithine transcarbamylase (OTC), associated with ornithine transcarbamylase deficiency; argininosuccinic acid synthetase (ASS1), associated with citrullinemia; lecithin-cholesterol acyltransferase (LCAT) deficiency; a methylmalonic acidemia (MMA); Niemann-Pick disease, type C1); propionic academia (PA); low density lipoprotein receptor (LDLR) protein, associated with familial hypercholesterolemia (FH); UDP-glucouronosyltransferase, associated with Crigler-Najjar disease; adenosine deaminase, associated with severe combined immunodeficiency disease; hypoxanthine guanine phosphoribosyl transferase, associated with Gout and n-Nyan syndrome; biotimidase, associated with biotimidase deficiency; alpha-galactosidase A (a-Gal A) associated with Fabry disease); ATP7B associated with Wilson's Disease; beta-glucocerebrosidase, associated with Gaucher disease type 2 and 3; peroxisome membrane protein 70 kDa, associated with Zellweger syndrome; arylsulfatase A (ARSA) associated with metachromatic leukodystrophy, galactocerebrosidase (GALC) enzyme associated with Krabbe disease, alpha-glucosidase (GAA) associated with Pompe disease; sphingomyelinase (SMPD1) gene associated with Nieman Pick disease type A; argininosuccinate synthase associated with adult onset type II citrullinemia (CTLN2); carbamoyl-phosphate synthase 1 (CPS1) associated with urea cycle disorders; survival motor neuron (SMN) protein, associated with spinal muscular atrophy; ceramidase associated with Farber lipogranulomatosis; b-hexosaminidase associated with GM2 gangliosidosis and Tay-Sachs and Sandhoff diseases; aspartylglucosaminidase associated with aspartyl-glucosaminuria; a-fucosidase associated with fucosidosis; α-mannosidase associated with alpha-mannosidosis; porphobilinogen deaminase, associated with acute intermittent *porphyria* (AIP); alpha-1 antitrypsin for treatment of alpha-1 antitrypsin deficiency (emphysema); erythropoietin for treatment of anemia due to thalassemia or to renal failure; vascular endothelial growth factor, angiopoietin-1, and fibroblast growth factor for the treatment of ischemic diseases; thrombomodulin and tissue factor pathway inhibitor for the treatment of occluded blood vessels as seen in, for example, atherosclerosis, thrombosis, or embolisms; aromatic amino acid decarboxylase (AADC), and tyrosine hydroxylase (TH) for the treatment of Parkinson's disease; the beta adrenergic receptor, anti-sense to, or a mutant form of, phospholamban, the sarco(endo)plasmic reticulum adenosine triphosphatase-2 (SERCA2), and the cardiac adenylyl cyclase for the treatment of congestive heart failure; a tumor suppressor gene such as p53 for the treatment of various cancers; a cytokine such as one of the various interleukins for the treatment of inflammatory and immune disorders and cancers; dystrophin or minidystrophin and utrophin or miniutrophin for the treatment of muscular dystrophies; and, insulin or GLP-1 for the treatment of diabetes.

Additional genes and diseases of interest include, e.g., dystonin gene related diseases such as Hereditary Sensory and Autonomic Neuropathy Type VI (the DST gene encodes dystonin; dual AAV vectors may be required due to the size of the protein (~7570 aa); SCN9A related diseases, in which loss of function mutants cause inability to feel pain and gain of function mutants cause pain conditions, such as erythromelagia. Another condition is Charcot-Marie-Tooth type 1F and 2E due to mutations in the NEFL gene (neurofilament light chain). characterized by a progressive peripheral motor and sensory neuropathy with variable clinical and electrophysiologic expression.

In certain embodiments, the rAAV described herein may be used in treatment of mucopolysaccaridoses (MPS) disorders. Such rAAV may contain carry a nucleic acid sequence encoding α-L-iduronidase (IDUA) for treating MPS I (Hurler, Hurler-Scheie and Scheie syndromes); a nucleic acid sequence encoding iduronate-2-sulfatase (IDS) for treating MPS II (Hunter syndrome); a nucleic acid sequence encoding sulfamidase (SGSH) for treating MPSIII A, B, C, and D (Sanfilippo syndrome); a nucleic acid sequence encoding N-acetylgalactosamine-6-sulfate sulfatase (GALNS) for treating MPS IV A and B (Morquio syndrome); a nucleic acid sequence encoding arylsulfatase B (ARSB) for treating MPS VI (Maroteaux-Lamy syndrome); a nucleic acid sequence encoding hyaluronidase for treating MPSI IX (hyaluronidase deficiency) and a nucleic acid sequence encoding beta-glucuronidase for treating MPS VII (Sly syndrome).

Immunogenic Transgenes

In some embodiments, an rAAV vector comprising a nucleic acid encoding a gene product associated with cancer (e.g., tumor suppressors) may be used to treat the cancer, by administering a rAAV harboring the rAAV vector to a subject having the cancer. In some embodiments, an rAAV vector comprising a nucleic acid encoding a small interfering nucleic acid (e.g., shRNAs, miRNAs) that inhibits the expression of a gene product associated with cancer (e.g., oncogenes) may be used to treat the cancer, by administering a rAAV harboring the rAAV vector to a subject having the cancer. In some embodiments, an rAAV vector comprising a nucleic acid encoding a gene product associated with cancer (or a functional RNA that inhibits the expression of a gene associated with cancer) may be used for research purposes, e.g., to study the cancer or to identify therapeutics that treat the cancer. The following is a non-limiting list of exemplary genes known to be associated with the development of cancer (e.g., oncogenes and tumor suppressors): AARS, ABCB1, ABCC4, ABI2, ABL 1, ABL2, ACK1, ACP2, ACY1, ADSL, AK1, AKR 1C2, AKT1, ALB, ANPEP, ANXA5, ANXA7, AP2M1, APC, ARHGAP5, ARHGEF5, ARID4A, ASNS, ATF4, ATM, ATP5B, ATP50, AXL, BARD1, BAX, BCL2, BHLHB2, BLMH, BRAF, BRCA1, BRCA2, BTK, CANX, CAP1, CAPN1, CAPNS1, CAV1, CBFB, CBLB, CCL2, CCND1, CCND2, CCND3, CCNE1, CCT5, CCYR61, CD24, CD44, CD59, CDC20, CDC25, CDC25A, CDC25B, CDC2L5, CDK10, CDK4, CDK5, CDK9, CDKL1, CDKN1A, CDKN1B, CDKN1C, CDKN2A, CDKN2B, CDKN2D, CEBPG, CENPC1, CGRRF1, CHAF1A, CIB1, CKMT1, CLK1, CLK2, CLK3, CLNS1A, CLTC, COL1A1, COL6A3, COX6C, COX7A2, CRAT, CRHR1, CSF1R, CSK, CSNK1G2, CTNNA1, CTNNB1, CTPS, CTSC, CTSD, CUL1, CYR61, DCC, DCN, DDX10, DEK, DHCR7, DHRS2, DHX8, DLG3, DVL1, DVL3, E2F1, E2F3, E2F5, EGFR, EGR1, EIF5, EPHA2, ERBB2, ERBB3, ERBB4, ERCC3, ETV1, ETV3, ETV6, F2R, FASTK, FBN1, FBN2, FES, FGFR1, FGR, FKBP8, FN1, FOS, FOSL1, FOSL2, FOXGIA, FOXOIA, FRAP1, FRZB, FTL, FZD2, FZD5, FZD9, G22P1, GAS6, GCN5L2, GDF15, GNA13, GNAS, GNB2, GNB2L1, GPR39, GRB2, GSK3A, GSPT1, GTF2I, HDAC1, HDGF, HMMR, HPRT1, HRB, HSPA4, HSPA5, HSPA8, HSPB1, HSPH1, HYAL1, HYOUl, ICAM1, ID1, ID2, IDUA, IER3, IFITMI, IGF1R, IGF2R, IGFBP3, IGFBP4, IGFBP5, IL1B, ILK, ING1, IRF3, ITGA3, ITGA6, ITGB4, JAK1, JARID IA, JUN, JUNB, JUND, K-ALPHA-1, KIT, KITLG, KLK10, KPNA2, KRAS2, KRT18, KRT2A, KRT9, LAMBI, LAMP2, LCK, LCN2, LEP, LITAF, LRPAP1, LTF, LYN, LZTR1, MADH1, MAP2K2, MAP3K8, MAPK12, MAPK13, MAPKAPK3, MAPRE1, MARS, MAS1, MCC, MCM2, MCM4, MDM2, MDM4, MET, MGST1, MICB, MLLT3, MME, MMP1, MMP14, MMP17, MMP2, MNDA, MSH2, MSH6, MT3, MYB, MYBL1, MYBL2, MYC, MYCL1, MYCN, MYD88, MYL9, MYLK, NEO1, NF1, NF2, NFKB1, NFKB2, NFSF7, NID, NINE, NMBR, NME1, NME2, NME3, NOTCH1, NOTCH2, NOTCH4, NPM1, NQO1, NR1D1, NR2F1, NR2F6, NRAS, NRG1, NSEP1, OSM, PA2G4, PABPC1, PCNA, PCTK1, PCTK2, PCTK3, PDGFA, PDGFB, PDGFRA, PDPK1, PEA15, PFDN4, PFDN5, PGAM1, PHB, PIK3CA, PIK3CB, PIK3CG, PIM1, PKM2, PKMYT1, PLK2, PPARD, PPARG, PPIH, PPP1CA, PPP2R5A, PRDX2, PRDX4, PRKARIA, PRKCBP1, PRNP, PRSS15, PSMA1, PTCH, PTEN, PTGS1, PTMA, PTN, PTPRN, RAB5A, RAC1, RAD50, RAF1, RALBP1, RAPIA, RARA, RARB, RASGRF1, RB1, RBBP4, RBL2, REA, REL, RELA, RELB, RET, RFC2, RGS19, RHOA, RHOB, RHOC, RHOD, RIPK1, RPN2, RPS6 KB1, RRM1, SARS, SELENBP1, SEMA3C, SEMA4D, SEPP1, SERPINHI, SFN, SFPQ, SFRS7, SHB, SHH, SIAH2, SIVA, SIVA TP53, SKI, SKIL, SLC16A 1, SLC1A4, SLC20A 1, SMO, sphingomyelin phosphodiesterase 1 (SMPD1), SNAI2, SND1, SNRPB2, SOCS1, SOCS3, SOD1, SORT1, SPINT2, SPRY2, SRC, SRPX, STAT1, STAT2, STAT3, STAT5B, STC1, TAF1, TBL3, TBRG4, TCF1, TCF7L2, TFAP2C, TFDP1, TFDP2, TGFA, TGFB1, TGFBI, TGFBR2, TGFBR3, THBS1, TIE, TIMP1, TIMP3, TJP1, TK1, TLEl, TNF, TNFRSF10A, TNFRSF10B, TNFRSFIA, TNFRSF1B, TNFRSF6, TNFSF7, TNK1, TOB1, TP53, TP53BP2, TP5313, TP73, TPBG, TPT1, TRADD, TRAM1, TRRAP, TSG101, TUFM, TXNRD1, TYRO3, UBC, UBE2L6, UCHL1, USP7, VDAC1, VEGF, VHL, VIL2, WEE1, WNT1, WNT2, WNT2B, WNT3, WNT5A, WT1, XRCC1, YES1, YWHAB, YWHAZ, ZAP70, and ZNF9.

A rAAV vector may comprise as a transgene, a nucleic acid encoding a protein or functional RNA that modulates apoptosis. The following is a non-limiting list of genes associated with apoptosis and nucleic acids encoding the products of these genes and their homologues and encoding small interfering nucleic acids (e.g., shRNAs, miRNAs) that inhibit the expression of these genes and their homologues are useful as transgenes in certain embodiments of the invention: RPS27A, ABL1, AKT1, APAF1, BAD, BAG1, BAG3, BAG4, BAK1, BAX, BCL 10, BCL2, BCL2A1, BCL2L 1, BCL2L 10, BCL2L11, BCL2L12, BCL2L13, BCL2L2, BCLAF1, BFAR, BID, BIK, NAIP, BIRC2, BIRC3, XIAP, BIRC5, BIRC6, BIRC7, BIRC8, BNIP1, BNIP2, BNIP3, BNIP3L, BOK, BRAF, CARDO, CARD11, NLRC4, CARD14, NOD2, NOD1, CARD6, CARDS, CARDS, CASP1, CASP10, CASP14, CASP2, CASP3, CASP4, CASP5, CASP6, CASP7, CASP8, CASP9, CFLAR, CIDEA, CIDEB, CRADD, DAPK1, DAPK2, DFFA, DFFB, FADD, GADD45A, GDNF, HRK, IGF1R, LTA, LTBR, MCL1, NOL3, PYCARD, RIPK1, RIPK2, TNF, TNFRSF10A, TNFRSF10B, TNFRSF10C, TNFRSF10D, TNFRSF11B, TNFRSF12A, TNFRSF14, TNFRSF19, TNFRSFIA, TNFRSFIB, TNFRSF21, TNFRSF25, CD40, FAS, TNFRSF6B, CD27, TNFRSF9, TNFSF10, TNFSF14, TNFSF18, CD40LG, FASLG, CD70, TNFSF8, TNFSF9, TP53, TP53BP2, TP73, TP63, TRADD, TRAF1, TRAF2, TRAF3, TRAF4, and TRAF5.

Useful gene products also include miRNAs. miRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

The following non-limiting list of miRNA genes, and their homologues, are useful as genes or as targets for small interfering nucleic acids encoded by genes (e.g., miRNA sponges, antisense oligonucleotides, TuD RNAs) in certain embodiments of the methods: hsa-let-7a, hsa-let-7a*, hsa-let-7b, hsa-let-7b*, hsa-let-7c, hsa-let-7c*, hsa-let-7d, hsa-let-7d*, hsa-let-7e, hsa-let-7e*, hsa-let-7f, hsa-let-7f-1*, hsa-let-7f-2*, hsa-let-7g, hsa-let-7g*, hsa-let-71, hsa-let-71*, hsa-miR-1, hsa-miR-100, hsa-miR-100*, hsa-miR-101, hsa-miR-101*, hsa-miR-103, hsa-miR-105, hsa-miR-105*, hsa-miR-106a, hsa-miR-106a*, hsa-miR-106b, hsa-miR-106b*, hsa-miR-107, hsa-miR-10a, hsa-miR-10a*, hsa-miR-10b, hsa-miR-10b*, hsa-miR-1178, hsa-miR-1179, hsa-miR-1180, hsa-miR-1181, hsa-miR-1182, hsa-miR-1183, hsa-miR-1184, hsa-miR-1185, hsa-miR-1197, hsa-miR-1200, hsa-miR-1201, hsa-miR-1202, hsa-miR-1203, hsa-miR-1204, hsa-miR-1205, hsa-miR-1206, hsa-miR-1207-3p, hsa-miR-1207-5p, hsa-miR-1208, hsa-miR-122, hsa-miR-122*, hsa-miR-1224-3p, hsa-miR-1224-5p, hsa-miR-1225-3p, hsa-miR-1225-5p, hsa-miR-1226, hsa-miR-1226*, hsa-miR-1227, hsa-miR-1228, hsa-miR-1228*, hsa-miR-1229, hsa-miR-1231, hsa-miR-1233, hsa-miR-1234, hsa-miR-1236, hsa-miR-1237, hsa-miR-1238, hsa-miR-124, hsa-miR-124*, hsa-miR-1243, hsa-miR-1244, hsa-miR-1245, hsa-miR-1246, hsa-miR-1247, hsa-miR-1248, hsa-miR-1249, hsa-miR-1250, hsa-miR-1251, hsa-miR-1252, hsa-miR-1253, hsa-miR-1254, hsa-miR-1255a, hsa-miR-1255b, hsa-miR-1256, hsa-miR-1257, hsa-miR-1258, hsa-miR-1259, hsa-miR-125a-3p, hsa-miR-125a-5p, hsa-miR-125b, hsa-miR-125b-1*, hsa-miR-125b-2*, hsa-miR-126, hsa-miR-126*, hsa-miR-1260, hsa-miR-1261, hsa-miR-1262, hsa-miR-1263, hsa-miR-1264, hsa-miR-1265, hsa-miR-1266, hsa-miR-1267, hsa-miR-1268, hsa-miR-1269, hsa-miR-1270, hsa-miR-1271, hsa-miR-1272, hsa-miR-1273, hsa-miR-127-3p, hsa-miR-1274a, hsa-miR-1274b, hsa-miR-1275, hsa-miR-127-5p, hsa-miR-1276, hsa-miR-1277, hsa-miR-1278, hsa-miR-1279, hsa-miR-128, hsa-miR-1280, hsa-miR-1281, hsa-miR-1282, hsa-miR-1283, hsa-miR-1284, hsa-miR-1285, hsa-miR-1286, hsa-miR-1287, hsa-miR-1288, hsa-miR-1289, hsa-miR-129*, hsa-miR-1290, hsa-miR-1291, hsa-miR-1292, hsa-miR-1293, hsa-miR-129-3p, hsa-miR-1294, hsa-miR-1295, hsa-miR-129-5p, hsa-miR-1296, hsa-miR-1297, hsa-miR-1298, hsamiR-1299, hsa-miR-1300, hsa-miR-1301, hsa-miR-1302, hsa-miR-1303, hsa-miR-1304, hsa-miR-1305, hsa-miR-1306, hsa-miR-1307, hsa-miR-1308, hsa-miR-130a, hsa-miR-130a*, hsa-miR-130b, hsa-miR-130b*, hsa-miR-132, hsa-miR-132*, hsa-miR-1321, hsa-miR-1322, hsa-miR-1323, hsa-miR-1324, hsa-miR-133a, hsa-miR-133b, hsa-miR-134, hsa-miR-135a, hsa-miR-135a*, hsa-miR-135b, hsa-miR-135b*, hsa-miR-136, hsa-miR-136*, hsa-miR-137, hsa-miR-138, hsa-miR-138-1*, hsa-miR-138-2*, hsa-miR-139-3p, hsa-miR-139-5p, hsa-miR-140-3p, hsa-miR-140-5p, hsa-miR-141, hsa-miR-141*, hsa-miR-142-3p, hsa-miR-142-5p, hsa-miR-143, hsa-miR-143*, hsa-miR-144, hsa-miR-144*, hsa-miR-145, hsa-miR-145*, hsa-miR-146a, hsa-miR-146a*, hsa-miR-146b-3p, hsa-miR-146b-5p, hsa-miR-147, hsa-miR-147b, hsa-miR-148a, hsa-miR-148a*, hsa-miR-148b, hsa-miR-148b*, hsa-miR-149, hsa-miR-149*, hsa-miR-150, hsa-miR-150*, hsa-miR-151-3p, hsa-miR-151-5p, hsa-miR-152, hsa-miR-153, hsa-miR-154, hsa-miR-154*, hsa-miR-155, hsa-miR-155*, hsa-miR-15a, hsa-miR-15a*, hsa-miR-15b, hsa-miR-15b*, hsa-miR-16, hsa-miR-16-1*, hsa-miR-16-2*, hsa-miR-17, hsa-miR-17*, hsa-miR-181a, hsa-miR-181a*, hsa-miR-181a-2*, hsa-miR-181b, hsa-miR-181c, hsa-miR-181c*, hsa-miR-181d, hsa-miR-182, hsa-miR-182*, hsa-miR-1825, hsa-miR-1826, hsa-miR-1827, hsa-miR-183, hsa-miR-183*, hsa-miR-184, hsa-miR-185, hsa-miR-185*, hsa-miR-186, hsa-miR-186*, hsa-miR-187, hsa-miR-187*, hsa-miR-188-3p, hsa-miR-188-5p, hsa-miR-18a, hsa-miR-18a*, hsa-miR-18b, hsa-miR-18b*, hsa-miR-190, hsa-miR-190b, hsa-miR-191, hsa-miR-191*, hsa-miR-192, hsa-miR-192*, hsa-miR-193a-3p, hsa-miR-193a-5p, hsa-miR-193b, hsa-miR-193b*, hsa-miR-194, hsa-miR-194*, hsa-miR-195, hsa-miR-195*, hsa-miR-196a, hsa-miR-196a*, hsa-miR-196b, hsa-miR-197, hsa-miR-198, hsa-miR-199a-3p, hsa-miR-199a-5p, hsa-miR-199b-5p, hsa-miR-19a, hsa-miR-19a*, hsa-miR-19b, hsa-miR-19b-1*, hsa-miR-19b-2*, hsa-miR-200a, hsa-miR-200a*, hsa-miR-200b, hsa-miR-200b*, hsa-miR-200c, hsa-miR-200c*, hsa-miR-202, hsa-miR-202*, hsa-miR-203, hsa-miR-204, hsa-miR-205, hsa-miR-206, hsa-miR-208a, hsa-miR-208b, hsa-miR-20a, hsa-miR-20a*, hsa-miR-20b, hsa-miR-20b*, hsa-miR-21, hsa-miR-21*, hsa-miR-210, hsa-miR-211, hsa-miR-212, hsa-miR-214, hsa-miR-214*, hsa-miR-215, hsa-miR-216a, hsa-miR-216b, hsa-miR-217, hsa-miR-218, hsa-miR-218-1*, hsa-miR-218-2*, hsa-miR-219-1-3p, hsa-miR-219-2-3p, hsa-miR-219-5p, hsa-miR-22, hsa-miR-22*, hsa-miR-220a, hsa-miR-220b, hsa-miR-220c, hsa-miR-221, hsa-miR-221*, hsa-miR-222, hsa-miR-222*, hsa-miR-223, hsa-miR-223*, hsa-miR-224, hsa-miR-23a, hsa-miR-23a*, hsa-miR-23b, hsa-miR-23b*, hsa-miR-24, hsa-miR-24-1*, hsa-miR-24-2*, hsa-miR-25, hsa-miR-25*, hsa-miR-26a, hsa-miR-26a-1*, hsa-miR-26a-2*, hsa-miR-26b, hsa-miR-26b*, hsa-miR-27a, hsa-miR-27a*, hsa-miR-27b, hsa-miR-27b*, hsa-miR-28-3p, hsa-miR-28-5p, hsa-miR-296-3p, hsa-miR-296-5p, hsa-miR-297, hsa-miR-298, hsa-miR-299-3p, hsa-miR-299-5p, hsa-miR-29a, hsa-miR-29a*, hsa-miR-29b, hsa-miR-296-1*, hsa-miR-296-2*, hsa-miR-29c, hsa-miR-29c*, hsa-miR-300, hsa-miR-301a, hsa-miR-30Ib, hsa-miR-302a, hsa-miR-302a*, hsa-miR-302b, hsa-miR-302b*, hsa-miR-302c, hsa-miR-302c*, hsa-miR-302d, hsa-miR-302d*, hsa-miR-302e, hsa-miR-302f, hsa-miR-30a, hsa-miR-30a*, hsa-miR-30b, hsa-miR-30b*, hsa-miR-30c, hsa-miR-30c-1*, hsa-miR-30c-2*, hsa-miR-30d, hsa-miR-30d*, hsa-miR-30e, hsa-miR-30e*, hsa-miR-31, hsa-miR-3I*, hsa-miR-32, hsa-miR-32*, hsa-miR-320a, hsa-miR-320b, hsa-miR-320c, hsa-miR-320d, hsa-miR-323-3p, hsa-miR-323-5p, hsa-miR-324-3p, hsa-miR-324-5p, hsa-miR-325, hsa-miR-326, hsa-miR-328, hsa-miR-329, hsa-miR-330-3p, hsa-miR-330-5p, hsa-miR-331-3p, hsa-miR-331-5p, hsa-miR-335, hsa-miR-335*, hsa-miR-337-3p, hsa-miR-337-5p, hsa-miR-338-3p, hsa-miR-338-5p, hsa-miR-339-3p, hsa-miR-339-5p, hsa-miR-33a, hsa-miR-33a*, hsa-miR-33b, hsa-miR-33b*, hsa-miR-340, hsa-miR-340*, hsa-miR-342-3p, hsa-miR-342-5p, hsa-miR-345, hsa-miR-346, hsa-miR-34a, hsa-miR-34a*, hsa-miR-34b, hsa-miR-34b*, hsa-miR-34c-3p, hsa-miR-34c-5p, hsa-miR-361-3p, hsa-miR-361-5p, hsa-miR-362-3p, hsa-miR-362-5p, hsa-miR-363, hsa-miR-363*, hsa-miR-365, hsa-miR-367, hsa-miR-367*, hsa-miR-369-3p, hsa-miR-369-5p, hsa-miR-370, hsa-miR-371-3p, hsa-miR-371-5p, hsa-miR-372, hsa-miR-373, hsa-miR-373*, hsa-miR-374a, hsa-miR-374a*, hsa-miR-374b, hsa-miR-374b*, hsa-miR-375, hsa-miR-376a, hsa-miR-376a*, hsa-miR-376b, hsa-miR-376c, hsa-miR-377, hsa-miR-377*, hsa-miR-378, hsa-miR-378*, hsa-miR-379, hsa-miR-379*, hsa-miR-380, hsa-miR-380*, hsa-miR-381, hsa-miR-382, hsa-miR-383, hsa-miR-384, hsa-miR-409-3p, hsa-miR-409-5p, hsa-miR-410, hsa-miR-411, hsa-miR-411*, hsa-miR-412, hsa-miR-421, hsa-miR-422a, hsa-miR423-3p, hsa-miR-423-5p, hsa-miR-424, hsa-miR-424*, hsa-miR-425, hsa-miR-425*, hsa-miR-429, hsa-miR-431, hsa-miR-431*, hsa-miR-432, hsa-miR-432*, hsa-miR-433, hsa-miR-448, hsa-miR-449a, hsa-miR-449b, hsa-miR-450a, hsa-miR-450b-3p, hsa-miR-450b-5p, hsa-miR-451, hsa-miR-452, hsa-miR-452*, hsa-miR-453, hsa-miR-454, hsa-miR-454*, hsa-miR-455-3p, hsa-miR-455-5p, hsa-miR-483-3p, hsa-miR-483-5p, hsa-miR-484, hsa-miR-485-3p, hsa-miR-485-5p, hsa-miR-486-3p, hsa-miR-486-5p, hsa-miR-487a, hsa-miR-487b, hsa-miR-488, hsa-miR-488*, hsa-miR-489, hsa-miR-490-3p, hsa-miR-490-5p, hsa-miR-491-3p, hsa-miR-491-5p, hsa-miR-492, hsa-miR-493, hsa-miR-493*, hsa-miR-494, hsa-miR-495, hsa-miR-496, hsa-miR-497, hsa-miR-497*, hsa-miR-498, hsa-miR-499-3p, hsa-miR-499-5p, hsa-miR-500, hsa-miR-500*, hsa-miR-501-3p, hsa-miR-501-5p, hsa-miR-502-3p, hsa-miR-502-5p, hsa-miR-503, hsa-miR-504, hsa-miR-505, hsa-miR-505*, hsa-miR-506, hsa-miR-507, hsa-miR-508-3p, hsa-miR-508-5p, hsa-miR-509-3-5p, hsa-miR-509-3p, hsa-miR-509-5p, hsa-miR-510, hsa-miR-511, hsa-miR-512-3p, hsa-miR-512-5p, hsa-miR-513a-3p, hsa-miR-513a-5p, hsa-miR-513b, hsa-miR-513c, hsa-miR-514, hsa-miR-515-3p, hsa-miR-515-5p, hsa-miR-516a-3p, hsa-miR-516a-5p, hsa-miR-516b, hsa-miR-517*, hsa-miR-517a, hsa-miR-517b, hsa-miR-517c, hsa-miR-518a-3p, hsa-miR-518a-5p, hsa-miR-518b, hsa-miR-518c, hsa-miR-518c*, hsa-miR-518d-3p, hsa-miR-518d-5p, hsa-miR-518e, hsa-miR-518e*, hsa-miR-518f, hsa-miR-518f*, hsa-miR-519a, hsa-miR-519b-3p, hsa-miR-519c-3p, hsa-miR-519d, hsa-miR-519c, hsa-miR-519c*, hsa-miR-520a-3p, hsa-miR-520a-5p, hsa-miR-520b, hsa-miR-520c-3p, hsa-miR-520d-3p, hsa-miR-520d-5p, hsa-miR-520e, hsa-miR-520f, hsa-miR-520g, hsa-miR-520h, hsa-miR-521, hsa-miR-522, hsa-miR-523, hsa-miR-524-3p, hsa-miR-524-5p, hsa-miR-525-3p, hsa-miR-525-5p, hsa-miR-526b, hsa-miR-526b*, hsa-miR-532-3p, hsa-miR-532-5p, hsa-miR-539, hsa-miR-541, hsa-miR-541*, hsa-miR-542-3p, hsa-miR-542-5p, hsa-miR-543, hsa-miR-544, hsa-miR-545, hsa-miR-545*, hsa-miR-548a-3p, hsa-miR-548a-5p, hsa-miR-548b-3p, hsa-miR-5486-5p, hsa-miR-548c-3p, hsa-miR-548c-5p, hsa-miR-548d-3p, hsa-miR-548d-5p, hsa-miR-548c, hsa-miR-548f, hsa-miR-548g, hsa-miR-548h, hsa-miR-548i, hsa-miR-548j, hsa-miR-548k, hsa-miR-548l, hsa-miR-548m, hsa-miR-548n, hsa-miR-548o, hsa-miR-548p, hsa-miR-549, hsa-miR-550, hsa-miR-550*, hsa-miR-551a, hsa-miR-55 lb, hsa-miR-551b*, hsa-miR-552, hsa-miR-553, hsa-miR-554, hsa-miR-555, hsa-miR-556-3p, hsa-miR-556-5p, hsa-miR-557, hsa-miR-558, hsa-miR-559, hsa-miR-561, hsa-miR-562, hsa-miR-563, hsa-miR-564, hsa-miR-566, hsa-miR-567, hsa-miR-568, hsa-miR-569, hsa-miR-570, hsa-miR-571, hsa-miR-572, hsa-miR-573, hsa-miR-574-3p, hsa-miR-574-5p, hsa-miR-575, hsa-miR-576-3p, hsa-miR-576-5p, hsa-miR-577, hsa-miR-578, hsa-miR-579, hsa-miR-580, hsa-miR-581, hsa-miR-582-3p, hsa-miR-582-5p, hsa-miR-583, hsa-miR-584, hsa-miR-585, hsa-miR-586, hsa-miR-587, hsa-miR- 588, hsa-miR-589, hsa-miR-589*, hsa-miR-590-3p, hsa-miR-590-5p, hsa-miR-591, hsa-miR-592, hsa-miR-593, hsa-miR-593*, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615-3p, hsa-miR-615-5p, hsa-miR-616, hsa-miR-616*, hsa-miR-617, hsa-miR-618, hsa-miR-619, hsa-miR-620, hsa-miR-621, hsa-miR-622, hsa-miR-623, hsa-miR-624, hsa-miR-624*, hsa-miR-625, hsa-miR-625*, hsa-miR-626, hsa-miR-627, hsa-miR-628-3p, hsa-miR-628-5p, hsa-miR-629, hsa-miR-629*, hsa-miR-630, hsa-miR-631, hsa-miR-632, hsa-miR-633, hsa-miR-634, hsa-miR-635, hsa-miR-636, hsa-miR-637, hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-653, hsa-miR-654-3p, hsa-miR-654-5p, hsa-miR-655, hsa-miR-656, hsa-miR-657, hsa-miR-658, hsa-miR-659, hsa-miR-660, hsa-miR-661, hsa-miR-662, hsa-miR-663, hsa-miR-663b, hsa-miR-664, hsa-miR-664*, hsa-miR-665, hsa-miR-668, hsa-miR-671-3p, hsa-miR-671-5p, hsa-miR-675, hsa-miR-7, hsa-miR-708, hsa-miR-708*, hsa-miR-7-1*, hsa-miR-7-2*, hsa-miR-720, hsa-miR-744, hsa-miR-744*, hsa-miR-758, hsa-miR-760, hsa-miR-765, hsa-miR-766, hsa-miR-767-3p, hsa-miR-767-5p, hsa-miR-768-3p, hsa-miR-768-5p, hsa-miR-769-3p, hsa-miR-769-5p, hsa-miR-770-5p, hsa-miR-802, hsa-miR-873, hsa-miR-874, hsa-miR-875-3p, hsa-miR-875-5p, hsa-miR-876-3p, hsa-miR-876-5p, hsa-miR-877, hsa-miR-877*, hsa-miR-885-3p, hsa-miR-885-5p, hsa-miR-886-3p, hsa-miR-886-5p, hsa-miR-887, hsa-miR-888, hsa-miR-888*, hsa-miR-889, hsa-miR-890, hsa-miR-891a, hsa-miR-891b, hsa-miR-892a, hsa-miR-892b, hsa-miR-9, hsa-miR-9*, hsa-miR-920, hsa-miR-921, hsa-miR-922, hsa-miR-923, hsa-miR-924, hsa-miR-92a, hsa-miR-92a-1*, hsa-miR-92a-2*, hsa-miR-92b, hsa-miR-92b*, hsa-miR-93, hsa-miR-93*, hsa-miR-933, hsa-miR-934, hsa-miR-935, hsa-miR-936, hsa-miR-937, hsa-miR-938, hsa-miR-939, hsa-miR-940, hsa-miR-941, hsa-miR-942, hsa-miR-943, hsa-miR-944, hsa-miR-95, hsa-miR-96, hsa-miR-%*, hsa-miR-98, hsa-miR-99a, hsa-miR-99a*, hsa-miR-99b, and hsa-miR-99b*. For example, miRNA targeting chromosome 8 open reading frame 72 (C9orf72) which expresses superoxide dismutase (SOD1), associated with amyotrophic lateral sclerosis (ALS) may be of interest.

A miRNA inhibits the function of the mRNAs it targets and, as a result, inhibits expression of the polypeptides encoded by the mRNAs. Thus, blocking (partially or totally) the activity of the miRNA (e.g., silencing the miRNA) can effectively induce, or restore, expression of a polypeptide whose expression is inhibited (derepress the polypeptide). In one embodiment, derepression of polypeptides encoded by mRNA targets of a miRNA is accomplished by inhibiting the miRNA activity in cells through any one of a variety of methods. For example, blocking the activity of a miRNA can be accomplished by hybridization with a small interfering nucleic acid (e.g., antisense oligonucleotide, miRNA sponge, TuD RNA) that is complementary, or substantially complementary to, the miRNA, thereby blocking interaction of the miRNA with its target mRNA. As used herein, a small interfering nucleic acid that is substantially complementary to a miRNA is one that is capable of hybridizing with a miRNA, and blocking the miRNA's activity. In some embodiments, a small interfering nucleic acid that is substantially complementary to a miRNA is an small interfering nucleic acid that is complementary with the miRNA at all but 1, 2, 3, 4, 5, 6, 7, 8, 9, 10, 11, 12, 13, 14, 15, 16, 17, or 18 bases. A "miRNA Inhibitor" is an agent that blocks miRNA function, expression and/or processing. For instance, these molecules include but are not limited to microRNA specific antisense, microRNA sponges, tough decoy RNAs (TuD RNAs) and microRNA oligonucleotides (double-stranded, hairpin, short oligonucleotides) that inhibit miRNA interaction with a Drosha complex.

Still other useful genes may include those encoding immunoglobulins which confer passive immunity to a pathogen. An "immunoglobulin molecule" is a protein containing the immunologically-active portions of an immunoglobulin heavy chain and immunoglobulin light chain covalently coupled together and capable of specifically combining with antigen. Immunoglobulin molecules are of any type (e.g., IgG, IgE, IgM, IgD, IgA and IgY), class (e.g., IgG1, IgG2, IgG3, IgG4, IgA1 and IgA2) or subclass. The terms "antibody" and "immunoglobulin" may be used interchangeably herein.

An "immunoglobulin heavy chain" is a polypeptide that contains at least a portion of the antigen binding domain of an immunoglobulin and at least a portion of a variable region of an immunoglobulin heavy chain or at least a portion of a constant region of an immunoglobulin heavy chain. Thus, the immunoglobulin derived heavy chain has significant regions of amino acid sequence homology with a member of the immunoglobulin gene superfamily. For example, the heavy chain in a Fab fragment is an immunoglobulin-derived heavy chain.

An "immunoglobulin light chain" is a polypeptide that contains at least a portion of the antigen binding domain of an immunoglobulin and at least a portion of the variable region or at least a portion of a constant region of an immunoglobulin light chain. Thus, the immunoglobulin-derived light chain has significant regions of amino acid homology with a member of the immunoglobulin gene superfamily.

An "immunoadhesin" is a chimeric, antibody-like molecule that combines the functional domain of a binding protein, usually a receptor, ligand, or cell-adhesion molecule, with immunoglobulin constant domains, usually including the hinge and Fc regions.

A "fragment antigen-binding" (Fab) fragment" is a region on an antibody that binds to antigens. It is composed of one constant and one variable domain of each of the heavy and the light chain.

The anti-pathogen construct is selected based on the causative agent (pathogen) for the disease against which protection is sought. These pathogens may be of viral, bacterial, or fungal origin, and may be used to prevent infection in humans against human disease, or in non-human mammals or other animals to prevent veterinary disease.

The rAAV may include genes encoding antibodies, and particularly neutralizing antibodies against a viral pathogen. Such anti-viral antibodies may include anti-influenza antibodies directed against one or more of Influenza A, Influenza B, and Influenza C. The type A viruses are the most virulent human pathogens. The serotypes of influenza A which have been associated with pandemics include, H1N1, which caused Spanish Flu in 1918, and Swine Flu in 2009; H2N2, which caused Asian Flu in 1957; H3N2, which caused Hong Kong Flu in 1968; H5N1, which caused Bird Flu in 2004; H7N7; H1N2; H9N2; H7N2; H7N3; and H10N7. Other target pathogenic viruses include, arenaviruses (including funin, machupo, and Lassa), filoviruses (including Marburg and Ebola), hantaviruses, picornoviridae (including rhinoviruses, echovirus), coronaviruses, paramyxovirus, morbillivirus, respiratory synctial virus, togavirus, coxsackievirus, JC virus, parvovirus B19, parainfluenza, adenoviruses, reoviruses, variola (Variola major (Smallpox)) and Vaccinia (Cowpox) from the poxvirus family, and varicella-zoster (pseudorabies). Viral hemorrhagic fevers are caused by members of the arenavirus family (Lassa fever) (which family is also associated with Lymphocytic choriomeningitis (LCM)), filovirus (ebola virus), and hantavirus (puremala). The members of picornavirus (a subfamily of rhinoviruses), are associated with the common cold in humans. The coronavirus family, which includes a number of non-human viruses such as infectious bronchitis virus (poultry), porcine transmissible gastroenteric virus (pig), porcine hemagglutinatin encephalomyelitis virus (pig), feline infectious peritonitis virus (cat), feline enteric coronavirus (cat), canine coronavirus (dog). The human respiratory coronaviruses, have been putatively associated with the common cold, non-A, B or C hepatitis, and sudden acute respiratory syndrome (SARS). The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus (RSV). The parvovirus family includes feline parvovirus (feline enteritis), feline panleucopeniavirus, canine parvovirus, and porcine parvovirus. The adenovirus family includes viruses (EX, AD7, ARD, O.B.) which cause respiratory disease. Thus, in certain embodiments, a rAAV vector as described herein may be engineered to express an anti-ebola antibody, e.g., 2G4, 4G7, 13C6, an anti-influenza antibody, e.g., FI6, CR8033, and anti-RSV antibody, e.g, palivizumab, motavizumab.

A neutralizing antibody construct against a bacterial pathogen may also be selected for use in the present invention. In one embodiment, the neutralizing antibody construct is directed against the bacteria itself. In another embodiment, the neutralizing antibody construct is directed against a toxin produced by the bacteria. Examples of airborne bacterial pathogens include, e.g., *Neisseria meningitidis* (meningitis), *Klebsiella pneumonia* (pneumonia), *Pseudomonas aeruginosa* (pneumonia), *Pseudomonas pseudomallei* (pneumonia), *Pseudomonas mallei* (pneumonia), *Acinetobacter* (pneumonia), *Moraxella catarrhalis, Moraxella lacunata, Alkaligenes, Cardiobacterium, Haemophilus influenzae* (flu). *Haemophilus parainfluenzae. Bordetella pertussis* (whooping cough), *Francisella tularensis* (pneumonia/fever). *Legionella pneumonia* (Legionnaires disease), *Chlamydia psittaci* (pneumonia), *Chlamydia pneumoniae* (pneumonia), *Mycobacterium tuberculosis* (tuberculosis (TB)), *Mycobacterium kansasii* (TB), *Mycobacterium avium* (pneumonia), *Nocardia asteroides* (pneumonia), *Bacillus anthracis* (anthrax), *Staphylococcus aureus* (pneumonia), *Streptococcus pyogenes* (scarlet fever), *Streptococcus pneumoniae* (pneumonia), *Corynebacteria diphtheria* (diphtheria), *Mycoplasma pneumoniae* (pneumonia).

The rAAV may include genes encoding antibodies, and particularly neutralizing antibodies against a bacterial pathogen such as the causative agent of anthrax, a toxin produced by *Bacillus anthracis*. Neutralizing antibodies against protective agent (PA), one of the three peptides which form the toxoid, have been described. The other two polypeptides consist of lethal factor (LF) and edema factor (EF). Anti-PA neutralizing antibodies have been described as being effective in passively immunization against anthrax. See, e.g., U.S. Pat. No. 7,442,373; R. Sawada-Hirai et al, J Immune Based Ther Vaccines. 2004; 2:5. (on-line 2004 May 12). Still other anti-anthrax toxin neutralizing antibodies have been described and/or may be generated. Similarly, neutralizing antibodies against other bacteria and/or bacterial toxins may be used to generate an AAV-delivered anti-pathogen construct as described herein.

Antibodies against infectious diseases may be caused by parasites or by fungi, including, e.g., *Aspergillus* species, *Absidia corymbifera, Rhixpus stolomfer, Mucor plumbeaus, Cryptococcus neoformans, Histoplasm capsulatum, Blastomyces dermatitidis, Coccidioides immitis, Penicillium* species, *Micropolyspora faeni, Thermoactinomyces vulgaris, Alternaria alternate, Cladosporium* species, *Helminthosporium*, and *Stachybotrys* species.

The rAAV may include genes encoding antibodies, and particularly neutralizing antibodies, against pathogenic factors of diseases such as Alzheimer's disease (AD), Parkinson's disease (PD), GBA-Parkinson's, Rheumatoid arthritis (RA), Irritable bowel syndrome (IBS), chronic obstructive pulmonary disease (COPD), cancers, tumors, systemic sclerosis, asthma and other diseases. Such antibodies may be, without limitation, e.g., alpha-synuclein, anti-vascular endothelial growth factor (VEGF) (anti-VEGF), anti-VEGFA, anti-PD-1, anti-PDL1, anti-CTLA-4, anti-TNF-alpha, anti-IL-17, anti-IL-23, anti-IL-21, anti-IL-6, anti-IL-6 receptor, anti-IL-5, anti-IL-7, anti-Factor XII, anti-IL-2, anti-HIV, anti-IgE, anti-tumour necrosis factor receptor-1 (TNFR1), anti-notch 2/3, anti-notch 1, anti-OX40, anti-erb-b2 receptor tyrosine kinase 3 (ErbB3), anti-ErbB2, anti-beta cell maturation antigen, anti-B lymphocyte stimulator, anti-CD20, anti-HER2, anti-granulocyte macrophage colony-stimulating factor, anti-oncostatin M (OSM), anti-lymphocyte activation gene 3 (LAG3) protein, anti-CCL20, anti-serum amyloid P component (SAP), anti-prolyl hydroxylase inhibitor, anti-CD38, anti-glycoprotein IIb/IIIa, anti-CD52, anti-CD30, anti-IL-lbeta, anti-epidermal growth factor receptor, anti-CD25, anti-RANK ligand, anti-complement system protein C5, anti-CD11a, anti-CD3 receptor, anti-alpha-4 ($\alpha$4) integrin, anti-RSV F protein, and anti-integrin $\alpha_4\beta_7$. Still other pathogens and diseases will be apparent to one of skill in the art. Other suitable antibodies may include those useful for treating Alzheimer's Disease, such as, e.g., anti-beta-amyloid (e.g., crenezumab, solanezumab, aducanumab), anti-beta-amyloid fibril, anti-beta-amyloid plaques, anti-tau, a bapineuzamab, among others. Other suitable antibodies for treating a variety of indications include those described, e.g., in PCT/US2016/058968, filed 27 Oct. 2016, published as WO 2017/075119A1.

II. rAAV Vector Production

For use in producing an AAV viral vector (e.g., a recombinant (r) AAV), the expression cassettes can be carried on any suitable vector, e.g., a plasmid, which is delivered to a packaging host cell. The plasmids useful in this invention may be engineered such that they are suitable for replication and packaging in vitro in prokaryotic cells, insect cells, mammalian cells, among others. Suitable transfection techniques and packaging host cells are known and/or can be readily designed by one of skill in the art.

Methods for generating and isolating AAVs suitable for use as vectors are known in the art. See generally, e.g., Grieger & Samulski, 2005, "Adeno-associated virus as a gene therapy vector: Vector development, production and clinical applications," *Adv. Biochem. Engin/Biotechnol.* 99: 119-145; Buning et al., 2008, "Recent developments in adeno-associated virus vector technology," *J. Gene Med.* 10:717-733; and the references cited below, each of which is incorporated herein by reference in its entirety. For packaging a gene into virions, the ITRs are the only AAV components required in cis in the same construct as the nucleic acid molecule containing the expression cassette(s). The cap and rep genes can be supplied in trans.

In one embodiment, the expression cassettes described herein are engineered into a genetic element (e.g., a shuttle plasmid) which transfers the immunoglobulin construct sequences carried thereon into a packaging host cell for production a viral vector. In one embodiment, the selected genetic element may be delivered to an AAV packaging cell by any suitable method, including transfection, electroporation, liposome delivery, membrane fusion techniques, high velocity DNA-coated pellets, viral infection and protoplast fusion. Stable AAV packaging cells can also be made. Alternatively, the expression cassettes may be used to generate a viral vector other than AAV, or for production of mixtures of antibodies in vitro. The methods used to make such constructs are known to those with skill in nucleic acid manipulation and include genetic engineering, recombinant engineering, and synthetic techniques. See, e.g., Molecular Cloning: A Laboratory Manual, ed. Green and Sambrook, Cold Spring Harbor Press, Cold Spring Harbor, NY (2012).

The term "AAV intermediate" or "AAV vector intermediate" refers to an assembled rAAV capsid which lacks the desired genomic sequences packaged therein. These may also be termed an "empty" capsid. Such a capsid may contain no detectable genomic sequences of an expression cassette, or only partially packaged genomic sequences which are insufficient to achieve expression of the gene product. These empty capsids are non-functional to transfer the gene of interest to a host cell.

The recombinant adeno-associated virus (AAV) described herein may be generated using techniques which are known. See. e.g., WO 2003/042397; WO 2005/033321, WO 2006/110689; U.S. Pat. No. 7,588,772 B2. Such a method involves culturing a host cell which contains a nucleic acid sequence encoding an AAV capsid protein; a functional rep gene; an expression cassette composed of, at a minimum, AAV inverted terminal repeats (ITRs) and a transgene; and sufficient helper functions to permit packaging of the expression cassette into the AAV capsid protein. Methods of generating the capsid, coding sequences therefor, and methods for production of rAAV viral vectors have been described. See. e.g., Gao, et al, Proc. Natl. Acad. Sci. U.S.A. 100 (10), 6081-6086 (2003) and US 2013/0045186A1.

In one embodiment, a production cell culture useful for producing a recombinant AAVhu68 is provided. Such a cell culture contains a nucleic acid which expresses the AAVhu68 capsid protein in the host cell; a nucleic acid molecule suitable for packaging into the AAVhu68 capsid, e.g., a vector genome which contains AAV ITRs and a non-AAV nucleic acid sequence encoding a gene product operably linked to sequences which direct expression of the product in a host cell; and sufficient AAV rep functions and adenovirus helper functions to permit packaging of the nucleic acid molecule into the recombinant AAVhu68 capsid. In one embodiment, the cell culture is composed of mammalian cells (e.g., human embryonic kidney 293 cells, among others) or insect cells (e.g., baculovirus).

Optionally the rep functions are provided by an AAV other than hu68. In certain embodiments, at least parts of the rep functions are from AAVhu68. See, e.g., the rep sequences encode the rep proteins of SEQ ID NO: 4, and functional fragments thereof. The AAV rep may be encoded by the nucleic acid sequence of SEQ ID NO: 3. In another embodiment, the rep protein is a heterologous rep protein other than AAVhu68rep, for example but not limited to, AAV1 rep protein, AAV2 rep protein, AAV3 rep protein, AAV4 rep protein, AAV5 rep protein, AAV6 rep protein, AAV7 rep protein, AAV8 rep protein; or rep 78, rep 68, rep 52, rep 40, rep68/78 and rep40/52; or a fragment thereof; or another source. Optionally, the rep and cap sequences are on the same genetic element in the cell culture. There may be a spacer between the rep sequence and cap gene. Optionally, the spacer is atgacttaaaccaggt, SEQ ID NO: 9. Any of these AAVhu68 or mutant AAV capsid sequences may be under the control of exogenous regulatory control sequences which direct expression thereof in a host cell.

In one embodiment, cells are manufactured in a suitable cell culture (e.g., HEK 293) cells. Methods for manufacturing the gene therapy vectors described herein include methods well known in the art such as generation of plasmid DNA used for production of the gene therapy vectors, generation of the vectors, and purification of the vectors. In some embodiments, the gene therapy vector is an AAV vector and the plasmids generated are an AAV cis-plasmid encoding the AAV genome and the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest. In yet another system, the gene therapy vectors are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

The crude cell harvest may thereafter be subject method steps such as concentration of the vector harvest, diafiltration of the vector harvest, microfluidization of the vector harvest, nuclease digestion of the vector harvest, filtration of microfluidized intermediate, crude purification by chromatography, crude purification by ultracentrifugation, buffer exchange by tangential flow filtration, and/or formulation and filtration to prepare bulk vector.

A two-step affinity chromatography purification at high salt concentration followed anion exchange resin chromatography are used to purify the vector drug product and to remove empty capsids. These methods are described in more detail in International Patent Application No. PCT/US2016/065970, filed Dec. 9, 2016 and its priority documents, US Patent Application Nos. 62/322,071, filed Apr. 13, 2016 and 62/226,357, filed Dec. 11, 2015 and entitled "Scalable Purification Method for AAV9", which is incorporated by reference herein. Purification methods for AAV8, International Patent Application No. PCT/US2016/065976, filed Dec. 9, 2016 and its priority documents US Patent Application Nos. 62/322,098, filed Apr. 13, 2016 and 62/266,341, filed Dec. 11, 2015, and rh10, International Patent Application No. PCT/US16/66013, filed Dec. 9, 2016 and its priority documents, U.S. Patent Application No. 62/322,055, filed Apr. 13, 2016 and 62/266,347, entitled "Scalable Purification Method for AAVrh10", also filed Dec. 11, 2015, and for AAV1, International Patent Application No. PCT/US2016/065974, filed Dec. 9, 2016 and its priority documents US Patent Application Nos. 62/322,083, filed Apr. 13, 2016 and 62/26,351, for "Scalable Purification Method for AAV1", filed Dec. 11, 2015, are all incorporated by reference herein.

To calculate empty and full particle content, VP3 band volumes for a selected sample (e.g., in examples herein an iodixanol gradient-purified preparation where # of GC=# of particles) are plotted against GC particles loaded. The resulting linear equation (y=mx+c) is used to calculate the number of particles in the band volumes of the test article peaks. The number of particles (pt) per 20 μL loaded is then multiplied by 50 to give particles (pt)/mL. Pt/mL divided by GC/mL gives the ratio of particles to genome copies (pt/GC). Pt/mL-GC/mL gives empty pt/mL. Empty pt/mL divided by pt/mL and ×100 gives the percentage of empty particles.

Generally, methods for assaying for empty capsids and AAV vector particles with packaged genomes have been known in the art. See, e.g., Grimm et al., *Gene Therapy*

(1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., *J. Virol.* (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions or other suitable staining method, i.e. SYPRO ruby or coomassie stains. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is used which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

In brief, the method for separating rAAVhu68 particles having packaged genomic sequences from genome-deficient AAVhu68 intermediates involves subjecting a suspension comprising recombinant AAVhu68 viral particles and AAVhu689 capsid intermediates to fast performance liquid chromatography, wherein the AAVhu68 viral particles and AAVhu68 intermediates are bound to a strong anion exchange resin equilibrated at a pH of 10.2, and subjected to a salt gradient while monitoring eluate for ultraviolet absorbance at about 260 and about 280. Although less optimal for rAAV9hu68, the pH may be in the range of about 10.0 to 10.4. In this method, the AAVhu68 full capsids are collected from a fraction which is eluted when the ratio of A260/A280 reaches an inflection point. In one example, for the Affinity Chromatography step, the diafiltered product may be applied to a Capture Select™ Poros-AAV2/9 affinity resin (Life Technologies) that efficiently captures the AAV2/hu68 serotype. Under these ionic conditions, a significant percentage of residual cellular DNA and proteins flow through the column, while AAV particles are efficiently captured.

III. Compositions and Uses

Provided herein are compositions containing at least one rAAV stock (e.g., an rAAVhu68 stock or a mutant rAAV stock) and an optional carrier, excipient and/or preservative. An rAAV stock refers to a plurality of rAAV vectors which are the same, e.g., such as in the amounts described below in the discussion of concentrations and dosage units.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host. Delivery vehicles such as liposomes, nanocapsules, microparticles, microspheres, lipid particles, vesicles, and the like, may be used for the introduction of the compositions of the present invention into suitable host cells. In particular, the rAAV vector delivered vector genomes may be formulated for delivery either encapsulated in a lipid particle, a liposome, a vesicle, a nanosphere, or a nanoparticle or the like.

In one embodiment, a composition includes a final formulation suitable for delivery to a subject, e.g., is an aqueous liquid suspension buffered to a physiologically compatible pH and salt concentration. Optionally, one or more surfactants are present in the formulation. In another embodiment, the composition may be transported as a concentrate which is diluted for administration to a subject. In other embodiments, the composition may be lyophilized and reconstituted at the time of administration.

A suitable surfactant, or combination of surfactants, may be selected from among non-ionic surfactants that are nontoxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxy-propylene (poly(propylene oxide)) flanked by two hydro-philic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodi-ment, the formulation contains a poloxamer. These copoly-mers are commonly named with the letter "P" (for polox-amer) followed by three digits: the first two digits×100 give the approximate molecular mass of the polyoxypropylene core, and the last digit×10 gives the percentage polyoxyeth-ylene content. In one embodiment Poloxamer 188 is selected. The surfactant may be present in an amount up to about 0.0005% to about 0.001% of the suspension.

The vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceuti-cally acceptable routes of administration include, but are not limited to, direct delivery to a desired organ (e.g., the liver (optionally via the hepatic artery), lung, heart, eye, kidney), oral, inhalation, intranasal, intrathecal, intratracheal, intraar-terial, intraocular, intravenous, intramuscular, subcutaneous, intradermal, and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 25 to about 1000 microliters to about 100 mL of solution contain-ing concentrations of from about $1 \times 10^9$ to $1 \times 10^{16}$ genomes virus vector. The dosage will be adjusted to balance the therapeutic benefit against any side effects and such dosages may vary depending upon the therapeutic application for which the recombinant vector is employed. The levels of expression of the transgene product can be monitored to determine the frequency of dosage resulting in viral vectors, preferably AAV vectors containing the minigene. Option-ally, dosage regimens similar to those described for thera-peutic purposes may be utilized for immunization using the compositions of the invention.

The replication-defective virus compositions can be for-mulated in dosage units to contain an amount of replication-defective virus that is in the range of about $1.0 \times 10^9$ GC to about $1.0 \times 10^{16}$ GC (to treat an average subject of 70 kg in body weight) including all integers or fractional amounts within the range, and preferably $1.0 \times 10^{12}$ GC to $1.0 \times 10^{14}$ GC for a human patient. In one embodiment, the composi-tions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, or $9 \times 10^{11}$ GC per dose including all integers or fractional amounts within the range. In another embodi-ment, the compositions are formulated to contain at least $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per dose including all integers or fractional amounts within the range. In another embodiment, the compositions are formulated to contain at least $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $1 \times 0^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $1 \times 10^{10}$ to about $1 \times 10^{12}$ GC per dose including all integers or fractional amounts within the range.

These above doses may be administered in a variety of volumes of carrier, excipient or buffer formulation, ranging from about 25 to about 1000 microliters, or higher volumes, including all numbers within the range, depending on the size of the area to be treated, the viral titer used, the route of administration, and the desired effect of the method. In one embodiment, the volume of carrier, excipient or buffer is at least about 25 µL. In one embodiment, the volume is about 50 µL. In another embodiment, the volume is about 75 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 225 µL. In yet another embodiment, the volume is about 250 µL. In yet another embodiment, the volume is about 275 µL. In yet another embodiment, the volume is about 300 µL. In yet another embodiment, the volume is about 325 µL. In another embodiment, the volume is about 350 µL. In another embodiment, the volume is about 375 µL. In another embodiment, the volume is about 400 µL. In another embodiment, the volume is about 450 µL. In another embodiment, the volume is about 500 µL. In another embodiment, the volume is about 550 µL. In another embodiment, the volume is about 600 µL. In another embodiment, the volume is about 650 µL. In another embodiment, the volume is about 700 µL. In another embodiment, the volume is between about 700 and 1000 µL.

In certain embodiments, the dose may be in the range of about $1 \times 10^9$ GC/g brain mass to about $1 \times 10^{12}$ GC/g brain mass. In certain embodiments, the dose may be in the range of about $3 \times 10^{10}$ GC/g brain mass to about $3 \times 10^{11}$ GC/g brain mass. In certain embodiments, the dose may be in the range of about $5 \times 10^{10}$ GC/g brain mass to about $1.85 \times 10^{11}$ GC/g brain mass.

In one embodiment, the viral constructs may be delivered in doses of from at least about least $1 \times 10^9$ GCs to about $1 \times 10^{15}$, or about $1 \times 10^{11}$ to $5 \times 10^{13}$ GC. Suitable volumes for delivery of these doses and concentrations may be deter-mined by one of skill in the art. For example, volumes of about 1 µL to 150 mL may be selected, with the higher volumes being selected for adults. Typically, for newborn infants a suitable volume is about 0.5 mL to about 10 mL, for older infants, about 0.5 mL to about 15 mL may be selected. For toddlers, a volume of about 0.5 mL to about 20 mL may be selected. For children, volumes of up to about 30 mL may be selected. For pre-teens and teens, volumes up to about 50 mL may be selected. In still other embodiments, a patient may receive an intrathecal administration in a vol-ume of about 5 mL to about 15 mL are selected, or about 7.5 mL to about 10 mL. Other suitable volumes and dosages may be determined. The dosage will be adjusted to balance the therapeutic benefit against any side effects and such dosages may vary depending upon the therapeutic applica-tion for which the recombinant vector is employed.

The above-described recombinant vectors may be deliv-ered to host cells according to published methods. The rAAV, preferably suspended in a physiologically compatible carrier, may be administered to a human or non-human mammalian patient. In certain embodiments, for administration to a human patient, the rAAV is suitably suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.5 to 7.5, pH 7.0 to 7.7, or pH 7.2 to 7.8. As the pH of the cerebrospinal fluid is about 7.28 to about 7.32, for intrathecal delivery, a pH within this range may be desired; whereas for intravenous delivery, a pH of about 6.8 to about 7.2 may be desired. However, other pHs within the broadest ranges and these subranges may be selected for other route of delivery.

In another embodiment, the composition includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV, from sticking to the infusion tubing but does not interfere with the rAAV binding activity in vivo. A suitable surfactant, or combination of surfactants, may be selected from among non-ionic surfactants that are nontoxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy-oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension. In one example, the formulation may contain, e.g., buffered saline solution comprising one or more of sodium chloride, sodium bicarbonate, dextrose, magnesium sulfate (e.g., magnesium sulfate·$7H_2O$), potassium chloride, calcium chloride (e.g., calcium chloride·$2H_2O$), dibasic sodium phosphate, and mixtures thereof, in water. Suitably, for intrathecal delivery, the osmolarity is within a range compatible with cerebrospinal fluid (e.g., about 275 to about 290); see, e.g., emedicine.medscape.com/article/2093316-overview. Optionally, for intrathecal delivery, a commercially available diluent may be used as a suspending agent, or in combination with another suspending agent and other optional excipients. See, e.g., Elliotts B® solution [Lukare Medical]. In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The compositions according to the present invention may comprise a pharmaceutically acceptable carrier, such as defined above. Suitably, the compositions described herein comprise an effective amount of one or more AAV suspended in a pharmaceutically suitable carrier and/or admixed with suitable excipients designed for delivery to the subject via injection, osmotic pump, intrathecal catheter, or for delivery by another device or route. In one example, the composition is formulated for intrathecal delivery.

As used herein, the terms "intrathecal delivery" or "intrathecal administration" refer to a route of administration for drugs via an injection into the spinal canal, more specifically into the subarachnoid space so that it reaches the cerebrospinal fluid (CSF). Intrathecal delivery may include lumbar puncture, intraventricular (including intracerebroventricular (ICV)), suboccipital/intracisternal, and/or C1-2 puncture. For example, material may be introduced for diffusion throughout the subarachnoid space by means of lumbar puncture. In another example, injection may be into the cisterna magna.

As used herein, the terms "intracisternal delivery" or "intracisternal administration" refer to a route of administration for drugs directly into the cerebrospinal fluid of the cisterna magna cerebellomedularis, more specifically via a suboccipital puncture or by direct injection into the cisterna magna or via permanently positioned tube.

IV. Apparatus and Method for Delivery of a Pharmaceutical Composition into Cerebrospinal Fluid In one aspect, the vectors provided herein may be administered intrathecally via the method and/or the device provided in this section and described further in FIG. 7. Alternatively, other devices and methods may be selected. The method comprises the steps of advancing a spinal needle into the cisterna magna of a patient, connecting a length of flexible tubing to a proximal hub of the spinal needle and an output port of a valve to a proximal end of the flexible tubing, and after said advancing and connecting steps and after permitting the tubing to be self-primed with the patient's cerebrospinal fluid, connecting a first vessel containing an amount of isotonic solution to a flush inlet port of the valve and thereafter connecting a second vessel containing an amount of a pharmaceutical composition to a vector inlet port of the valve. After connecting the first and second vessels to the valve, a path for fluid flow is opened between the vector inlet port and the outlet port of the valve and the pharmaceutical composition is injected into the patient through the spinal needle, and after injecting the pharmaceutical composition, a path for fluid flow is opened through the flush inlet port and the outlet port of the valve and the isotonic solution is injected into the spinal needle to flush the pharmaceutical composition into the patient.

In another aspect, a device for intracisternal delivery of a pharmaceutical composition is provided. The device includes a first vessel containing an amount of a pharmaceutical composition, a second vessel containing an isotonic solution, and a spinal needle through which the pharmaceutical composition may be ejected from the device directly into cerebrospinal fluid within the cisterna magna of a patient. The device further includes a valve having a first inlet port interconnected to the first vessel, a second inlet port interconnected to the second vessel, an outlet port interconnected to the spinal needle, and a luer lock for controlling flow of the pharmaceutical composition and isotonic solution through the spinal needle.

As used herein, the term Computed Tomography (CT) refers to radiography in which a three-dimensional image of a body structure is constructed by computer from a series of plane cross-sectional images made along an axis.

Figure 7:
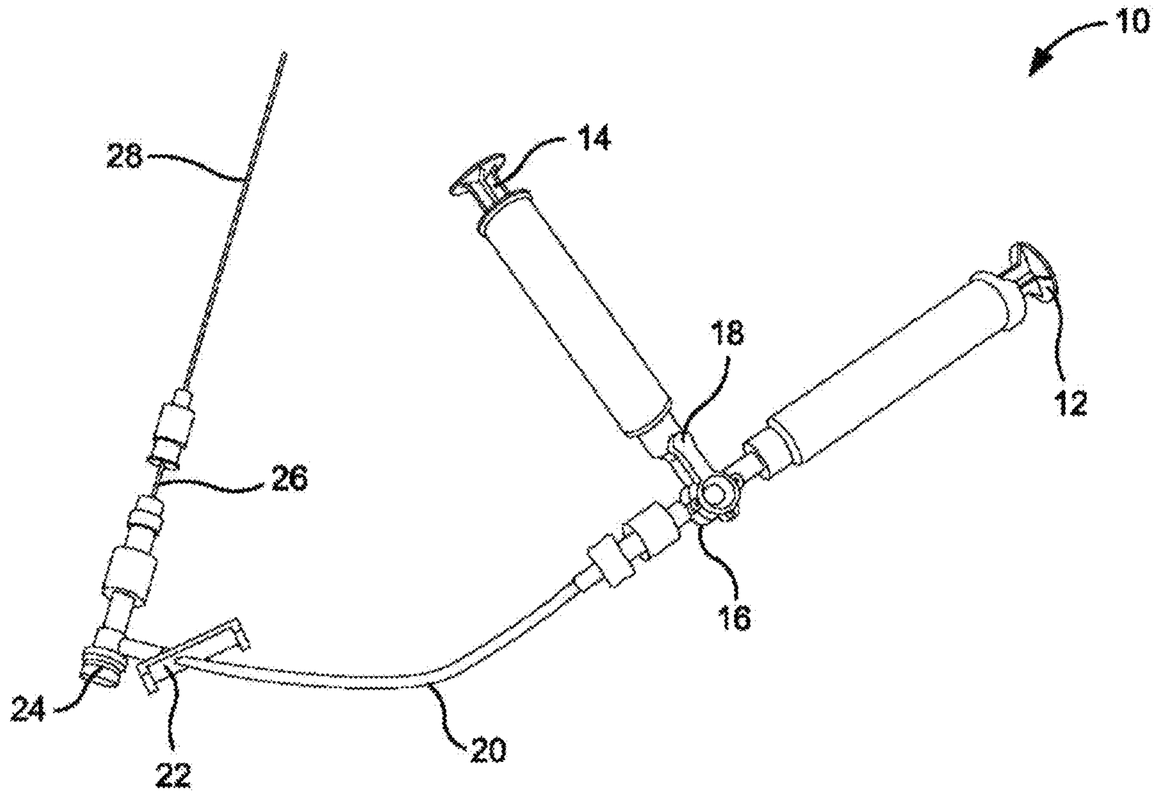
FIG. 7 is an image of an apparatus for intracisternal delivery, including optional introducer needle for coaxial insertion method, which includes a 10 cc vector syringe, a 10 cc prefilled flush syringe, a T-connector extension set, a 22G×5" spinal needle, an optional 18G×3.5" introducer needle.

The apparatus or medical device 10 as shown in FIG. 7 includes one or more vessels, 12 and 14, interconnected via a valve 16. The vessels, 12 and 14, provide a fresh source of a pharmaceutical composition, drug, vector, or like substance and a fresh source of an isotonic solution such as saline, respectively. The vessels, 12 and 14, may be any form of medical device that enables injection of fluids into a patient.

By way of example, each vessel, 12 and 14, may be provided in the form of a syringe, cannula, or the like. For instance, in the illustrated embodiment, the vessel 12 is provided as a separate syringe containing an amount of a pharmaceutical composition and is referred to herein as a "vector syringe". Merely for purposes of example, the vessel 12 may contain about 10 cc of a pharmaceutical composition or the like.

Likewise, the vessel 14 may be provided in the form of a separate syringe, cannula, or the like that contains an amount of saline solution and may be referred to as a "flush syringe". Merely for purposes of example, the vessel 14 may contain about 10 cc of a saline solution.

As an alternative, the vessels 12 and 14 may be provided in forms other than syringes and may be integrated into a single device, such as an integrated medical injection device have a pair of separate chambers, one for the pharmaceutical composition and one for saline solution. Also, the size of the chambers or vessels may be provided as needed to contain a desired amount of fluid.

In the illustrated embodiment, the valve 16 is provided as a 4-way stopcock having a swivel male luer lock 18. The valve 16 interconnects the vessels 12 and 14 (i.e., the vector syringe and flush syringe in the illustrated embodiment), and the swivel male luer lock enables a path through the valve 16 to be closed or opened to each of the vessels 12 and 14. In this way, the path through the valve 16 may be closed to both the vector syringe and flush syringe or may be open to a selected one of the vector syringe and flush syringe. As an alternative to a 4-way stopcock, the valve may be a 3-way stopcock or fluid control device.

In the illustrated embodiment, the valve 16 is connected to one end of a length of extension tubing 20 or the like conduit for fluid. The tubing 20 may be selected based on a desired length or internal volume. Merely by way of example, the tubing may be about 6 to 7 inches in length.

In the illustrated embodiment, an opposite end 22 of the tubing 12 is connected to a T-connector extension set 24 which, in turn, is connected to a spinal needle 26. By way of example, the needle 26 may be a five inch, 22 or 25 gauge spinal needle. In addition, as an option, the spinal needle 26 may be connected to an introducer needle 28, such as a three and a half inch, 18 gauge introducer needle.

In use, the spinal needle 26 and/or optional introducer needle 28 may be advanced into a patient towards the cisterna magna. After needle advancement, Computed Tomography (CT) images may be obtained that permit visualization of the needle 26 and/or 28 and relevant soft tissues (e.g., paraspinal muscles, bone, brainstem, and spinal cord). Correct needle placement is confirmed by observation of Cerebrospinal Fluid (CSF) in the needle hub and visualization of a needle tip within the cisterna magna. Thereafter, the relatively short extension tubing 20 may be attached to the inserted spinal needle 26, and the 4-way stopcock 16 may then be attached to the opposite end of the tubing 20.

The above assembly is permitted to become "self-primed" with the patient's CSF. Thereafter, the prefilled normal saline flush syringe 14 is attached to a flush inlet port of the 4-way stopcock 16 and then the vector syringe 12 containing a pharmaceutical composition is attached to a vector inlet port of the 4-way stopcock 16. Thereafter, the output port of the stopcock 16 is opened to the vector syringe 12, and the contents of the vector syringe may be slowly injected through the valve 16 and assembled apparatus and into the patient over a period of time. Merely for purposes of example, this period of time may be approximately 1-2 minutes and/or any other time of desire.

After the contents of the vector syringe 12 are injected, the swivel lock 18 on the stopcock 16 is turned to a second position so that the stopcock 16 and needle assembly can be flushed with a desired amount of normal saline using the attached prefilled flush syringe 14. Merely by way of example, 1 to 2 cc of normal saline may be used; although greater or lesser amounts may be used as needed. The normal saline ensures that all or most of the pharmaceutical composition is forced to be injected through the assembled device and into the patient and so that little or none of the pharmaceutical composition remains in the assembled device.

After the assembled device has been flushed with the saline, the assembled device in its entirely, including the needle(s), extension tubing, stopcock, and syringes are slowly removed from the subject and placed onto a surgical tray for discarding into a biohazard waste receptacle or hard container (for the needle(s)).

A screening process may be undertaken by a principal investigator which may ultimately lead to an intracisternal (IC) procedure. The principal investigator may describe the process, procedure, the administration procedure itself, and all potential safety risks in order for the subject (or designated caregiver) to be fully informed. Medical history, concomitant medications, physical exam, vital signs, electrocardiogram (ECG), and laboratory testing results are obtained or performed and provided to a neuroradiologist, neurosurgeon, and anesthesiologist for use in screening assessment of subject eligibility for the IC procedure.

To allow adequate time to review eligibility, the following procedures may be performed at any time between the first screening visit and up to one week prior to a study visit. For example, on "Day 0", Head/Neck Magnetic Resonance Imaging (MRI) with and without gadolinium (i.e., eGFR>30 mL/min/1.73 m2) may be obtained. In addition to the Head/Neck MRI, the investigator may determine the need for any further evaluation of the neck via flexion/extension studies. The MRI protocol may include T1, T2, DTI, FLAIR, and CINE protocol images.

In addition, Head/Neck MRA/MRV may be obtained as per institutional protocol (i.e., subjects with a history of intra/transdural operations may be excluded or may need further testing (e.g., radionucleotide cisternography)) that allows for adequate evaluation of CSF flow and identification of possible blockage or lack of communication between CSF spaces.

The neuroradiologist, neurosurgeon, and anesthesiologist ultimately discuss and determine the eligibility of each subject for the IC procedures based on all available information (scans, medical history, physical exam, labs, etc.). An Anesthesia pre-op evaluation may also be obtained from "Day −28" to "Day 1" that provides a detailed assessment of airway, neck (shortened/thickened) and head range-of-motion (degree of neck flexion), keeping in mind the special physiologic needs of a MPS subject.

Prior to an IC procedure, the CT Suite will confirm the following equipment and medications are present: Adult lumbar puncture (LP) kit (supplied per institution); BD (Becton Dickinson) 22 or 25 gauge×3-7" spinal needle (Quincke bevel); Coaxial introducer needle, used at the discretion of the interventionalist (for introduction of spinal needle); 4 way small bore stopcock with swivel (Spin) male luer lock; T-connector extension set (tubing) with female luer lock adapter, approximate length of 6.7 inches; Omnipaque 180 (iohexol), for intrathecal administration; Iodinated contrast for intravenous (IV) administration; 1% lidocaine solution for injection (if not supplied in adult LP kit); Prefilled 10 cc normal saline (sterile) flush syringe; Radiopaque marker(s); Surgical prep equipment/shaving razor; Pillows/supports to allow proper positioning of intubated subject; Endotracheal intubation equipment, general anesthesia machine and mechanical ventilator; Intraoperative neurophysiological monitoring (IONM) equipment (and required personnel); and 10 cc syringe containing vector; prepared and transported to CT/Operating Room (OR) suite in accordance with separate Pharmacy Manual.

Informed Consent for the procedure are confirmed and documented within the medical record and/or study file. Separate consent for the procedure from radiology and anesthesiology staff is obtained as per institutional requirements. Subject has intravenous access placed within the appropriate hospital care unit according to institutional guidelines (e.g., two IV access sites). Intravenous fluids are administered at the discretion of the anesthesiologist. At the discretion of the anesthesiologist and per institutional guidelines, subject may be induced and undergo endotracheal intubation with administration of general anesthesia in an appropriate patient care unit, holding area or the surgical/CT procedure suite.

A lumbar puncture is performed, first to remove 5 cc of cerebrospinal fluid (CSF) and subsequently to inject contrast (Omnipaque 180) intrathecally to aid visualization of the cisterna magna. Appropriate subject positioning maneuvers may be performed to facilitate diffusion of contrast into the cisterna magna.

Intraoperative neurophysiological monitoring (IONM) equipment is attached to the subject. Subject is placed onto the CT scanner table in the prone or lateral decubitus position. Adequate staff must be present to assure subject safety during transport and positioning. If deemed appropriate, subject may be positioned in a manner that provides neck flexion to the degree determined to be safe during pre-operative evaluation and with normal neurophysiologic monitor signals documented after positioning.

The following staff may be confirmed to be present and identified on-site: Interventionalist/neurosurgeon performing the procedure; Anesthesiologist and respiratory technician(s); Nurses and physician assistants; CT (or OR) technicians; Neurophysiology technician; and Site Coordinator. A "time-out" may be completed per Joint Commission/hospital protocol to verify correct subject, procedure, site, positioning, and presence of all necessary equipment in the room. The lead site investigator may then confirm with staff that he/she may proceed with prepping the subject.

The subject's skin under the skull base is shaved as appropriate. CT scout images are performed, followed by a pre-procedure planning CT with IV contrast, if deemed necessary by the interventionalist to localize the target location and to image vasculature. After the target site (cisterna magna) is identified and needle trajectory planned, the skin is prepped and draped using sterile technique as per institutional guidelines. A radiopaque marker is placed on the target skin location as indicated by the interventionalist. The skin under the marker is anesthetized via infiltration with 1% lidocaine. A 22G or 25G spinal needle is than advanced towards the cisterna magna, with the option to use a coaxial introducer needle.

After needle advancement, CT images are obtained using the thinnest CT slice thickness feasible using institutional equipment (ideally ≤2.5 mm). Serial CT images using the lowest radiation dose possible that allows for adequate visualization of the needle and relevant soft tissues (e.g., paraspinal muscles, bone, brainstem, and spinal cord) are obtained. Correct needle placement is confirmed by observation of CSF in the needle hub and visualization of needle tip within the cisterna magna.

The interventionalist confirms that the vector syringe is positioned close to, but outside of the sterile field. Prior to handling or administering the pharmaceutical composition in the vector syringe, gloves, mask, and eye protection are donned by staff assisting the procedure within the sterile field.

The extension tubing is attached to the inserted spinal needle, which is then attached to the 4-way stopcock. Once this apparatus is "self-primed" with the subject's CSF, the 10 cc prefilled normal saline flush syringe is attached to a flush inlet port of the 4-way stopcock. The vector syringe is then provided to the interventionalist and attached to a vector inlet port on the 4-way stop cock.

After the outlet port of the stopcock is opened to the vector syringe by placing the swivel lock of the stopcock in a first position, the contents of the vector syringe are injected slowly (over approximately 1-2 minutes), with care taken not to apply excessive force onto the plunger of the syringe during the injection. After the contents of the vector syringe are injected, the swivel lock of stopcock is turned to a second position so that the stopcock and needle assembly can be flushed with 1-2 cc of normal saline using the attached prefilled flush syringe.

When ready, the interventionist then alerts staff that he/she will remove the apparatus from the subject. In a single motion, the needle, extension tubing, stopcock, and syringes are slowly removed from the subject and placed onto a surgical tray for discarding into a biohazard waste receptacle or hard container (for the needle).

The needle insertion site is examined for signs of bleeding or CSF leakage and treated as indicated by the investigator. Site is dressed using gauze, surgical tape and/or Tegaderm dressing, as indicated. Subject is then removed from the CT scanner and placed supine onto a stretcher. Adequate staff is present to assure subject safety during transport and positioning.

Anesthesia is discontinued and subject cared for following institutional guidelines for post-anesthesia care. Neurophysiologic monitors are removed from the subject. The head of the stretcher on which the subject lies should be slightly raised (~30 degrees) during recovery. Subject is transported to a suitable post-anesthesia care unit as per institutional guidelines. After subject has adequately recovered consciousness and is in stable condition, he/she will be admitted to the appropriate floor/unit for protocol mandated assessments. Neurological assessments will be followed as per the protocol and the Primary Investigator oversees subject care in collaboration with hospital and research staff.

In one embodiment, a method for delivery of a composition provided herein comprises the steps of: advancing a spinal needle into the cisterna magna of a patient; connecting a length of flexible tubing to a proximal hub of the spinal needle and an output port of a valve to a proximal end of the flexible tubing; after said advancing and connecting steps and after permitting the tubing to be self-primed with the patient's cerebrospinal fluid, connecting a first vessel containing an amount of isotonic solution to a flush inlet port of the valve and thereafter connecting a second vessel containing an amount of a pharmaceutical composition to a vector inlet port of the valve; after connecting said first and second vessels to the valve, opening a path for fluid flow between the vector inlet port and the outlet port of the valve and injecting the pharmaceutical composition into the patient through the spinal needle; and after injecting the pharmaceutical composition, opening a path for fluid flow through the flush inlet port and the outlet port of the valve and injecting the isotonic solution into the spinal needle to flush the pharmaceutical composition into the patient. In certain embodiment, the method further comprises confirming proper placement of a distal tip of the spinal needle within the cisterna magna before connecting the tubing and valve to the hub of the spinal needle. In certain embodiments, the confirming step includes visualizing the distal tip of the spinal needle within the cisterna magna with Computed Tomography (CT) imaging. In certain embodiments, the confirming step includes observing the presence of the patient's cerebrospinal fluid in the hub of the spinal needle.

In the above-described method, the valve may be a stopcock with a swivel luer lock adapted to swivel to a first position permitting flow from the vector inlet port to the outlet port while simultaneously blocking flow through the flush inlet port and to a second position permitting flow from the flush inlet port to the outlet port while simultaneously blocking flow through the vector inlet port, and wherein the swivel luer lock is positioned into said first position when said pharmaceutical composition is injected the patient and is positioned into said second position when said pharmaceutical composition is being flushed into said patient by the isotonic solution. In certain embodiments, after injecting the isotonic solution into the spinal needle to flush the pharmaceutical composition into the patient, the spinal needle is withdrawn from the patient with the tubing, valve, and first and second vessels connected thereto as an assembly. In certain embodiments, the valve is a 4-way stopcock with a swivel male luer lock. In certain embodiments, the first and second vessels are separate syringes. In certain embodiments, a T-connector is located at the hub of the spinal needle and interconnects the tubing to the spinal needle. Optionally, the spinal needle includes an introducer needle at the distal end of the spinal needle. The spinal needle may be a five inch, 22 or 24 gauge spinal needle. In certain embodiments, the introducer needle is a 3.5 inch, 18 gauge introducer needle.

In certain aspects, the method utilizes a device which is composed of, at a minimum, a first vessel for containing an amount of a pharmaceutical composition; a second vessel for containing an isotonic solution; a spinal needle through which the pharmaceutical composition may be ejected from the device directly into cerebrospinal fluid within the cisterna magna of a patient; and a valve having a first inlet port interconnected to the first vessel, a second inlet port interconnected to the second vessel, an outlet port interconnected to the spinal needle, and a luer lock for controlling flow of the pharmaceutical composition and isotonic solution through the spinal needle. In certain embodiments, the valve is a stopcock with a swivel luer lock adapted to swivel to a first position permitting flow from the first inlet port to the outlet port while simultaneously blocking flow through the second inlet port and to a second position permitting flow from the second inlet port to the outlet port while simultaneously blocking flow through the first inlet port. Optionally, the valve is a 4-way stopcock with a swivel male luer lock. In certain embodiments, the first and second vessels are separate syringes. In certain embodiments, the spinal needle is interconnected to the valve via a length of flexible tubing. A T-connector may interconnect the tubing to the spinal needle. In certain embodiments, the spinal needle is a five inch, 22 or 24 gauge spinal needle. In certain embodiments, the device further comprises an introducer needle connected to a distal end of the spinal needle. Optionally, the introducer needle is a 3.5 inch, 18 gauge introducer needle.

This method and this device may each optionally be used for intrathecal delivery of the compositions provided herein. Alternatively, other methods and devices may be used for such intrathecal delivery.

In certain embodiments, a composition is provided which comprises the rAAVhu68.anti-HER2 antibody so that AAV vectors carry the nucleic acid expression cassettes encoding the immunoglobulin constructs and regulatory sequences which direct expression of the immunoglobulin thereof in the selected cell. Following administration of the vectors into the CNS, the vectors deliver the expression cassettes to the CNS and express the proteinaceous immunoglobulin constructs in vivo. The use of compositions described herein in an anti-neoplastic method are described, as are uses of these compositions in anti-neoplastic regimens, which may optionally involve delivery of one or more other anti-neoplastic or other active agents.

A composition may contain a single type of AAVhu68 vector as described herein which contains the expression cassette for delivering the anti-neoplastic immunoglobulin construct in vivo. Alternatively, a composition may contain two or more different AAV vectors, each of which has packaged therein different expression cassettes. For example, the two or more different AAV may have different expression cassettes which express immunoglobulin polypeptides which assemble in vivo to form a single functional immunoglobulin construct. In another example, the two or more AAV may have different expression cassettes which express immunoglobulin polypeptides for different targets, e.g., two provide for two functional immunoglobulin constructs (e.g., an anti-Her2 immunoglobulin construct and a second anti-neoplastic immunoglobulin construct). In still another alternative, the two or more different AAV may express immunoglobulin constructs directed to the same target, wherein one of the immunoglobulin constructs has been modified to ablate FcRn binding and a second immunoglobulin construct which retains its ability or has enhanced ability to bind to FcRn. Such a composition may be useful to simultaneously provide antibodies with increased retention in the brain area and antibodies for systemic delivery of the immunoglobulin construct.

Optionally, one or both of these immunoglobulin constructs described herein has enhanced ADCC activity. A regimen as described herein may comprise, in addition to one or more of the combinations described herein, further combination with one or more of an anti-neoplastic biological drug, an anti-neoplastic small molecule drug, a chemotherapeutic agent, immune enhancers, radiation, surgery, and the like. A biological drug as described herein, is based on a peptide, polypeptide, protein, enzyme, nucleic acid molecule, vector (including viral vectors), or the like.

Suitably, the compositions described herein comprise an anti-neoplastic effective amount of one or more AAVhu68 suspended in a pharmaceutically suitable carrier designed for delivery to the subject via injection, osmotic pump, intrathecal catheter, or for delivery by another device or route. In one example, the composition is formulated for intrathecal delivery. As used herein, intrathecal delivery encompasses an injection into the spinal canal, more specifically into the subarachnoid space. However, other routes of delivery may be selected and the pharmaceutically acceptable carriers for the AAV compositions including, e.g., intracranial, intranasal, intracisternal, intracerebrospinal fluid delivery, among other suitable direct or systemic routes, i.e. Ommaya reservoir.

The compositions can be formulated in dosage units to contain an amount of AAV that is in the range of about $1\times10^9$ genome copies (GC) to about $5\times10^{13}$ GC (to treat an average subject of 70 kg in body weight). In one embodiment, a spinal tap is performed in which from about 15 mL (or less) to about 40 mL CSF is removed and in which vector is admixed with the CSF and/or suspended in a compatible carrier and delivered to the subject. In one example, the vector concentration is about $3\times10^{13}$ GC, but other amounts such as about $1\times10^9$ GC, about $5\times10^9$ GC, about $1\times10^{10}$ GC, about $5\times10^{10}$ GC, about $1\times10^{11}$ GC, about $5\times10^{11}$ GC, about $1\times10^{12}$ GC, about $5\times10^{12}$ GC, or about $1.0\times10^{13}$ GC.

In one embodiment, the compositions described herein are used in a method for retarding the growth of a tumor. In still another embodiment, the compositions described herein are useful for decreasing tumor size in a subject. In a further embodiment, the compositions described herein are useful in reducing the number of cancer cells in a non-solid tumor cancer. In another embodiment, a composition as provided herein is used in a method for increasing overall survival and/or progression-free survival in a patient. The anti-neoplastic immunoglobulin constructs are selected with a view to the neoplasm to be treated. For example, for treatment of a metastatic breast cancer in the brain, one may engineer an expression cassette for an anti-HER antibody into a recombinant AAV as described herein. Optionally, the AAV compositions as described herein are administered in the absence of an additional extrinsic pharmacological or chemical agent, or other physical disruption of the blood brain barrier. In a combination therapy, the AAV-delivered immunoglobulin construct described herein is administered before, during, or after commencing therapy with another agent, as well as any combination thereof, i.e., before and during, before and after, during and after, or before, during and after commencing the anti-neoplastic therapy. For example, the AAV can be administered between 1 and 30 days, preferably 3 and 20 days, more preferably between 5 and 12 days before commencing radiation therapy. In another embodiment of the invention, chemotherapy is administered concurrently with or, more preferably, subsequent to AAV-mediated immunoglobulin (antibody) therapy. In still other embodiments, the compositions of the invention may be combined with other biologics, e.g., recombinant monoclonal antibody drugs, antibody-drug conjugates, or the like. Further, combinations of different AAV-delivered immunoglobulin constructs such as are discussed above may be used in such regimens. Any suitable method or route can be used to administer an AAVhu68.anti-Her2-containing composition as described herein, and optionally, to co-administer anti-neoplastic agents and/or antagonists of other receptors. The anti-neoplastic agent regimens utilized according to the invention, include any regimen believed to be optimally suitable for the treatment of the patient's neoplastic condition. Different malignancies can require use of specific antitumor antibodies and specific anti-neoplastic agents, which will be determined on a patient to patient basis. Routes of administration include, for example, systemic, oral, intravenous, intraperitoneal, subcutaneous, or intramuscular administration. The dose of antagonist administered depends on numerous factors, including, for example, the type of antagonists, the type and severity tumor being treated and the route of administration of the antagonists.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% (±10%) from the reference given, unless otherwise specified.

As used herein, "disease", "disorder" and "condition" are used interchangeably, to indicate an abnormal state in a subject.

Unless defined otherwise in this specification, technical and scientific terms used herein have the same meaning as commonly understood by one of ordinary skill in the art and by reference to published texts, which provide one skilled in the art with a general guide to many of the terms used in the present application.

The term "expression" is used herein in its broadest meaning and comprises the production of RNA or of RNA and protein. With respect to RNA, the term "expression" or "translation" relates in particular to the production of peptides or proteins. Expression may be transient or may be stable.

As used herein, the term "NAb titer" a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199(3): p. 381-390, which is incorporated by reference herein.

As used herein, an "expression cassette" refers to a nucleic acid molecule which comprises a coding sequence, promoter, and may include other regulatory sequences therefor. In certain embodiments, a vector genome may contain two or more expression cassettes. In other embodiments, the term "transgene" may be used interchangeably with "expression cassette". Typically, such an expression cassette for generating a viral vector contains the coding sequence for the gene product described herein flanked by packaging signals of the viral genome and other expression control sequences such as those described herein.

The abbreviation "sc" refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See. e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

As used herein, the term "operably linked" refers to both expression control sequences that are contiguous with the gene of interest and expression control sequences that act in trans or at a distance to control the gene of interest.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the gene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

In many instances, rAAV particles are referred to as DNase resistant. However, in addition to this endonuclease (DNase), other endo- and exo-nucleases may also be used in the purification steps described herein, to remove contaminating nucleic acids. Such nucleases may be selected to degrade single stranded DNA and/or double-stranded DNA, and RNA. Such steps may contain a single nuclease, or mixtures of nucleases directed to different targets, and may be endonucleases or exonucleases.

The term "nuclease-resistant" indicates that the AAV capsid has fully assembled around the expression cassette which is designed to deliver a gene to a host cell and protects these packaged genomic sequences from degradation (digestion) during nuclease incubation steps designed to remove contaminating nucleic acids which may be present from the production process.

As used herein, an "effective amount" refers to the amount of the rAAV composition which delivers and expresses in the target cells an amount of the gene product from the vector genome. An effective amount may be determined based on an animal model, rather than a human patient. Examples of a suitable murine model are described herein.

In certain embodiments, a rAAV or composition as provided herein excludes an anti-influenza antibody or immunoglobulin construct. In certain embodiments, a rAAV or composition as provided herein excludes an spinal muscular atrophy (SMA) gene or SMN coding sequence.

The term "translation" in the context of the present invention relates to a process at the ribosome, wherein an mRNA strand controls the assembly of an amino acid sequence to generate a protein or a peptide.

As used throughout this specification and the claims, the terms "comprising", "containing", "including", and its variants are inclusive of other components, elements, integers, steps and the like. Conversely, the term "consisting" and its variants are exclusive of other components, elements, integers, steps and the like.

It is to be noted that the term "a" or "an", refers to one or more, for example, "an enhancer", is understood to represent one or more enhancer(s). As such, the terms "a" (or "an"), "one or more," and "at least one" is used interchangeably herein.

As described above, the term "about" when used to modify a numerical value means a variation of ±10%, unless otherwise specified.

The following examples are illustrative only and are not intended to limit the present invention.

EXAMPLES

In certain embodiments, AAVhu68 capsid has been observed to have better yield AAV9, which is also in Clade F. One or both changes of amino acids the glutamic acid (Glu) at position 67 and the valine (Val) at position 157 may confer this increased yield. In certain embodiments, vectors having the AAVhu68 capsids provide at least a 15% increase in yield of packaged vector as compared to vectors based on AAV9. In a comparison between AAVhu68 and AAVrh10, AAVhu68 has been found to provide better transduction efficiency than AAVrh10 at low dose (e.g. about $1\times10^9$) following intracerebroventricular administration.

Example 1

A. Identification of AAVhu68

Tissue DNA was extracted from human tissue samples as PCR template with QIAamp columns (Qiagen) following the manufacturer's recommendations with the following modifications. Q5 DNA polymerase (Q5@ Hot Start High-Fidelity 2X Master Mix, NEB) was chosen for its extraordinary high fidelity and robust efficiency to recover full length VP1 gene of potential AAVs in the samples with as described by Gao, et al [Proc Natl Acad Sci USA, 2002 Sep. 3, 99(18): 11854-11859 (Epub 2002 Aug. 21)] with the primer set modified as follows: in the place of the AVINS, GCTGCGYCAACTGGACCAATGAGAAC primer, prm504 [SEQ ID NO: 7], was used and in the place of reverse primer AV2CAS, prm505:CGCAGAGACCAAGTTCAACTGAAACGA [SEQ ID NO: 8], was used. The PCR conditions were modified as follows:

| | μL |
|---|---|
| Water | 9 |
| prm504 | 1.25 |
| prm505 | 1.25 |
| template | 1 |
| 2 × Q5 | 12.5 |

PCR Program

| | Time (seconds) | Cycle(s) |
|---|---|---|
| 98 | 30 | 1 |
| 98 | 10 | 50 |
| 59 | 10 | |
| 72 | 93 | |
| 72 | 120 | 1 |

The bands of ~3 kb from the PCR were cut out from the gel; DNA was extracted with QIAquick Gel Extraction Kit (Qiagen) and cloned into Zero Blunt® TOPO® PCR Cloning Kit (Thermo Fisher Scientific). Plasmids were sequenced to get the full length of AAV VP1 gene. For most of the samples, at least three plasmids were fully sequenced and consensus sequences were drawn as the final AAV sequence for that sample.

Figures 1, 2A:
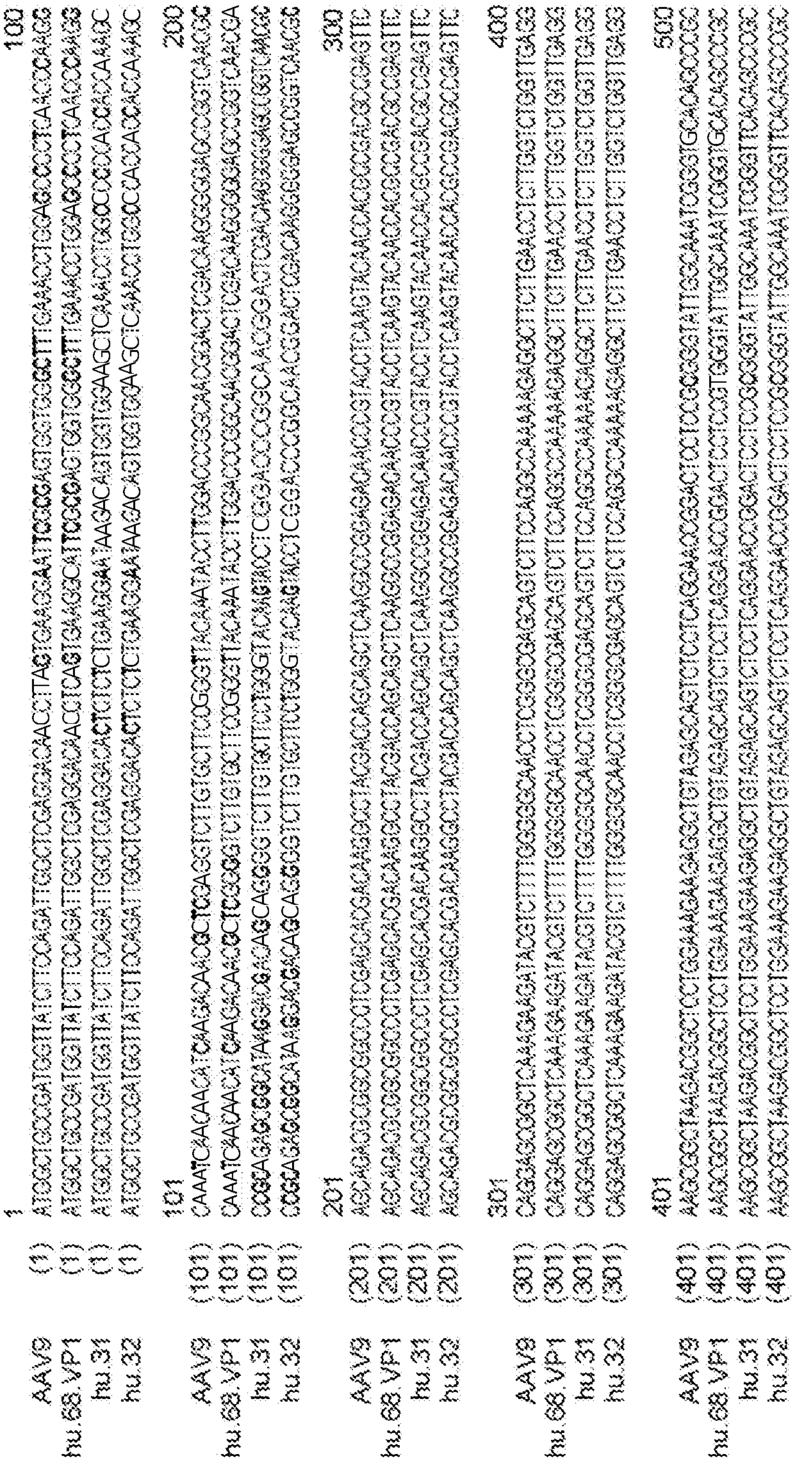
Figures 2, 2B:
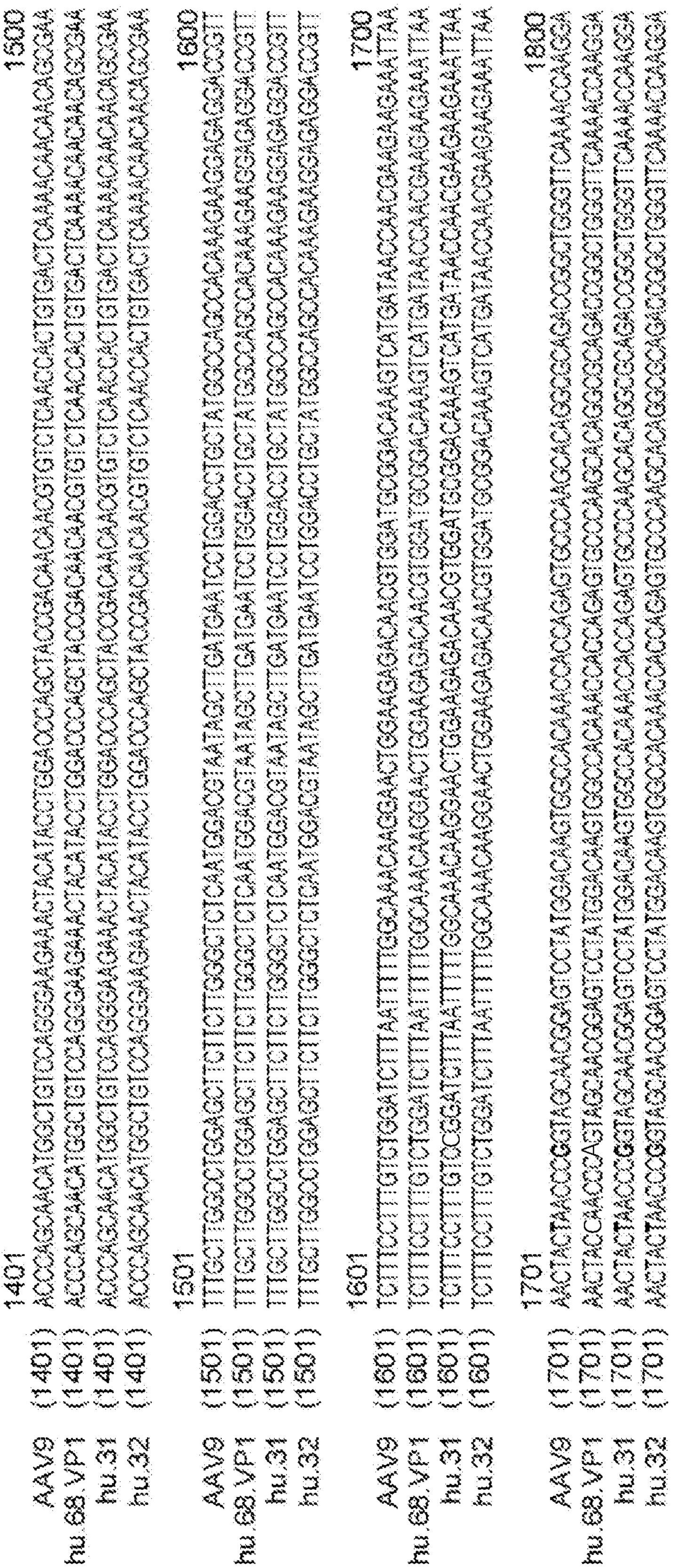

The acquired nucleic acid sequence encoding the vp1 capsid protein of AAVhu68 is provided in SEQ ID NO: 1. See, also, FIGS. 2A-2C. The vp1 amino acid sequence of AAVhu68 is provided in FIG. 1 and SEQ ID NO: 2. Compared to AAV9, AAVhu31 and AAVhu32, two mutations (A67E and A 157V) were identified critical in AAVhu68 (circled in FIG. 1).

This amplification method also provided a spacer sequence between the vp1 coding sequence and the rep coding sequences. This coding sequence is: atgacttaaaccaggt, SEQ ID NO: 9. The coding sequence for rep52 of AAVhu68 is reproduced in SEQ ID NO: 3. The rep52 protein sequence is also reproduced in SEQ ID NO: 4.

pAAV2/hu68 trans plasmid was then made by loading the VP1 gene of hu68 into a pAAV2/9 backbone in the place of the AAV9 VP1 gene in order to assess packaging efficiency, yield, and transduction properties. The pAAV2/9 plasmid contains AAV2 5' and 3' ITRs flanking the capsid gene and is available from the Penn Vector Core [University of Pennsylvania, Phila, PA US, pennvectorcore.med.upenn.edu].

B. Characterization of AAVhu68

Although this phenomenon has not been previously observed or described in adeno-associated virus capsids, other proteins and peptides have been found to be susceptible, both in vivo as well in vitro, to a variety of chemical modifications. One of the most frequent modifications is the deamidation of asparagine, a spontaneous non-enzymatic reaction. In general, the half-times of asparaginyl deamidation under physiological conditions (pH 7.4, 37° C.) vary between about 1 and 1000 days. A similar series of reactions occur in glutamine to glutamate residues, but these reactions are much slower than those of their asparagine counter parts.

In short peptides, formation of cyclic intermediates is controlled by primary sequence, while in proteins secondary, tertiary, and quaternary structures have an additional effect. Thus, the deamidation rate of each protein amide is uniquely determined. Mass spectrometric identification of deamidated peptides is relatively straightforward, as deamidation adds to the mass of intact molecule+0.984 Da (the mass difference between —OH and —$NH_2$ groups). Since deamidation is a modification stable in the gas phase, MS/MS spectra can reveal the position of deamidation even in the presence of several potential deamidation sites.

Four AAVhu68 vectors were produced using one of four vector genomes which are not relevant to this study, each produced using conventional triple transfection methods in 293 cells. For a general description of these techniques see. e.g., Bell C L, et al., "The AAV9 receptor and its modification to improve in vivo lung gene transfer in mice.", J Clin Invest. 2011; 121:2427-2435. Briefly, a plasmid encoding the sequence to be packaged (a gene product expressed from a chicken β-actin promoter, an intron, and a growth hormone poly A) flanked by AAV2 inverted terminal repeats, was packaged by triple transfection of HEK293 cells with plasmids encoding the AAV2 rep gene and the AAVhu68 cap gene and an adenovirus helper plasmid (pAdΔF6). The resulting AAV viral particles can be purified using CsCl gradient centrifugation, concentrated, and frozen for later use.

Denaturation and alkylation: To 100 μg of the thawed viral preparation (protein solution), add 2 μl of 1M Dithiothreitol (DTT) and 2 μl of 8M guanidine hydrochloride (GndHCl) and incubate at 90° C. for 10 minutes. Allow the solution to cool to room temperature then add 5 μl of freshly prepared 1M iodoacetamide (IAM) and incubate for 30 minutes at room temperature in the dark. After 30 minutes, quench alkylation reaction by adding 1 μl of 1M DTT.

Digestion: To the denatured protein solution add 20 mM Ammonium Bicarbonate, pH 7.5-8 at a volume that dilutes the final GndHCl concentration to 800 mM. Add protease solution (trypsin or chymotrypsin) for a 1:20 protease to protein ratio and incubate at 37° C. overnight. After digestion, add TFA to a final of 0.5% to quench digestion reaction.

Mass Spectrometry: Approximately 1 microgram of the combined digestion mixture is analyzed by UHPLC-MS/MS. LC is performed on an UltiMate 3000 RSLCnano System (Thermo Scientific). Mobile phase A is MilliQ water with 0.1% formic acid. Mobile phase B is acetonitrile with 0.1% formic acid. The LC gradient is run from 4% B to 6% B over 15 min, then to 10% B for 25 min (40 minutes total), then to 30% B for 46 min (86 minutes total). Samples are loaded directly to the column. The column size is 75 cm×15 um I.D. and is packed with 2 micron C18 media (Acclaim PepMap). The LC is interfaced to a quadrupole-Orbitrap mass spectrometer (Q-Exactive HF, Thermo Scientific) via nanoflex electrospray ionization using a source. The column is heated to 35° C. and an electrospray voltage of 2.2 kV is applied. The mass spectrometer is programmed to acquire tandem mass spectra from top 20 ions. Full MS resolution to 120,000 and MS/MS resolution to 30,000. Normalized collision energy is set to 30, automatic gain control to 1e5, max fill MS to 100 ms, max fill MS/MS to 50 ms.

Data Processing: Mass spectrometer RAW data files were analyzed by BioPharma Finder 1.0 (Thermo Scientific). Briefly, all searches required 10 ppm precursor mass tolerance, 5 ppm fragment mass tolerance, tryptic cleavage, up to 1 missed cleavages, fixed modification of cysteine alkylation, variable modification of methionine/tryptophan oxidation, asparagine/glutamine deamidation, phosphorylation, methylation, and amidation.

In the following table, T refers to the trypsin and C refers to chymyotrypsin.

| | Enzyme | | | | | | | | | | | |
|---|---|---|---|---|---|---|---|---|---|---|---|---|
| | T | T | T | T | C | C | C | C | T | T | T | |
| | % Coverage | | | | | | | | | | | |
| Modification | 93.6 | 92 | 93.1 | 92.5 | 90.2 | 89.7 | 91.1 | 88.9 | 98.9 | 97 | 94.6 | 92.4 |
| +Deamidation (Deamid) ~N35 | | | | | | | | | | | | |
| N57 + Deamid | 87.6 | 95.5 | 89.3 | 88.2 | 90.5 | 96.3 | 86.4 | 84.8 | 100.0 | 100.0 | 99.0 | 92.7 |
| N66 + Deamid | 4.7 | | | | | | | | | | | |
| N94 + Deamid | 11.3 | 10.9 | 11.0 | 5.3 | 11.6 | 10.4 | 10.8 | 5.6 | 5.0 | 11.1 | 5.4 | 16.0 |
| N113 + Deamid | | | 1.8 | | | | | | | | | |
| ~N253 + Deamid | 17.7 | 22.0 | 21.1 | 15.0 | 17.0 | 22.6 | 20.5 | 15.6 | 4.2 | 5.5 | | |
| Q259 + Deamid | 35.2 | 25.6 | 21.0 | | 35.4 | 26.3 | 20.9 | 9.2 | | | | |
| ~N270 + Deamid | 16.4 | 25.1 | 23.2 | 16.6 | 15.9 | 24.9 | 23.5 | 16.1 | 0.2 | | | |
| ~N304 + Deamid | 2.6 | 2.9 | 2.8 | 1.3 | 2.5 | 2.8 | 2.9 | 1.3 | 16.6 | 10.3 | | |
| ~N314 + Deamid | | | | | | | | | 6.5 | | | |
| N319 + Deamid | 0.3 | 2.8 | 2.8 | 0.2 | | 2.9 | 2.8 | 0.2 | | | | |
| N329 + Deamid | 72.7 | 85.6 | 89.1 | 86.8 | 71.0 | 87.2 | 88.7 | 84.7 | 85.5 | 79.4 | 78.9 | 91.8 |
| N336 + Deamid | | 30.8 | 9.3 | 100.0 | | 31.0 | 9.2 | 95.7 | | | | |
| ~N409 + Deamid | 21.3 | 22.9 | 23.9 | 24.0 | 22.0 | 23.4 | 24.7 | 24.2 | | | | |
| N452 + Deamid | 98.8 | 99.7 | 99.2 | 100.0 | 98.9 | 97.3 | 98.1 | 95.2 | 98.2 | 68.7 | 67.4 | 49.4 |
| N477 + Deamid | 4.4 | 4.3 | 4.3 | 2.6 | 4.5 | 4.4 | 4.3 | 2.6 | | | 0.8 | |
| N512 + Deamid | 97.5 | 97.9 | 95.3 | 95.7 | 92.2 | 91.8 | 99.2 | 96.1 | 99.7 | 98.2 | 87.9 | 75.7 |
| ~N515 + Deamid | 8.2 | 21.0 | 16.0 | | 8.3 | 21.0 | 16.5 | 0.0 | 2.5 | 3.0 | | 15.1 |
| ~Q599 + Deamid | 4.0 | 15.4 | 10.1 | 13.6 | 4.0 | 15.5 | 10.0 | 13.8 | 15.8 | | | |
| N628 + Deamid | 5.3 | | 5.6 | | 5.4 | 0.0 | 5.4 | 0.0 | | | | |
| N651 + Deamid | 0.9 | 1.6 | 1.6 | | | | | | 0.5 | | | |
| N663 + Deamid | 3.4 | | 3.5 | 3.7 | 3.4 | 0.0 | 3.4 | 3.6 | | | | |
| N709 + Deamid | 0.6 | 0.8 | 20.2 | 0.6 | 0.6 | 0.8 | 19.8 | 0.6 | 0.3 | 1.3 | 0.1 | 0.2 |
| N735 | | | | | | | | 25.0 | 42.7 | | 21.7 | |

-continued

| | Enzyme | | | | | | | | | | | |
|---|---|---|---|---|---|---|---|---|---|---|---|---|
| | T | T | T | T | C | C | C | C | T | T | T | |
| | % Coverage | | | | | | | | | | | |
| Modification | 93.6 | 92 | 93.1 | 92.5 | 90.2 | 89.7 | 91.1 | 88.9 | 98.9 | 97 | 94.6 | 92.4 |
| +Acetylation (Ac): | | | | | | | | | | | | |
| K332 + Ac | | | | 100.0 | | | | | | | | |
| ~K693 + Ac | 13.0 | | 13.5 | | | | | | | | | |
| ~K666 + Ac | | | | 93.8 | | | | | | | | |
| ~K68 + Ac | | 59.2 | | | | | | | | | | |
| +Isomerization (Iso): | | | | | | | | | | | | |
| D97 + Iso | 0.5 | 0.4 | 0.4 | 0.2 | 0.5 | | 0.4 | 0.2 | | | | |
| D107 + Iso | | 0.3 | | 0.3 | | 0.3 | | | | | | |
| D384 + Iso | 0.8 | | | | 0.9 | | | | | | | |
| +Phosphorylation (Phos) | | | | | | | | | | | | |
| S149 + Phos | 5.8 | 5.7 | 5.2 | 9.8 | 5.7 | 5.9 | 5.2 | 9.9 | | | | |
| ~S499 + Phos | | | | 30.6 | | | | | | | | |
| ~T569 + Phos | 0.9 | | | | | | | | | | | |
| ~S586 + Phos | | 3.6 | | | | | | | | | | |
| +Oxidation | | | | | | | | | | | | |
| ~W23 + Oxi | | 4.7 | 5.5 | | | 4.8 | 5.5 | | | | | |
| W247 + Oxi | 1.5 | 0.4 | 0.7 | | 1.4 | | | | | | | |
| W247 + Oxi to kynurenine | | 0.1 | | | | 0.1 | | | | | | |
| W306 + Oxi | 0.7 | 0.9 | 1.6 | 1.8 | 0.7 | 1.0 | 1.6 | 1.8 | | | | |
| W306 + Oxidation to kynurenine | | | 0.3 | | | | 0.3 | | | | | |
| M404 + Oxi | 0.1 | | 0.2 | | 0.1 | | 0.2 | | | | | |
| M436 + Oxi | 4.9 | | 10.2 | 23.0 | 4.8 | | 10.2 | 22.6 | | | | |
| ~M518 + Oxi | 29.9 | | 1.5 | 10.6 | 29.9 | | 1.5 | 10.5 | | | | |
| ~M524 + Oxi | 18.8 | 31.6 | 52.7 | | 18.4 | 31.1 | 52.5 | 14.2 | | | | |
| M559 + Oxi | 19.0 | 21.6 | 19.6 | 20.9 | 19.6 | 21.3 | 20.1 | 20.9 | | | | |
| ~M605 + Oxi | 12.2 | 15.2 | | | 12.8 | 14.8 | | | | | | |
| W619 + Oxi | 1.0 | | 0.6 | 1.5 | 1.0 | | 0.6 | 1.5 | | | | |
| W619 + Oxidation | | | 20.3 | | | | | | | | | |
| ~M640 + Oxi | 23.5 | 64.2 | 24.6 | | 22.4 | 21.1 | 25.6 | | | | | |
| W695 + Oxi | 0.3 | | 0.4 | 0.4 | 0.3 | | 0.4 | 0.4 | | | | |
| +Amidation | | | | | | | | | | | | |
| ~D297 + Amidation | | 72.9 | | 73.3 | | | | | | | | |

In the case of the AAVhu68 capsid protein, 4 residues (N57, N329, N452, N512) routinely display high levels of deamidation and it most cases >90% across various lots. Additional asparagine residues (N94, N253, N270, N304, N409, N477) and Q599) also display deamidation levels up to ~20% across various lots. The deamidation levels were initially identified using a trypsin digest and verified with a chymotrypsin digestion.

Example 2—Yield of AAVhu68 Vectors

AAVhu68 and AAV9 vectors carrying various tags, such as GFP and LacZ were generated and evaluated. Each of the vectors was generated using the triple transfection technique in 293 cells, as described by Gao et al [Gao, Guang-Ping, et al. "Novel adeno-associated viruses from rhesus monkeys as vectors for human gene therapy." Proceedings of the National Academy of Sciences 99.18 (2002): 11854-11859.]

A. Production of pAAVhu68 Trans Plasmid

The nucleic acid sequence encoding the vp1 capsid protein is provided in SEQ ID NO: 1.

pAAV2/hu68 trans plasmid was made by loading the VP1 gene of hu68 into a pAAV2/9 backbone in the place of the AAV9 VP1 gene in order to assess packaging efficiency, yield, and transduction properties. The pAAV2/9 plasmid contains AAV2 5' and 3' ITRs flanking the capsid gene and is available from the Penn Vector Core [University of Pennsylvania, Phila, PA US, pennvectorcore.med.upenn.edu].

B. Yield of AAVhu68 Vectors 293 cells were cultured and maintained in DMEM, 1× (Dulbecco's Modification of Eagle's Minimum Essential Medium) with 4.5 g/L glucose, L-glutamine & sodium pyruvate supplemented with 10% of fetal bovine serum under the atmosphere with 5% $CO_2$ at 37° C. Transfections were performed as described by Gao et al [Gao, Guang-Ping, et al. "Novel adeno-associated viruses from rhesus monkeys as vectors for human gene therapy." Proceedings of the National Academy of Sciences 99.18 (2002): 11854-11859.] with the vector plasmid replaced by pAAV2/hu68 or pAAV2/9. The transgene (expression cassette) utilized was CB7.CI.ffLuciferase.RBG. The transfected cells were further cultured in 6-well plates. Total lysate of the cells as well as the supernatant was collected for virus quantification via TaqMan (Applied Biosystems) analysis by using probes and primers targeting the rabbit beta-globin polyA region of the transgene (expression cassette) as described in Gao et al [Gao, Guangping, et al. "Purification of recombinant adeno-associated virus vectors by column chromatography and its performance in vivo." Human gene therapy 11.15 (2000): 2079-2091.]. The yields of six pAAV2/9 plasmids and six pAAV2/hu.68 plasmids were compared in 6-well plate, head to head, in terms of both supernatant titer and the total lysate titer. Each plasmid was from an individual bacteria colony.

Figure 3A:
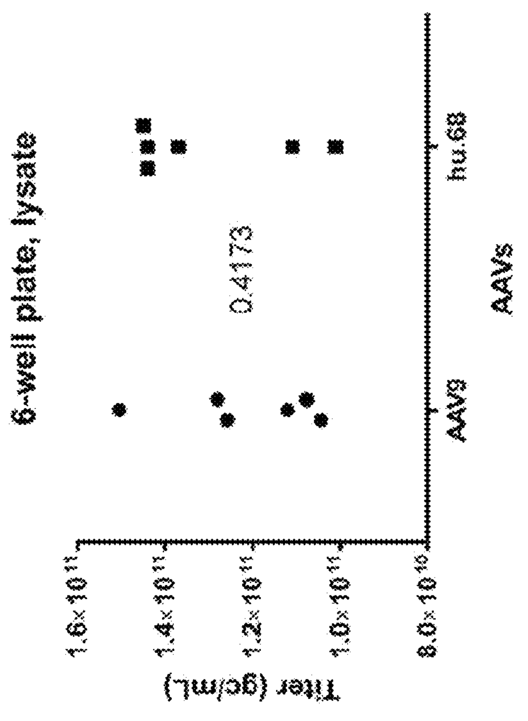
FIGS. 3A-3B provide graphs showing yields of AAVhu.68 compared with that of AAV9. The experiment was performed as described in Example 2. n=6. P value was calculated and shown in the figures.
Figure 3B:
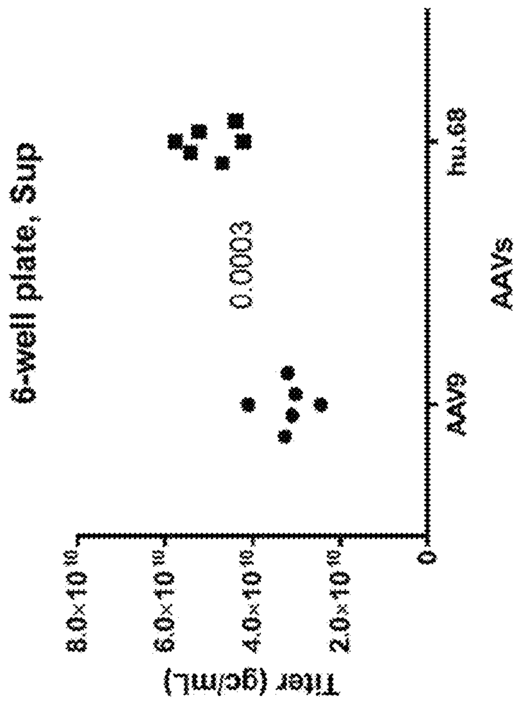

The yield of AAVhu68 was found to be similar to that of AAV9 in terms of total lysate (FIG. 3A, n=6, p=0.42). However, in the supernatant, the yield of AAVhu68 was significantly higher than that of AAV9 (FIG. 3B, n=6, p=0.0003). Thus, AAVhu68 was demonstrated as a better vector compared to AAV9 in terms of production since supernatant is harvested during cell-stack scale and virus production.

Example 3—In Vivo Transduction of AAVhu68.LacZ

AAVhu68.CB7.nLacZ (also referred as AAVhu68.LacZ) was generated via inserting a sequence encoding nuclear-localized bacterial β-galactosidase (nLacZ) and then produced as described in Example 2. To assess the packaging efficiency, yield, transduction properties, transduction efficiency and tropism of AAVhu68 in vivo, mice were injected with $5\times10^{11}$ genome copies of the AAVhu68.LacZ vector via various administration methods, such as intravenous, intramuscular and intranasal administration. Muscle, lung, liver and heart were collected after sacrificing the mice two weeks after vector administration. Frozen sections of each organ were prepared, processed and analyzed as conventional protocol detecting LacZ gene expression [Bell, Peter, et al. "An optimized protocol for detection of *E. coli* β-galactosidase in lung tissue following gene transfer." Histochemistry and cell biology 124.1 (2005): 77-85.]. A positive staining for LacZ shown in blue (FIG. 4A-4C) indicates a successful transduction of AAVhu68.

Figure 4A:
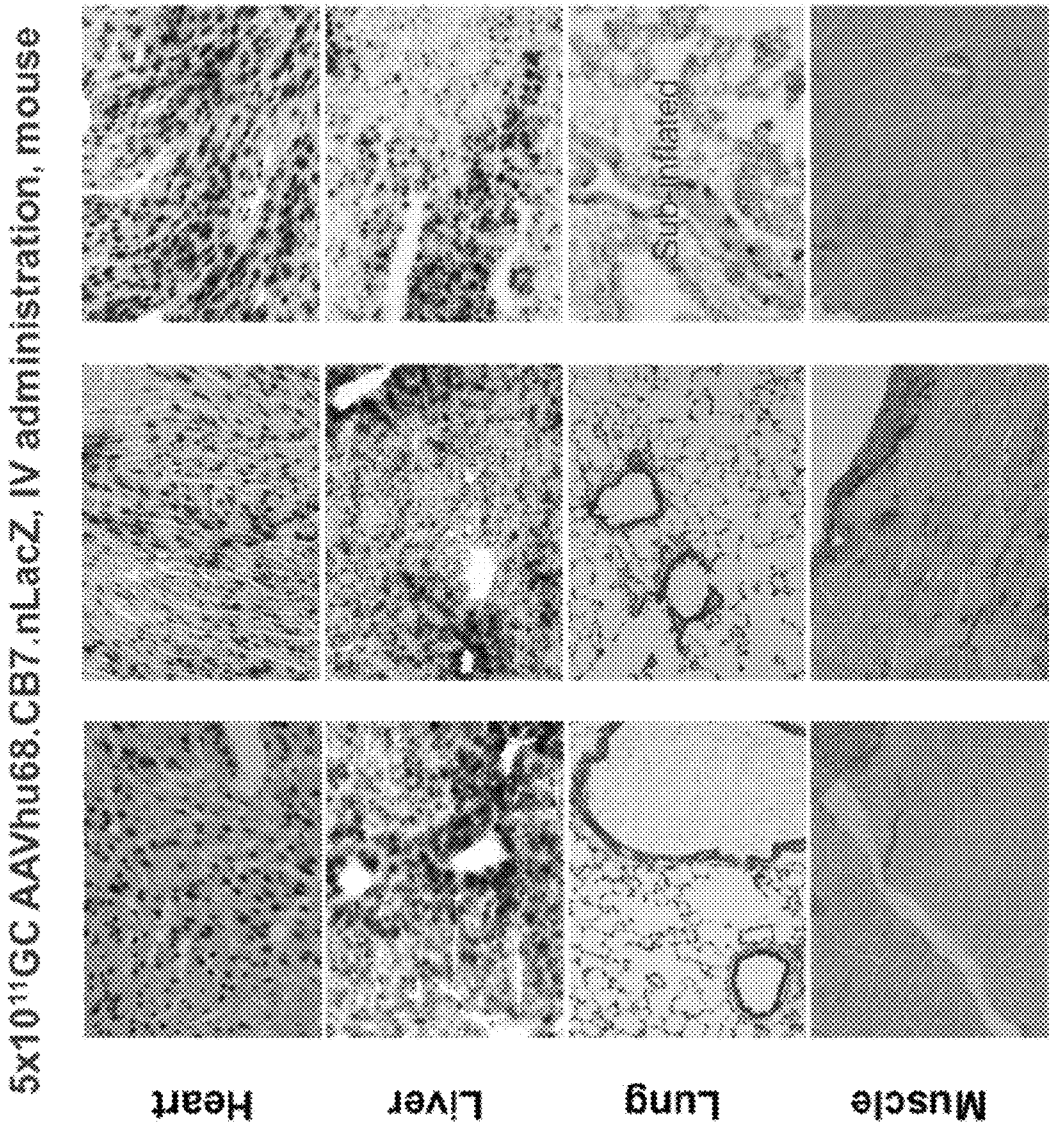
FIGS. 4A-4C provide immunohistochemistry staining of various organs (heart, liver, lung and muscle) from mice administrated with $5\times10^{11}$ GC AAVhu68.CB7.nLacZ. Samples were prepared and processed as described in Example 3. Samples were counterstained by Eosin shown in red. A positive staining for LacZ shown in blue indicates a successful transduction of AAVhu68.
Figure 4B:
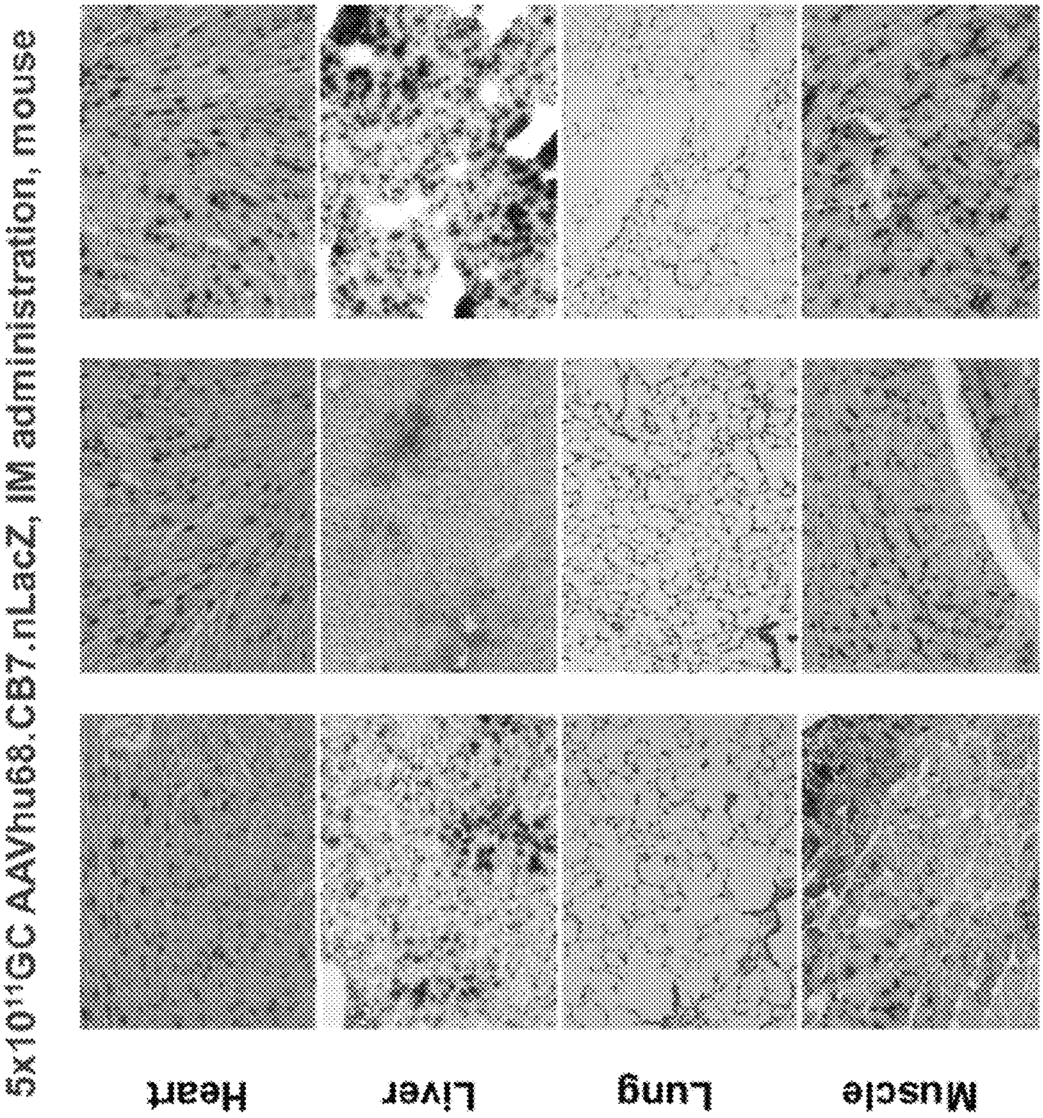
Figure 4C:
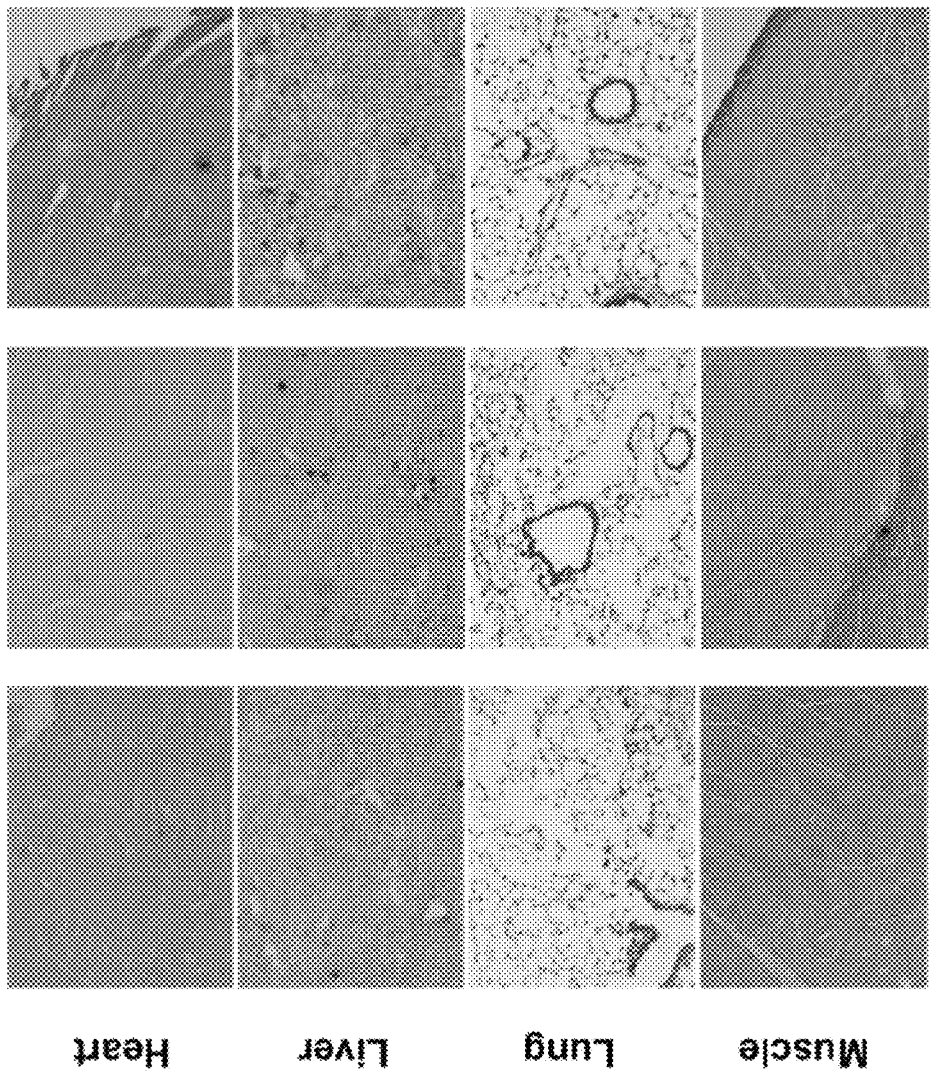
Figure 5A:
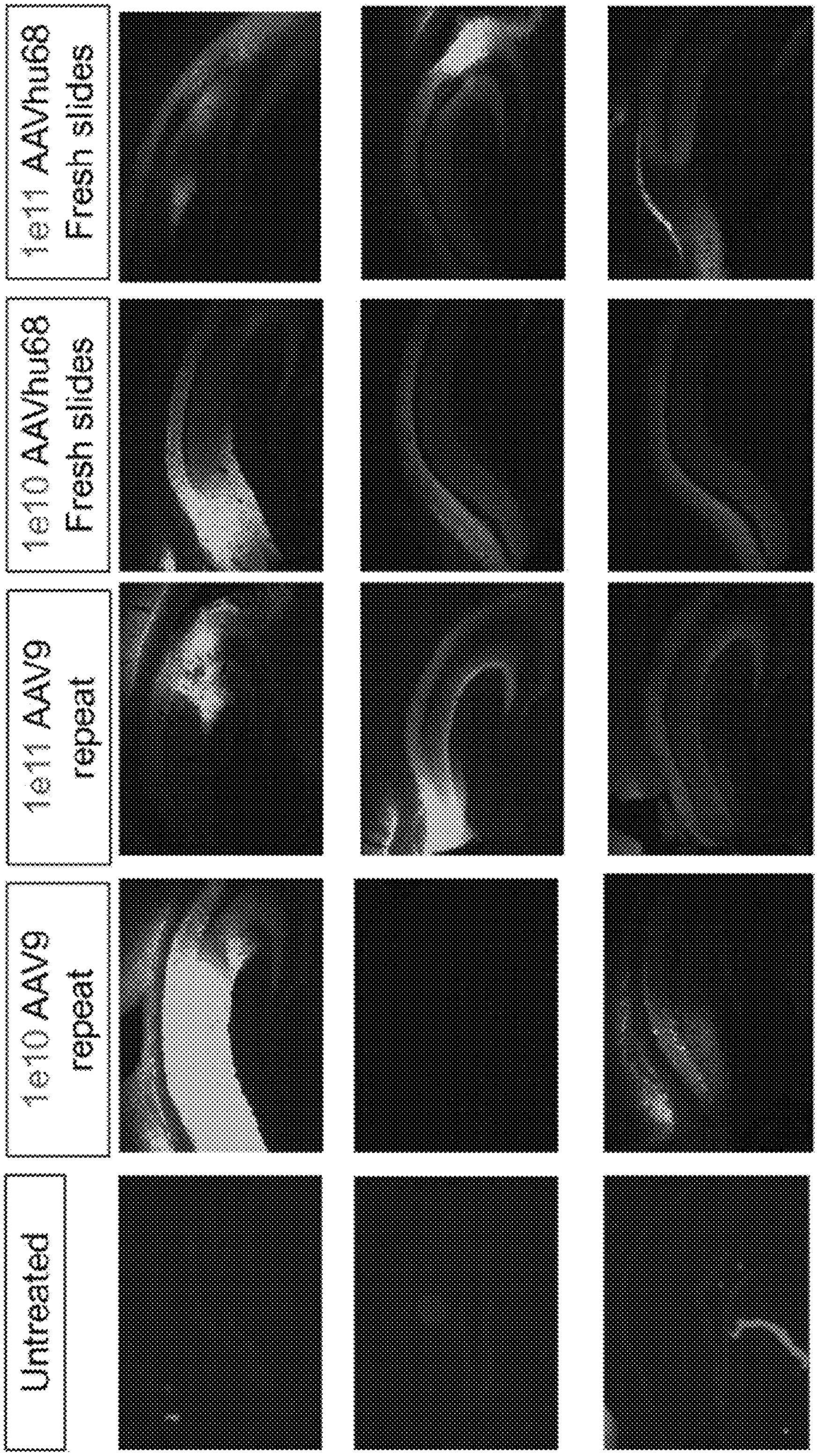
FIGS. 5A-5C provide fluorescent microscopic images of various brain regions (hippocampus, FIG. 5A; motor cortex, FIG. 5B; and cerebellum, FIG. 5C) from mice administrated with AAVhu68.GFP or AAV9.GFP at the doses of $1\times10^{10}$ GC or $1\times10^{11}$ GC. Samples were prepared and processed as described in Example 4. A positive signal from GFP shown in green indicates a successful transduction of the AAV vectors.
Figure 5B:
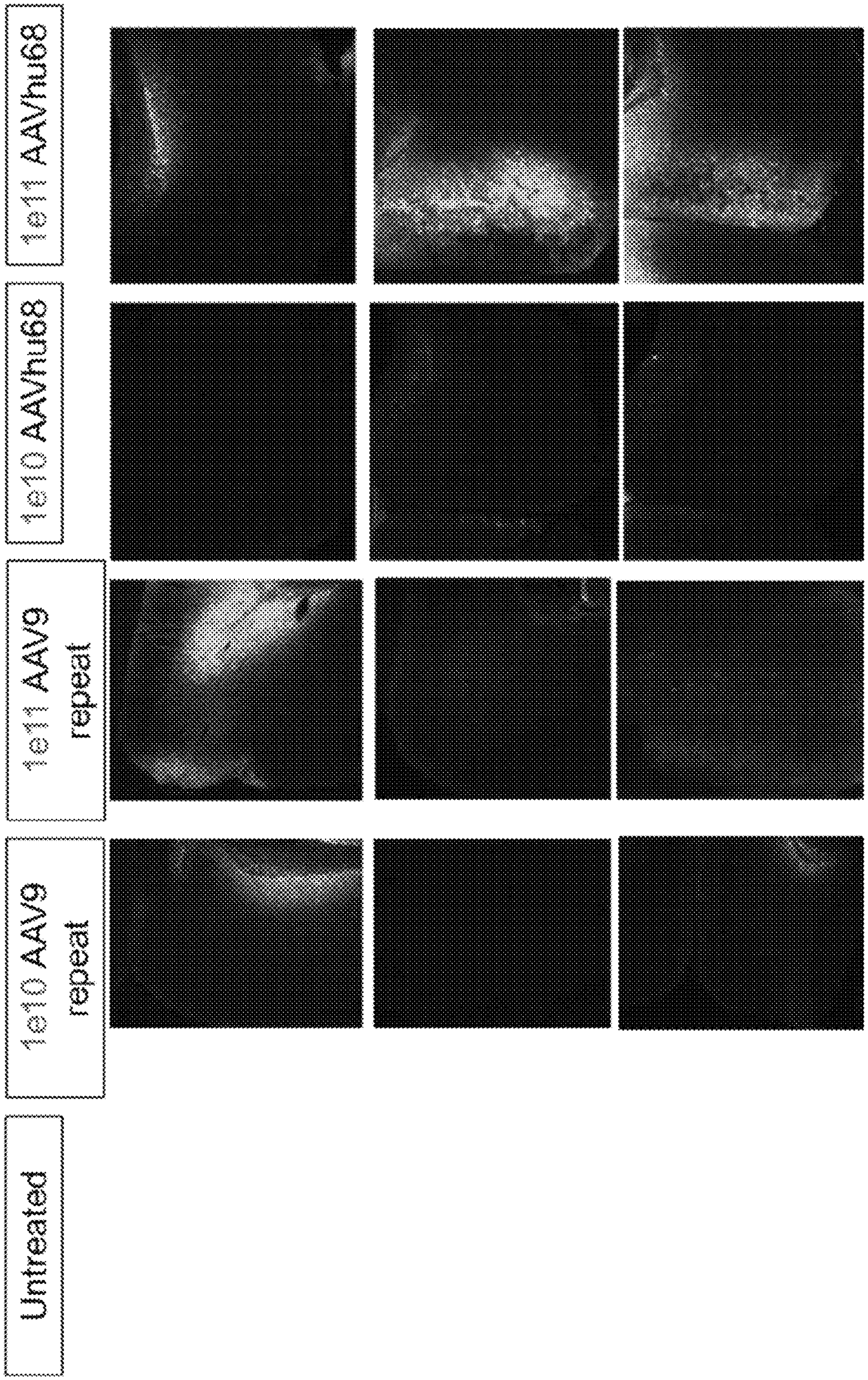
Figure 5C:
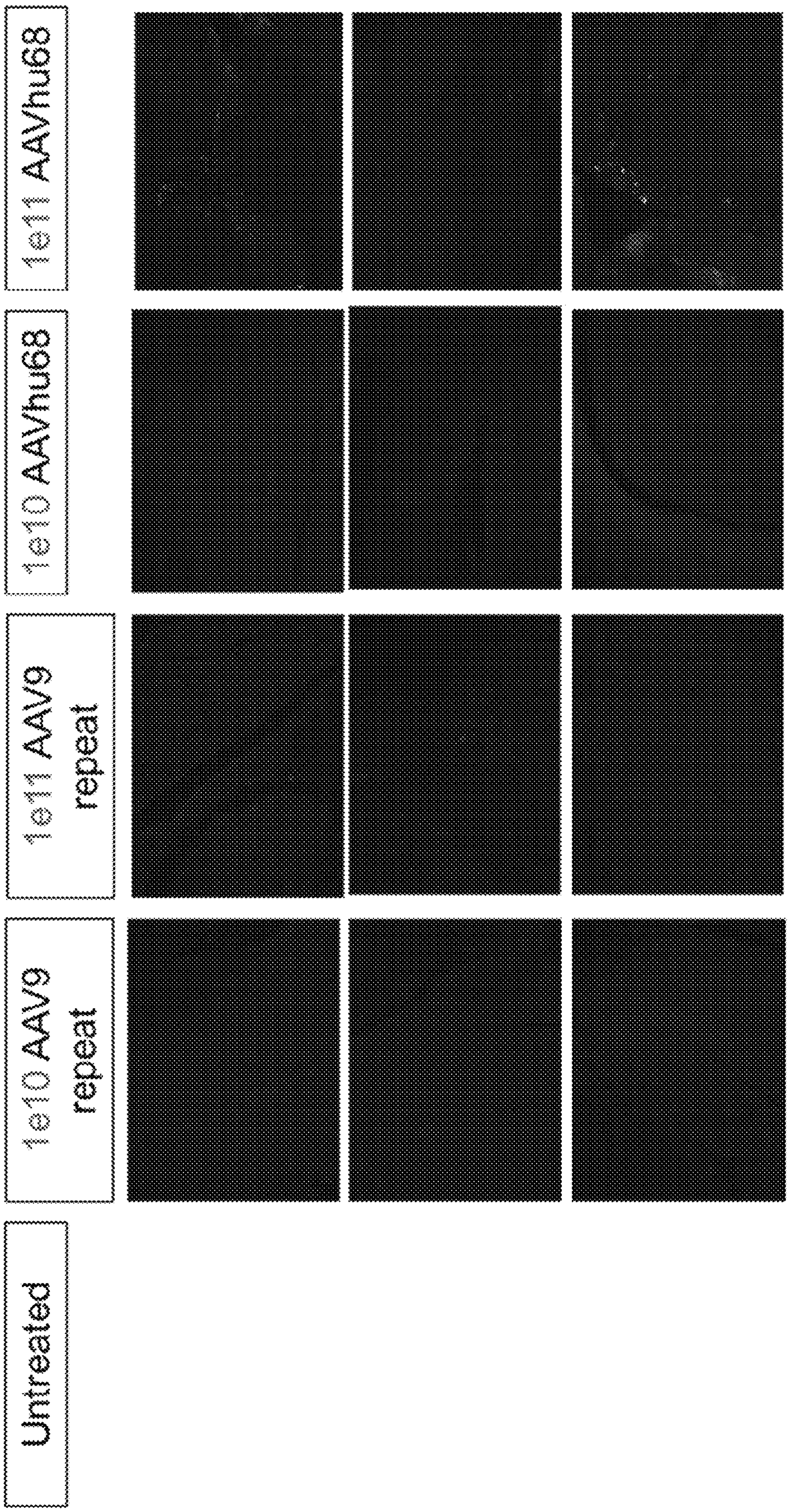
Figure 6A:
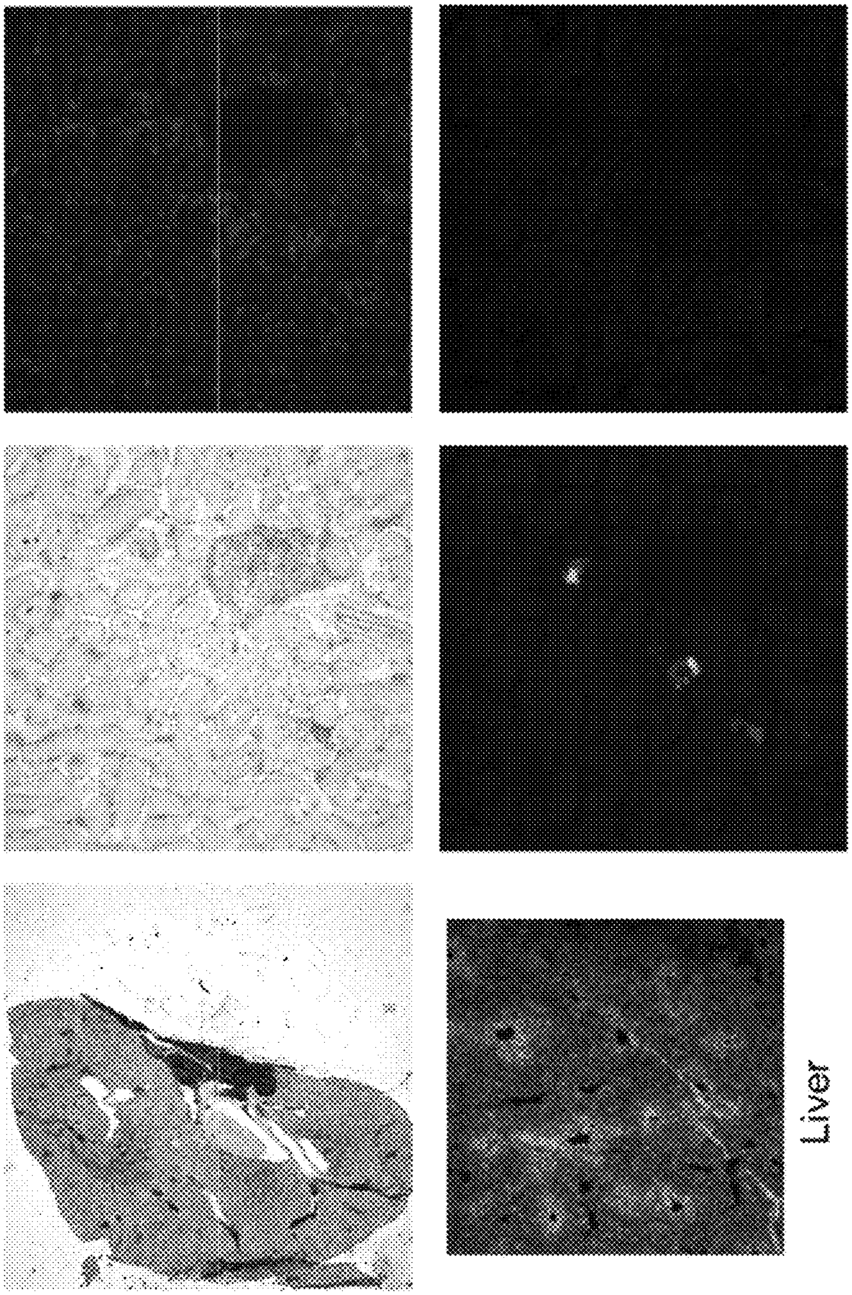
FIGS. 6A-6D provide microscopic images of various organs (liver, kidney, heart and pancreas) from mice administrated with AAVhu68.GFP intravenously. Samples were prepared and processed as described in Example 4. A positive signal from GFP shown in green indicates a successful transduction of the said AAV vectors. Bright field images shown in black and white were provided for the organ morphology while the corresponding red fluorescent channel were provided as a negative control where applicable.
Figure 6B:
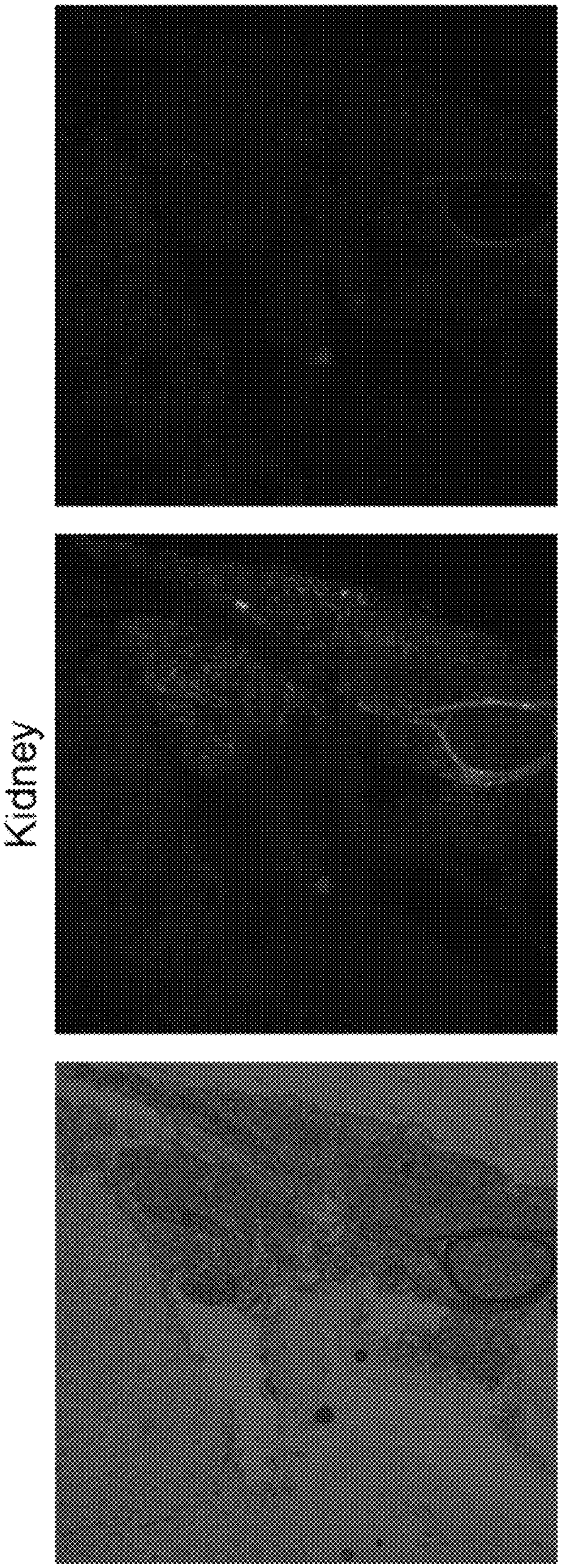
Figure 6C:
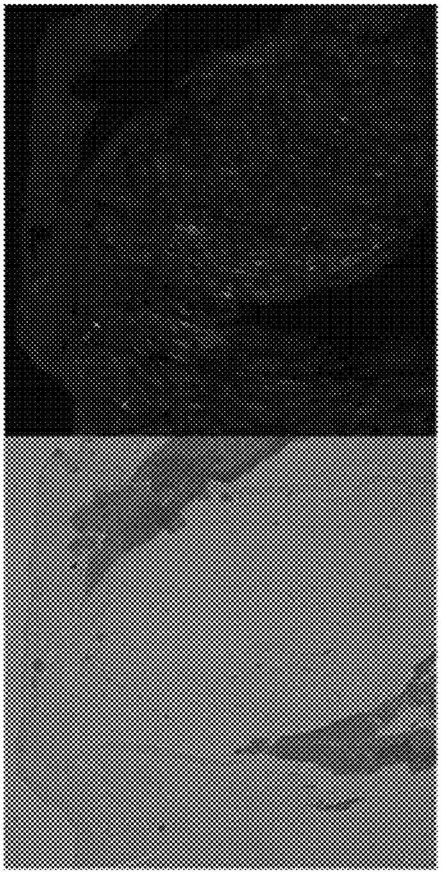
Figure 6D:
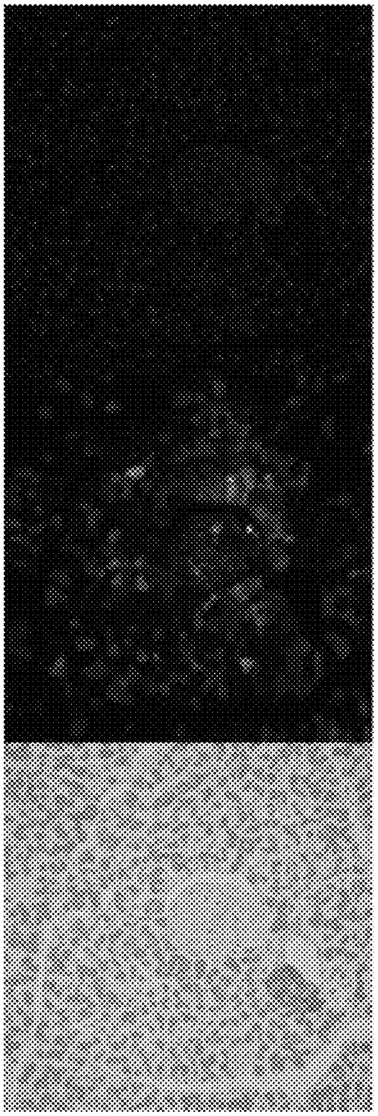

As shown in FIG. 4A, after the vectors introduced to mice via intravenous injection (IV), all tested organs (heart, liver, lung and muscle) demonstrated AAVhu68 transduction while a tropism favoring heart and liver over lung and muscle was observed. After the vectors introduced to mice via intramuscular injection (IM), heart, liver and muscle demonstrated high transduction rate of AAVhu68 while no detectable transduction in lung was observed. If intranasal administration was performed, scattered transduction was observed in heart, liver, muscle and lung.

These results revealed that AAVhu68 demonstrated a high transduction efficiency and a broad tissue/organ tropism.

Example 4—In Vivo Transduction of AAVhu68.GFP Compared to AAV9.GFP

AAVhu68.GFP and AAV9.GFP were generated via inserting a gene encoding green fluorescent protein (GFP) as the genes which are then produced as described in Example 2. To assess the packaging efficiency, yield, transduction properties, transduction efficiency and tropism of AAVhu68 and AAV9 in vivo, mice were administrated with AAVhu68.GFP or AAV9.GFP at the doses of $1\times10^{10}$ GC or $1\times10^{11}$ GC. Brain, muscle, lung, liver and heart were collected after sacrificing the mice two weeks after vector administration. Frozen sections of each organ were prepared and processed to visualized GFP expression as described by Wang et al [Wang L, et al., Hum Gene Ther. 2011 November; 22(11): 1389-401; Wang L, et al., Mol Ther. 2010 January; 18(1): 126-34]. A positive staining for GFP shown in green (FIG. 5A-5C and FIG. 6A-6D) indicates a successful transduction of the tested vectors.

Sections from various brain regions (hippocampus, motor cortex and cerebellum) of mice with intracerebroventricular administration of the vectors were investigated. Transduction of the AAV vectors was observed in all tested hippocampal samples except one from mice injected with $1\times10^{10}$ GC of AAV9.GFP. A better transduction of AAVhu68.GFP compared to that of AAV9 was observed in the motor cortex. Furthermore, transduction in cerebellum of AAVhu68.GFP was observed when mice were injected with $1\times10^{11}$ GC of the vector only. Therefore, AAVhu68 displayed a higher transduction efficiency as well as a broader tropism in the brain compared to AAV9.

In a further experiment, various organs, such as liver, kidney, heart and pancreas, from mice administrated with AAVhu68.GFP intravenously were prepared and processed as described by Wang et al [Wang L, Calcedo R, Bell P, Lin J, Grant R L, Siegel D L, Wilson J M, Hum Gene Ther. 2011 November; 22(11):1389-401; Wang L, Calcedo R, Wang H, Bell P, Grant R, Vandenberghe L H, Sanmiguel J, Morizono H, Batshaw M L, Wilson J M, Mol Ther. 2010 January; 18(1):126-34]. A positive signal from GFP shown in green indicates a successful transduction of the said AAV vectors. Bright field images shown in black and white were provided for the organ morphology while the corresponding red fluorescent channel was provided as a negative control.

Strong positive signal shown in green was observed in liver while kidney, heart and pancreas demonstrated transduction of the said vector as well, indicating a broad tissue/organ tropism of AAVhu68 vector.

Example 5—Yield and In Vivo Transduction of AAV Vectors with A67E and A157V Mutation To increase yield and/or packaging efficiency of a recombinant adeno-associated (rAAV) vector, an AAV capsid gene to express a vp1 protein with a Glu at amino acid position 67 and/or a Val at amino acid position 157 is engineered to the AAV vectors, such as AAV9, AAVhu31 and AAVhu32, wherein the numbering of the amino acid residues is based on AAVhu68 [SEQ ID NO: 5].

Said AAV vectors are produced and evaluated for yield of each vector according to Example 2. In vivo transduction efficiency and tissue/organ/region tropism is further assessed by conventional methods, such as illustrated in Example 3.

Example 6—Intrathecal AAVhu68.CMV.PI.Htrastuzumab.SV40 for the Prophylaxis of Human HER2+ Breast Cancer Brain Metastases

| | |
|---|---|
| AAV9 | Adeno-Associated Virus 9 |
| AAV9.trastuzumab | AAV9.CMV.PI.htrastuzumab.SV40 (AAV9 carrying a trastuzumab expression cassette) |
| BCA | Bicinchoninic acid assay |
| BCBM | Breast cancer brain metastases |
| CI | Chimeric intron |
| CMV (Promoter) | Cytomegalovirus immediate early enhancer/chicken beta-actin promoter |
| CSF | Cerebrospinal fluid |
| ddPCR | Droplet digital polymerase chain reaction |
| DNA | Deoxyribonucleic acid |
| GC | Genome copies |
| GLP | Good laboratory practices |
| GTP | Gene Therapy Program |
| HER2 | Human epidermal growth factor receptor 2 |
| AAVhu68 | Adeno-Associated Virus serotype hu68 |
| AAVhu68.trastuzumab | hu68.CMV.PI.htrastuzumab.SV40 (AAVhu68 carrying a trastuzumab expression cassette) |
| ICV | Intracerebroventricular |
| ID | Identification number |
| IT | Intrathecal |
| mAb | Monoclonal antibody |
| MED | Minimal essential dose |
| n | Number of animals |
| PBS | Phosphate buffered saline |
| qPCR | Quantitative polymerase chain reaction |
| $RAG1^{-/-}$ | Recombination activating gene 1 knock-out |

-continued

| | |
|---|---|
| RAG1 | Recombination activating gene 1 |
| rBG | Rabbit β-globin poly A sequence |
| RPM | Rotation per minute |
| SD | Standard deviation |
| SOP | Standard operating procedure |
| SV40 (Poly A signal) | Simian virus 40 polyadenylation signal |

A. Summary

The purpose of this study was to test the therapeutic efficacy of AAVhu68.CMV.PI.htrastuzumab.SV40 (AAVhu68.trastuzumab), a recombinant adeno-associated virus of serotype AAVhu68 containing a trastuzumab expression cassette, for the prophylaxis of human HER2+ breast cancer brain metastases in a xenograft mouse model. Trastuzumab (Herceptin®, Roche) is a humanized monoclonal antibody (mAb) directed against HER2 which extends the survival of patients when used intravenously with chemotherapy to treat systemic HER2+ disease. However, the blood-brain barrier excludes Herceptin® that is administered intravenously from entering the central nervous system, rendering it unable to effectively treat HER2+ breast cancer brain metastases. Several case reports indicate that intrathecally-administered Herceptin® can increase survival of patients with HER2+ leptomeningeal disease or halt the progression of HER2+ focal metastases [J. C. Bendell, et al, Central nervous system metastases in women who receive trastuzumab-based therapy for metastatic breast carcinoma. Cancer. 97, 2972-2977 (2003); D. J. Slamon, et al., Use of Chemotherapy plus a Monoclonal Antibody against HER2 for Metastatic Breast Cancer That Overexpresses HER2. N. Engl. J. Med. 344, 783-792 (2001), M. A. Cobleigh, et al, Multinational study of the efficacy and safety of humanized anti-HER2 monoclonal antibody in women who have HER2-overexpressing metastatic breast cancer that has progressed after chemotherapy for metastatic disease. J. Clin. Oncol. 17, 2639-2648 (1999), Zagouri F, et al, (2013). Intrathecal administration of trastuzumab for the treatment of meningeal carcinomatosis in HER2-positive metastatic breast cancer: a systematic review and pooled analysis. Breast Cancer Res Treat, 139(1):13-22., Bousquet G, et al. (2016). Intrathecal Trastuzumab Halts Progression of CNS Metastases in Breast Cancer. J Clin Oncol. 34(16): e151-155]. However, CSF turns over rapidly, likely compromising the therapeutic effect of IT Herceptin® due to a widely fluctuating CSF pharmacokinetic profile. The aim of AAVhu68.trastuzumab treatment is to prevent the occurrence, slow the growth, improve survival, or increase the clinical quality of life measures associated with HER2+ BCBM by providing localized, long-term expression of AAVhu68.trastuzumab in the brain parenchyma itself.

AAVhu68.trastuzumab was administered at four different doses ($1.00\times10^{10}$, $3.00\times10^{10}$, $1.00\times10^{11}$, and $3.00\times10^{11}$ GC/animal) by intracranioventricular injection (ICV) in $RAG1^{-/-}$ mice at 6-9-weeks age. BT474.M1.ffluc cells, derived from a HER2+ human ductal carcinoma cell line, were implanted at least 21 days later. Mice were observed daily and euthanized at study end-point. Brain tissue was collected at necropsy for measuring tumor volume. It was concluded that prophylactic ICV administration of AAVhu68.CMV.PI.htrastuzumab.SV40 in a $RAG1^{-/-}$ xenograft model of HER2+ breast cancer brain metastases resulted in significantly reduced tumor volume at all doses test in this experiment. Altogether, these results demonstrated the potential therapeutic efficacy of AAVhu68.trastuzumab to improve the survival of patients with HER2+ BCBM.

B. The objective of this study was to investigate minimal essential dose (MED) of AAVhu68.trastuzumab for tumor prophylaxis in a $RAG1^{-/-}$ xenograft model of HER2+ BCBM by way of studying tumor volume. The vector is AAVhu68.CMV.PI.htrastuzumab.SV40 or AAVhu68.trastuzumab.

ddPCR Titer: $7.38\times10^{13}$ GC/ml

Endotoxin: <2.0 EU/ml

Purity: 100%

Phosphate Buffer Saline (PBS) (No treatment Control)

The ability of AAVhu68.trastuzumab to provide tumor prophylaxis was evaluated using a RAG1−/−murine xenograft model of HER2+ BCBM. An immunodeficient mouse model allows for the growth of orthotopic tumors of human origin in a mouse without rejection by the mouse immune system. Additionally, the RAG1−/−mouse possesses no intrinsic IgG, allowing the trastuzumab to be quantified by protein A ELISA.

TABLE

Study Design

| Group No. | Treatment | Dose (GC/mice) | Genotype (n) | Dose Volume (μl) | ROA | Tumor Cell Implantation |
|---|---|---|---|---|---|---|
| 1 | AAVhu68.trastuzumab | $1.0\times10^{10}$ | $RAG1^{-/-}$ (10) | 5 | ICV | 21 days post-treatment |
| 2 | AAVhu68.trastuzumab | $3.0\times10^{10}$ | $RAG1^{-/-}$ (10) | 5 | ICV | |
| 3 | AAVhu68.trastuzumab | $1.0\times10^{11}$ | $RAG1^{-/-}$ (10) | 5 | ICV | |
| 4 | AAVhu68.trastuzumab | $3.0\times10^{11}$ | $RAG1^{-/-}$ (10) | 5 | ICV | |
| 5 | PBS | No treatment | $RAG1^{-/-}$ (10) | 5 | ICV | |

The test article and negative control were diluted with sterile phosphate buffered saline (PBS) to the appropriate concentration. Vector was administered ICV into the left lateral ventricle.

Intrathecal AAV delivery can be performed using a variety of routes for CSF access. The ICV route was chosen because it is minimally invasive and requires no surgical procedure in the mouse (compared to the cisterna magna route that necessitates incisions through skin and muscles of the neck). It was demonstrated previously in our laboratory and by others that a single injection of AAV9 vector into the cerebrospinal fluid (ICV or cisterna magna) in both mice and large animals targets neurons throughout the whole brain [Dirren at al. (2014). Intracerebroventricular Injection Of Adeno-Associated Virus 6 And 9 Vectors For Cell Type-Specific Transgene Expression In The Spinal Cord. Hum. Gene. Therapy 25, 109-120, Snyder et al. (2011). Comparison Of Adeno-Associated Viral Vector Serotypes For Spinal Cord And Motor Neuron Gene Delivery. Hum. Gene Ther 22, 1129-1135, Bucher et al. (2014). Intracisternal Delivery Of AAV9 Results In Oligodendrocyte And Motor Neuron Transduction In The Whole Central Nervous System Of Cats. Gene Therapy 21, 522-528, Hinderer et al. (2014). Intrathecal Gene Therapy Corrects CNS Pathology In A Feline Model Of Mucopolysaccharidosis I. Mol Ther: 22, 2018-2027].

C. Tumor Cell Implantation in RAG1−/− Mice

For creating a mice xenograft model for HER2+ BCBM, a human HER2+ ductal cell carcinoma cell line transduced with firefly luciferase, BT474-M1.ffluc, was employed. For the injection procedure, mice were anesthetized with ketamine/xylazine. Fur on the scalp and neck was sheared. A time-release 17-β estradiol pellet (1.7 mg, 90-day release, Innovative Research of America) was implanted subcutaneously in the dorsum of the neck and re-administered every 90 days during the study. Mice were fixed in a stereotaxic apparatus. Exposed skin was cleansed with povidone-iodine and 70% ethanol. A 1 cm anterior-posterior incision was made over the top of the skull. Bregma was identified. A pneumatic drill was positioned at bregma then moved 0.8 mm posterior and 2.2 mm left of bregma where a burr hole was drilled in the skull. A 25 μL Hamilton syringe was loaded with 5 μL tumor cell suspension (100,000 cells total in 50:50 MatriGel®:PBS). The needle was brought to bregma and moved to the coordinates indicated above before penetrating 4.0 mm into the brain parenchyma. The needle was then lifted 1.0 mm back up the needle track to create a pocket into which to inject tumor cells. The needle was left in place for 5 minutes. Next, 5 μL of cell suspension was injected over 10 minutes using a motorized injection apparatus. The needle was left in place for 5 minutes after the injection finished then removed slowly. The incision over the skull was sutured with 4.0 vicryl, and the mice received 15 mg/kg enrofloxacin (Bayer) in sterile PBS along with 0.3 mg/kg buprenorphine in sterile PBS, both subcutaneously.

Mice were monitored daily. When moribund, mice were euthanized by overexposure to CO2 followed by cervical dislocation. At necropsy, brains were isolated and cut coronally through the tumor injection needle track.

Tumor volume: Measurement of day 35 tumor diameter was performed with digital Vernier calipers (Thermo-Fisher). Brains were harvested at necropsy. Blunt dissection at the tumor injection needle track was used to isolate tumors from surrounding brain tissue. The tumor diameter was then measured in 3 dimensions (x, y, and z), and the tumor volume was calculated as the volume of an ellipsoid, 4/3*π*x/2*y/2*z/2. The right cerebral hemisphere, the hemisphere contralateral to the site of vector injection and tumor implantation, was preserved in formalin. Dissected tumors were pooled by dose cohort and preserved in formalin. Tumor volume comparisons were carried out using the Mann-Whitney test in GraphPad Prism 7.

D. Results

Tumor Volume: To determine if IT AAVhu68.trastuzumab tumor prophylaxis slows tumor growth, we measured tumor diameter 35 days after implantation. The median volume of tumors from the group that received a highest dose of AAVhu68.trastuzumab tumor prophylaxis (0.4 $mm^3$, n=10) was significantly smaller than mice that received no treatment (26.1 $mm^3$, n=9). Mice that received lower doses of AAVhu68.trastuzumab all had significantly smaller tumors compared to no treatment. The median tumor volume of mice that received $1.00\times10^{10}$ GC/mouse was calculated to be statistically the same as the median tumor volume of mice that received $3.00\times10^{10}$ GC/mouse (p=0.6029). Of note, two mice in group 1, one mouse in group 2, three mice in group 3, and three mice in group 4 had no grossly appreciable tumor upon dissection,

| Group | Dose (GC/ mouse) | Number of mice | Median tumor volume ($mm^3$) | p value compared to no treatment |
|---|---|---|---|---|
| 1 | $1.00 \times 10^{10}$ | 9* | 6.4 | 0.0375 |
| 2 | $3.00 \times 10^{10}$ | 10 | 8.1 | 0.0053 |
| 3 | $1.00 \times 10^{11}$ | 9* | 1.3 | 0.0026 |
| 4 | $3.00 \times 10^{11}$ | 10 | 0.4 | <0.0001 |

*One animal in each of these groups was euthanized before the scheduled necropsy date and hence was not included in the analysis.

At all doses, IT administration of AAVhu68.trastuzumab led to significantly smaller median tumor volume at D35 post-tumor implantation when administered prophylactically in a RAG1$^{-/-}$ murine xenograft model of HER2+ BCBM, which uses the HER2+BT474.M1 human ductal carcinoma cell line. The AAVhu68.trastuzumab MED measured in this study was $1.00\times10^{10}$ GC/mouse.

Example 7—Production Yield and Purity for AAVhu68 Vectors

To compare production yield and/or purity of a recombinant adeno-associated (rAAV) vector having different capsids, two different sets of vectors having different capsids, including AAVhu68, AAV8triple, AAV8 and AAV9 were generated and prepared.

Briefly, one set of vectors having an indicated capsid and a vector genome comprising a cytomegalovirus promoter (CMV), a firefly luciferase coding sequence, and an SV40 poly A (CMV.ffLuciferase.SV40) were produced and evaluated for yield of each vector at small scale. The results show that AAV9 vectors provided the highest yield while the AAVhu68 vector followed as the second (FIG. 8A). AAV8 and AAV8 triple vectors also provided a yield of above $4\times10^{13}$ GC (FIG. 8A).

The other set of vectors having an indicated capsid and a vector genome comprising a CMV promoter, an intron, an immunoadhesin coding sequence (201Ig IA), and an SV40 poly A (CMV.PI.201Ig IA.SV40) were produced and evaluated for yield and purity of each vector at mega scale according to conventional methods. The results are shown in FIGS. 8B and 9.

Figure 8B:
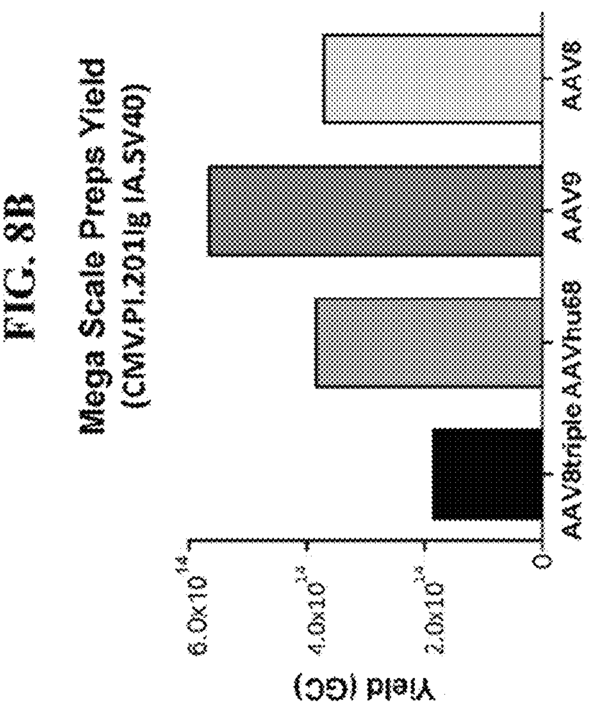
FIGS. 8A-8B illustrate production yield for two different AAVhu68 vectors prepared at small scale (FIG. 8A) and very large scale (mega, FIG. 8B) compared to vectors having different capsids. The data for the small-scale vector preparations were generated using vectors having a AAVhu68, AAV9, AAV8, or AAV8triple capsid and having a vector genome comprising a cytomegalovirus promoter (CMV), a firefly luciferase coding sequence, and an SV40 poly A (CMV.ffLuciferase.SV40). The mega scale preparations were assessed using AAVhu68, AAV9, AAV8 or AAV8triple vectors having a vector genome having a CMV promoter, an intron, an immunoadhesin coding sequence (201Ig IA), and an SV40 poly A.
Figure 8A:
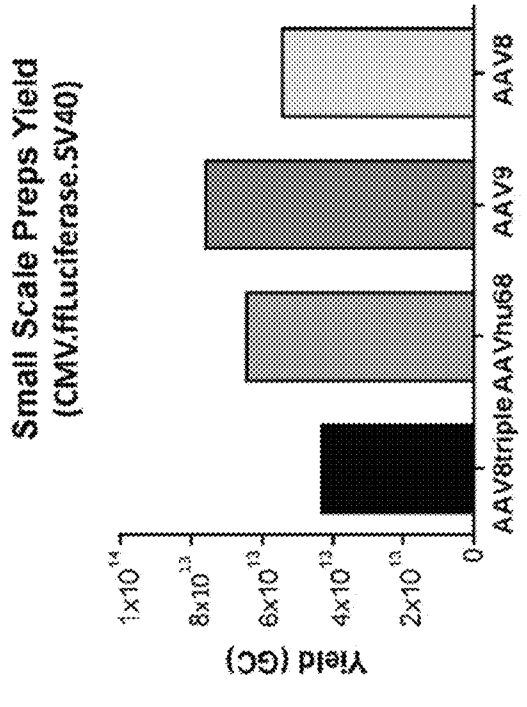
Figure 9:
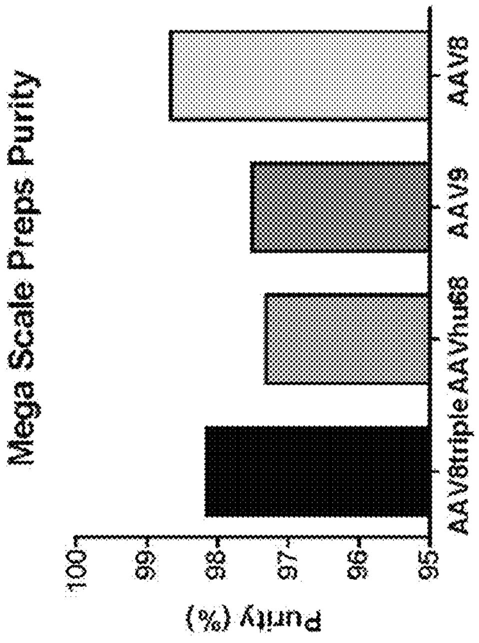
FIG. 9 provides production purity for AAVhu68 vectors prepared at mega scale compared to vectors having different capsids, including AAV8triple, AAV9 and AAV8. The preparations were assessed using AAVhu68, AAV9, AAV8 or AAV8triple vectors having a vector genome comprising a CMV promoter, an intron, an immunoadhesin coding sequence (201Ig IA), and an SV40 poly A.

Similar to yields of preparations at small scale, AAV9 vectors provided the highest yield at about $5.7\times10^{14}$ GC while the AAVhu68 vector followed as the second at about $3.8\times10^{14}$ GC (FIG. 8B). AAV8 vectors provided a yield of about $3.6\times10^{14}$ GC and AAV8triple at about $1.8\times10^{14}$ GC (FIG. 8B). The purities of the tested preparations are comparable, ranging from about 97.4% to about 98.6%.

Example 8—rAAV Vectors in Male RAG KO Mice

The gene expression was tested in vivo using rAAV vectors having different capsids, including AAVhu68, AAV8triple, AAV8 and AAV9 and expressing a secreted transgene product, 201Ig IA.

Male RAG KO mice at 6-8 weeks of age (n=5/group) were intramuscularly into gastrocnemius muscle with either $3\times10^{11}$ GC/mouse or $3\times10^{10}$ GC/mouse of the tested vector using a Hamilton syringe. Serum was collected weekly from mice administered with vectors expressing secreted proteins by submandibular bleeds into serum collection tubes. Transgene expression levels were measured in serum by ELISA as described in Greig et al., Intramuscular Injection of AAV8 in Mice and Macaques Is Associated with Substantial Hepatic Targeting and Transgene Expression, PLoS One. 2014 Nov. 13; 9(11):el12268. doi: 10.1371/journal.pone.0112268. eCollection 2014.

Figure 10A:
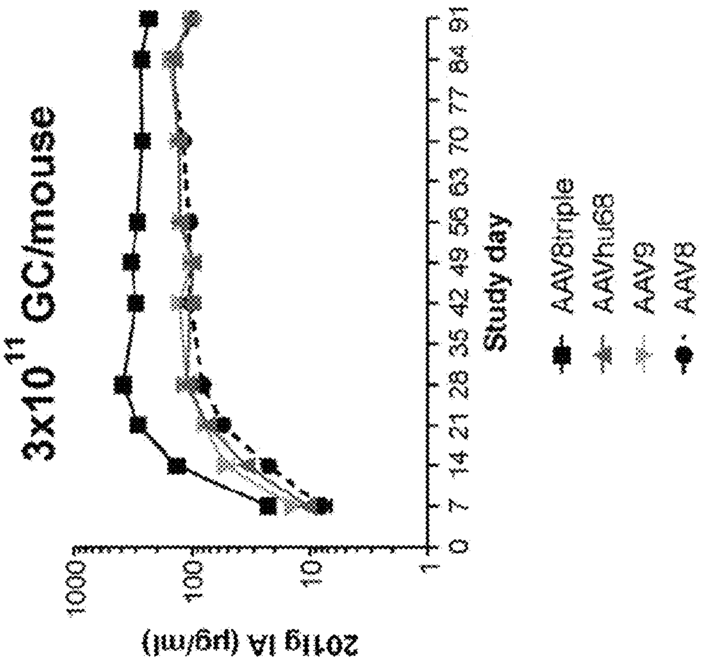
FIGS. 10A-10B provide transgene expression level of AAVhu68 vectors in male RAG KO mice (n=5/group) injected intramuscularly with either $3\times10^{11}$ GC/mouse (FIG. 10A) or $3\times10^{10}$ GC/mouse (FIG. 10B) of vector compared to that of vectors having different capsids, including AAV8triple, AAV9 and AAV8. The transgene expressed by the rAAV vectors is an immunoadhesin coding sequence (201Ig IA). The Experiment was performed as described in detail in Example 8.
Figure 10B:
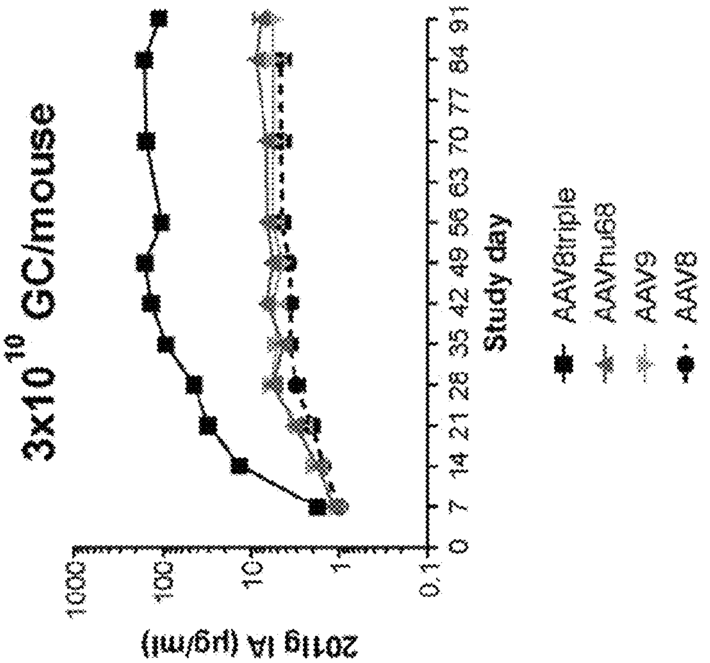

As shown in FIGS. 10A and 10B, AAVhu68, AAV8 and AAV9 vectors expressed the transgene at a similar level while AAV8triple vector expresses better following IM injection in mice. At the lower dose tested (i.e., $3\times10^{10}$ GC/mouse), the difference in expression from AAV8triple is substantial.

Example 9—Transgene Expression of rAAV Vectors in Male C57BL/6J Mice

The expression in liver and muscle was tested in vivo using rAAV vectors having different capsids, including AAVhu68, AAV8triple, AAV8 and AAV9 and expressing a firefly luciferase (ffLuc) as the transgene.

Male C57BL/6J mice at 6-8 weeks of age (n=5/group) were intramuscularly into gastrocnemius muscle with $3\times10^{11}$ GC/mouse of the tested vector using a Hamilton syringe. ffLuc expression was visualized by whole-body bioluminescence imaging weekly as previously described (Greig et al., PLoS One 2014, cited above).

Figure 11B:
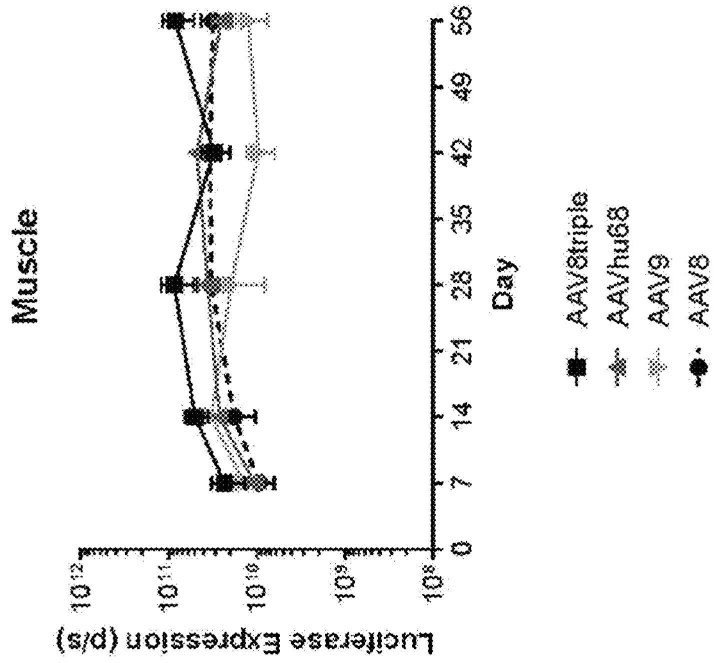
FIGS. 11A-11B provide transgene expression level of AAVhu68 vectors in either the liver (FIG. 11A) or the muscle (FIG. 11B) of male C57BL/6J mice (n=5/group) injected intramuscularly with $3\times10^{11}$ GC/mouse of vector compared to that of vectors having different capsids, including AAV8triple, AAV9 and AAV8. The transgene expressed by the rAAV vectors is firefly luciferase. The Experiment was performed as described in detail in Example 9.
Figure 11A:
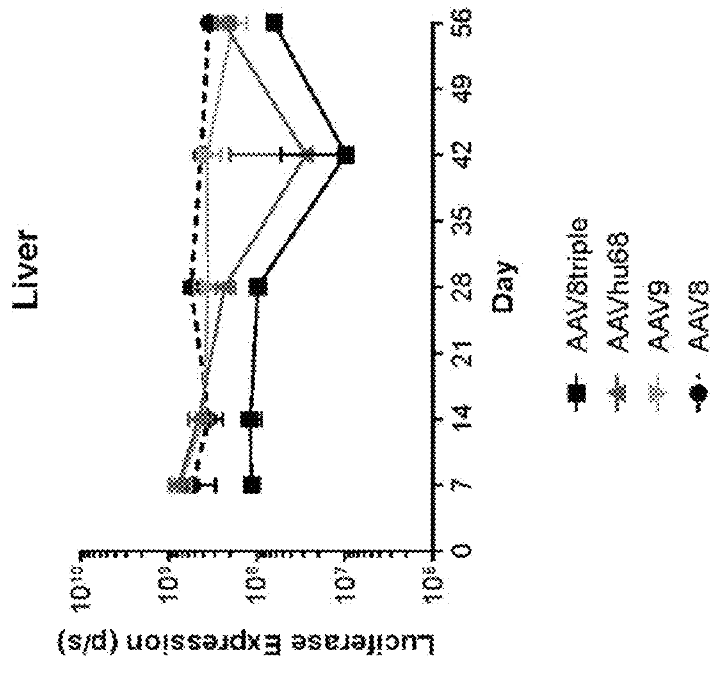

As shown in FIGS. 11A and 11B, AAVhu68, AAV8 and AAV9 vectors were expressed at a similar level in both muscle and liver while AAV8triple vector has reduced expression in liver and enhanced expression in muscle.

Example 10—rAAV Vectors in Male and Female Cynomolgus Macaques

The transgene expression was tested in Cynomolgus Macaques using rAAV vectors having different capsids, including AAVhu68, AAV8triple, AAV8 and AAV9 and expressing a secreted transgene, 201Ig IA.

Male and female cynomolgus macaques having NAb titers to the injected vector of <1:5 at the start of the studies, were administered with a dose of $10^{13}$ GC/kg body weight of vector expressing 201Ig IA from one of four vector capsids (AAV8triple, AAVhu68, AAV9, or AAV8) intramuscularly into the vastus lateralis muscle of both the right and left legs as 1 ml injections per kg body weight (vector concentration of $10^{13}$ GC/ml) for the vector biodistribution study. Blood samples were taken pre-study and weekly during the study via venipuncture of the femoral vein. Transgene expression levels were measured in serum by ELISA as previously described (Greig et al., PLoS One 2014, cited above).

Figure 12:
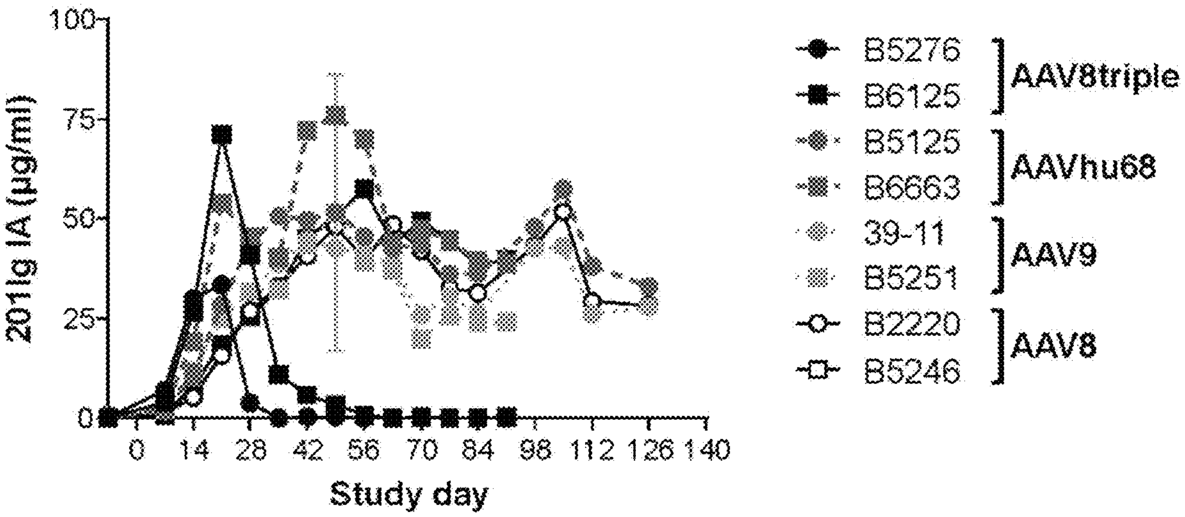
FIG. 12 provides transgene expression level of AAVhu68 vectors in male and female cynomolgus macaques injected intramuscularly with $1\times10^{13}$ GC/kg body weight of vector compared to that of vectors having different capsids, including AAV8triple, AAV9 and AAV8. The transgene expressed by the rAAV vectors is an immunoadhesin coding sequence (201Ig IA). The Experiment was performed as described in detail in Example 10.

As shown in FIG. 12, AAVhu68 and AAV8triple expresses better compared to AAV9 and AAV8 vectors following IM injection.

All documents cited in this specification are incorporated herein by reference, as is U.S. Provisional Patent Application No. 62/614,002, filed Jan. 5, 2018, U.S. Provisional Patent Application No. 62/591,002, filed Nov. 27, 2017 and U.S. Provisional Patent Application No. 62/464,748, filed Feb. 28, 2017. The Sequence Listing filed herewith, labelled "UPN-17-7986.US.C1_ST26_Seq Listing", 55,265 bytes, and the sequences and text therein are incorporated by reference. While the invention has been described with reference to particular embodiments, it will be appreciated that modifications can be made without departing from the spirit of the invention. Such modifications are intended to fall within the scope of the appended claims.

The invention claimed is:

1. A method for purifying a rAAVhu68 vector comprising:

(a) culturing a packaging host cell comprising (i) an AAVhu68 capsid nucleic acid sequence encoding the amino acid sequence of SEQ ID NO:2 operably linked to regulatory sequences which direct expression of AAVhu68 VP1 capsid proteins, AAVhu68 VP2 capsid proteins and AAVhu68 VP3 capsid proteins, wherein said capsid proteins which assemble into an AAVhu68 capsid in the cells of the culture;

(ii) a nucleic acid molecule comprising a vector genome for packaging into the AAVhu68 capsid, said vector genome comprising a 5' AAV inverted terminal repeat (ITR), a non-AAV nucleic acid sequence encoding a gene product operably linked to regulatory control sequences, and a 3' AAV ITR;

(iii) a nucleic acid sequence comprising AAV rep functions and a nucleic acid sequence comprising helper functions for packaging of the vector genome into the AAVhu68 capsid;

(b) harvesting vector-containing cells and/or culture media comprising rAAVhu68 viral particles and one or more of: concentrating the rAAVhu68 vector harvest, diafaltering the vector harvest, microfluidizing the vector harvest, nuclease digestion of the vector harvest, filtering the microfluidized intermediate, performing crude purification by chromatography, performing crude purification by ultracentrifugation, performing buffer exchange by tangential flow filtration, and/or formulation and/or filtration to prepare bulk rAAVhu68.

2. The method according to claim 1, wherein the method comprises concentrating the vector harvest.

3. The method according to claim 2, wherein the method further comprises nuclease digestion of the vector harvest.

4. The method according to claim 2, wherein the method further comprises performing crude purification by chromatography and/or ultracentrifugation.

5. The method according to claim 2, wherein the method further comprises performing tangential flow filtration.

6. A method for separating recombinant adeno-associated virus hu68 (rAAVhu68) particles having packaged genomic sequences from genome-deficient AAVhu68 intermediates from an rAAVhu68 vector harvest comprising:

(a) culturing a packaging host cell comprising (i) an AAVhu68 capsid nucleic acid sequence encoding the amino acid sequence of SEQ ID NO:2 operably linked to regulatory sequences which direct expression of AAVhu68 VP1 capsid proteins, AAVhu68 VP2 capsid proteins and AAVhu68 VP3 capsid proteins, wherein said capsid proteins which assemble into an AAVhu68 capsid in the cells of the culture;

(ii) a nucleic acid molecule comprising a vector genome for packaging into the AAVhu68 capsid, said vector genome comprising a 5' AAV inverted terminal repeat (ITR), a non-AAV nucleic acid sequence encoding a gene product operably linked to regulatory control sequences, and a 3' AAV ITR;

(iii) a nucleic acid sequence comprising AAV rep functions and a nucleic acid sequence comprising helper functions for packaging of the vector genome into the AAVhu68 capsid;

(b) harvesting vector-containing cells and/or culture media comprising rAAVhu68 viral particles and one or more of subjecting a suspension comprising the harvested recombinant AAVhu68 viral particles and AAVhu68 capsid intermediates to fast performance liquid chromatography, equilibrating a strong anion exchange resin at a pH of 10.0 to 10.4 for binding of the AAVhu68 viral particles and AAVhu68 intermediates; subjecting the resin to a salt gradient while monitoring eluate for ultraviolet absorbance at about 260 and about 280, and/or monitoring ultraviolet absorbance of the eluate for an inflection point in a ratio of A260/A280 and, collecting the full particles from the resulting fraction.

7. The method according to claim 6, wherein the anion exchange resin is equilibrated at a pH of 10.2.

* * * * *

SEQUENCE LISTING

```
Sequence total quantity: 14
SEQ ID NO: 1            moltype = DNA  length = 2211
FEATURE                 Location/Qualifiers
misc_feature            1..2211
                        note = AAVhu68 vp1 capsid of Homo Sapiens origin
source                  1..2211
                        mol_type = other DNA
                        organism = synthetic construct
CDS                     1..2211
SEQUENCE: 1
atggctgccg atggttatct tccagattgg ctcgaggaca acctcagtga aggcattcgc  60
gagtggtggg ctttgaaacc tggagcccct caacccaagg caaatcaaca acatcaagac  120
aacgctcggg gtcttgtgct tccgggttac aaataccttg gacccggcaa cggactcgac  180
aaggggggagc cggtcaacga agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgt gggtattggc  480
aaatcgggtg cacagcccgc taaaaagaga ctcaatttcg gtcagactgg cgacacagag  540
tcagtccccg accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcaaaga  900
ctcatcaaca acaactgggg attccggcct aagcgactca acttcaagct cttcaacatt  960
caggtcaaag aggttacgga caacaatgga gtcaagacca tcgctaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatcta  1140
acgcttaatg atggaagcca agccgtgggt cgttcgtcct tttactgcct ggaatatttc  1200
ccgtcgcaaa tgctaagaac gggtaacaac ttccagttca gctacgagtt tgagaacgta  1260
cctttccata gcagctatgc tcacagccaa agcctggacc gactcatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaatttttg gcaaacaagg aactggaaga gacaacgtgg atgcggacaa agtcatgata  1680
accaacgaag aagaaattaa aactaccaac ccagtagcaa cggagtccta tggacaagtg  1740
gccacaaacc accagagtgc ccaagcacag gcgcagaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gctttcaaca aggacaagct gaactctttc atcacccagt attctactgg ccaagtcagc  2040
gtggagattg agtgggagct gcagaaggaa aacagcaagc gctggaaccc ggagatccag  2100
tacacttcca actattacaa gtctaataat gttgaatttg ctgttaatac tgaaggtgtt  2160
tattctgaac cccgccccat tggcaccaga tacctgactc gtaatctgta a           2211
```

-continued

```
SEQ ID NO: 2            moltype = AA  length = 736
FEATURE                 Location/Qualifiers
REGION                  1..736
                        note = Synthetic Construct
source                  1..736
                        mol_type = protein
                        organism = synthetic construct
SEQUENCE: 2
MAADGYLPDW LEDNLSEGIR EWWALKPGAP QPKANQQHQD NARGLVLPGY KYLGPGNGLD  60
KGEPVNEADA AALEHDKAYD QQLKAGDNPY LKYNHADAEF QERLKEDTSF GGNLGRAVFQ  120
AKKRLLEPLG LVEEAAKTAP GKKRPVEQSP QEPDSSVGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 3            moltype = DNA  length = 1866
FEATURE                 Location/Qualifiers
misc_feature            1..1866
                        note = AAVhu68 rep gene of homo sapiens origin
source                  1..1866
                        mol_type = other DNA
                        organism = synthetic construct
CDS                     1..1866
SEQUENCE: 3
atgccggggt tttacgagat tgtgattaag gtccccagcg accttgacga gcatctgccc  60
ggcatttctg acagctttgt gaactgggtg gccgagaagg aatgggagtt gccgccagat  120
tctgacatgg atctgaatct gattgagcag gcacccctga ccgtggccga gaagctgcag  180
cgcgactttc tgacggaatg gcgccgtgtg agtaaggccc cggaggctct tttctttgtg  240
caatttgaga agggagagag ctacttccac atgcacgtgc tcgtggaaac caccggggtg  300
aaatccatgg ttttgggacg tttcctgagt cagattcgcg aaaaactgat tcagagaatt  360
taccgcggga tcgagccgac tttgccaaac tggttcgcgg tcacaaagac cagaaatggc  420
gccggaggcg ggaacaaggt ggtggatgag tgctacatcc ccaattactt gctccccaaa  480
acccagcctg agctccagtg ggcgtggact aatatggaac agtatttaag cgcctgtttg  540
aatctcacgg agcgtaaacg gttggtggcg cagcatctga cgcacgtgtc gcagacgcag  600
gagcagaaca aagagaatca gaatcccaat tctgatgcgc cggtgatcag atcaaaaact  660
tcagccaggt acatggagct ggtcgggtgg ctcgtggaca aggggattac ctcggagaag  720
cagtggatcc aggaggacca ggcctcatac atctccttca atgcggcctc caactcgcgg  780
tcccaaatca aggtcgcctt ggacaatgcg ggaaagatta tgagcctgac taaaaccgcc  840
cccgactacc tggtgggcca gcagcccgtg gaggacattt ccagcaatcg gatttataaa  900
attttggaac taaacgggta cgatccccaa tatgcggctt ccgtctttct gggatgggcc  960
acgaaaaagt tcggcaagag gaacaccatc tggctgtttg ggcctgcaac taccgggaag  1020
accaacatcg cggaggccat agcccacact gtgcccttct acgggtgcgt aaactggacc  1080
aatgagaact ttcccttcaa cgactgtgtc gacaagatgg tgatctggtg ggaggagggg  1140
aagatgaccg ccaaggtcgt ggagtcggcc aaagccattc tcggaggaag caaggtgcgc  1200
gtggaccaga aatgcaagtc ctcggcccag atagacccga ctcccgtgat cgtcacctcc  1260
aacaccaaca tgtgcgccgt gattgacggg aactcaacga ccttcgaaca ccagcagccg  1320
ttgcaagacc ggatgttcaa atttgaactc acccgccgtc tggatcatga ctttgggaag  1380
gtcaccaagc aggaagtcaa agactttttc cggtgggcaa aggatcacgt ggttgaggtg  1440
gagcatgaat tctacgtcaa aaagggtgga gccaagaaaa gacccgcccc cagtgacgca  1500
gatataagtg agcccaaacg ggtgcgcgag tcagttgcgc agccatcgac gtcagacgcg  1560
gaagcttcga tcaactacgc ggacaggtac caaaacaaat gttctcgtca cgtgggcatg  1620
aatctgatgc tgtttccctg cagacaatgc gagagactga atcagaattc aaatatctgc  1680
ttcactcacg gtgtcaaaga ctgtttagag tgctttcccg tgtcagaatc tcaacccgtt  1740
tctgtcgtca aaaaggcgta tcagaaactg tgctacattc atcacatcat gggaaaggtg  1800
ccagacgctt gcactgcttg cgacctggtc aatgtggact tggatgactg tgtttctgaa  1860
caataa                                                            1866

SEQ ID NO: 4            moltype = AA  length = 621
FEATURE                 Location/Qualifiers
REGION                  1..621
                        note = Synthetic Construct
source                  1..621
                        mol_type = protein
                        organism = synthetic construct
SEQUENCE: 4
MPGFYEIVIK VPSDLDEHLP GISDSFVNWV AEKEWELPPD SDMDLNLIEQ APLTVAEKLQ  60
RDFLTEWRRV SKAPEALFFV QFEKGESYFH MHVLVETTGV KSMVLGRFLS QIREKLIQRI  120
YRGIEPTLPN WFAVTKTRNG AGGGNKVVDE CYIPNYLLPK TQPELQWAWT NMEQYLSACL  180
NLTERKRLVA QHLTHVSQTQ EQNKENQNPN SDAPVIRSKT SARYMELVGW LVDKGITSEK  240
QWIQEDQASY ISFNAASNSR SQIKVALDNA GKIMSLTKTA PDYLVGQQPV EDISSNRIYK  300
ILELNGYDPQ YAASVFLGWA TKKFGKRNTI WLFGPATTGK TNIAEAIAHT VPFYGCVNWT  360
NENFPFNDCV DKMVIWWEEG KMTAKVVESA KAILGGSKVR VDQKCKSSAQ IDPTPVIVTS  420
```

-continued

```
NTNMCAVIDG NSTTFEHQQP LQDRMFKFEL TRRLDHDFGK VTKQEVKDFF RWAKDHVVEV  480
EHEFYVKKGG AKKRPAPSDA DISEPKRVRE SVAQPSTSDA EASINYADRY QNKCSRHVGM  540
NLMLFPCRQC ERLNQNSNIC FTHGVKDCLE CFPVSESQPV SVVKKAYQKL CYIHHIMGKV  600
PDACTACDLV NVDLDDCVSE Q                                            621

SEQ ID NO: 5            moltype = DNA  length = 2208
FEATURE                 Location/Qualifiers
misc_feature            1..2208
                        note = AAV9 VP1 capsid of homo sapiens origin
source                  1..2208
                        mol_type = other DNA
                        organism = synthetic construct
CDS                     1..2208
                        note = AAV9 VP1 Capsid
SEQUENCE: 5
atggctgccg atggttatct tccagattgg ctcgaggaca accttagtga aggaattcgc  60
gagtggtggg ctttgaaacc tggagcccct caacccaagg caaatcaaca acatcaagac  120
aacgctcgag gtcttgtgct tccgggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctgggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctg            2208

SEQ ID NO: 6            moltype = AA  length = 736
FEATURE                 Location/Qualifiers
REGION                  1..736
                        note = Synthetic Construct
source                  1..736
                        mol_type = protein
                        organism = synthetic construct
SEQUENCE: 6
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 7            moltype = DNA  length = 26
FEATURE                 Location/Qualifiers
misc_feature            1..26
                        note = primer prm504
```

-continued

```
source                  1..26
                        mol_type = other DNA
                        organism = synthetic construct
SEQUENCE: 7
gctgcgycaa ctggaccaat gagaac                                        26

SEQ ID NO: 8            moltype = DNA  length = 27
FEATURE                 Location/Qualifiers
misc_feature            1..27
                        note = primer prm505
source                  1..27
                        mol_type = other DNA
                        organism = synthetic construct
SEQUENCE: 8
cgcagagacc aagttcaact gaaacga                                       27

SEQ ID NO: 9            moltype = DNA  length = 16
FEATURE                 Location/Qualifiers
misc_feature            1..16
                        note = AAVhu68 spacer sequence
source                  1..16
                        mol_type = other DNA
                        organism = synthetic construct
SEQUENCE: 9
atgacttaaa ccaggt                                                   16

SEQ ID NO: 10           moltype = AA  length = 736
FEATURE                 Location/Qualifiers
REGION                  1..736
                        note = AAVhu31 vp1 capsid protein
source                  1..736
                        mol_type = protein
                        organism = synthetic construct
SEQUENCE: 10
MAADGYLPDW LEDTLSEGIR QWWKLKPGPP PPKPAERHKD DSRGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGSQPAKKK LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGGQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVSTEGV  720
YSEPRPIGTR YLTRNL                                                   736

SEQ ID NO: 11           moltype = AA  length = 736
FEATURE                 Location/Qualifiers
REGION                  1..736
                        note = AAVhu32 vp1 capsid protein
source                  1..736
                        mol_type = protein
                        organism = synthetic construct
SEQUENCE: 11
MAADGYLPDW LEDTLSEGIR QWWKLKPGPP PPKPAERHKD DSRGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGSQPAKKK LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                   736

SEQ ID NO: 12           moltype = DNA  length = 2211
FEATURE                 Location/Qualifiers
misc_feature            1..2211
                        note = AAVhu31 vp1 coding sequence
source                  1..2211
                        mol_type = other DNA
                        organism = synthetic construct
SEQUENCE: 12
atggctgccg atggttatct tccagattgg ctcgaggaca accttagtga aggaattcgc  60
```

-continued

```
gagtggtggg ctttgaaacc tggagcccct caacccaagg caaatcaaca acatcaagac  120
aacgctcgag gtcttgtgct tccgggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctgggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 13           moltype = DNA  length = 2211
FEATURE                 Location/Qualifiers
misc_feature            1..2211
                        note = AAVhu32 vp1 coding sequence
source                  1..2211
                        mol_type = other DNA
                        organism = synthetic construct
SEQUENCE: 13
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtt cacagcccgc taaaaagaaa ctcaatttcg gtcagactgg cgacacagag  540
tcagtccccg accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctgggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atgggagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gcgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc taatgggagg gtttggaatg  1920
aagcacccgc ctcctcagat cctcatcaaa aacacacctg tacctgcgga tcctccaacg  1980
gctttcaata aggacaagct gaactctttc atcacccagt attctactgg ccaagtcagc  2040
```

-continued

```
gtggagattg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 14           moltype = AA  length = 736
FEATURE                 Location/Qualifiers
REGION                  1..736
                        note = modified hu68vp1
VARIANT                 23
                        note = Xaa may be W (Trp, tryptophan), or oxidated W.
VARIANT                 35
                        note = Xaa may be Asn, or deamidated to Asp, isoAsp, or
                         Asp/isoAsp
VARIANT                 57
                        note = Xaa may be Asn, or deamidated to Asp, isoAsp, or
                         Asp/isoAsp
VARIANT                 66
                        note = Xaa may be Asn, or deamidated to Asp, isoAsp, or
                         Asp/isoAsp
VARIANT                 94
                        note = Xaa may be Asn, or deamidated to Asp, isoAsp, or
                         Asp/isoAsp
VARIANT                 97
                        note = Xaa may be D (asp, aspartic acid), or isomerized D.
VARIANT                 107
                        note = Xaa may be D (asp, aspartic acid), or isomerized D.
VARIANT                 113
                        note = Xaa can be any naturally occurring amino acid
VARIANT                 149
                        note = Xaa may be S (Ser, serine), or Phosphorilated S
VARIANT                 149
                        note = Xaa may be S (Ser, serine), or Phosphorylated S
VARIANT                 247
                        note = Xaa may be W (Trp, tryptophan), or oxidated W (e.g.,
                         kynurenine).
VARIANT                 253
                        note = Xaa may be Asn, or deamidated to Asp, isoAsp, or
                         Asp/isoAsp
VARIANT                 259
                        note = Xaa represents Q, or Q deamidated to glutamic acid
                         (alpha-glutamic acid), gamma-glutamic acid (Glu), or a
                         blend of alpha- and gamma-glutamic acid
VARIANT                 270
                        note = Xaa may be Asn, or deamidated to Asp, isoAsp, or
                         Asp/isoAsp
VARIANT                 297
                        note = Xaa represents D (Asp, aspartic acid) or amindated D
                         to N (Asn, asparagine)
VARIANT                 304
                        note = Xaa may be Asn, or deamidated to Asp, isoAsp, or
                         Asp/isoAsp
VARIANT                 306
                        note = Xaa may be W (Trp, tryptophan), or oxidated W (e.g.,
                         kynurenine).
VARIANT                 314
                        note = Xaa may be Asn, or deamidated to Asp, isoAsp, or
                         Asp/isoAsp
VARIANT                 319
                        note = Xaa may be Asn, or deamidated to Asp, isoAsp, or
                         Asp/isoAsp
VARIANT                 329
                        note = Xaa may be Asn, or deamidated to Asp, isoAsp, or
                         Asp/isoAsp
VARIANT                 332
                        note = Xaa may be K (lys, lysine), or acetylated K
VARIANT                 336
                        note = Xaa may be Asn, or deamidated to Asp, isoAsp, or
                         Asp/isoAsp
VARIANT                 384
                        note = Xaa may be D (asp, aspartic acid), or isomerized D.
VARIANT                 404
                        note = Xaa may be M (Met, Methionine), or oxidated M.
VARIANT                 409
                        note = Xaa may be Asn, or deamidated to Asp, isoAsp, or
                         Asp/isoAsp
VARIANT                 436
                        note = Xaa may be M (Met, Methionine), or oxidated M.
VARIANT                 452
                        note = Xaa may be Asn, or deamidated to Asp, isoAsp, or
```

-continued

```
                     Asp/isoAsp
VARIANT             477
                    note = Xaa may be Asn, or deamidated to Asp, isoAsp, or
                     Asp/isoAsp
VARIANT             499
                    note = Xaa may be S (Ser, serine), or Phosphorylated S
VARIANT             512
                    note = Xaa may be Asn, or deamidated to Asp, isoAsp, or
                     Asp/isoAsp
VARIANT             515
                    note = Xaa may be Asn, or deamidated to Asp, isoAsp, or
                     Asp/isoAsp
VARIANT             518
                    note = Xaa may be M (Met, Methionine), or oxidated M.
VARIANT             524
                    note = Xaa may be M (Met, Methionine), or oxidated M.
VARIANT             559
                    note = Xaa may be M (Met, Methionine), or oxidated M.
VARIANT             569
                    note = Xaa may be T (Thr, threonine), or Phosphorylated T
VARIANT             586
                    note = Xaa may be S (Ser, serine), or Phosphorylated S
VARIANT             599
                    note = Xaa represents Q, or Q deamidated to glutamic acid
                     (alpha-glutamic acid), gamma-glutamic acid (Glu), or a
                     blend of alpha- and gamma-glutamic acid
VARIANT             605
                    note = Xaa may be M (Met, Methionine), or oxidated M.
VARIANT             619
                    note = Xaa may be W (Trp, tryptophan), or oxidated W (e.g.,
                     kynurenine).
VARIANT             628
                    note = Xaa may be Asn, or deamidated to Asp, isoAsp, or
                     Asp/isoAsp
VARIANT             640
                    note = Xaa may be M (Met, Methionine), or oxidated M.
VARIANT             651
                    note = Xaa may be Asn, or deamidated to Asp, isoAsp, or
                     Asp/isoAsp
VARIANT             663
                    note = Xaa may be Asn, or deamidated to Asp, isoAsp, or
                     Asp/isoAsp
VARIANT             666
                    note = Xaa may be K (lys, lysine), or acetylated K
VARIANT             689
                    note = Xaa may be K (lys, lysine), or acetylated K
VARIANT             693
                    note = Xaa may be K (lys, lysine), or acetylated K
VARIANT             695
                    note = Xaa may be W (Trp, tryptophan), or oxidated W.
VARIANT             709
                    note = Xaa may be Asn, or deamidated to Asp, isoAsp, or
                     Asp/isoAsp
VARIANT             735
                    note = Xaa may be Asn, or deamidated to Asp, isoAsp, or
                     Asp/isoAsp
source              1..736
                    mol_type = protein
                    organism = synthetic construct
SEQUENCE: 14
MAADGYLPDW LEDNLSEGIR EWXALKPGAP QPKAXQQHQD NARGLVLPGY KYLGPGXGLD  60
KGEPVXEADA AALEHDKAYD QQLKAGDNPY LKYXHAXAEF QERLKEXTSF GGXLGRAVFQ  120
AKKRLLEPLG LVEEAAKTAP GKKRPVEQXP QEPDSSVGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTXALP TYXNHLYKXI SNSTSGGSSX DNAYFGYSTP WGYFDFNRFH CHFSPRXWQR  300
LINXNXGFRP KRLXFKLFXI QVKEVTDNXG VXTIAXNLTS TVQVFTDSDY QLPYVLGSAH  360
EGCLPPFPAD VFMIPQYGYL TLNXGSQAVG RSSFYCLEYF PSQXLRTGXN FQFSYEFENV  420
PFHSSYAHSQ SLDRLXNPLI DQYLYYLSKT IXGSGQNQQT LKFSVAGPSN MAVQGRXYIP  480
GPSYRQQRVS TTVTQNNNXE FAWPGASSWA LXGRXSLXNP GPAXASHKEG EDRFFPLSGS  540
LIFGKQGTGR DNVDADKVXI TNEEEIKTXN PVATESYGQV ATNHQXAQAQ AQTGWVQNQG  600
ILPGXVWQDR DVYLQGPIXA KIPHTDGXFH PSPLMGGFGX KHPPPQILIK XTPVPADPPT  660
AFXKDXLNSF ITQYSTGQVS VEIEWELQXE NSXRXNPEIQ YTSNYYKSXN VEFAVNTEGV  720
YSEPRPIGTR YLTRXL                                                   736
```